US007737155B2

(12) United States Patent
Palani et al.

(10) Patent No.: US 7,737,155 B2
(45) Date of Patent: *Jun. 15, 2010

(54) NITROGEN-CONTAINING HETEROCYCLIC COMPOUNDS AND METHODS OF USE THEREOF

(75) Inventors: Anandan Palani, Bridgewater, NJ (US); Dong Xiao, Warren, NJ (US); Xianhai Huang, Warren, NJ (US); Ashwin U. Rao, Avenel, NJ (US); Xiao Chen, Edison, NJ (US); Jun Qin, Edison, NJ (US); Ying R. Huang, Berkeley Heights, NJ (US); Robert G. Aslanian, Rockaway, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/771,538

(22) Filed: Jun. 29, 2007

(65) Prior Publication Data

US 2008/0019978 A1    Jan. 24, 2008

Related U.S. Application Data

(63) Continuation-in-part of application No. 11/600,216, filed on Nov. 15, 2006, which is a continuation-in-part of application No. 11/432,133, filed on May 11, 2006.

(60) Provisional application No. 60/681,848, filed on May 17, 2005, provisional application No. 60/715,565, filed on Sep. 9, 2005, provisional application No. 60/731,039, filed on Oct. 28, 2005.

(51) Int. Cl.
C07D 491/052 (2006.01)
A61K 31/519 (2006.01)
A61P 9/00 (2006.01)
A61P 25/00 (2006.01)
A61P 33/00 (2006.01)
A61P 29/00 (2006.01)
A61P 1/00 (2006.01)
A61P 3/10 (2006.01)

(52) U.S. Cl. .................... 514/260.1; 544/278
(58) Field of Classification Search ............. 514/260.1; 544/278
See application file for complete search history.

(56) References Cited

U.S. PATENT DOCUMENTS

| 2,826,580 | A | 3/1958 | Fischer et al. |
| 6,399,653 | B1 | 6/2002 | Henke |
| 2003/0019956 | A1* | 1/2003 | Rodriguez-Amaya ...... 239/533.2 |
| 2003/0199526 | A1 | 10/2003 | Choquette et al. |
| 2004/0122033 | A1 | 6/2004 | Nargund et al. |
| 2004/0142377 | A1 | 7/2004 | Unett et al. |
| 2004/0229844 | A1 | 11/2004 | Cheng et al. |
| 2005/0251869 | A1 | 11/2005 | Cai et al. |
| 2006/0264489 | A1 | 11/2006 | Palani et al. |
| 2007/0065917 | A1 | 3/2007 | Chen et al. |
| 2007/0066630 | A1 | 3/2007 | Palani et al. |
| 2007/0167469 | A1 | 7/2007 | Bourrie et al. |
| 2007/0173495 | A1 | 7/2007 | Palani et al. |

FOREIGN PATENT DOCUMENTS

| DE | 263 891 A3 | | 1/1989 |
| DE | 265 760 A3 | | 3/1989 |
| FR | 2563223 | * | 1/1985 |
| WO | WO 00/69829 A1 | | 11/2000 |
| WO | WO 02/084298 A2 | | 10/2002 |
| WO | WO 2004/037159 A2 | | 5/2004 |
| WO | WO 2004/047755 A2 | | 6/2004 |
| WO | WO 2004/083388 A2 | | 9/2004 |
| WO | WO 2004/110368 A2 | | 12/2004 |
| WO | WO 2004/110375 A2 | | 12/2004 |
| WO | WO 2005/000217 A2 | | 1/2005 |
| WO | WO 2005/077950 A2 | | 8/2005 |
| WO | WO 2005/105097 A2 | | 11/2005 |
| WO | WO 2006/045564 A1 | | 5/2006 |
| WO | WO 2006/045565 A1 | | 5/2006 |
| WO | WO 2006/078834 A1 | | 7/2006 |
| WO | WO 2006/089009 A2 | | 8/2006 |
| WO | WO 2006/092430 A1 | | 9/2006 |
| WO | WO 2007/021744 A1 | | 2/2007 |
| WO | WO 2007/027661 A2 | | 3/2007 |
| WO | WO 2008/127591 | | 10/2008 |

OTHER PUBLICATIONS

Vippagunta et al. ,Advanced Drug Delivery Reviews, 2001, 48, 3-26.*
Griesser, Chapter 8, The Importance of Solvates (pp. 211-230), in the text, Polymorphism: In the Pharmaceutical Industry, Hilfiker, 2006.*
Ahluwalia et al., "Base Catalysed Condensation of Acetone with Uracil Derivatives: One Step Synthesis of Pyranopyrimidines", *Synthetic Communications*, 17(12):1435-1440 (1987).
Kvita et al., "158. Reaktionen des Cumalinsaure-methylesters and Cumalinaldehyds mit ambidenten Nucleophilen", *Helv. Chim, Acta.*, 71:1467-1473 (1988).
Selles et al., "Expedient Synthesis of Highly Substituted Fused Heterocoumarins"; *Organic Letters*, 6( 2):277-279 (1997).
Tietze et al., "Multicomponent Domino Reactions for the Synthesis of Biologically Active Natural Products and Drugs", *Medicinal Research Reviews*, 20:304-322 (2000).
Zooroob et al., 1,3-Dimethylpyrimidoheterozyklen als antibakterielle Substanzen, *Arzneimittel-Forschung*, 47:958-962 (1997).
Database Beilstein, Beilstein Institute for Organic Chemistry, Frankfurt-Main, DE; XP002482949 retrieved from CrossFire Database accession Nos. 5954253, 595391 and 5975043 Abstract.
Database Beilstein, Beilstein Institute for Organic Chemistry, Frankfurt-Main, DE; XP002482950 retrieved from CrossFire Database accession No. 233231 Abstract.
Database Beilstein, Beilstein Institute for Organic Chemistry, Frankfurt-Main, DE; XP002482951 retrieved from CrossFire Database accession Nos. 5935847, 5942970, 5959486 Abstract.
Database Beilstein, Beilstein Institute for Organic Chemistry, Frankfurt-Main, DE; XP002482952 retrieved from CrossFire Database accession No. 191230 Abstract.
Database Beilstein, Beilstein Institute for Organic Chemistry, Frankfurt-Main, DE; XP002482953 retrieved from CrossFire Database accession No. 1037486 Abstract.
Database Beilstein, Beilstein Institute for Organic Chemistry, Frankfurt-Main, DE; XP002482954 retrieved from CrossFire Database accession No. 617130 Abstract.
Database Beilstein, Beilstein Institute for Organic Chemistry, Frankfurt-Main, DE; XP002482955 retrieved from CrossFire Database accession No. 1018983 Abstract.
Database Beilstein, Beilstein institute for Organic Chemistry, Frankfurt-Main, DE; XP002482956 retrieved from CrossFire Database accession No. 1128908 Abstract.
Chemical Abstract No. 45:8600 for Ridi, Mario, et al., "Barbituric acid and its derivatives. VII. Some reactions with ethyl acetate", Gazzetta Chimica Italiana 80:121-128, (1950) (which is attached to said abstract).

Chemical Abstract No. 48:3424 for Ridi, Mario, et al., "Barbituric acid and its derivatives. XI. Some reactions with esters of ketonic acids", Gazzetta Chimica Italiana 82:23-30, (1952) (which is attached to said abstract).

Paterson, Thomas, et al, "Specific Enzyme Inhibitors in Vitamin Biosynthesis; Part I. The Synthesis of 8-Substituted Pyrido [2,3-d] Pyrimidines", J. Chem. Soc., Perkin Trans. I, 8:1041-1050 (1972).

Rao, A. Subba, et al., "Synthesis of Heterocycles: Part ll—Pyrano[2,3-d]pyrimidines", Indian Journal of Chemistry, 12:1028-1030 (1974).

Skof, Marko, et al. "A One-Step Transformation of (S)-1-Benzoyl-3-[(E)-Dimethylaminomethylidene]-5-Methoxycarbonyl-Pyrrolidin-2-One Into quinolizinyl-AND 2H-2- Pyranonyl-Substituted Alanine Derivatives", Heterocycles, 51(5):1051-1058 (1999).

Toplak, Renata, et al. "The Synthesis of Methyl-2-(Benzyloxycarbonyl)amino-3-dimethylaminopropenoate. The Synthesis of Trisubstituted Pyrroles, 3-Amino-2H-pyran-2ones, Fused 2H-Pyran-2-ones and 4H Pyridin-4-ones", J. Heterocyclic Chem., 36:225-235 (1999).

Habib, Nargues S., et al., "Synthesis of 2H-Pyrano[2,3-d]pyrimidine Derivatives", Monatshefte fur Chemie, 115:1459-1466 (1984).

PCT International Search Report dated Dec. 28, 2006 for corresponding PCT Application No. PCT/US2006/018186.

Office Action mailed Oct. 26, 2007 in connection with U.S. Appl. No. 11/432,133 (10 Pages).

Office Action mailed Feb. 29, 2008 in connection with U.S. Appl. No. 11/432,133 (16 Pages).

Office Action mailed Oct. 3, 2008 in connection with U.S. Appl. No. 11/432,133 (15 Pages).

Office Action mailed Oct. 26, 2007 in connection with U.S. Appl. No. 11/600,216 (9 Pages).

Office Action mailed Jan. 8, 2008 in connection with U.S. Appl. No. 11/600,216 (15 Pages).

Office Action mailed Sep. 19, 2008 in connection with U.S. Appl. No. 11/600,216 (6 Pages).

Office Action mailed Oct. 3, 2008 in connection with U.S. Appl. No. 11/654,137 (6 Pages).

* cited by examiner

*Primary Examiner*—James O Wilson
*Assistant Examiner*—Cecilia M Jaisle
(74) *Attorney, Agent, or Firm*—Jeffrey P. Bergman; Palaiyur S. Kalyanaraman

(57) ABSTRACT

The present invention provides compounds of Formula (I):

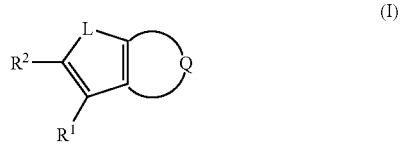

(I)

and pharmaceutically acceptable salts, solvates, esters, and tautomers thereof, wherein:

Q is selected from the group consisting of:

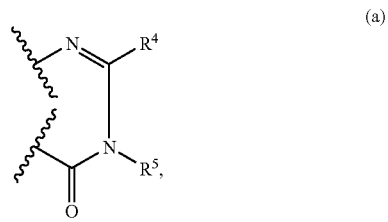

(a)

-continued

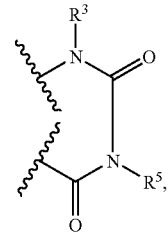

(b)

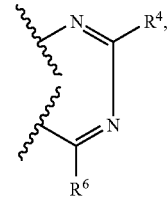

(c)

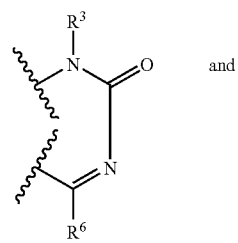

(d)

and

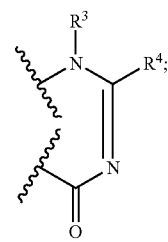

(e)

and

L is selected from the group consisting of:

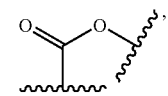

(f)

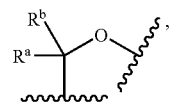

(g)

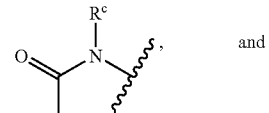

(h)

and

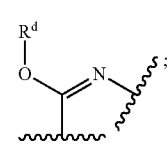

(i)

pharmaceutically compositions comprising one or more compounds of formula (I), and methods of using the compounds of formula (I).

35 Claims, No Drawings

NITROGEN-CONTAINING HETEROCYCLIC COMPOUNDS AND METHODS OF USE THEREOF

REFERENCE TO PRIORITY APPLICATIONS

This application is a continuation-in-part of U.S. patent application Ser. No. 11/600,216, filed Nov. 15, 2006, which is a continuation-in-part of U.S. patent application Ser. No. 11/432,133, filed May 11, 2006, which claims the benefit of priority from U.S. provisional patent applications, Ser. No. 60/681,848 filed May 17, 2005; U.S. provisional patent applications, Ser. No. 60/715,565 filed Sep. 9, 2005; and U.S. provisional patent applications, Ser. No. 60/731,039 filed Oct. 28, 2005, each of which is incorporated herein by reference in its entirety.

FIELD OF THE INVENTION

The present invention relates to nicotinic acid receptor agonist compounds useful for treating metabolic syndrome, dyslipidemia, cardiovascular diseases, disorders of the peripheral and central nervous system, hematological diseases, cancer, inflammation, respiratory diseases, gastroenterological diseases, diabetes, and non-alcoholic fatty liver disease; pharmaceutical compositions comprising such compounds; pharmaceutical compositions comprising nicotinic acid receptor agonist compounds in combination with other therapeutic agents; and methods of treatment using the compounds and compositions to treat conditions such as metabolic syndrome, dyslipidemia, cardiovascular diseases, disorders of the peripheral and central nervous system, hematological diseases, cancer, inflammation, respiratory diseases, gastroenterological diseases, diabetes, hepatic steatosis and non-alcoholic fatty liver disease.

BACKGROUND OF THE INVENTION

Nicotinic acid has been used to treat metabolic syndrome and dyslipidemia. However, nicotinic acid has undesirable side effects such as flushing and diarrhea. It is therefore desirable to provide improved nicotinic acid receptor agonists with improved efficacy at treating metabolic syndrome and dyslipidemia, yet without the undesirable side effects. The compounds of the present invention provide such improved nicotinic acid receptor agonists.

M. Ridi, *Gazzetta Chim. Ital.* (1950) vol. 80, p. 121 and M. Ridi, *Gazzetta Chim. Ital.* (1952) vol. 82, p 23 disclose syntheses of barbituric acid derivatives. FR 2563223 discloses nucleoside analogs. T. Paterson et al. *J. Chem. Soc., Perkins Trans. I* (1972), vol. 8, pp. 1041-1050 discloses the synthesis of 8-substituted pyrido[2,3-d]pyrimidines. S. Rao, *Indian J. Chem.* (1974), 12(10), pp. 1028-1030 discloses the synthesis of pyrano[2,3-d]pyrimidines. M. Skof, *Heterocycles*, (1999), 51(5), pp. 1051-1058 discloses one step transformations of (S)-1-benzoyl-3-[(E)-dimethylaminomethylidene]-5-methoxycarbonyl-pyrrolidin-2-one into quinolizinyl- and 2H-2-pyranonyl-substituted alanine derivatives. R. Toplak *J. Heterocyclic Chem.* (1999), 36(1), pp. 225-235 discloses the synthesis of pyran-2-ones. However, the compounds of the above references differ from those of the present invention.

WO 2004/110368 describes combination therapies for the treatment of hypertension comprising the combination of an anti-obesity agent and an anti-hypertensive agent. However, WO 2004/110368 fails to describe nicotinic acid receptor agonists, or combinations of one or more nicotinic acid receptor agonists with a second therapeutic agent.

WO 2005/000217 describes combination therapies for the treatment of dyslipidemia comprising the administration of a combination of an anti-obesity agent and an anti-dyslipidemic agent. However, WO 2005/000217 fails to describe nicotinic acid receptor agonists, or combinations of one or more nicotinic acid receptor agonists with a second therapeutic agent.

WO 2004/110375 describes combination therapies for the treatment of diabetes comprising the administration of a combination of an anti-obesity agent and an anti-diabetic agent. However, WO 2004/110375 fails to describe nicotinic acid receptor agonists, or combinations of one or more nicotinic acid receptor agonists with a second therapeutic agent.

U.S Pat. No. 2004/0122033 describes combination therapies for the treatment of obesity comprising the administration of a combination of an appetite suppressant and/or metabolic rate enhancers and/or nutrient absorption inhibitors. However, U.S Pat. No. 2004/0122033 fails to describe nicotinic acid receptor agonists, or combinations of one or more nicotinic acid receptor agonists with a second therapeutic agent. U.S Pat. No. 2004/0229844 describes combination therapies for treating atherosclerosis comprising the administration of a combination of nicotinic acid or another nicotinic acid receptor agonist and a DP receptor antagonist. However, the nicotinic acid agonists of U.S Pat. No. 2004/0229844 are quite different from those of the present invention.

WO2005/077950 describes xanthine derivatives which are agonists of the nicotinic acid receptor HM74A. However, the xanthine derivatives of WO2005/077950 are quite different from the compounds of the present invention.

SUMMARY OF THE INVENTION

In one embodiment, the present invention is directed to a compound of Formula (I):

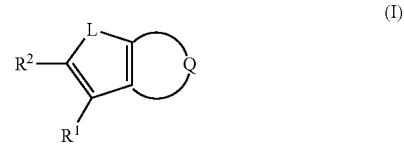

(I)

and pharmaceutically acceptable salts, solvates, esters, and tautomers thereof, wherein:

Q is selected from the group consisting of:

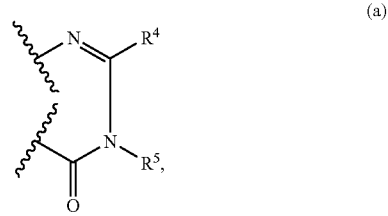

(a)

-continued

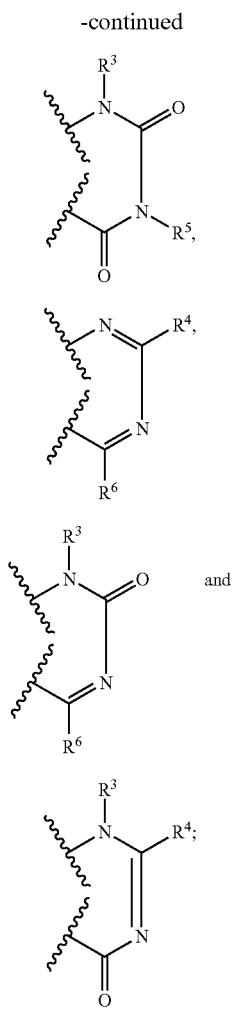

L is selected from the group consisting of:

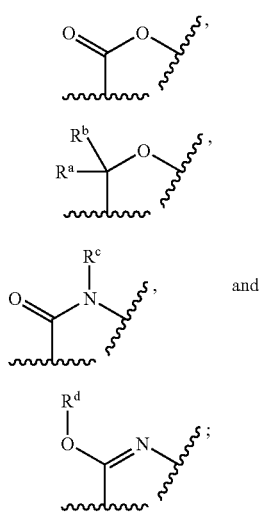

$R^1$ is selected from the group consisting of H, alkyl, arylalkyl, -alkylene-S-alkyl, alkenyl, alkynyl, haloalkyl, wherein an alkyl group can be optionally substituted with one or more of the following groups, which can be the same or different: —OH, cycloalkyl, —C(O)-alkyl, -alkylene-C(O)—O-alkyl, —O—$R^{10}$, -alkylene-O-alkyl, aryl, -alkylene-aryl, heteroaryl, -alkylene-heteroaryl, halogen, —$(CH_2)_n$—$N(R^7)_2$, -alkylene-cycloalkyl, or -alkylene-cycloalkenyl, wherein the cycloalkyl or the cycloalkyl portion of said -alkylene-cycloalkyl of $R^1$ is unsubstituted or substituted with one or more X groups, said aryl or the aryl portion of said -alkylene-aryl of $R^1$ is unsubstituted or substituted with one or more Y groups, and said heteroaryl or the heteroaryl portion of said -alkylene-heteroaryl of $R^1$ is unsubstituted or substituted with one or more Y groups;

$R^2$ is selected from the group consisting of H, halogen, alkyl, haloalkyl, alkyl substituted with one or more —OH, —C(O)-alkyl, —C(O)—O-alkyl, —C(O)—OH, —O—$R^{10}$, -alkylene-O-alkyl, unsubstituted aryl, aryl substituted with one or more Y groups, unsubstituted heteroaryl, heteroaryl substituted with one or more Y groups, and halogen; or $R^1$ and $R^2$ together with the ring carbon atoms to which they are shown attached, form a 5- or 6-membered cycloalkenyl ring or a 5- or 6-membered heterocyclic ring having 1 or 2 heteroatoms;

$R^3$ is selected from the group consisting of H, alkyl, alkyl substituted with one or more hydroxyl groups, -alkylene-O-alkyl, cycloalkyl, -alkylene-cycloalkyl, -alkylene-C(O)—O-alkyl, -alkylene-O—C(O)-alkyl, alkenyl, aryl, and heteroaryl, wherein the cycloalkyl or the cycloalkyl portion of said -alkylene-cycloalkyl of $R^3$ is unsubstituted or substituted with one or more X groups, said aryl of $R^3$ is unsubstituted or substituted with one or more Y groups, and said heteroaryl of $R^3$ is unsubstituted or substituted with one or more Y groups;

$R^4$ is selected from the group consisting of H, halogen, alkyl, haloalkyl, —O-cycloalkyl, —O-alkynyl, —O—$R^{10}$, —C(O)—O-alkyl, —$S(O)_m$—$R^9$, —$N(R^7)_2$, —$N(R^7)$—NH—C(O)-alkyl, —$N(R^7)$—NH—C(O)—O-alkyl, —O—N=$C(R^{12})_2$, —$N(R^7)$—N=$C(R^{12})_2$, —C(O)-alkyl, unsubstituted heterocyclyl, heterocyclyl substituted with one or more X groups, —O—$N(R^7)$—C(O)—O-alkyl, —C(O)—$N(R^7)_2$, —CN, —$N_3$, and —O—C(O)-alkyl;

$R^5$ is selected from the group consisting of H, alkyl, —OH, haloalkyl, arylalkyl, —O-alkyl, —O-aryl, cycloalkyl, heterocyclyl, —O-cycloalkyl, —O-heterocyclyl, —O-arylalkyl or -alkylene-O-alkyl-alkylene-C(O)—$R^8$, -alkylene-C(O)—$N(R^{11})_2$, -alkylene-C(=N—O-alkyl)-aryl, cycloalkyl, -alkylene-cycloalkyl, -alkylene-C(O)—O-alkyl, -alkylene-O—C(O)-alkyl, -alkylene-C(O)-heterocyclyl, and alkenyl, wherein the cycloalkyl or the cycloalkyl portion of said -alkylene-cycloalkyl of $R^5$ is unsubstituted or substituted with one or more X groups, and the aryl portion of said -alkylene-C(=N—O-alkyl)-aryl of $R^5$ is unsubstituted or substituted with one or more Y groups;

$R^6$ is selected from the group consisting of H, alkyl, alkenyl, alkyl substituted with one or more hydroxyl groups, -alkylene-O-alkyl, —O—$R^{10}$, halogen, aryl, heteroaryl, and —$N(R^7)_2$, wherein the aryl of $R^6$ is unsubstituted or substituted with one or more Y groups, and said heteroaryl of $R^6$ is unsubstituted or substituted with one or more Z groups;

each $R^7$ is independently selected from the group consisting of H, alkyl, cycloalkyl, aryl, —C(O)-alkyl, and —C(O)-aryl, wherein the cycloalkyl of $R^7$ is unsubstituted or substituted with one or more X groups, and the aryl portion of said —C(O)-aryl or said aryl of $R^7$ is unsubstituted or substituted with one or more Y groups;

two $R^7$ groups, together with the N atom to which they are bonded form a heterocyclyl;

$R^8$ is selected from the group consisting of aryl, —OH, and heterocyclyl, wherein the heterocyclyl of $R^8$ is unsubstituted or substituted with one or more X groups, and said aryl of $R^8$ is unsubstituted or substituted with one or more Y groups;

$R^9$ is selected from the group consisting of alkyl, -alkylene-cycloalkyl, alkenyl, —N$(R^{11})_2$, and -alkylene-aryl, wherein the cycloalkyl portion of said alkylene-cycloalkyl of $R^9$ is unsubstituted or substituted with one or more X groups, and the aryl portion of said -alkylene-aryl of $R^9$ is unsubstituted or substituted with one or more Y groups, and with the proviso that when $R^9$ is —N$(R^{11})_2$, m is 1 or 2;

$R^{10}$ is selected from the group consisting of H, alkyl, cycloalkyl, arylalkyl, haloalkyl, -alkylene-O-alkyl, -alkylene-aryl, -alkenylene-aryl, -alkylene-heteroaryl, alkenyl, —C(O)-alkyl, alkynyl, and -alkylene-cycloalkyl, wherein an the alkynyl portion of an —O-alkynyl group can be optionally substituted with —OH or alkoxy; the cycloalkyl portion of an —O-cycloalkyl group can be optionally substituted with an -alkylene-O-alkylene-aryl group; the cycloalkyl portion of said -alkylene-cycloalkyl of $R^{10}$ is unsubstituted or substituted with one or more X groups; the aryl portion of said -alkylene-aryl or -alkenylene-aryl of $R^{10}$ is unsubstituted or substituted with one or more Y groups; and the heteroaryl portion of said -alkylene-heteroaryl of $R^{10}$ is unsubstituted or substituted with one or more Z groups;

$R^{11}$ is selected from the group consisting of H, alkyl, and aryl, wherein the aryl of $R^{11}$ is unsubstituted or substituted with one or more Y groups; or two $R^{11}$ groups, together with the N atom to which they are attached, form a heterocyclyl;

each $R^{12}$ is independently selected from the group consisting of alkyl, aryl, and heteroaryl, wherein the aryl of $R^{12}$ is unsubstituted or substituted with one or more Y groups and said heteroaryl of $R^{12}$ is unsubstituted or substituted with one or more Z groups; or wherein both $R^{12}$ groups, together with the carbon atom to which they are attached, combine to form a heterocyclyl group;

$R^a$ and $R^b$ are each independently selected from the group consisting of H, alkyl, aryl, and heteroaryl, wherein the aryl of $R^a$ and $R^b$ is unsubstituted or substituted with one or more Y groups, and said heteroaryl of $R^a$ and $R^b$ is unsubstituted or substituted with one or more Z groups;

$R^c$ is selected from the group consisting of H, alkyl, alkylene-aryl, and —C(O)-alkyl, wherein the aryl portion of said alkylene-aryl of $R^c$ is unsubstituted or substituted with one or more Y groups;

$R^d$ is selected from the group consisting of H, alkyl, and alkylene-aryl, wherein the aryl portion of said alkylene-aryl of $R^d$ is unsubstituted or substituted with one or more Y groups;

each X is independently selected from the group consisting of halogen, alkyl, haloalkyl, —O-alkyl, —O-haloalkyl, and —OH;

each Y is independently selected from the group consisting of halogen, alkyl, haloalkyl, —O-alkyl, —O-haloalkyl, —CN, —NO$_2$, —OH, —S(O$_2$)-alkyl, —S(O$_2$)-aryl, —S(O$_2$)—NH$_2$, —S(O$_2$)—NH-alkyl, —S(O$_2$)—NH-aryl, —S(O$_2$)—N(alkyl)$_2$, —S(O$_2$)—N(aryl)$_2$, —S(O$_2$)—N(alkyl)(aryl), and aryl;

each Z is independently selected from the group consisting of alkyl, haloalkyl, halogen, —O-alkyl, —O-haloalkyl, —CN, —OH, aryl, and N-oxide;

n is 0, 1, 2, or 3;

m is 0, 1, or 2; and with the proviso that when L is (f), and $R^2$, $R^3$ and $R^5$ are each H, then $R^1$ is not —CH$_3$.

In another embodiment, the present invention is directed to a pharmaceutical composition comprising a therapeutically effective amount of at least one compound of Formula (I), or a pharmaceutically acceptable salt, solvate, ester, or tautomer thereof, and at least one pharmaceutically acceptable carrier.

In another embodiment, the present invention is directed to a method of treating a disease or disorder in a patient, such as metabolic syndrome, dyslipidemia, cardiovascular diseases, disorders of the peripheral and central nervous system, hematological diseases, cancer, inflammation, respiratory diseases, gastroenterological diseases, diabetes, and non-alcoholic fatty liver disease. The method comprises administering to the patient an effective amount of at least one compound of Formula (I), or a pharmaceutically acceptable salt, solvate, ester, or tautomer thereof.

In another embodiment, the present invention is directed to a method of treating a disease or disorder in a patient, such as metabolic syndrome, dyslipidemia, cardiovascular diseases, disorders of the peripheral and central nervous system, hematological diseases, cancer, inflammation, respiratory diseases, gastroenterological diseases, diabetes, hepatic steatosis, and non-alcoholic fatty liver disease. The method comprises administering to the patient an effective amount of at least one compound of Formula (I), or a pharmaceutically acceptable salt, solvate, ester, or tautomer thereof, in combination with at least one additional active ingredient selected from the group consisting of hydroxy-substituted azetidinone compounds, substituted β-lactam compounds, HMG CoA reductase inhibitor compounds, HMG CoA synthetase inhibitors, squalene synthesis inhibitors, squalene epoxidase inhibitors, sterol biosynthesis inhibitors, nicotinic acid derivatives, bile acid sequestrants, inorganic cholesterol sequestrants, AcylCoA:Cholesterol O-acyltransferase inhibitors, cholesteryl ester transfer protein inhibitors, fish oils containing Omega 3 fatty acids, natural water soluble fibers, plant stanols and/or fatty acid esters of plant stanols (e.g., Omacor® from Pronova Biocare, Oslo, Norway), low-density lipoprotein receptor activators, anti-oxidants, PPAR α agonists, PPAR γ-agonists, FXR receptor modulators, LXR receptor agonists, lipoprotein synthesis inhibitors, renin angiotensin inhibitors, microsomal triglyceride transport protein inhibitors, bile acid reabsorption inhibitors, PPAR δ agonists, triglyceride synthesis inhibitors, squalene epoxidase inhibitors, low density lipoprotein receptor inducers, platelet aggregation inhibitors, 5-LO or FLAP inhibitors, PPAR δ partial agonists, niacin or niacin receptor agonists, 5HT transporter inhibitors, NE transporter inhibitors, $CB_1$ antagonists/inverse agonists, ghrelin antagonists, $H_3$ antagonists/inverse agonists, MCH1R antagonists, MCH2R agonists/antagonists, NPY1 antagonists, NPY5 antagonists, NPY2 agonists, NPY4 agonists, mGluR5 antagonists, leptins, leptin agonists/modulators, leptin derivatives, opioid antagonists, orexin receptor antagonists, BRS3 agonists, CCK-A agonists, CNTF, CNTF derivatives, CNTF agonists/modulators, 5HT2c agonists, Mc4r agonists, monoamine reuptake inhibitors, serotonin reuptake inhibitors, GLP-1 agonists, phentermine, topiramate, phytopharm compound 57, ghrelin antibodies, Mc3r agonists, ACC2 inhibitors, β3 agonists, DGAT1 inhibitors, DGAT2 inhibitors, FAS inhibitors, PDE inhibitors, thyroid hormone β agonists, UCP-1 activators. UCP-2 activators, UCP-3 activators, acyl-estrogens, glucocorticoid agonists/antagonists, 11β HSD-1 inhibitors, SCD-1 inhibitors, lipase inhibitors, fatty acid transporter inhibitors, dicarboxylate transporter inhibitors, glucose transporter inhibitors, phosphate transporter inhibitors, antidiabetic agents, anti-hypertensive agents, anti-dyslipidemic agents, DP receptor antagonists, apolipoprotein-B secretion/microsomal triglyceride transfer protein (apo-B/MTP) inhibitors, sympathomimetic agonists, dopamine agonists, melanocyte-stimulating hormone receptor analogs, melanin concentrating hormone antagonists, leptons, galanin receptor antagonists, bombesin agonists, neuropeptide-Y antagonists, thyromimetic agents, dehydroepiandrosterone, analogs of dehydroepiandrosterone, urocortin binding protein antagonists, glucagons-like peptide-1 receptor agonists, human agouti-related proteins (AGRP), neuromedin U receptor agonists, noradrenergic anorectic agents, appetite suppressants, hormone sensitive lipase antagonists, MSH-receptor analogs, α-glucosidase inhibitors, apo A1 milano reverse cholesterol transport inhibitors, fatty acid binding protein inhibitors (FABP), and fatty acid transporter protein inhibitors (FATP).

DETAILED DESCRIPTION OF THE INVENTION

The nicotinic acid receptor agonist compounds of the present invention are useful for treating conditions such as metabolic syndrome, dyslipidemia, cardiovascular diseases, disorders of the peripheral and central nervous system, hematological diseases, cancer, inflammation, respiratory diseases, gastroenterological diseases, diabetes, hepatic steatosis, and non-alcoholic fatty liver disease and other diseases listed herein. One or more compounds of the present invention can be administered alone or in combination with one or more other therapeutic agents as described herein.

The present invention provides compound of Formula (I):

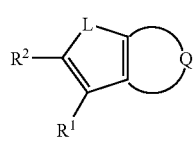

(I)

and pharmaceutically acceptable salts, solvates, esters, and tautomers thereof, wherein L, Q, $R^1$ and $R^2$ are defined above for the compound of formula (I).

In one embodiment, $R^1$ is alkyl.
In another embodiment, $R^1$ is haloalkyl.
In another embodiment, $R^1$ is arylalkyl.
In still another embodiment, $R^1$ is -alkylene-S-alkyl.
In yet another embodiment, $R^1$ is -alkylene-cycloalkyl.
In another embodiment, $R^1$ is -alkylene-cyclopropyl, -alkylene-cyclobutyl, -alkylene-cyclopentyl or -alkylene-cyclohexyl.
In a further embodiment, $R^1$ is -alkylene-cycloalkenyl.
In another embodiment, $R^1$ is a straight chain alkyl having from 1 to 6 carbon atoms.
In one embodiment, $R^1$ is methyl.
In another embodiment, $R^1$ is ethyl.
In another embodiment, $R^1$ is n-propyl.
In still another embodiment, $R^1$ is n-butyl.
In one embodiment, $R^1$ is n-pentyl.
In another embodiment, $R^1$ is n-hexyl.
In yet another embodiment, $R^1$ is a branched chain alkyl having from 3 to 6 carbon atoms.
In a further embodiment, $R^1$ is isopropyl.
In one embodiment, $R^1$ is isobutyl.
In another embodiment, $R^1$ is isopentyl.
In another embodiment, $R^1$ is sec-butyl.
In still another embodiment, $R^1$ is tert-butyl.
In yet another embodiment, $R^1$ is haloalkyl, having from 1 to 3 F atoms.
In another embodiment, $R^1$ is $-(CH_2)_3CF_3$.
In one embodiment, $R^2$ is $-H$.
In another embodiment, $R^2$ is $-CN$.
In another embodiment, $R^2$ is $-NHC(O)$-alkyl.
In still another embodiment, $R^2$ is $-NHC(O)CH_3$.
In one embodiment, $R^3$ is $-H$.
In another embodiment, $R^3$ is $-OH$.
In another embodiment, $R^3$ is alkyl.
In another embodiment, $R^3$ is haloalkyl.
In still another embodiment, $R^3$ is $-O$-alkyl.
In yet another embodiment, $R^3$ is cycloalkyl.
In a further embodiment, $R^3$ is heterocyclyl.
In one embodiment, $R^3$ is $-O$-arylalkyl.
In another embodiment, $R^3$ is -alkylene-O-alkyl.
In one embodiment, $R^3$ is $-OCH_3$.
In another embodiment, $R^3$ is cyclobutyl.
In another embodiment, $R^3$ is ethyl.
In still another embodiment, $R^3$ is N-morpholinyl.
In one embodiment, $R^3$ is $-O$-benzyl.
In another embodiment, $R^3$ is $-CH_2CH_2OCH_3$.
In yet another embodiment, $R^3$ is $-OCH_2CH_3$.
In another embodiment, $R^3$ is $-CH_2F$.
In one embodiment, $R^3$ is $-CH_2CH_2F$.
In another embodiment, $R^3$ is $-OH$.
In one embodiment, $R^4$ is $-CF_3$.
In another embodiment, $R^4$ is $-H$.
In another embodiment, $R^4$ is $-O$-cycloalkyl.
In another embodiment, $R^4$—O-alkynyl.
In still another embodiment, $R^4$ is $-O$-alkynylene-cycloalkyl.
In yet another embodiment, $R^4$ is haloalkyl.
In a further embodiment, $R^4$ is $-O-N=C(R^7)_2$.
In one embodiment, $R^4$ is is $-CH_2F$.
In another embodiment, $R^4$ is $-CH(F)_2$.
In another embodiment, $R^4$ is $-CF_3$.
In another embodiment, $R^4$ is $-OCH_2C\equiv CCH_2H_3$.
In another embodiment, $R^4$ is $-OCH_2C\equiv C(CH_2)_3CH_3$.
In still another embodiment, $R^4$ is $-OCH_2C\equiv CCH_2CH_3$.
In yet another embodiment, $R^4$ is $-OCH_2C\equiv C$-cyclopropyl.

In a further embodiment, $R^4$ is —OCH$_2$C≡CCH(OCH$_3$)CH$_3$.

In one embodiment, $R^4$ is —OCH$_2$C≡CCH(OH)CH$_3$.

In another embodiment, $R^4$ is —OCH$_2$C≡CCH(OH)CH$_2$CH$_3$.

In another embodiment, $R^4$ is —OCH$_2$C≡CCH$_2$CH$_2$OCH$_3$.

In still another embodiment, $R^4$ is —OCH$_2$C≡CCH$_2$CH$_2$OH.

In yet another embodiment, $R^4$ is —OCH$_2$C≡C(CH$_2$)$_3$OH.

In a further embodiment, $R^4$ is —OCH(CH$_3$)C≡CCH$_2$CH$_3$.

In another embodiment, $R^4$ is —OCH$_2$C≡C-cyclohexyl.

In one embodiment, $R^4$ is —O-cyclobutyl.

In another embodiment, $R^4$ is:

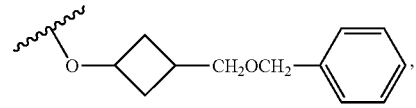

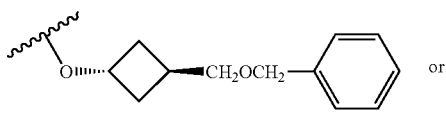 or

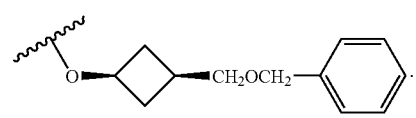

In one embodiment, $R^4$ is:

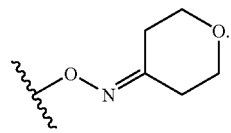

In one embodiment, $R^5$ is —H.
In another embodiment, $R^5$ is —OH.
In another embodiment, $R^5$ is alkyl.
In another embodiment, $R^5$ is haloalkyl.
In still another embodiment, $R^5$ is —O-alkyl.
In yet another embodiment, $R^5$ is cycloalkyl.
In a further embodiment, $R^5$ is heterocyclyl.
In one embodiment, $R^5$ is —O-arylalkyl.
In another embodiment, $R^5$ is -alkylene-O-alkyl.
In one embodiment, $R^5$ is —OCH$_3$.
In another embodiment, $R^5$ is cyclobutyl.
In another embodiment, $R^5$ is ethyl.
In still another embodiment, $R^5$ is N-morpholinyl.
In one embodiment, $R^5$ is —O-benzyl.
In another embodiment, $R^5$ is —CH$_2$CH$_2$OCH$_3$.
In yet another embodiment, $R^5$ is —OCH$_2$CH$_3$.
In another embodiment, $R^5$ is —CH$_2$F.
In one embodiment, $R^5$ is —CH$_2$CH$_2$F.
In another embodiment, $R^5$ is —OH.
In one embodiment, $R^6$ is alkoxy.

In another embodiment, $R^6$ is —O-alkylene-O-alkyl.
In another embodiment, $R^6$ is —O-arylalkyl.
in still another embodiment, $R^6$ is —O-haloalkyl.
In yet another embodiment, $R^6$ is —OCH$_2$-(4-methoxyphenyl).
In one embodiment, $R^6$ is —OCH$_2$F.
In another embodiment, $R^6$ is —OCH$_2$CH$_2$F.
In another embodiment, $R^6$ is —OCH$_2$CH$_3$.
In still another embodiment, $R^6$ is —OCH$_2$CH$_2$OCH$_3$.
In one embodiment, Q is:

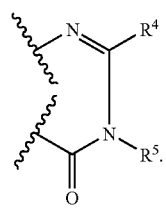

(a)

In another embodiment, Q is:

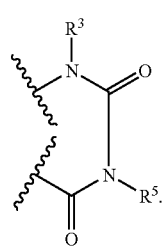

(b)

In another embodiment, Q is:

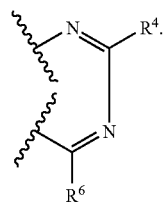

(c)

In still another embodiment, Q is:

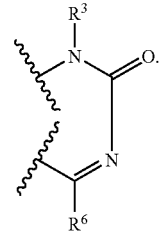

(d)

In yet another embodiment, Q is:

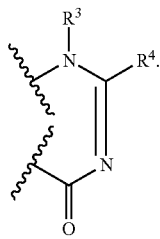
(e)

In one embodiment, L is:

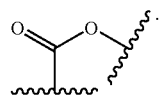
(f)

In another embodiment, L is:

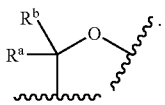
(g)

In another embodiment, L is:

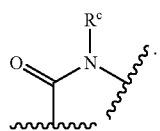
(h)

In still another embodiment, L is:

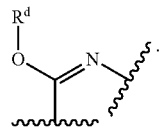
(i)

In another embodiment of the compounds of Formula (I), $R^1$ is selected from the group consisting of —$(C_1-C_6)$alkyl, —$(C_1-C_6)$alkenyl, —$(C_1-C_6)$alkynyl, —$(C_1-C_6)$haloalkyl, —$(C_1-C_6)$alkyl substituted with one hydroxyl group, —$(C_3-C_7)$cycloalkyl, —$(C_1-C_6)$alkylene-O—$(C_1-C_6)$alkyl, —$(C_1-C_6)$alkylene-$(C_6-C_{10})$aryl, —$C_1$-$C_6$)alkylene-$(C_2-C_{10})$heteroaryl, —$(C_1-C_6)$alkylene-C(O)—O—$(C_1-C_6)$alkyl, —$(CH_2)_n$—N$(R^7)_2$, —$(C_1-C_6)$alkylene-$(C_3-C_7)$cycloalkyl, and —$(C_1-C_6)$alkylene-$(C_3-C_7)$cycloalkenyl wherein the —$(C_3-C_7)$cycloalkyl or the $(C_3-C_7)$cycloalkyl portion of said —$(C_1-C_6)$alkylene-$(C_3-C_7)$cycloalkyl is unsubstituted or substituted with one or more X groups, the $(C_6-C_{10})$aryl portion of said —$(C_1-C_6)$alkylene-$(C_6-C_{10})$aryl is unsubstituted or substituted with one or more Y groups, and the $(C_2-C_{10})$heteroaryl portion of said —$(C_1-C_6)$alkylene-$(C_2-C_{10})$heteroaryl is unsubstituted or substituted with one or more Z groups;

$R^2$ is H, halogen, unsubstituted aryl, aryl substituted with one or more independently selected Y groups, unsubstituted heteroaryl, heteroaryl substituted with one or more independently selected Y groups; or $R^1$ and $R^2$ together with the ring carbon atoms to which they are shown attached, form a 5- or 6-membered cycloalkenyl ring;

$R^3$ is selected from the group consisting of H, $(C_1-C_6)$alkyl, —$(C_3-C_6)$alkylene-O—$(C_1-C_6)$alkyl, $(C_3-C_7)$cycloalkyl, —$(C_1-C_6)$alkylene-$(C_3-C_7)$cycloalkyl, —$(C_1-C_6)$alkylene-C(O)—O-alkyl, and $(C_1-C_6)$alkenyl, wherein the $(C_3-C_7)$cycloalkyl or the $(C_3-C_7)$cycloalkyl portion of said —$(C_3-C_6)$alkylene-$(C_3-C_7)$cycloalkyl of $R^3$ is unsubstituted or substituted with one or more X groups;

$R^4$ is selected from the group consisting of halogens —O—$R^{10}$, —C(O)—O—$(C_1-C_6)$alkyl, —S(O)$_m$—$R^9$, —N$(R^7)_2$, —O—N=C$(R^{12})_2$, —N$(R^7)$—NH—C(O)—O—$(C_1-C_6)$alkyl and —C(O)—$(C_1-C_6)$alkyl;

$R^5$ is selected from the group consisting of H, —$(C_1-C_6)$alkyl, —$(C_1-C_6)$alkylene-C(O)—$R^8$, —$(C_1-C_6)$alkylene-C(=N—O—$(C_1-C_6)$alkyl)-$(C_6-C_{10})$aryl, $(C_3-C_7)$cycloalkyl, —$(C_1-C_6)$alkylene-$(C_3-C_7)$cycloalkyl, —$(C_1-C_6)$alkylene-C(O)—O—$(C_1-C_6)$alkyl, and $(C_2-C_6)$alkenyl wherein the $(C_3-C_7)$cycloalkyl or the $(C_3-C_7)$cycloalkyl portion of said —$(C_1-C_6)$alkylene-$(C_3-C_7)$cycloalkyl of $R^5$ is unsubstituted or substituted with one or more X groups, and the $(C_6-C_{10})$aryl portion of said —$(C_1-C_6)$alkylene-C(N=O—$(C_1-C_6)$alkyl)-$(C_6-C_{10})$aryl of $R^5$ is unsubstituted or substituted with one or more Y groups;

$R^6$ is selected from the group consisting of —O—$R^{10}$, halogen, and —N$(R^7)_2$;

each $R^7$ is independently selected from the group consisting of H, $(C_1-C_6)$alkyl, $(C_3-C_7)$cycloalkyl, and $(C_6-C_{10})$aryl, wherein the $(C_3-C_7)$cycloalkyl of $R^7$ is unsubstituted or substituted with one or more X groups, and said $(C_6-C_{10})$aryl of $R^7$ is unsubstituted or substituted with one or more Y groups;

$R^8$ is selected from the group consisting of unsubstituted $(C_6-C_{10})$aryl, $(C_6-C_{10})$aryl substituted with one or more Y groups, —OH, unsubstituted $(C_2-C_{10})$heterocyclyl, and $(C_2-C_{10})$heterocyclyl substituted with one or more X groups;

$R^9$ is selected from the group consisting of $(C_1-C_6)$alkyl, —$(C_1-C_6)$alkylene-$(C_3-C_7)$cycloalkyl, $(C_2-C_6)$alkenyl, and —$(C_1-C_6)$alkylene-$(C_6-C_{10})$aryl, wherein the $(C_3-C_7)$cycloalkyl portion of said —$(C_1-C_6)$alkylene-$(C_3-C_7)$cycloalkyl of $R^9$ is unsubstituted or substituted with one or more X groups, and the $(C_6-C_{10})$aryl portion of said —$(C_1-C_6)$alkylene-$(C_6-C_{10})$aryl of $R^9$ is unsubstituted or substituted with one or more groups Y;

$R^{10}$ is selected from the group consisting of H, $(C_1-C_6)$alkyl, —$(C_1-C_6)$alkylene-$(C_6-C_{10})$aryl, —$(C_2-C_6)$alkenylene-$(C_6-C_{10})$aryl, —$(C_1-C_6)$alkylene-$(C_2-C_{10})$heteroaryl, $(C_2-C_6)$alkenyl, $(C_2-C_6)$alkynyl, and —$(C_1-C_6)$alkylene-$(C_3-C_7)$cycloalkyl, wherein the $(C_3-C_7)$cycloalkyl portion of said —$(C_1-C_6)$alkylene-$(C_3-C_7)$cycloalkyl of $R^{10}$ is unsubstituted or substituted with one or more X groups, and the $(C_6$-$C_{10})$aryl portion of said —$(C_1$-$C_6)$alkylene-$(C_5$-$C_{10})$aryl or —$(C_2$-$C_6)$alkenylene-$(C_6$-$C_{10})$aryl of $R^{10}$ is unsubstituted or substituted with one or more Y groups, and the $(C_2$-$C_{10})$heteroaryl portion of said —$(C_1$-$C_6)$alkylene-$(C_2$-$C_{10})$heteroaryl of $R^{10}$ is unsubstituted or substituted with one or more Z groups;

each $R^{12}$ is independently a $(C_1$-$C_6)$alkyl;

$R^a$ and $R^b$ are each independently a $(C_1$-$C_6)$alkyl;

$R^c$ is H;

$R^d$ is selected from the group consisting of H, $(C_1$-$C_6)$alkyl, and —$(C_1$-$C_6)$alkylene-$(C_6$-$C_{10})$aryl,
wherein the $(C_6$-$C_{10})$aryl portion of said —$(C_1$-$C_6)$alkylene-$(C_6$-$C_{10})$aryl of $R^d$ is unsubstituted or substituted with one or more Y groups;

each X is independently selected from the group consisting of F, Cl, Br, $(C_1$-$C_6)$alkyl, $(C_1$-$C_6)$haloalkyl, —O—$(C_1$-$C_6)$alkyl, —O—$(C_1$-$C_6)$haloalkyl, and —OH;

each Y is independently selected from the group consisting of F, Br, Cl, $(C_1$-$C_6)$alkyl, $(C_1$-$C_6)$haloalkyl, —O—$(C_1$-$C_6)$alkyl, —O—$(C_1$-$C_6)$haloalkyl, —CN, —NO$_2$, —OH, , —S(O$_2$)—$(C_1$-$C_6)$alkyl, —S(O$_2$)—$(C_6$-$C_{10})$aryl, —S(O$_2$)—NH$_2$, —S(O$_2$)—NH—$(C_1$-$C_6)$alkyl, —S(O$_2$)—NH—$(C_6$-$C_{10})$aryl, —S(O$_2$)—N(($C_1$-$C_6)$alkyl)$_2$, —S(O$_2$)—N(($C_6$-$C_{10})$aryl)$_2$, —S(O$_2$)—N(($C_1$-$C_6)$alkyl)(($C_6$-$C_{10})$aryl), and $(C_1$-$C_{10})$aryl; and each Z is independently selected from the group consisting of $(C_1$-$C_6)$alkyl, $(C_1$-$C_6)$haloalkyl, F, Br, and Cl, —O—$(C_1$-$C_6)$alkyl, —CN, —OH, $(C_6$-$C_{10})$aryl, and N-oxide.

In another embodiment of the compounds of Formula (I), $R^1$ is selected from the group consisting of —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CH$_2$CH$_2$CH(CH$_3$)$_2$, —CH$_2$CH$_2$CH$_2$CH(CH$_3$)$_2$, —CH(CH$_3$)$_2$, —CH$_2$CH$_2$CH=CH$_2$, —CH$_2$CH$_2$CH=CHCH$_3$, —CH$_2$CH$_2$CH$_2$CH$_2$CH=CH$_2$, —CH$_2$CH$_2$CH$_2$CH=CH$_2$, —CH$_2$—OH, —CH(CH$_3$)—OH, cyclobutyl, —CH$_2$—C(O)—O—CH$_2$CH$_3$, —CH$_2$CH$_2$CH$_2$—O—CH$_3$, —CH$_2$CF$_3$, —CHBrCH$_3$, —CH$_2$CH$_2$CF$_3$, —CH$_2$CH$_2$CH$_2$CF$_3$, —CH$_2$CH$_2$CH$_2$CH$_2$CF$_3$, —CH$_2$CH$_2$CH$_2$Cl, —CH$_2$-(2-thiophenyl), —CH$_2$CH$_2$CH$_2$-(2-thiophenyl), —CH$_2$-cyclopropyl, —CH$_2$CH$_2$-cyclopropyl, —CH$_2$CH$_2$CH$_2$-cyclopropyl, —CH$_2$CH$_2$CH$_2$CH$_2$-cyclopropyl, —CH$_2$-cyclobutyl, —CH$_2$CH$_2$-cyclobutyl, —CH$_2$CH$_2$CH$_2$-cyclobutyl, —CH$_2$CH$_2$CH$_2$CH$_2$-cyclobutyl, —CH$_2$-cyclopentyl, —CH$_2$CH$_2$-cyclopentyl, —CH$_2$CH$_2$CH$_2$-cyclopentyl, —CH$_2$CH$_2$CH$_2$CH$_2$-cyclopentyl, —CH$_2$-cyclohexyl, —CH$_2$-(4-methylcyclohexyl), —CH$_2$CH$_2$-cyclohexyl, —CH$_2$-cycloheptyl, —CH$_2$-(2-cyclopentenyl, —CH$_2$CH$_2$C≡CH, —CH$_2$CH$_2$CH$_2$C≡CH, —CH$_2$-phenyl, —CH$_2$-(2-fluorophenyl), —CH$_2$-(3-fluorophenyl), and —CH$_2$—NH(3-methoxyphenyl);

$R^2$ is selected from the group consisting of H, F, Cl, Br, unsubstituted aryl, aryl substituted with one or more Y groups, unsubstituted heteroaryl, heteroaryl substituted with one or more Y groups; or $R^1$ and $R^2$ together with the ring carbon atoms to which they are shown attached, form a cyclopentenyl or cyclohexenyl ring;

$R^3$ is selected from the group consisting of H, —CH$_2$-cyclopropyl, —CH$_2$—C(O)—O—CH$_3$, cyclopropyl, cyclobutyl, cyclopentyl, cyclopentyl, —CH$_3$, —CH$_2$CH$_3$, —CH$_2$CH$_2$CH$_3$, —CH$_2$CH=CH$_2$, and —CH$_2$—O—CH$_3$;

$R^4$ is selected from the group consisting of Cl, —O—$R^{10}$, —C(O)—O—CH$_3$, —S(O)$_2$—CH$_3$, —S(O)—CH$_3$, —S(O)—CH$_2$CH$_3$, —S(O)—CH(CH$_3$)$_2$, —S(O)—C(CH$_3$)$_3$, —S(O)—CH$_2$-cyclopropyl, —S(O)—CH$_2$-phenyl, —S(O)—CH(CH$_3$)-phenyl, —S—CH$_2$—CH=CH$_2$, —N(R$^7$)$_2$, —O—N=C(CH$_3$)$_2$, —NH—NH—C(O)—O—CH$_3$, and —C(O)—CH$_3$,
wherein the phenyl portion of said —S(O)—CH$_2$-phenyl, or —S(O)—CH(CH$_3$)-phenyl of $R^4$ is unsubstituted or substituted with one or more groups Y;

$R^5$ is selected from the group consisting of H, —CH$_3$, —CH$_2$CH$_3$, —CH$_2$CH$_2$CH$_3$, —CH$_2$—C(O)-phenyl, —CH$_2$—C(O)—OH, —CH$_2$—C(=N—O—CH$_3$)-phenyl, cyclopropyl, cyclobutyl, cyclopentyl, —CH$_2$—C(O)-piperidyl, —CH$_2$-cyclopropyl, —CH$_2$—C(O)—O—CH$_3$, and —CH$_2$—CH=CH$_3$,
wherein the phenyl portion of said —CH$_2$—C(O)-phenyl is unsubstituted or substituted with one or more Y groups;

$R^6$ is selected from the group consisting of —OR$^{10}$, Cl, and —N(R$^7$)$_2$;

each $R^7$ is independently selected from the group consisting of H, cyclobutyl, unsubstituted phenyl, and phenyl substituted with one or more Y groups;

$R^{10}$ is selected from the group consisting of H, —CH$_3$, —CH$_2$-cyclopropyl, —CH$_2$—CH=CH$_3$, —CH$_2$C≡C—CH$_3$, —CH$_2$-phenyl, —CH(CH$_3$)-phenyl, —CH(CH$_2$CH$_3$)-phenyl, —CH(CH$_2$CH$_2$CH$_3$)-phenyl, —CH(CH(CH$_3$)$_2$)-phenyl, —CH(CH$_2$CH=CH$_2$)-phenyl, —CH$_2$-pyridyl, —CH(CH$_3$)-thiazolyl, and —CH$_2$-pyrimidinyl,
wherein the phenyl portion of said —CH$_2$-phenyl, —CH(CH$_3$)-phenyl, —CH(CH$_2$CH$_3$)-phenyl, —CH(CH$_2$CH$_2$CH$_3$)-phenyl, —CH(CH(CH$_3$)$_2$)-phenyl, or —CH(CH$_2$CH=CH$_2$)-phenyl of $R^{10}$ is unsubstituted or substituted with one or more groups Y, and the pyridyl, thiazolyl, or pyrimidinyl portion of said —CH$_2$-pyridyl, —CH$_2$-thiazolyl, or —CH$_2$-pyrimidinyl of $R^{10}$ is unsubstituted or substituted with one or more groups Z;

$R^a$ and $R^b$ are each —CH$_3$;

$R^c$ is H;

$R^d$ is selected from the group consisting of H, —CH$_3$, and —CH$_2$-phenyl,
wherein the phenyl portion of said —CH$_2$-phenyl of $R^d$ is unsubstituted or substituted with one or more Y groups;

each Y is independently selected from the group consisting of F, Cl, Br, —CH$_3$, —CF$_3$, —O—CH$_3$, —O—CF$_3$, —CN, —OH, and phenyl; and each Z is independently selected from the group consisting of —CH$_3$, —CF$_3$, F, Br, and Cl, —O—CH$_3$, —CN, —OH, phenyl, and N-oxide.

In another embodiment of the compounds of Formula (I), Q is:

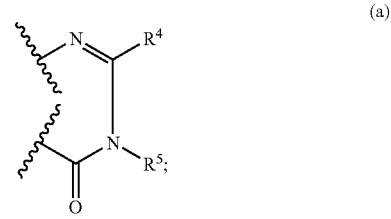

(a)

L is:

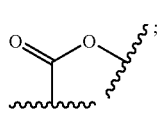

(f)

$R^1$ is selected from the group consisting of —($C_1$-$C_6$)alkyl, —($C_1$-$C_6$)alkylene-O—($C_1$-$C_6$)alkyl, unsubstituted ($C_6$-$C_{10}$)aryl, and ($C_6$-$C_{10}$)aryl substituted with one or more substituents Y;

$R^2$ is H or halogen;

$R^4$ is selected from the group consisting of halogen, —O—$R^{10}$, —C(O)—O—($C_1$-$C_6$)alkyl, —S(O)$_m$—$R^9$, —N($R^7$)$_2$, —O—N=C($R^{12}$)$_2$, —N($R^7$)—NH—C(O)—O—($C_1$-$C_6$)alkyl, and —C(O)—($C_1$-$C_6$)alkyl;

$R^5$ is H or ($C_1$-$C_6$)alkyl;

each $R^7$ is independently selected from the group consisting of H, ($C_1$-$C_6$)alkyl, ($C_3$-$C_6$)cycloalkyl, unsubstituted ($C_6$-$C_{10}$)aryl, and ($C_6$-$C_{10}$)aryl substituted with one or more Y groups;

$R^9$ is selected from the group consisting of ($C_1$-$C_6$)alkyl, —($C_1$-$C_6$)alkylene-($C_3$-$C_6$)cycloalkyl, ($C_2$-$C_6$)alkenyl, and —($C_1$-$C_6$)alkylene-($C_6$-$C_{10}$)aryl, wherein the ($C_6$-$C_{10}$)aryl of said —($C_1$-$C_6$)alkylene-($C_6$-$C_{10}$)aryl of $R^9$ is unsubstituted or substituted with one or more groups Y;

$R^{10}$ is selected from the group consisting of H, ($C_1$-$C_6$)alkyl, —($C_1$-$C_6$)alkylene-($C_6$-$C_{10}$)aryl, —($C_1$-$C_6$)alkenylene-($C_6$-$C_{10}$)aryl, —($C_1$-$C_6$)alkylene-($C_2$-$C_{10}$)heteroaryl, ($C_2$-$C_6$)alkenyl, ($C_2$-$C_6$)alkynyl, and —($C_1$-$C_6$)alkylene-($C_3$-$C_6$)cycloalkyl wherein the aryl of said —($C_1$-$C_6$)alkylene-($C_6$-$C_{10}$)aryl or —($C_1$-$C_6$)alkenylene-($C_6$-$C_{10}$)aryl of $R^{10}$ is unsubstituted or substituted with one or more groups Y, and the ($C_2$-$C_{10}$)heteroaryl of said —($C_1$-$C_6$)alkylene-($C_2$-$C_{10}$)heteroaryl of $R^{10}$ is unsubstituted or substituted with one or more groups Z;

each $R^{12}$ is independently selected from the group consisting of ($C_1$-$C_6$)alkyl, ($C_6$-$C_{10}$)aryl, and ($C_2$-$C_{10}$)heteroaryl, wherein the ($C_6$-$C_{10}$)aryl is unsubstituted or substituted with one or more Y group, and said ($C_2$-$C_{10}$)heteroaryl is unsubstituted or substituted with one or more Z group;

each Y is independently selected from the group consisting of halogen, ($C_1$-$C_6$)alkyl, ($C_1$-$C_6$)haloalkyl, —O—($C_1$-$C_6$)haloalkyl, —O—($C_1$-$C_6$)alkyl, —CN, —NO$_2$, —OH, —S(O$_2$)—($C_1$-$C_6$)alkyl, —S(O$_2$)—($C_6$-$C_{10}$)aryl, —S(O$_2$)—NH$_2$, —S(O$_2$)—NH—($C_1$-$C_6$)alkyl, —S(O$_2$)—NH—($C_6$-$C_{10}$)aryl, —S(O$_2$)—N(($C_1$-$C_6$)alkyl)$_2$, —S(O$_2$)—N(($C_6$-$C_{10}$)aryl)$_2$, —S(O$_2$)—N(($C_1$-$C_6$)alkyl)(($C_6$-$C_{10}$)aryl), and ($C_6$-$C_{10}$)aryl; and each Z is independently selected from the group consisting of ($C_1$-$C_6$)alkyl, ($C_1$-$C_6$)haloalkyl, halogen, —O-alkyl, —O—($C_1$-$C_6$)haloalkyl, —CN, —OH, ($C_6$-$C_{10}$)aryl, and, and N-oxide.

In another embodiment of the compounds of Formula (I), Q is:

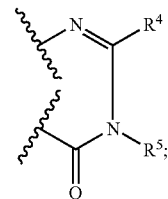

(a)

L is:

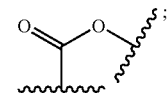

(f)

$R^1$ is —OH$_2$OH$_3$, butyl, pentyl, —CH$_2$—CH$_2$—CH$_2$-cyclopropyl;

$R^2$ is H, Br, unsubstituted aryl, aryl substituted with one or more Y groups, unsubstituted heteroaryl, heteroaryl substituted with one or more Y groups;

$R^4$ is selected from the group consisting of Cl, —O—$R^{10}$, —C(O)—O—CH$_3$, —S(O)—CH$_3$, —S(O)—CH$_2$CH$_3$, —S(O)—CH(CH$_3$)$_2$, —S(O)—C(CH$_3$)$_3$, —S(O)—CH$_2$-cyclopropyl, —S—CH$_2$—CH=CH$_2$, —S(O)—CH$_2$-phenyl, —S(O)—CH(CH$_3$)-phenyl, —N($R^7$)$_2$, —O—N=C(CH$_3$)$_2$, —NH—NH—C(O)—O—CH$_3$, and —C(O)—CH$_3$, wherein the phenyl portion of said —S(O)—CH$_2$-phenyl, or —S(O)—CH(CH$_3$)-phenyl of $R^4$ is unsubstituted or substituted with one or more groups Y;

$R^5$ is H or —CH$_2$CH$_3$;

each $R^7$ is independently selected from the group consisting of H and cyclobutyl;

$R^{10}$ is selected from the group consisting of H, —CH$_3$, —CH$_2$-cyclopropyl, —CH$_2$—CH=CH$_2$, —CH$_2$C≡C—CH$_3$, —CH$_2$-phenyl, —CH(CH$_3$)-phenyl, —CH(CH$_2$CH$_3$)-phenyl, —CH(CH(CH$_3$)$_2$)-phenyl, —CH(CH$_2$CH$_2$CH$_3$)-phenyl, —CH(CH$_2$CH=CH$_2$)-phenyl, —CH$_2$-pyridyl, —CH(CH$_3$)-thiazolyl, —CH$_2$-pyrimidinyl, wherein the phenyl portion of said —CH$_2$-phenyl, —CH(CH$_3$)-phenyl, —CH(CH$_2$CH$_3$)-phenyl, —CH(CH(CH$_3$)$_2$)-phenyl, —CH(CH$_2$CH=CH$_2$)-phenyl, or —CH(CH$_2$CH$_2$CH$_3$)-phenyl, of $R^{10}$ is unsubstituted or substituted with one or more groups Y, and the pyridyl, thiazolyl, or pyrimidinyl portion of said —CH$_2$-pyridyl, —CH(CH$_3$)-thiazolyl, or —CH$_2$-pyrimidinyl of $R^{10}$ is unsubstituted or substituted with one or more groups Z;

each Y is independently selected from the group consisting of F, Cl, Br, —CH$_3$, —CF$_3$, —O—CH$_3$, —O—CF$_3$, and phenyl; and each Z is independently selected from the group consisting of —CH$_3$, phenyl, and N-oxide.

In another embodiment of the compounds of Formula (I), Q is:

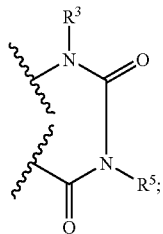
(b)

L is:

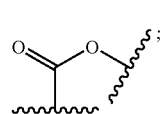
(f)

is selected from the group consisting of —(C$_1$-C$_6$)alkyl, —(C$_1$-C$_6$)alkenyl, —(C$_1$-C$_6$)alkynyl, —(C$_1$-C$_6$)alkylene-C(O)—O—(C$_1$-C$_6$)alkyl, —(C$_3$-C$_7$)cycloalkyl, —(C$_1$-C$_6$)alkylene-O—(C$_1$-C$_6$)alkyl, —(C$_1$-C$_6$)alkylene-(C$_6$-C$_{10}$)aryl, —(C$_1$-C$_6$)alkylene-(C$_2$-C$_{10}$)heteroaryl, —(C$_1$-C$_6$)alkylene-(C$_3$-C$_7$)cycloalkyl, —(C$_1$-C$_6$)alkylene-(C$_3$-C$_7$)cycloalkenyl, (C$_1$-C$_6$)alkyl substituted with one or more hydroxyl groups, —(CH$_2$)$_n$—N(R$^7$)$_2$, and —(C$_1$-C$_6$)haloalkyl
wherein the —(C$_3$-C$_7$)cycloalkyl or the (C$_3$-C$_7$)cycloalkyl portion of said —(C$_1$-C$_6$)alkylene-(C$_3$-C$_7$)cycloalkyl is unsubstituted or substituted with one or more X groups, the (C$_6$-C$_{10}$)aryl portion of said —(C$_1$-C$_6$)alkylene-(C$_6$-C$_{10}$)aryl is unsubstituted or substituted with one or more Y groups, and the (C$_2$-C$_{10}$)heteroaryl portion of said —(C$_1$-C$_6$)alkylene-(C$_2$-C$_{10}$)heteroaryl is unsubstituted or substituted with one or more Z groups;

R$^2$ is H;
R$^3$ is selected from the group consisting of H, (C$_1$-C$_6$)alkyl, (C$_3$-C$_6$)cycloalkyl, —(C$_1$-C$_3$)alkylene-(C$_3$-C$_6$)cycloalkyl, —(C$_1$-C$_6$)alkylene-C(O)—O—(C$_1$-C$_6$)alkyl, (C$_2$-C$_6$)alkenyl, and —(C$_1$-C$_6$)alkylene-O—(C$_1$-C$_6$)alkyl;
R$^5$ is selected from the group consisting of H, —(C$_1$-C$_6$)alkyl, (C$_2$-C$_6$)alkenyl, —(C$_1$-C$_6$)alkylene-C(O)—R$^8$, —(C$_1$-C$_6$)alkylene-C(=N—O—(C$_1$-C$_6$)alkyl)-(C$_6$-C$_{10}$)aryl, (C$_3$-C$_6$)cycloalkyl, —(C$_1$-C$_6$)alkylene-(C$_3$-C$_6$)cycloalkyl, and —(C$_1$-C$_6$)alkylene-C(O)—O—(CO—C$_6$)alkyl;
each R$^7$ is independently selected from the group consisting of H and aryl,
wherein the aryl of R$^7$ is unsubstituted or substituted with one or more Y groups;
R$^8$ is selected from the group consisting of unsubstituted (C$_6$-C$_{10}$)aryl, (C$_6$-C$_{10}$)aryl substituted with one or more Y groups, —OH, unsubstituted (C$_2$-C$_{10}$)heterocyclyl and (C$_2$-C$_{10}$)heterocyclyl substituted with one or more X groups;
each X is independently selected from the group consisting of halogen, (C$_1$-C$_6$)alkyl, (C$_1$-C$_6$)haloalkyl, —O—(C$_1$-C$_6$)alkyl, —O—(C$_1$-C$_6$)haloalkyl, and —OH;

each Y is independently selected from the group consisting of halogen, (C$_1$-C$_6$)alkyl, (C$_1$-C$_6$)haloalkyl, —O—(C$_1$-C$_6$)haloalkyl, —O—(C$_1$-C$_6$)alkyl, —CN, —NO$_2$, —OH, —S(O$_2$)—(C$_1$-C$_6$)alkyl, —S(O$_2$)—(CO—C$_{10}$)aryl, —S(O$_2$)—NH$_2$, —S(O$_2$)—NH—(C$_1$-C$_6$)alkyl, —S(O$_2$)—NH—(C$_6$-C$_{10}$)aryl, —S(O$_2$)—N((C$_1$-C$_6$)alkyl)$_2$, —S(O$_2$)—N((C$_6$-C$_{10}$)aryl)$_2$, —S(O$_2$)—N((C$_1$-C$_6$)alkyl)((C$_6$-C$_{10}$)aryl), and (C$_6$-C$_{10}$)aryl; and
each Z is independently selected from the group consisting of (C$_1$-C$_6$)alkyl, (C$_1$-C$_6$)haloalkyl, F, Br, and Cl, —O—(C$_1$-C$_6$)alkyl, —CN, —OH, (C$_6$-C$_{10}$)aryl, and N-oxide.

In another embodiment of the compounds of Formula (I), Q is:

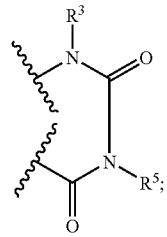
(b)

L is:

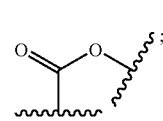
(f)

R$^1$ is selected from the group consisting of —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CH$_2$CH$_2$CH(CH$_3$)$_2$, —CH$_2$CH$_2$CH$_2$CH(CH$_3$)$_2$, —CH(CH$_3$)$_2$, —CH$_2$—C(O)—O—CH$_2$CH$_3$, —CH$_2$CF$_3$, —CH$_2$CH$_2$CH=CH$_2$, —CH$_2$CH$_2$CH=CHCH$_3$, —CH$_2$CH$_2$CH$_2$CH$_2$CH=CH$_2$, —CH$_2$CH$_2$CH$_2$CH=CH$_2$, —CH$_2$OH, —CH(CH$_3$)OH, —CH$_2$N(R$^7$)$_2$, cyclobutyl, —CH$_2$CH$_2$CH$_2$—O—CH$_3$, —CH$_2$CH$_2$CF$_3$, —CH$_2$CH$_2$CH$_2$CF$_3$, —CH$_2$CH$_2$CH$_2$CH$_2$CF$_3$, —CH$_2$CH$_2$CH$_2$Cl, —CH$_2$-(2-thiophenyl), —CH$_2$CH$_2$CH$_2$-(2-thiophenyl), —CH$_2$-cyclopropyl, —CH$_2$CH$_2$-cyclopropyl, —CH$_2$CH$_2$CH$_2$-cyclopropyl, —CH$_2$CH$_2$CH$_2$CH$_2$-cyclopropyl, —CH$_2$-cyclopentyl, —CH$_2$CH$_2$-cyclopentyl, —CH$_2$-cyclohexyl, —CH$_2$-(4-methylcyclohexyl), —CH$_2$CH$_2$-cyclohexyl, —CH$_2$-cycloheptyl, —CH$_2$-(2-cyclopentenyl, —CH$_2$CH$_2$C≡CH, —CH$_2$CH$_2$CH$_2$C≡CH, —CH$_2$-phenyl, —CH$_2$-(2-fluorophenyl), —CH$_2$-(3-fluorophenyl), and —CHBrCH$_3$;

R$^2$ is H; or
R$^1$ and R$^2$ together with the ring carbon atoms to which they are shown attached, form a cyclopentenyl or cyclohexenyl ring;
R$^3$ is selected from the group consisting of H, —CH$_2$-cyclopropyl, —CH$_2$—C(O)—O—CH$_3$, -cyclopropyl, cyclobutyl, cyclopentyl, —CH$_3$, —CH$_2$CH$_3$, —CH$_2$CH$_2$CH$_3$, —CH$_2$CH=CH$_2$, and —CH$_2$—O—CH$_3$;
R$^5$ is selected from the group consisting of H, —CH$_2$-cyclopropyl, —CH$_2$—C(O)—O—CH$_3$, —CH$_2$—C(O)—R$^8$, —CH$_2$—C(=N—O—CH$_3$)-phenyl, cyclopropyl, cyclobutyl, cyclopentyl, —CH$_3$, —CH$_2$CH$_3$, —CH$_2$CH$_2$CH$_3$, and —CH$_2$CH=CH$_2$;

each R$^7$ is independently H or phenyl,
  wherein the phenyl of R$^7$ is unsubstituted or substituted with one or more Y groups;

R$^8$ is selected from the group consisting of unsubstituted phenyl, phenyl substituted with one or more Y groups, —OH, and piperidyl; and each Y is independently selected from the group consisting of F, —CF$_3$, —OCH$_3$, —CN, and —OH.

In another embodiment of the compounds of Formula (I), Q is:

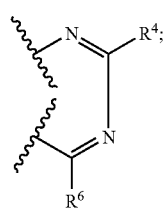
(c)

L is:

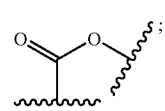
(f)

R$^1$ is selected from the group consisting of —(C$_1$-C$_6$)alkyl, —(C$_1$-C$_6$)alkenyl, —(C$_1$-C$_6$)alkynyl, —(C$_1$-C$_6$)alkylene-C(O)—O—(C$_1$-C$_6$)alkyl, —(C$_3$-C$_7$)cycloalkyl, —(C$_1$-C$_6$)alkylene-O—(C$_1$-C$_6$)alkyl, —(C$_1$-C$_6$)alkylene-(C$_6$-C$_{10}$)aryl, —(C$_1$-C$_6$)alkylene-(C$_2$-C$_1$)heteroaryl, —(C$_1$-C$_6$)alkylene-(C$_3$-C$_7$)cycloalkyl, —(C$_1$-C$_6$)alkylene-(C$_3$-C$_7$)cycloalkenyl, —(C$_1$-C$_6$)alkyl substituted with one or more hydroxyl groups, —(CH$_2$)$_n$—N(R$^7$)$_2$, and —(C$_1$-C$_6$)haloalkyl
  wherein the —(C$_3$-C$_7$)cycloalkyl or the (C$_3$-C$_7$)cycloalkyl portion of said —(C$_1$-C$_6$)alkylene-(C$_3$-C$_7$)cycloalkyl is unsubstituted or substituted with one or more X groups, the (C$_6$-C$_{10}$)aryl portion of said —(C$_1$-C$_6$)alkylene-(C$_6$-C$_{10}$)aryl is unsubstituted or substituted with one or more Y groups, and the (C$_2$-C$_{10}$)heteroaryl portion of said —(C$_1$-C$_6$)alkylene-(C$_2$-C$_{10}$)heteroaryl is unsubstituted or substituted with one or more Z groups;

R$^2$ is H; or

R$^1$ and R$^2$ together with the ring carbon atoms to which they are shown attached, form a 5- or 6-membered cycloalkenyl ring;

R$^4$ is selected from the group consisting of halogen, —O—R$^{10}$, —C(O)—O—(C$_1$-C$_{10}$)alkyl, —S(O)$_m$—R$^9$, —N(R$^7$)$_2$, —O—N=C(R$^{12}$)$_2$, —N(R$^7$)—NH—C(O)—O—(C$_1$-C$_6$)alkyl, and —C(O)—(C$_1$-C$_6$)alkyl;

R$^6$ is selected from the group consisting of —O—R$^{10}$, halogen, and —N(R$^7$)$_2$;

each R$^7$ is independently selected from the group consisting of H, (C$_1$-C$_6$)alkyl, (C$_3$-C$_6$)cycloalkyl, unsubstituted (C$_6$-C$_{10}$)aryl, and (C$_6$-C$_{10}$)aryl substituted with one or more Y groups;

R$^9$ is selected from the group consisting of (C$_1$-C$_6$)alkyl, —(C$_1$-C$_6$)alkylene-(C$_3$-C$_6$)cycloalkyl, (C$_2$-C$_6$)alkenyl, and —(C$_1$-C$_6$)alkylene-(C$_6$-C$_{10}$)aryl,
  wherein the (C$_6$-C$_{10}$)aryl portion of said —(C$_1$-C$_6$)alkylene-(C$_6$-C$_{10}$)aryl of R$^9$ is unsubstituted or substituted with one or more groups Y;

R$^{10}$ is selected from the group consisting of H, (C$_1$-C$_6$c)alkyl, —(C$_1$-C$_6$)alkylene-(C$_6$-C$_{10}$)aryl, —(C$_1$-C$_6$)alkenylene-(C$_6$-C$_{10}$)aryl, —(C$_1$-C$_6$)alkylene-(C$_2$-C$_{10}$)heteroaryl, (C$_2$-C$_6$)alkenyl, (C$_2$-C$_6$)alkynyl, and —(C$_1$-C$_6$)alkylene-(C$_3$-C$_6$)cycloalkyl,
  wherein the (C$_6$-C$_{10}$)aryl portion of said —(C$_1$-C$_6$)alkylene-(C$_6$-C$_{10}$)aryl or —(C$_1$-C$_6$)alkenylene-(C$_6$-C$_{10}$)aryl of R$^{10}$ is unsubstituted or substituted with one or more groups Y, and the (C$_2$-C$_{10}$)heteroaryl portion of said —(C$_1$-C$_6$)alkylene-(C$_2$-C$_{10}$)heteroaryl of R$^{10}$ is unsubstituted or substituted with one or more groups Z;

each Y is independently selected from the group consisting of F, Br, Cl, (C$_1$-C$_6$)alkyl, (C$_1$-C$_6$)haloalkyl, —O—(C$_1$-C$_6$)alkyl, —O—(C$_1$-C$_6$)haloalkyl, —CN, —NO$_2$, —OH, —S(O$_2$)—(C$_1$-C$_6$)alkyl, —S(O$_2$)—(C$_6$-C$_{10}$)aryl, —S(O$_2$)—NH$_2$, —S(O$_2$)—NH—(C$_1$-C$_6$)alkyl, —S(O$_2$)—NH—(C$_6$-C$_{10}$)aryl, —S(O$_2$)—N((C$_1$-C$_6$)alkyl)$_2$, —S(O$_2$)—N((C$_6$-C$_{10}$)aryl)$_2$, —S(O$_2$)—N((C$_1$-C$_6$)alkyl)((C$_6$-C$_{10}$)aryl), and (C$_6$-C$_{10}$)aryl; and each Z is independently selected from the group consisting of (C$_1$-C$_6$)alkyl, (C$_1$-C$_6$)haloalkyl, F, Br, and Cl, —O—(C$_1$-C$_6$)alkyl, —CN, —OH, (C$_6$-C$_{10}$)aryl, and N-oxide.

In another embodiment of the compounds of Formula (I), Q is:

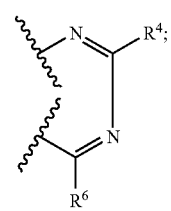
(c)

L is:

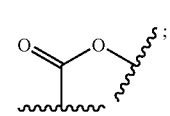
(f)

R$^1$ is selected from the group consisting of —CH$_3$, —CH$_2$CH$_3$, —CH$_2$CH$_2$CH$_3$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CH$_2$CH$_2$CH(CH$_3$)$_2$, —CH$_2$CH$_2$CH$_2$CH(CH$_3$)$_2$, —CH(CH$_3$)$_2$, —CH$_2$—C(O)—O—CH$_2$CH$_3$, —CH$_2$—OH, —CH(CH$_3$)—OH, —CH$_2$CH$_2$CH=CH$_2$, —CH$_2$CH$_2$CH=CHCH$_3$, —CH$_2$CH$_2$CH$_2$CH$_2$CH=CH$_2$, —CH$_2$CH$_2$CH$_2$CH=CH$_2$, cyclobutyl, —CH$_2$CH$_2$CH$_2$—O—CH$_3$, —CH$_2$CH$_2$CF$_3$, —CH$_2$CH$_2$CH$_2$CF$_3$, —CH$_2$CH$_2$CH$_2$CH$_2$CF$_3$, —CH$_2$CH$_2$Cl, —CH$_2$-(2-thiophenyl), —CH$_2$CH$_2$-(2-thiophenyl), —CH$_2$-cyclopropyl, —CH$_2$CH$_2$-cyclopropyl, —CH$_2$CH$_2$CH$_2$-cyclopropyl, —CH$_2$CH$_2$CH$_2$CH$_2$-cyclopropyl, —CH$_2$-cyclopentyl, —CH$_2$CH$_2$-cyclopentyl, —CH$_2$-cyclohexyl, —CH$_2$-(4-methylcyclohexyl), —CH$_2$CH$_2$-cyclohexyl, —CH$_2$-cycloheptyl, —CH$_2$-(2-cyclopentenyl, —CH$_2$CH$_2$C≡CH, —CH$_2$CH$_2$CH$_2$C≡CH, —CH$_2$-phenyl, —CH$_2$-(2-fluorophenyl), —CH$_2$-(3-fluorophenyl), —CHBrCH$_3$ and —CH$_2$CF$_3$;

R$^2$ is H; or

R$^1$ and R$^2$ together with the ring carbon atoms to which they are shown attached, form a cyclopentenyl or cyclohexenyl ring R$^4$ is selected from the group consisting of Cl, —O—R$^{10}$, —C(O)—O—CH$_3$, —S(O)$_2$—CH$_3$, —S(O)—CH$_3$, —S(O)—CH$_2$CH$_3$, —S(O)—CH(CH$_3$)$_2$, —S(O)—C(CH$_3$)$_3$, —S(O)—CH$_2$-cyclopropyl, —S—CH$_2$—CH=CH$_2$, —S(O)—CH$_2$-phenyl, —S(O)—CH(CH$_3$)-phenyl, —N(R$^7$)$_2$, —O—N=C(CH$_3$)$_2$, —NH—NH—C(O)—O—CH$_3$, and —C(O)—CH$_3$, wherein the phenyl portion of said —S(O)—CH$_2$-phenyl, or —S(O)—CH(CH$_3$)-phenyl of R$^4$ is unsubstituted or substituted with one or more groups Y;

R$^6$ is selected from the group consisting of —O—R$^{10}$, —N(R$^7$)$_2$, and Cl;

each R$^7$ is independently selected from the group consisting of H, unsubstituted phenyl, phenyl substituted with one or more Y groups, and cyclobutyl;

R$^{10}$ is selected from the group consisting of H, CH$_3$, —CH$_2$-cyclopropyl, —CH$_2$—C≡C—H$_3$, —CH$_2$—CH=CH$_2$, —CH$_2$-phenyl, —CH(CH$_3$)-phenyl, —CH(CH$_2$CH$_3$)-phenyl, —CH(CH(CH$_3$)$_2$)-phenyl, —CH(CH$_2$CH$_2$CH$_3$)-phenyl, —CH(CH$_2$CH=CH$_2$)-phenyl, —CH$_2$-pyridyl, —CH(CH$_3$)-thiazolyl, —CH$_2$-pyrimidinyl, wherein the phenyl portion of said —CH$_2$-phenyl, —CH(CH$_3$)-phenyl, —CH(CH$_2$CH$_3$)-phenyl, —CH(CH$_2$CH=CH$_2$)-phenyl, or —CH(CH$_2$CH$_2$CH$_3$)-phenyl of R$^{10}$ is unsubstituted or substituted with one or more groups Y, and the pyridyl, thiazolyl, or pyrimidinyl portion of said —CH$_2$-pyridyl, —CH(CH$_3$)-thiazolyl, or —CH$_2$-pyrimidinyl of R$^{10}$ is unsubstituted or substituted with one or more groups Z;

each Y is independently selected from the group consisting of F, Cl, Br, —CH$_3$, —CF$_3$, —O—CH$_3$, —O—CF$_3$, —CN, —OH, and phenyl; and each Z is independently selected from the group consisting of —CH$_3$, F, Br, and Cl, —O—CH$_3$, —CN, —OH, phenyl, and N-oxide.

In another embodiment of the compounds of Formula (I), Q is:

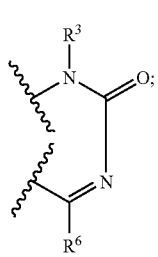
(d)

L is:

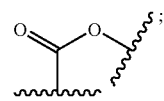
(f)

R$^1$ is —(C$_1$-C$_6$)alkyl;
R$^2$ is H;
R$^3$ is H or —(C$_2$-C$_6$)alkenyl; and
R$^6$ is —OH or —O—(C$_1$-C$_6$)alkylene-(C$_1$-C$_6$)cycloalkyl.

In another embodiment of the compounds of Formula (I), Q is:

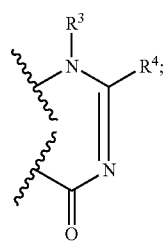
(e)

L is:

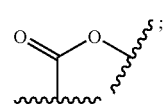
(f)

R$^1$ is —(C$_1$-C$_6$)alkyl or —(C$_1$-C$_6$)haloalkyl;
R$^2$ is H;
R$^3$ is selected from the group consisting of H, —(C$_1$-C$_6$)alkylene-(C$_1$-C$_6$)cycloalkyl, —(C$_1$-C$_6$)alkylene-C(O)—O—(C$_1$-C$_6$)alkyl, —(C$_1$-C$_6$)cycloalkyl, (C$_1$-C$_6$)alkyl, (C$_2$-C$_6$)alkenyl, and —(C$_1$-C$_6$)alkylene-O—(C$_1$-C$_6$)alkyl; and
R$^4$ is —O—N=C((C$_1$-C$_6$)alkyl)$_2$.

In another embodiment of the compounds of Formula (I), Q is:

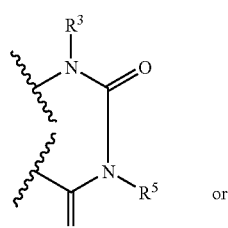
(b)

or

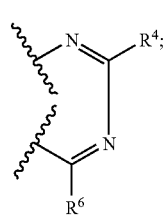
(c)

L is selected from the group consisting of:

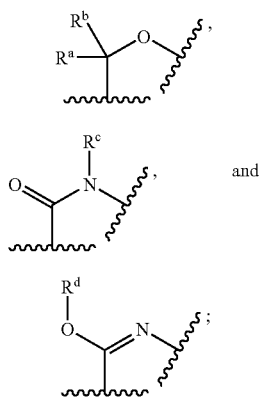

$R^a$ and $R^b$ are each independently selected from the group consisting of H, $(C_1$-$C_6)$alkyl, $(C_6$-$C_{10})$aryl, and $(C_2$-$C_{10})$heteroaryl,
  wherein the $(C_6$-$C_{10})$aryl of $R^a$ and $R^b$ is unsubstituted or substituted with one or more Y groups, and said $(C_2$-$C_{10})$heteroaryl of $R^a$ and $R^b$ is unsubstituted or substituted with one or more Z groups;

$R^c$ is selected from the group consisting of H, $(C_1$-$C_6)$alkyl, —$(C_1$-$C_6)$alkylene-$(C_6$-$C_{10})$aryl, and —C(O)—$(C_1$-$C_6)$alkyl,
  wherein the $(C_6$-$C_{10})$aryl portion of said —$(C_1$-$C_6)$alkylene-$(C_6$-$C_{10})$aryl of $R^c$ is unsubstituted or substituted with one or more Y groups;

$R^d$ is selected from the group consisting of H, $(C_1$-$C_6)$alkyl, and —$(C_1$-$C_6)$alkylene-$(C_6$-$C_{10})$aryl,
  wherein the $(C_6$-$C_{10})$aryl portion of said —$(C_1$-$C_6)$alkylene-$(C_6$-$C_{10})$aryl of $R^d$ is unsubstituted or substituted with one or more Y groups;

$R^1$ is $(C_1$-$C_6)$alkyl or or —$(C_1$-$C_6)$haloalkyl;
$R^2$ is H;
$R^3$ is H;
$R^4$ is —O—$R^{10}$;
$R^5$ is H or —$(C_1$-$C_6)$alkylene-$(C_3$-$C_6)$cycloalkyl;
$R^6$ is —O—$R^{10}$;
$R^{10}$ is H, $(C_1$-$C_5)$alkyl, or —$(C_1$-$C_6)$alkylene-$(C_6$-$C_{10})$aryl; and
each Y is independently selected from the group consisting of F, Br, Cl, $(C_1$-$C_6)$alkyl, $(C_1$-$C_6)$haloalkyl, —O—$(C_1$-$C_6)$alkyl, —O—$(C_1$-$C_6)$haloalkyl, —CN, —$NO_2$, —OH, —$S(O_2)$—$(C_1$-$C_6)$alkyl, —$S(O_2)$—$(C_6$-$C_{10})$aryl, —$S(O_2)$—$NH_2$, —$S(O_2)$—NH—$(C_1$-$C_6)$alkyl, —$S(O_2)$—NH—$(C_6$-$C_{10})$aryl, —$S(O_2)$—N$((C_1$-$C_6)$alkyl$)_2$, —$S(O_2)$—N$((C_6$-$C_{10})$aryl$)_2$, —$S(O_2)$—N$((C_1$-$C_6)$alkyl$)((C_6$-$C_{10})$aryl$)$, and $(C_6$-$C_{10})$aryl; and
each Z is independently selected from the group consisting of $(C_1$-$C_6)$alkyl, $(C_1$-$C_6)$haloalkyl, F, Br, and Cl, —O—$(C_1$-$C_6)$alkyl, —CN, —OH, $(C_6$-$C_{10})$aryl, and N-oxide.

In another embodiment of the Formula (I), $R^1$ is —$CH_3$, —$CH_2CH_3$, —$CH_2CH_2CH_3$, —$CH_2CH_2CH_2CH_3$, —CH$(CH_3)_2$, —$CH_2$—C(O)—O—$CH_2CH_3$, —$CH_2CF_3$, —$CH_2$—OH, —CH$(CH_3)$OH, —$OH_2$—N$(R^7)_2$, —$CH_2$—NH(3-methoxyphenyl), —$CH_2CH_2CH_2CH_2CH_3$, —$CH_2CH_2CH_2CH_2CH_2CH_3$, —$CH_2CH_2CH(CH_3)_2$, —$CH_2CH_2CH_2CH(CH_3)_2$, —$CH_2CH_2CH$=$CH_2$, —$CH_2CH_2CH$=$CHCH_3$, —$CH_2CH_2CH_2CH_2CH$=$CH_2$, —$CH_2CH_2CH_2CH$=$CH_2$, cyclobutyl, —$CH_2CH_2$—O—$CH_3$, —$CH_2CF_3$, —$CHBrCH_3$, —$CH_2CH_2CF_3$, —$CH_2CH_2CH_2CF_3$, —$CH_2CH_2CH_2CH_2CF_3$, —$CH_2CH_2CH_2Cl$, —$CH_2$-(2-thiophenyl), —$CH_2CH_2$-(2-thiophenyl), —$CH_2$-cyclopropyl, —$CH_2CH_2$-cyclopropyl, —$CH_2CH_2CH_2$-cyclopropyl, —$CH_2CH_2CH_2CH_2$-cyclopropyl, —$CH_2CH_2$-cyclopentyl, —$CH_2$-cyclopentyl, —$CH_2$-cyclohexyl, —$CH_2$-(4-methylcyclohexyl), —$CH_2CH_2$-cyclohexyl, —$CH_2$-cycloheptyl, —$CH_2$-(2-cyclopentenyl), —$CH_2CH_2$C≡CH, —$CH_2CH_2CH_2$C≡CH, —$CH_2$-phenyl, —$CH_2$-(2-fluorophenyl), —$CH_2$-(3-fluorophenyl), or —$CHBrCH_3$.

In another embodiment of the Formula (I), $R^2$ is H.

In another embodiment of the Formula (I), $R^2$ is Br.

In another embodiment, $R^1$ and $R^2$ together with the ring carbon atoms to which they are shown attached in Formula (I), form a cyclopentenyl or cyclohexenyl ring.

In another embodiment of the Formula (I), $R^3$ is H, —$CH_2$-cyclopropyl, —$CH_2$—C(O)—O—$CH_3$, -cyclopropyl, cyclobutyl, cyclopentyl, —$CH_3$, —$CH_2CH_3$, —$CH_2$—$CH_2CH_3$, —$CH_2CH$=$CH_2$, or —$CH_2$—O—$CH_3$.

In another embodiment of the Formula (I), $R^4$ is Cl, —OH, —O—$CH_3$, —O—$CH_2$-cyclopropyl, —$CH_2$—C≡C—$CH_3$, —O—$CH_2$-phenyl, —O—CH$(CH_3)$-phenyl, —O—CH$(CH_2CH_3)$-phenyl, —O—CH$(CH_2CH_2CH_3)$-phenyl, —O—CH$(CH(CH_3)_2)$-phenyl, —O—CH$(CH_2CH$=$CH_2)$-phenyl, —O—$CH_2$-pyridyl, —O—$CH_2$-thiazolyl, —O—CH$(CH_3)$-thiazolyl, —O—$CH_2$-pyrimidinyl, —C(O)—O—$CH_3$, —$S(O_2)$—$CH_3$, —S(O)—$CH_3$, —S(O)—$CH_2CH_3$, —S(O)—CH$(CH_3)_2$, —S(O)—C$(CH_3)_3$, —S(O)—$CH_2$-cyclopropyl, —S(O)—$CH_2$-phenyl, —S(O)—CH$(CH_3)$-phenyl, —S(O)—N$(R^{11})_2$, —$S(O_2)$—N$(R^{11})_2$, —S—$CH_2$—CH=$CH_2$, —N(H)cyclobutyl, —N(H)phenyl, —NH—NH—C(O)—O—$CH_3$, —O—$CH_2$—CH=$CH_2$, —O—N=C$(CH_3)_2$, or —C(O)—$CH_3$, wherein the phenyl portions of any of these groups can be unsubstituted or substituted with one or more Y groups as defined herein, the cyclobutyl portions of any of these groups may be unsubstituted or substituted with one or more X groups as defined herein, and the pyridyl, thiazolyl, or pyrimidinyl portions of any of these groups can be unsubstituted or substituted with one or more Z groups as defined herein.

In another embodiment of the compound of Formula (I), $R^5$ is H, —$CH_3$, —$CH_2CH_3$, —$CH_2CH_2CH_3$, —$CH_2$—C(O)-phenyl, —$CH_2$—C(O)—OH, —$CH_2$—C(=N—O—$CH_3$)-phenyl, cyclopropyl, cyclobutyl, cyclopentyl, —$CH_2$—C(O)-piperidyl, —$CH_2$-cyclopropyl, —$CH_2$—C(O)—O—$CH_3$, or —$CH_2$—CH=$CH_3$, wherein the phenyl of said —$CH_2$—C(O)-phenyl of $R^5$ is unsubstituted or substituted with one or more Y groups as defined herein, said cyclopropyl the cyclopropyl of said —$CH_2$-cyclopropyl, cyclobutyl, cyclopentyl, or the piperidyl of said —$CH_2$—C(O)-piperidyl of $R^5$ are unsubstituted or substituted with one or more X groups as defined herein.

In another embodiment of the compound of Formula (I), $R^6$ is —OH, Cl, —O—$CH_3$, —O—$CH_2$-cyclopropyl, —O—$CH_2$—CH=$CH_3$, —O—$CH_2$-phenyl, —O—CH$(CH_3)$-phenyl, —O—CH$(CH_2CH_3)$-phenyl, —O—CH$(CH_2CH_2CH_3)$-phenyl, —O—CH$(CH(CH_3)_2)$-phenyl, —O—CH$(CH_2CH$=$CH_2)$-phenyl, —O—$CH_2$-pyridyl, —O—$CH_2$-thiazolyl, —O—$CH_2$-pyrimidinyl, and —N(H)cyclobutyl, —N(H)phenyl, —NH—NH—C(O)—O—$CH_3$, wherein the phenyl of said —O—$CH_2$-phenyl, —O—CH$(CH_3)$-phenyl, —O—CH$(CH_2CH_3)$-phenyl, —O—CH$(CH_2CH_2CH_3)$-phenyl, —O—CH$(CH(CH_3)_2)$-phenyl, or —O—CH$(CH_2CH$=$CH_2)$-phenyl of $R^6$ is unsubstituted or substituted with one or more groups Y as defined herein, and the pyridyl, thiazolyl, or pyrimidinyl of said —O—$CH_2$- pyridyl, —O—CH$_2$-thiazolyl, or —O—CH$_2$-pyrimidinyl of R$^6$ is unsubstituted or substituted with one or more groups Z as defined herein.

In another embodiment of the compound of Formula (I), each R$^7$ is independently H, —CH$_3$, —CH$_2$CH$_3$, —CH$_2$CH$_2$CH$_3$, unsubstituted phenyl, phenyl substituted with one or more Y groups, cyclopropyl, cyclobutyl, cyclopentyl, cyclohexyl, —C(O)—CH$_3$, and —C(O)-phenyl. Alternatively, two groups R$^7$, together with the N atom to which they are attached, form an azetidinyl, pyrrolidinyl, piperidinyl, piperazinyl, morpholinyl, pyrrolidinonyl, triazolyl, or pyrrolyl ring.

In another embodiment of the compound of Formula (I), R$^8$ is —CH$_3$, unsubstituted phenyl, phenyl substituted with one or more Y groups, piperidyl, and —OH.

In another embodiment of the compound of Formula (I), R$^9$ is —CH$_3$, —CH$_2$CH$_3$, —CH(CH$_3$)$_2$, —C(CH$_3$)$_3$, —CH$_2$-cyclopropyl, —CH$_2$—CH=CH$_2$ (allyl), —CH$_2$-phenyl, and —CH(CH$_3$)-phenyl.

In another embodiment of the compound of Formula (I), R$^{10}$ is H, —CH$_2$C≡CCH$_3$, —CH$_2$-cyclopropyl, —CH$_2$CH=CH$_2$, —CH$_2$-phenyl, —CH(CH$_3$)-phenyl, —CH(CH$_2$CH$_3$)-phenyl, —CH(CH(CH$_3$)$_2$)-phenyl, —CH$_2$-pyridyl, —CH$_2$-thiazolyl, —CH(CH$_3$)-thiazolyl, —CH$_2$-pyrimidyl, —CH(CH$_2$CH=CH$_2$)-phenyl, —CH(CH$_2$CH$_2$CH$_3$)-phenyl, wherein the phenyl portion of —CH$_2$-phenyl, —CH(CH$_3$)-phenyl, —CH(CH$_2$CH$_3$)-phenyl, —CH(CH(CH$_3$)$_2$)-phenyl, —CH(CH$_2$CH=CH$_2$)-phenyl, and —CH(CH$_2$CH$_2$CH$_3$)-phenyl of R$^{10}$ are unsubstituted or substituted with one or more Y groups, and the pyridyl, thiazolyl, and pyrimidyl portion of said —CH$_2$-pyridyl, —CH$_2$-thiazolyl, —CH(CH$_3$)-thiazolyl, —CH$_2$-pyrimidyl are unsubstituted or substituted with one or more Z groups.

In another embodiment of the compound of Formula (I), R$^{11}$ is H, —CH$_3$, or phenyl, wherein the phenyl is unsubstituted or substituted with one or more Y groups. Alternatively, two groups R$^{11}$, together with the N atom to which they are attached, form an azetidinyl, pyrrolidinyl, piperidinyl, piperazinyl, morpholinyl, pyrrolidinonyl, triazolyl, or pyrrolyl ring.

In another embodiment of the compound of Formula (I), R$^{12}$ is H, —CH$_3$, —CH$_2$CH$_3$, or unsubstituted pyridyl or pyridyl substituted with one or more Z groups.

In another embodiment of the compound of Formula (I), R$^a$ is H or —CH$_3$.

In another embodiment of the compound of Formula (I), R$^b$ is H or —CH$_3$.

In another embodiment of the compound of Formula (I), R$^a$ and R$^b$ are both —CH$_3$.

In another embodiment of the compound of Formula (I), R$^c$ is H or —CH$_3$.

In another embodiment of the compound of Formula (I), R$^d$ is H, —CH$_3$, or —CH$_2$-phenyl, wherein the phenyl portion of said —CH$_2$-phenyl of R$^d$ is unsubstituted or substituted with one or more Y groups as defined herein.

In another embodiment of the compound of Formula (I), each X is independently selected from the group consisting of —CH$_3$, —CF$_3$, F, Br, and Cl, —O—CH$_3$, —O—CF$_3$, —CN, —OH, phenyl, and N-oxide;

In another embodiment of the compound of Formula (I), each Y is independently selected from the group consisting of F, Cl, Br, —CH$_3$, —CF$_3$, —O—CH$_3$, —O—CF$_3$, —CN, —OH, and phenyl; and In another embodiment of the compound of Formula (I), each Z is independently selected from the group consisting of —CH$_3$, —CF$_3$, F, Br, and Cl, —O—CH$_3$, —O—CF$_3$, —CN, —OH, phenyl, and N-oxide.

Non-limiting illustrative examples of the compounds of formula (I), include the following compounds:

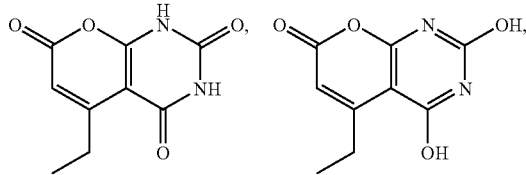

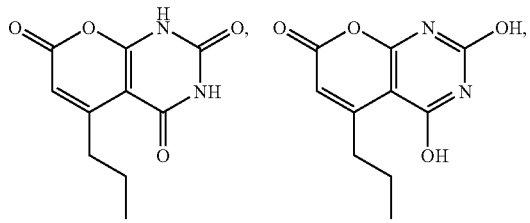

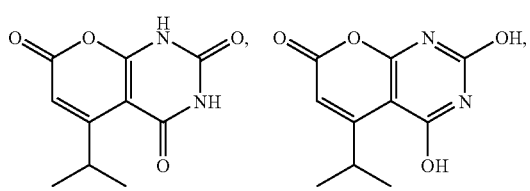

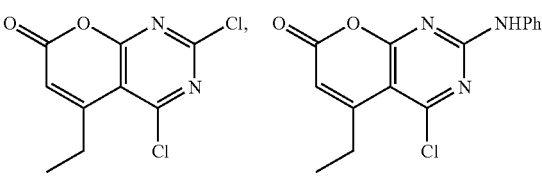

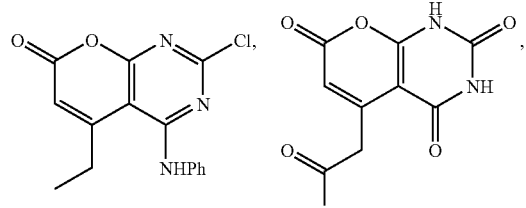

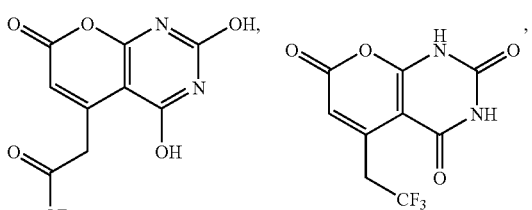

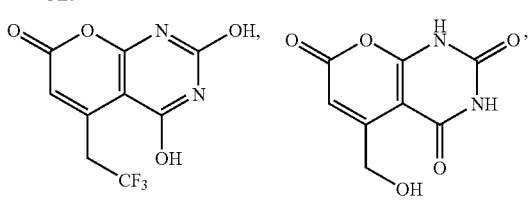

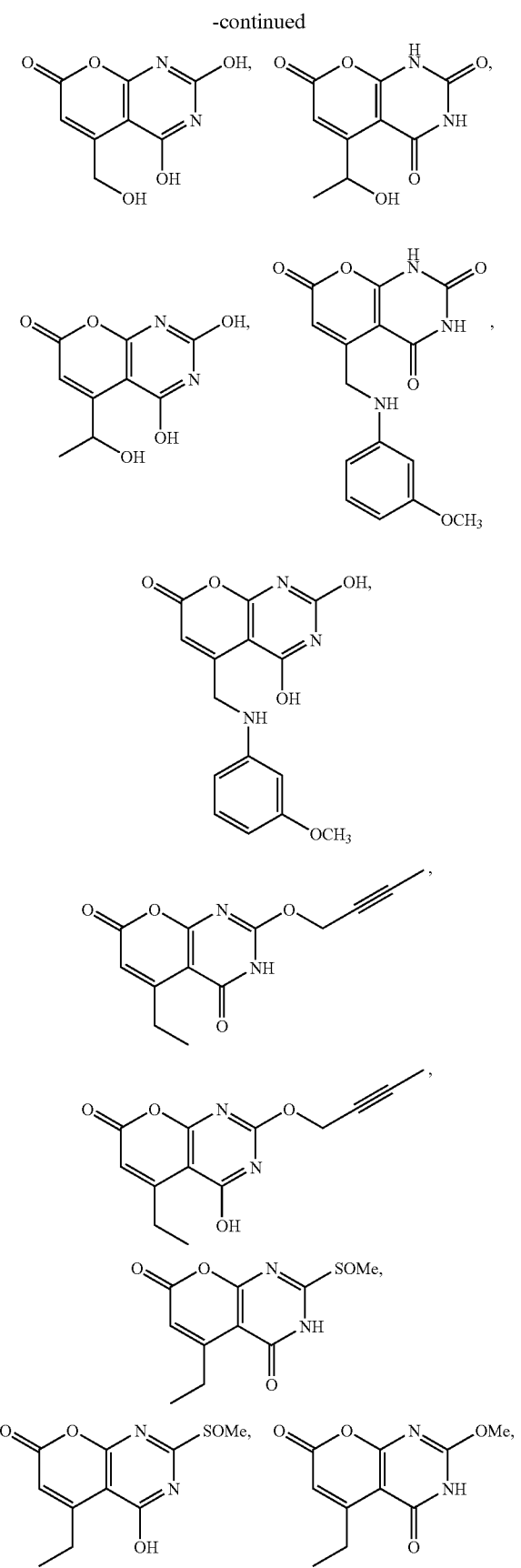
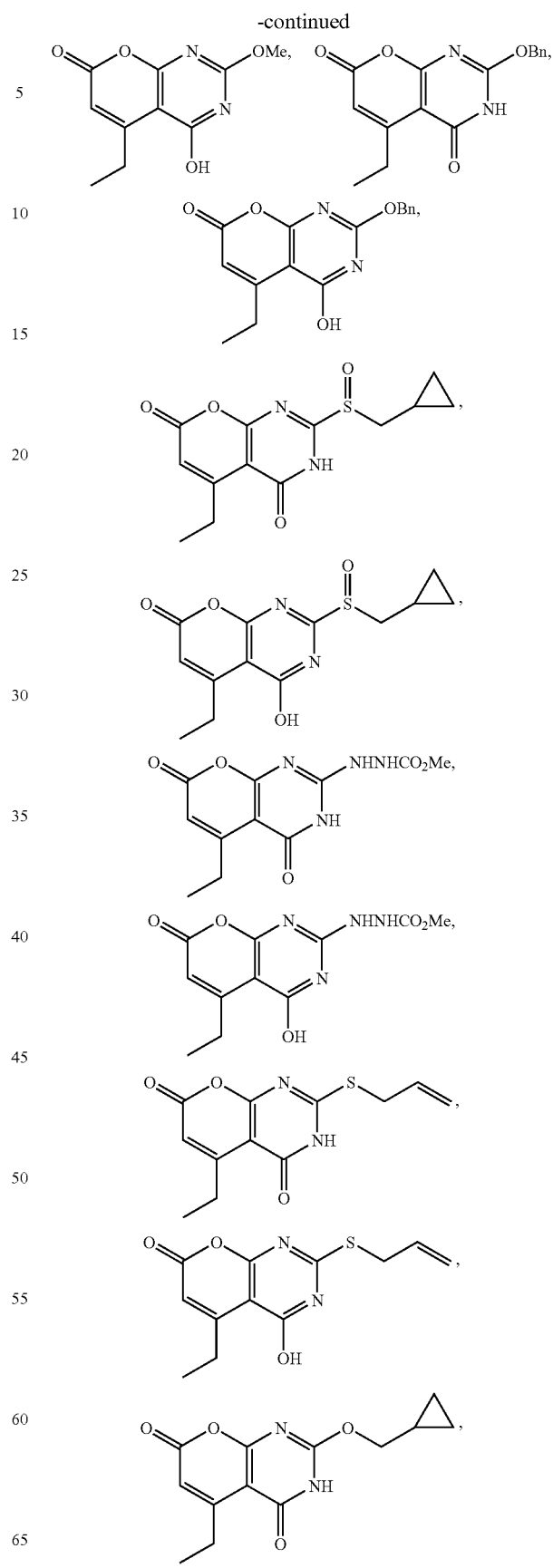

-continued
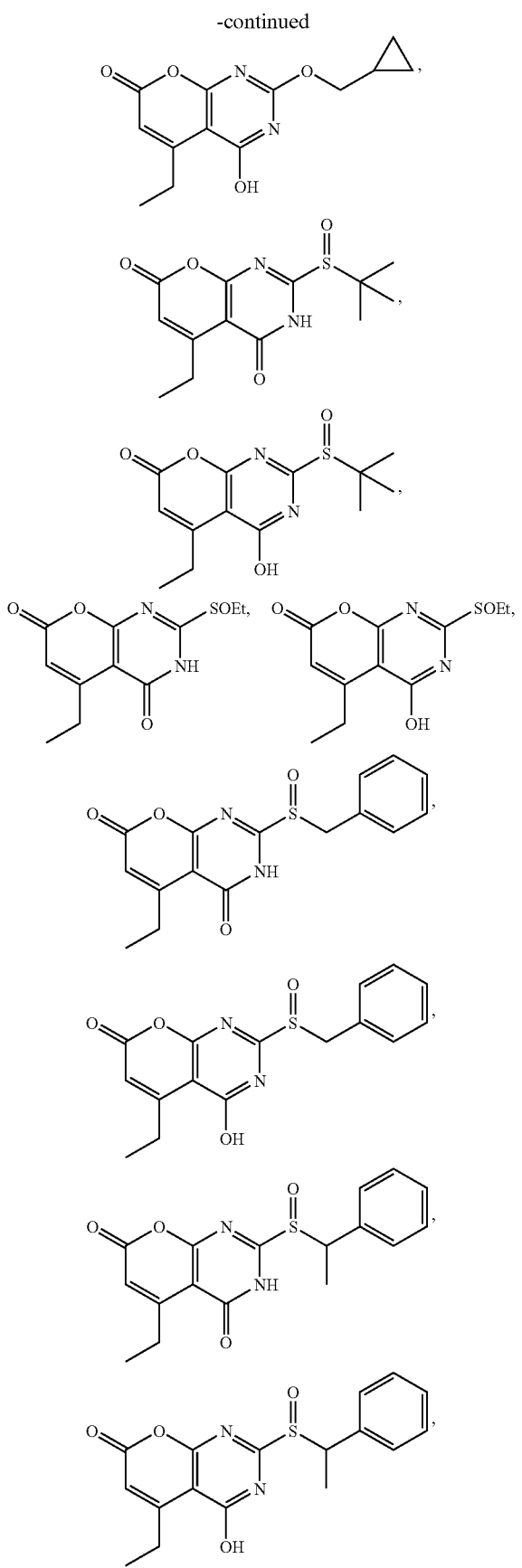
-continued
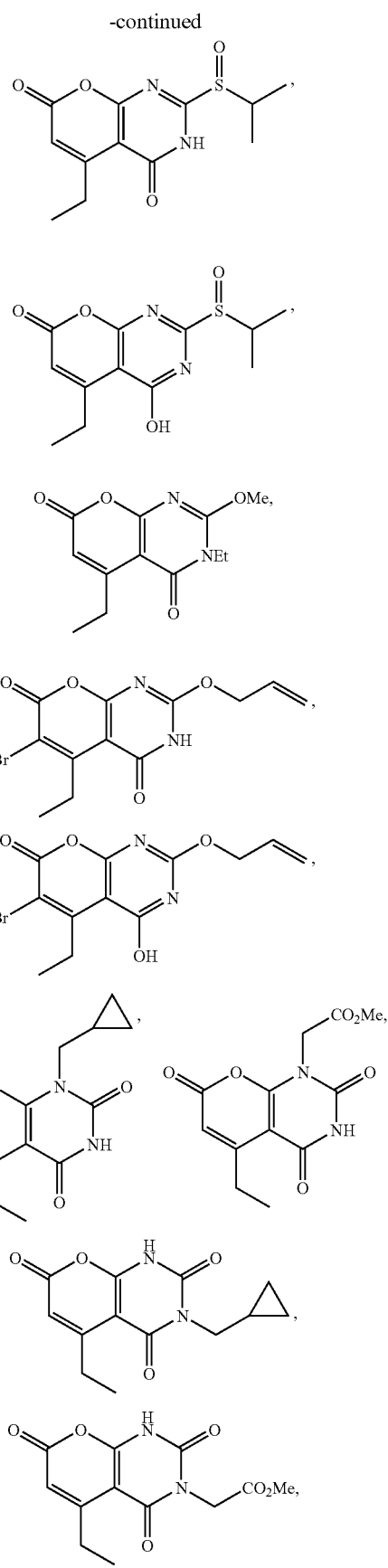

-continued
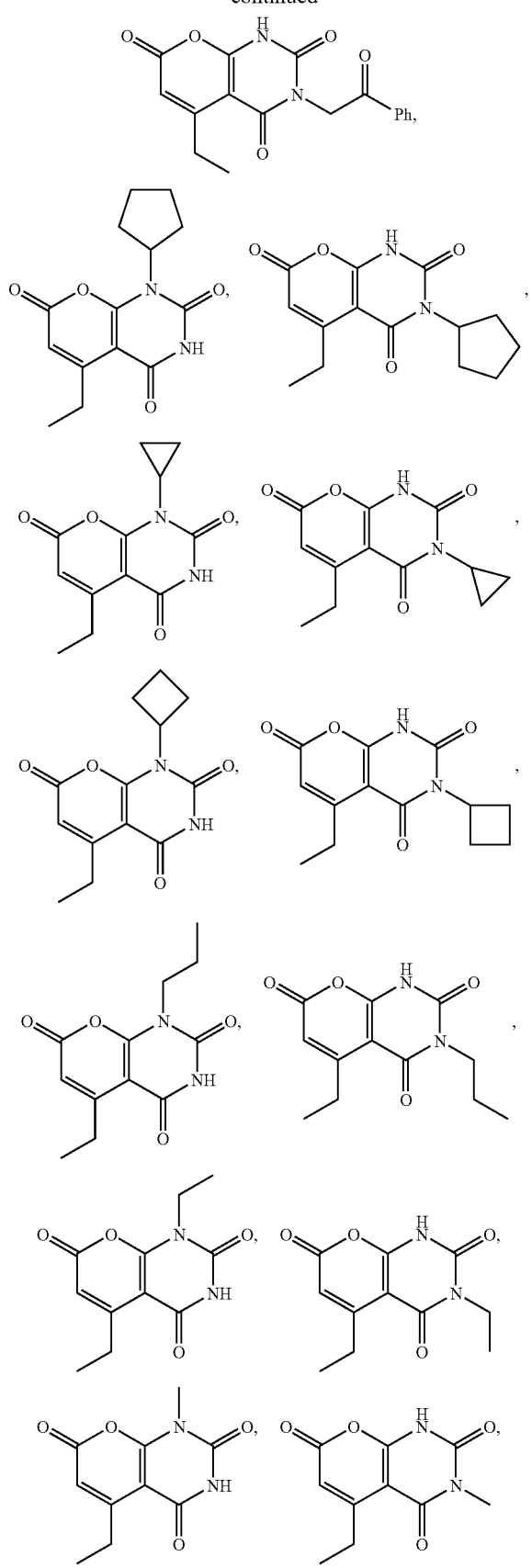
-continued
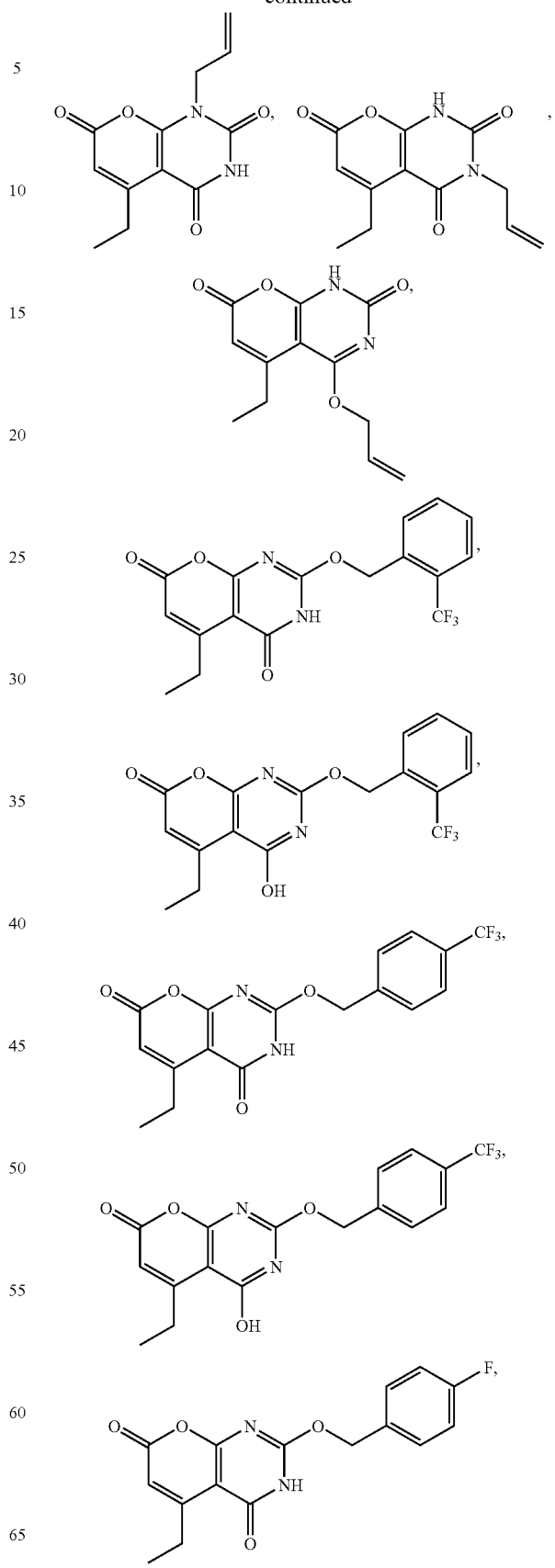

-continued
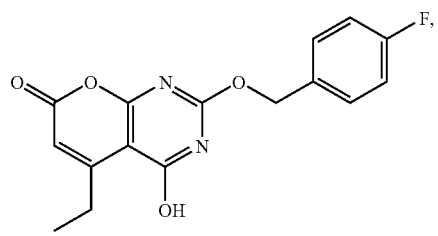
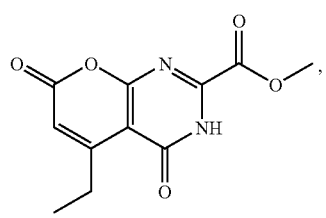
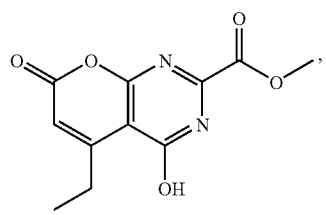
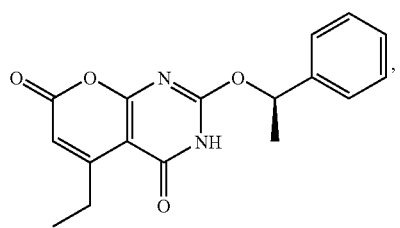
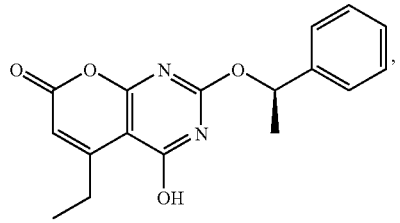
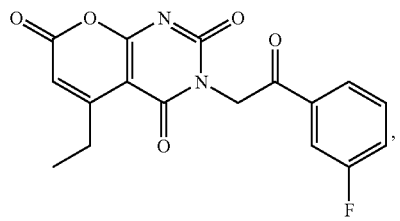
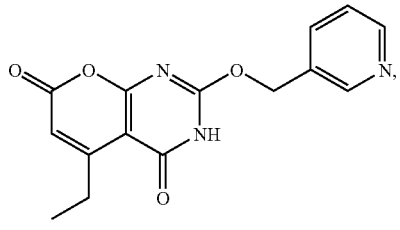
-continued
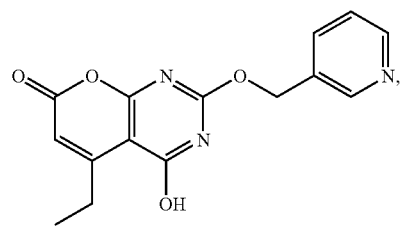
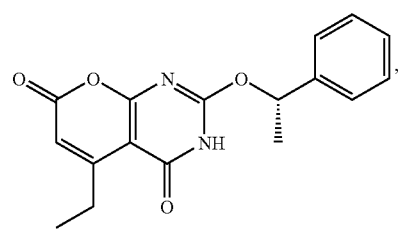
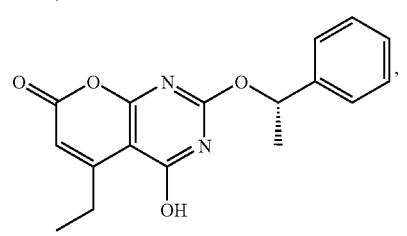
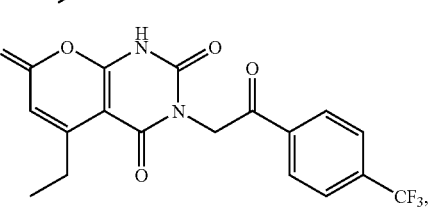
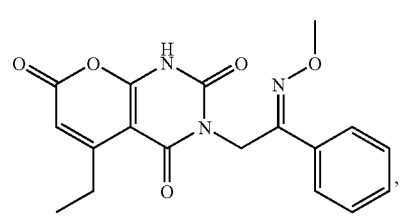
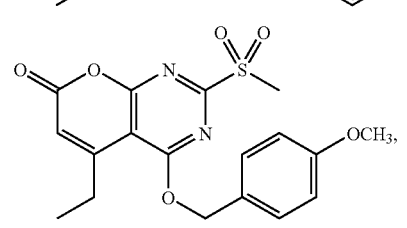
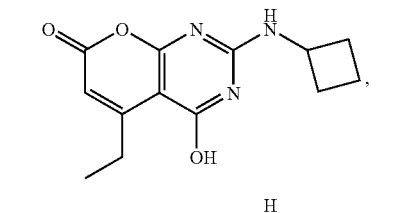
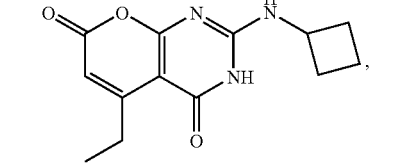

-continued
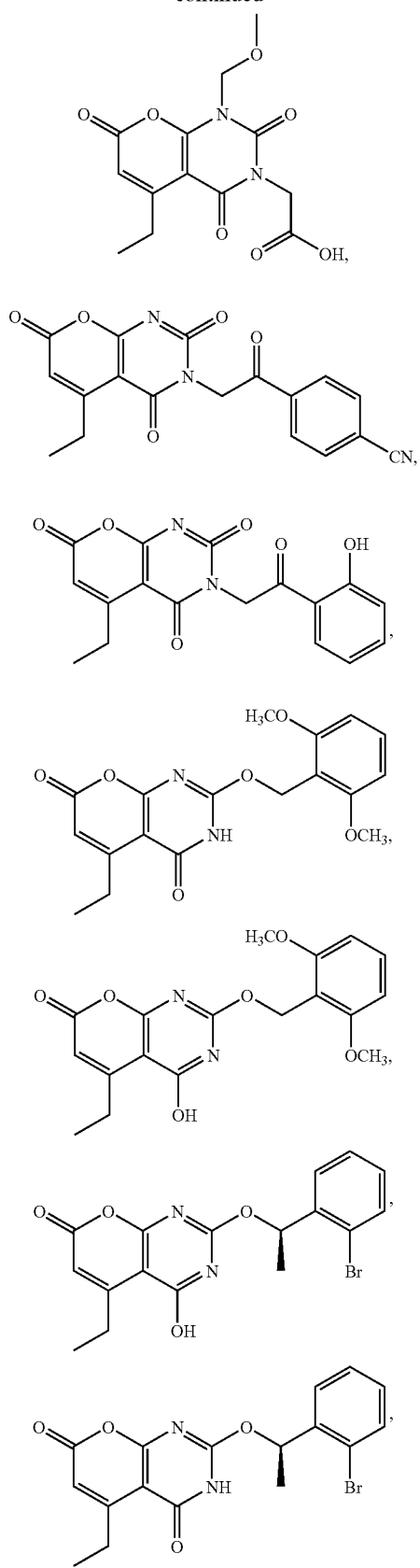
-continued
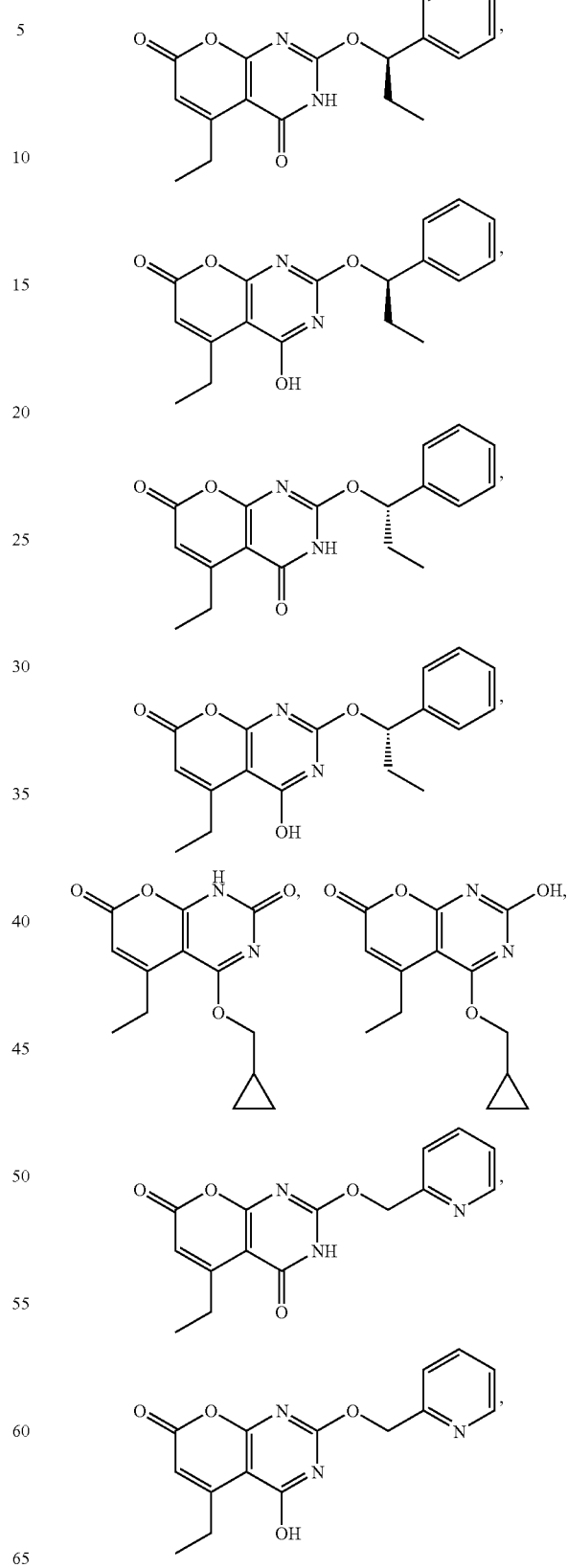

-continued
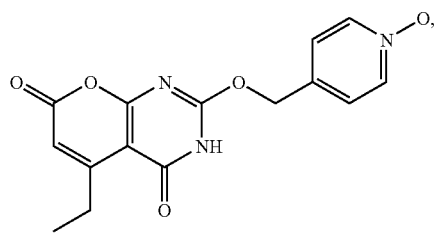
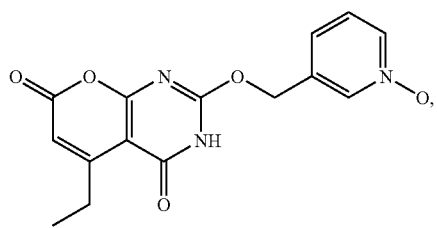
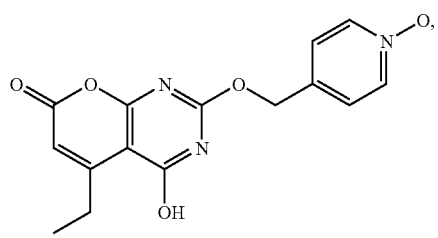
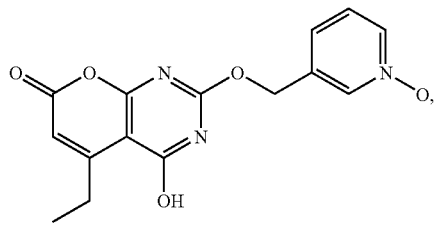
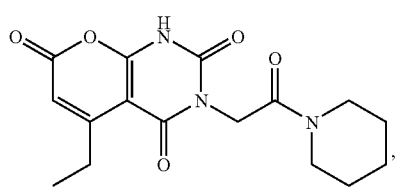
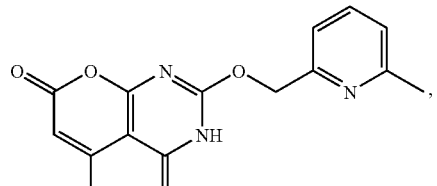
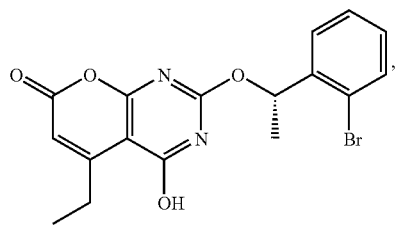
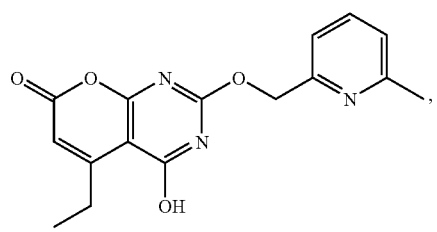
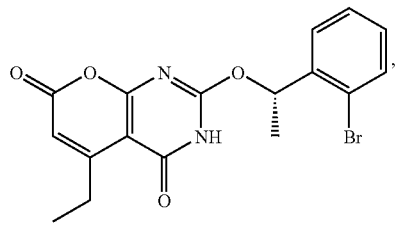
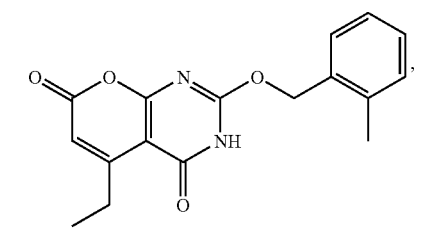
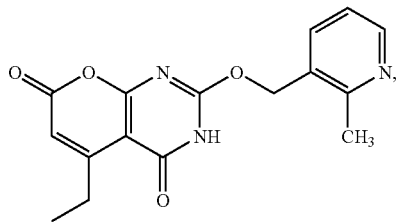
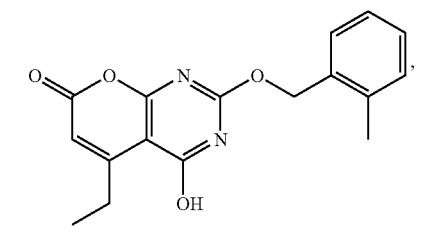
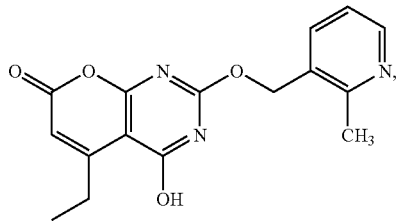
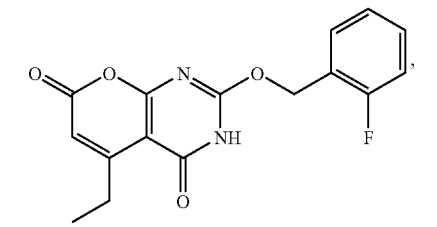

-continued
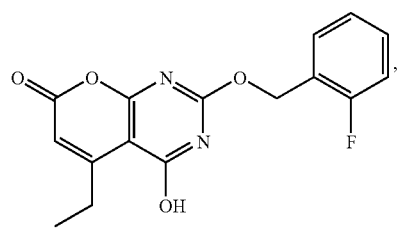
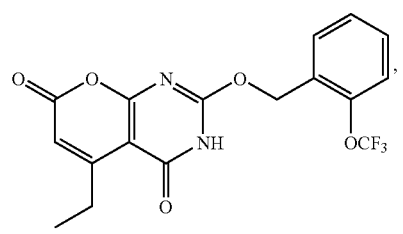
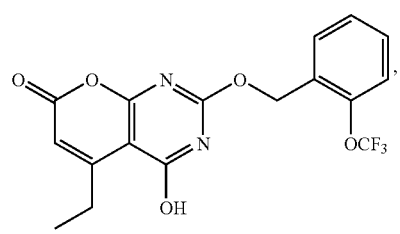
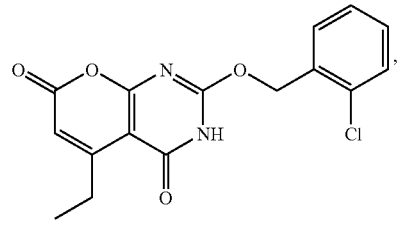
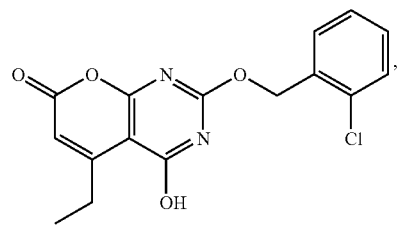
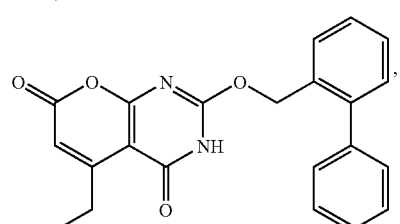
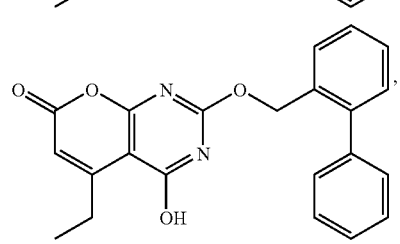
-continued
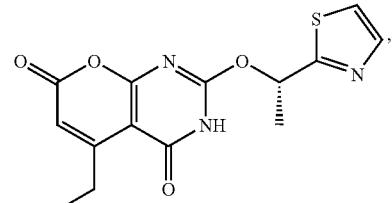
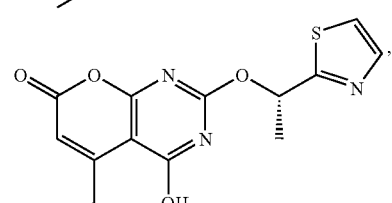
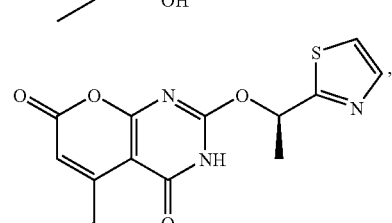
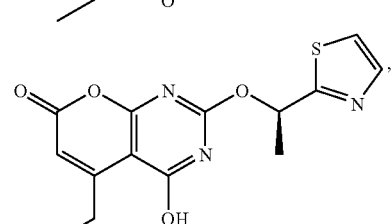
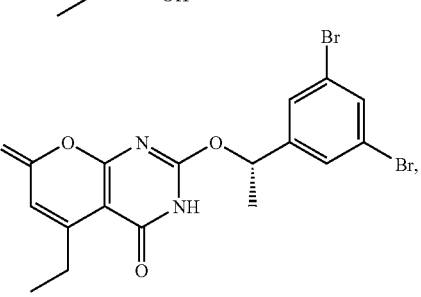
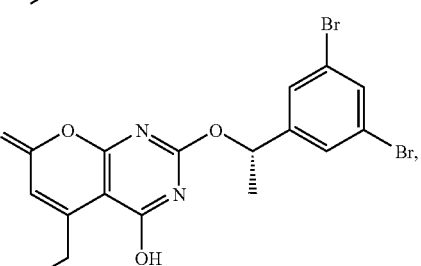
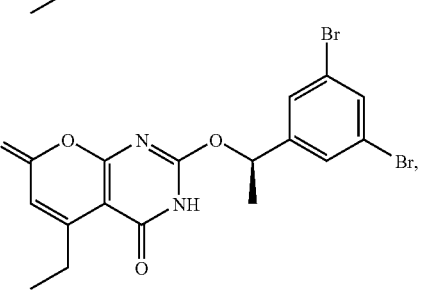

-continued
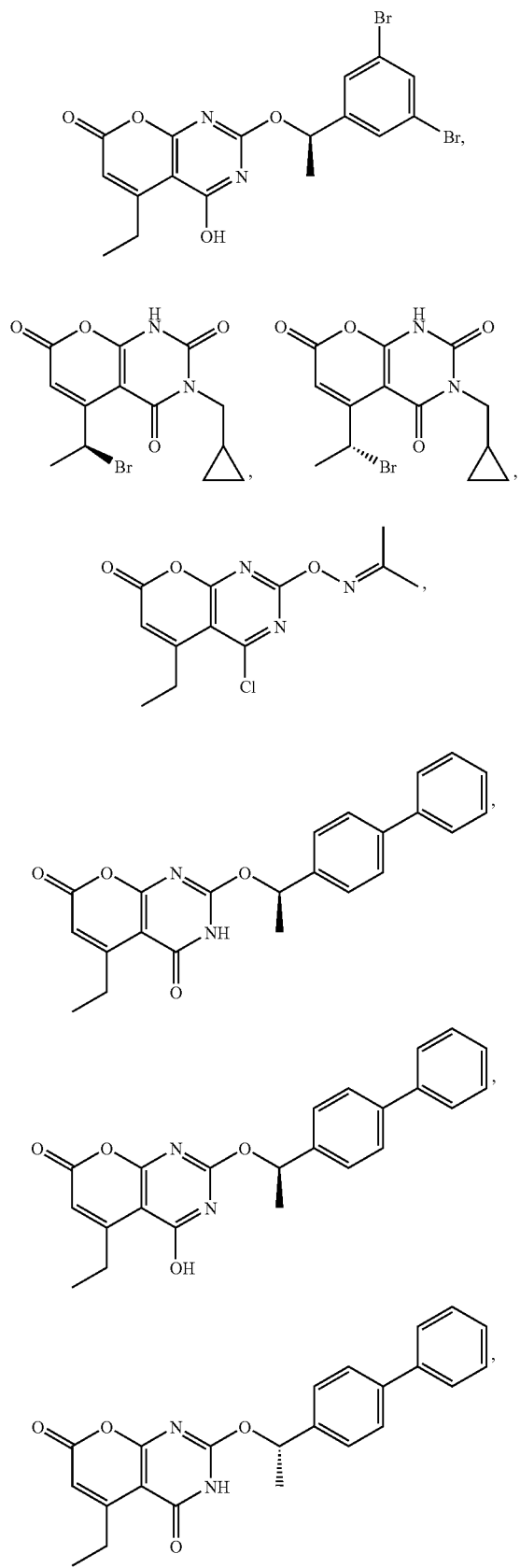
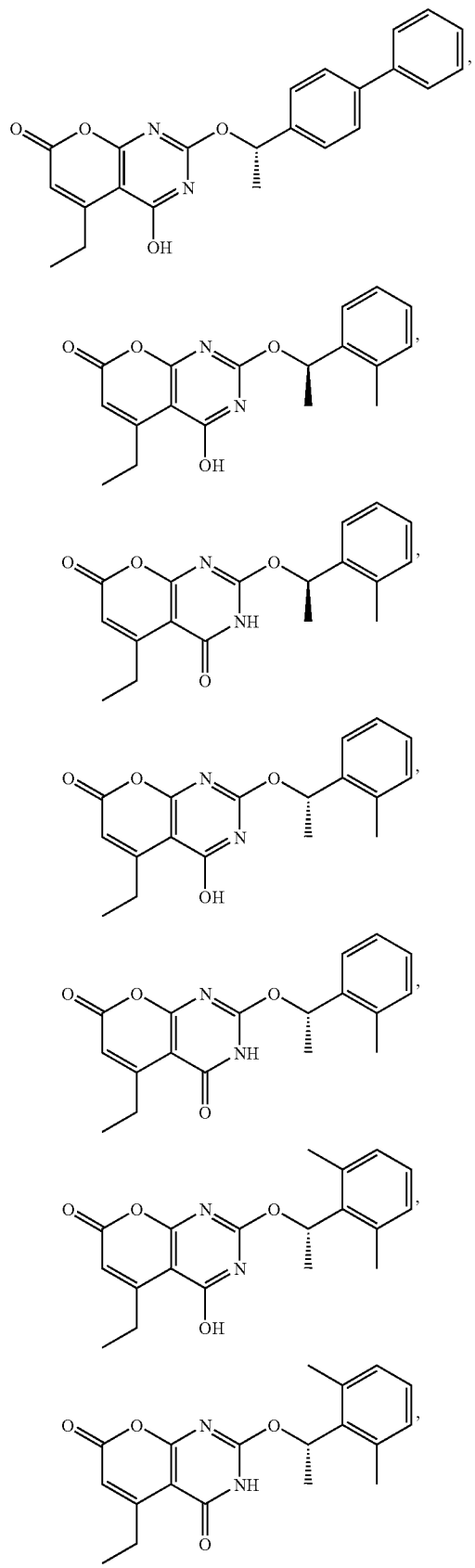

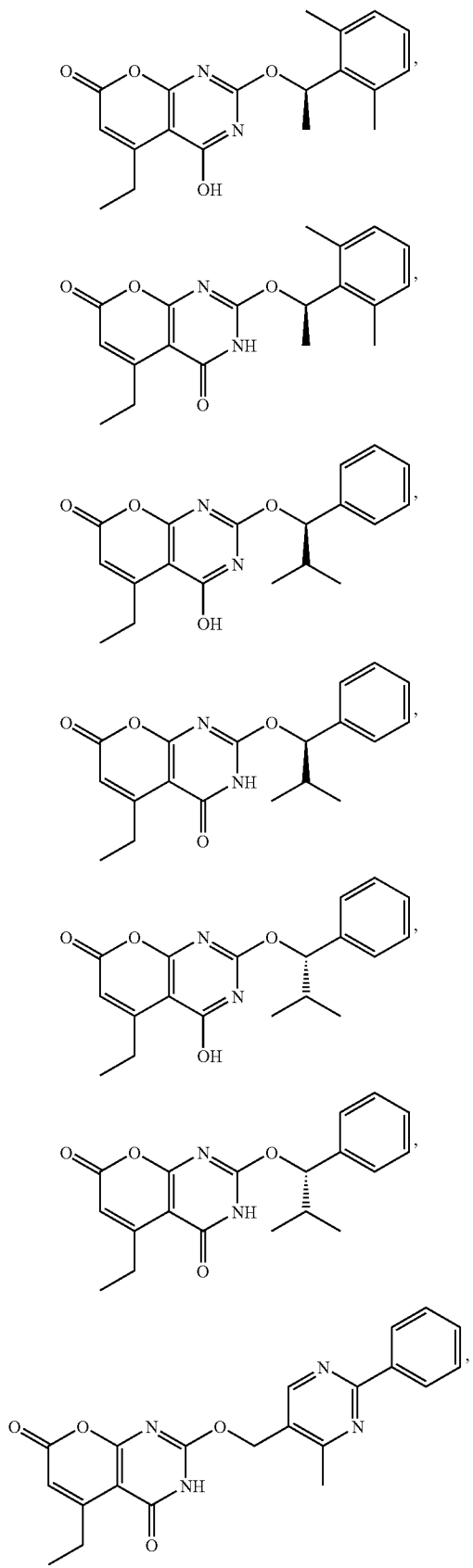
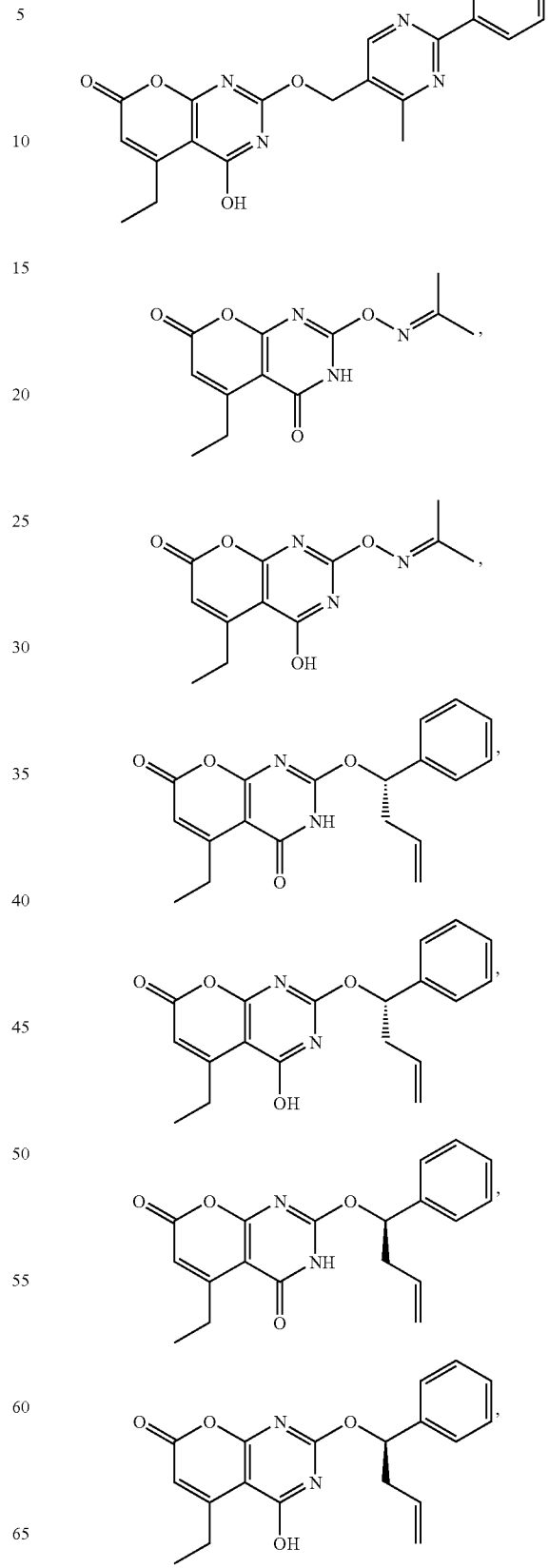

-continued
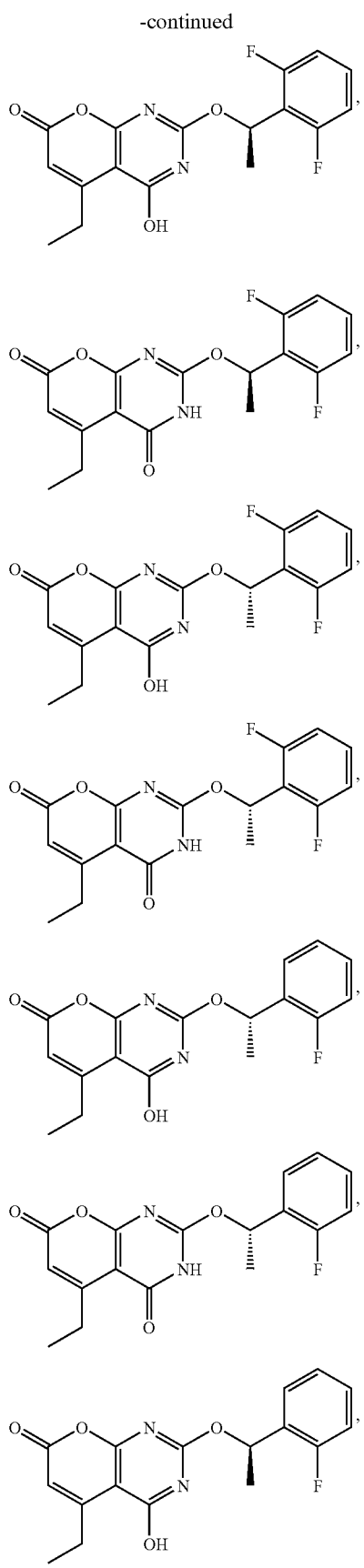
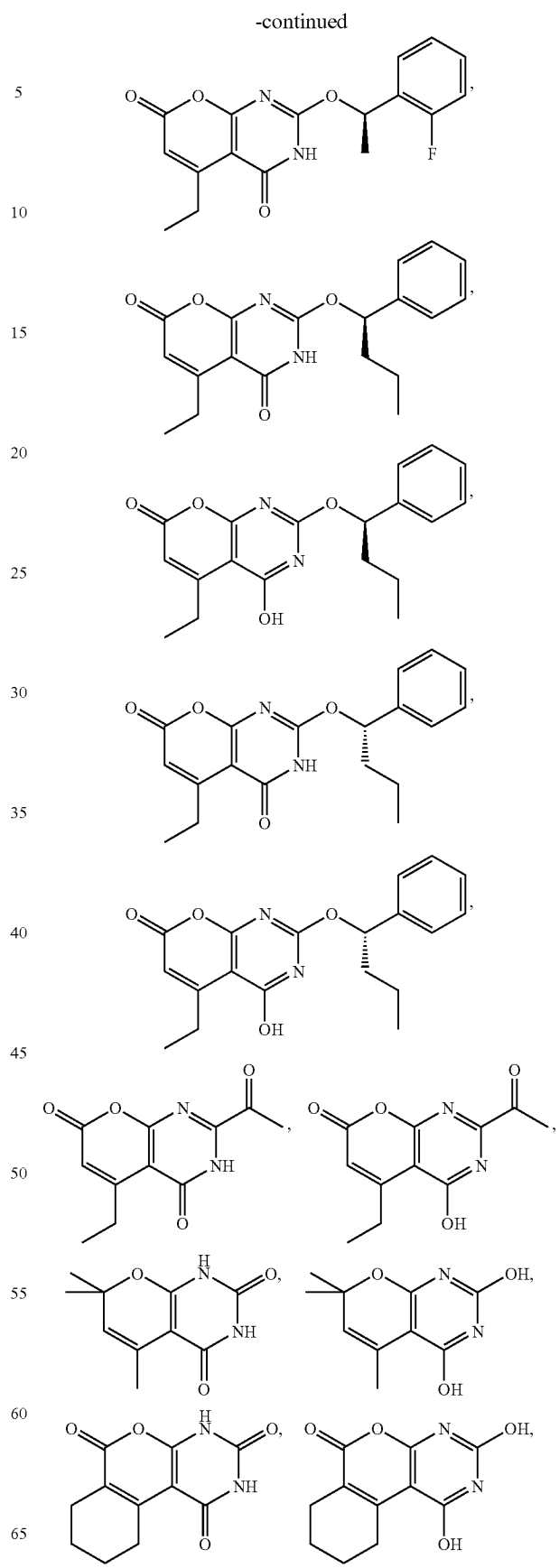

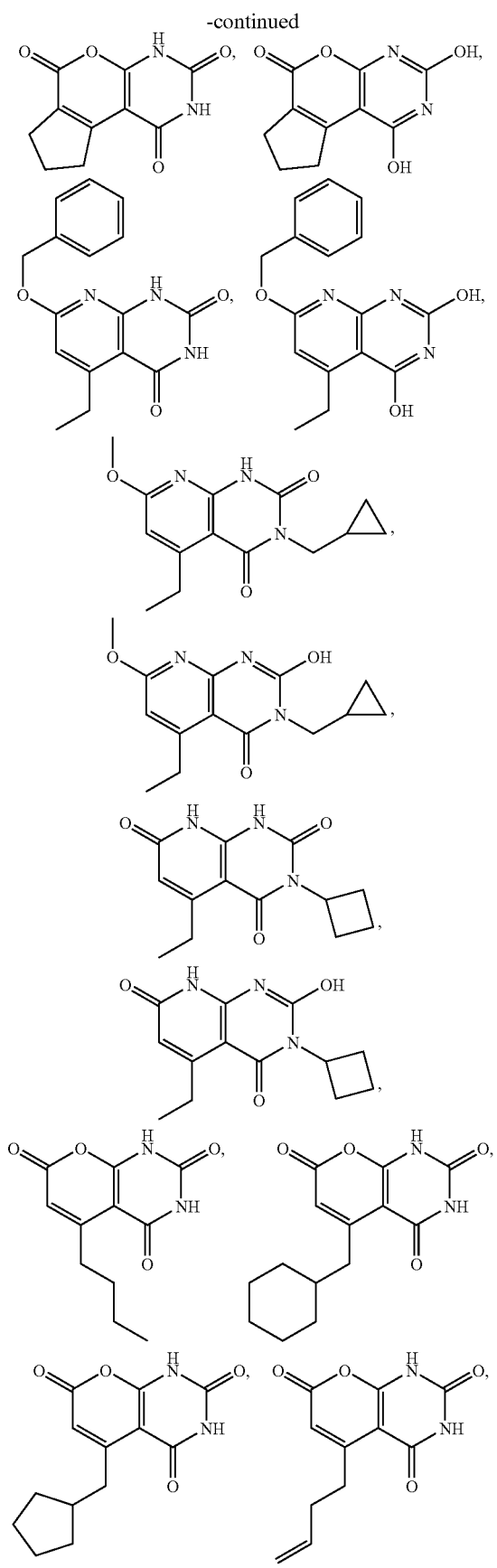
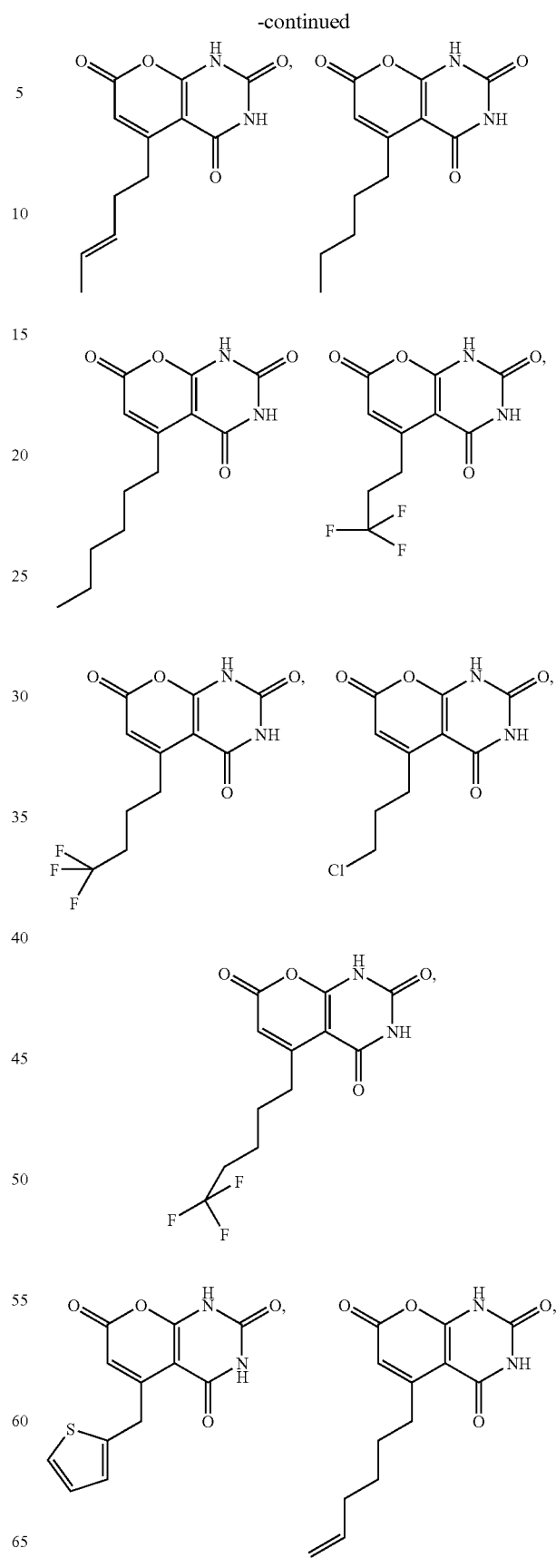

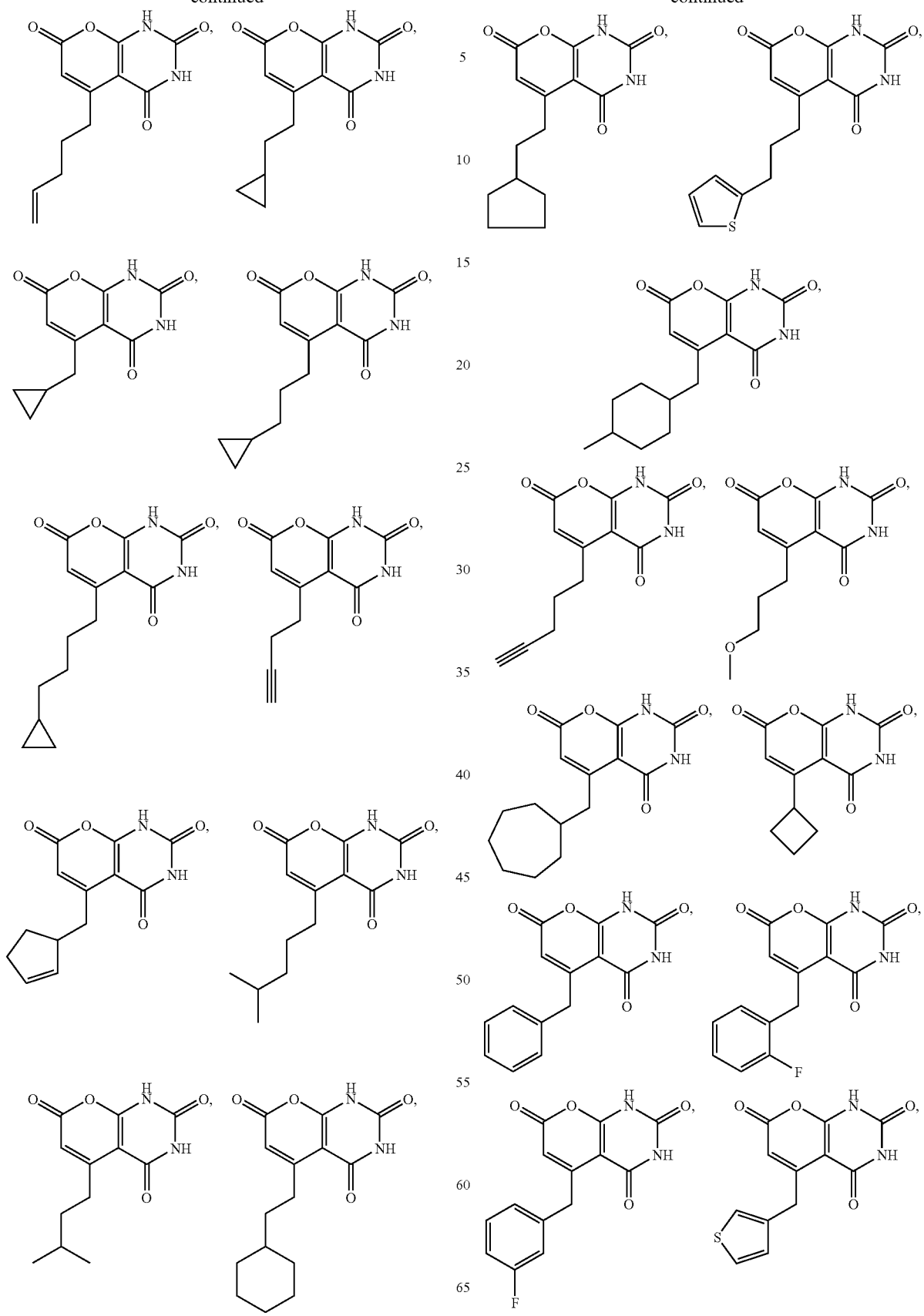

51
-continued
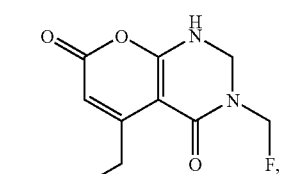
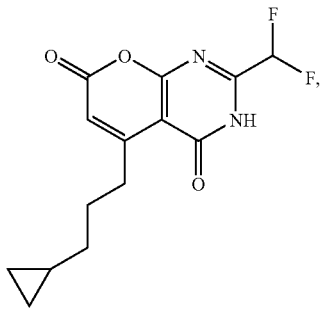
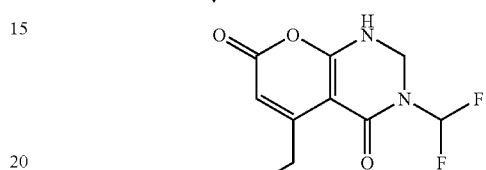
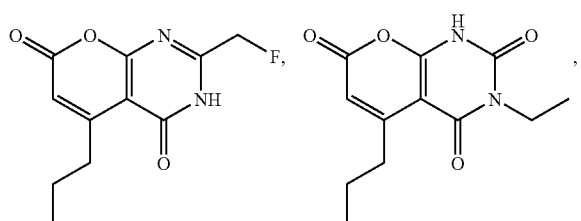
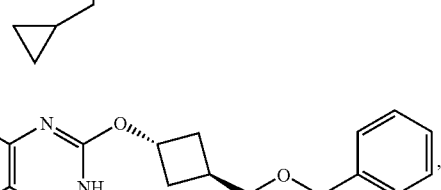
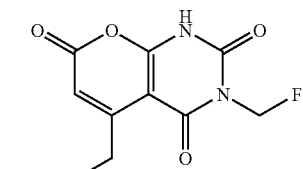
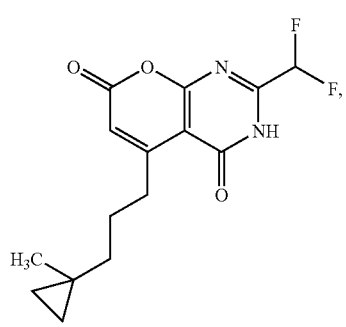
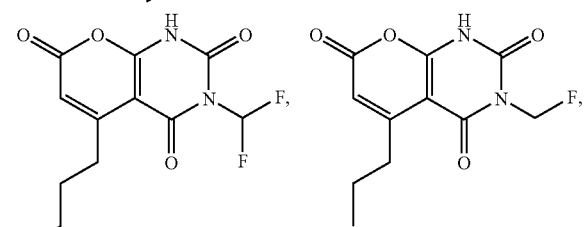
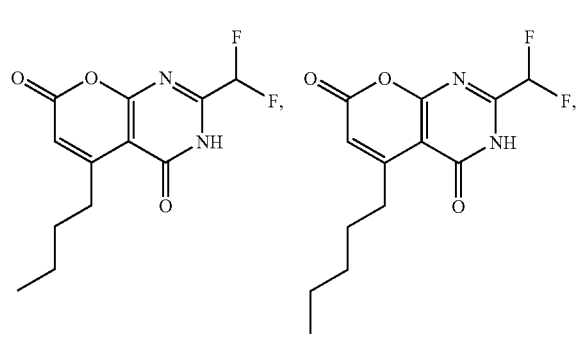
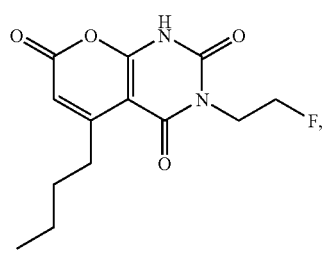
52
-continued

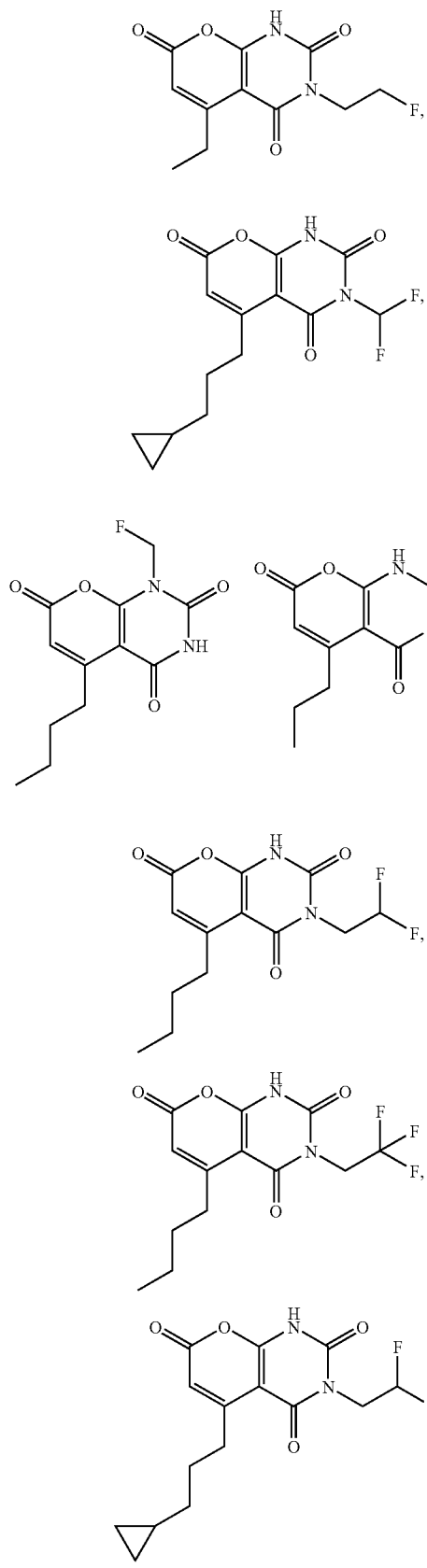
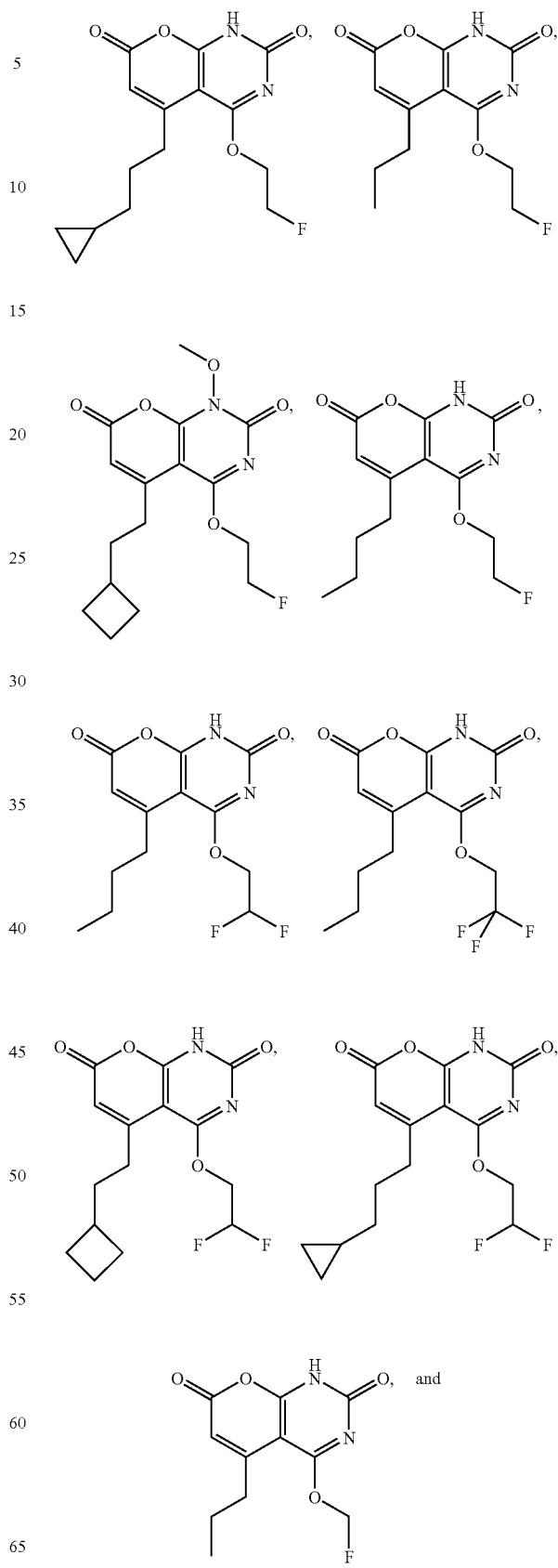

-continued

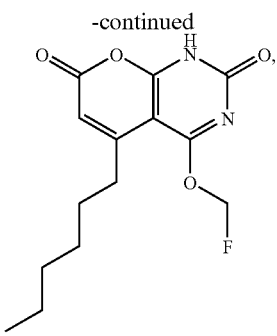

and pharmaceutically acceptable salts, solvates, esters, or tautomers thereof.

In one embodiment, the compounds of formula (I) have the formula (II):

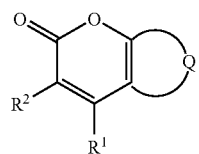

(II)

and pharmaceutically acceptable salts, solvates, esters, and tautomers thereof, wherein:

Q is selected from the group consisting of:

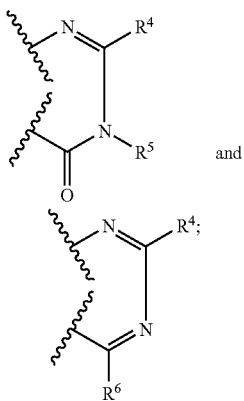

$R^1$ is —H, alkyl, haloalkyl, arylalkyl, -alkylene-S-alkyl or -alkylene-cycloalkyl;

$R^2$ is —H, —CN, or —NHC(O)-alkyl;

$R^4$ is —O-cycloalkyl, —O-alkynyl, —O-alkynylene-cycloalkyl, haloalkyl or —O—N=C($R^{12}$)$_2$, wherein both $R^{12}$ groups, together with the carbon atom to which they are attached, combine to form a heterocyclyl group, and wherein the alkynyl portion of an —O-alkynyl group can be optionally substituted with —OH or alkoxy; and wherein the cycloalkyl portion of an —O-cycloalkyl group can be optionally substituted with an -alkylene-O-alkylene-aryl group;

$R^5$ is —H, —OH, alkyl, haloalkyl, arylalkyl, —O-alkyl, —O-aryl, cycloalkyl, heterocyclyl, —O-cycloalkyl, —O-heterocyclyl, —O-arylalkyl or -alkylene-O-alkyl; and $R^6$ is alkoxy, —O-alkylene-O-alkyl, —O-arylalkyl or —O-haloalkyl.

The following embodiments refer to the compounds of formula (II), wherein Q is:

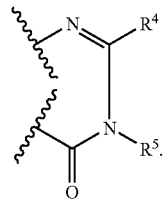

In one embodiment, $R^1$ is alkyl.
In another embodiment, $R^1$ is haloalkyl.
In another embodiment, $R^1$ is arylalkyl.
In still another embodiment, $R^1$ is -alkylene-S-alkyl.
In yet another embodiment, $R^1$ is -alkylene-cycloalkyl.
In another embodiment, $R^1$ is -alkylene-cyclopropyl, -alkylene-cyclobutyl, -alkylene-cyclopentyl or -alkylene-cyclohexyl.
In a further embodiment, $R^1$ is -alkylene-cycloalkenyl.
In another embodiment, $R^1$ is a straight chain alkyl having from 1 to 6 carbon atoms.
In one embodiment, $R^1$ is methyl.
In another embodiment, $R^1$ is ethyl.
In another embodiment, $R^1$ is n-propyl.
In still another embodiment, $R^1$ is n-butyl.
In one embodiment, $R^1$ is n-pentyl.
In another embodiment, $R^1$ is n-hexyl.
In yet another embodiment, $R^1$ is a branched chain alkyl having from 3 to 6 carbon atoms.
In a further embodiment, $R^1$ is isopropyl.
In one embodiment, $R^1$ is isobutyl.
In another embodiment, $R^1$ is isopentyl.
In another embodiment, $R^1$ is sec-butyl.
In still another embodiment, $R^1$ is tert-butyl.
In yet another embodiment, $R^1$ is haloalkyl, having from 1 to 3 F atoms.
In another embodiment, $R^1$ is —(CH$_2$)$_3$CF$_3$.
In one embodiment, $R^4$ is —CF$_3$.
In another embodiment, $R^4$ is —H.
In another embodiment, $R^4$ is —O-cycloalkyl.
In another embodiment, $R^4$—O-alkynyl.
In still another embodiment, $R^4$ is —O-alkynylene-cycloalkyl.
In yet another embodiment, $R^4$ is haloalkyl.
In a further embodiment, $R^4$ is —O—N=C($R^7$)$_2$.
In one embodiment, $R^4$ is is —CH$_2$F.
In another embodiment, $R^4$ is —CH(F)$_2$.
In another embodiment, $R^4$ is —CF$_3$.
In another embodiment, $R^4$ is —OCH$_2$C≡CCH$_2$CH$_3$.
In another embodiment, $R^4$ is —OCH$_2$C≡C(CH$_2$)$_3$CH$_3$.
In still another embodiment, $R^4$ is —OCH$_2$C≡CCH$_2$CH$_2$CH$_3$.
In yet another embodiment, $R^4$ is —OCH$_2$C≡C-cyclopropyl.
In a further embodiment, $R^4$ is —OCH$_2$C≡CCH(OCH$_3$)CH$_3$.
In one embodiment, $R^4$ is —OCH$_2$C≡CCH(OH)CH$_3$.
In another embodiment, $R^4$ is —OCH$_2$C≡CCH(OH)CH$_2$CH$_3$.
In another embodiment, $R^4$ is —OCH$_2$C≡CCH$_2$CH$_2$OCH$_3$.
In still another embodiment, $R^4$ is —OCH$_2$C≡CCH$_2$CH$_2$OH.

In yet another embodiment, $R^4$ is —OCH$_2$C≡C(CH$_2$)$_3$OH.

In a further embodiment, $R^4$ is —OCH(CH$_3$)C≡CCH$_2$CH$_3$.

In another embodiment, $R^4$ is —OCH$_2$C≡C-cyclohexyl.

In one embodiment, $R^4$ is —O-cyclobutyl.

In another embodiment, $R^4$ is:

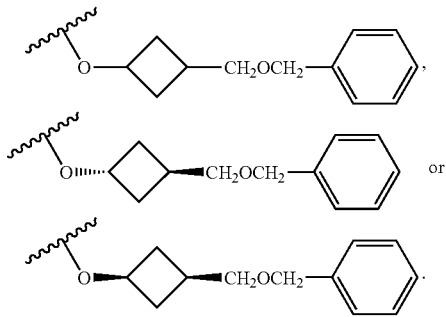

In one embodiment, $R^4$ is:

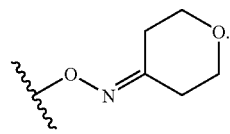

In one embodiment, $R^5$ is —H.
In another embodiment, $R^5$ is —OH.
In another embodiment, $R^5$ is alkyl.
In another embodiment, $R^5$ is haloalkyl.
In still another embodiment, $R^5$ is —O-alkyl.
In yet another embodiment, $R^5$ is cycloalkyl.
In a further embodiment, $R^5$ is heterocyclyl.
In one embodiment, $R^5$ is —O-arylalkyl.
In another embodiment, $R^5$ is -alkylene-O-alkyl.
In one embodiment, $R^5$ is —OCH$_3$.
In another embodiment, $R^5$ is cyclobutyl.
In another embodiment, $R^5$ is ethyl.
In still another embodiment, $R^5$ is N-morpholinyl.
In one embodiment, $R^5$ is —O-benzyl.
In another embodiment, $R^5$ is —CH$_2$CH$_2$OCH$_3$.
In yet another embodiment, $R^5$ is —OCH$_2$CH$_3$.
In another embodiment, $R^5$ is —CH$_2$F.
In one embodiment, $R^5$ is —CH$_2$CH$_2$F.
In another embodiment, $R^5$ is —OH.
In one embodiment, $R^1$ is alkyl and $R^5$ is —H.
In another embodiment, $R^1$ is haloalkyl and $R^5$ is —H.
In another embodiment, $R^1$ is arylalkyl and $R^5$ is —H.
In still another embodiment, $R^1$ is -alkylene-S-alkyl and $R^5$ is —H.
In yet another embodiment, $R^1$ is -alkylene-cycloalkyl and $R^5$ is —H.
In one embodiment, $R^1$ is alkyl and $R^5$ is —H.
In another embodiment, $R^1$ is haloalkyl and $R^5$ is —H.
In another embodiment, $R^1$ is arylalkyl and $R^5$ is —H.
In still another embodiment, $R^1$ is -alkylene-S-alkyl and $R^5$ is —H.
In yet another embodiment, $R^1$ is -alkylene-cycloalkyl and $R^5$ is —H.
In one embodiment, $R^1$ is alkyl, $R^5$ is —H and $R^4$ is —O-alkynyl.

In another embodiment, $R^1$ is alkyl, $R^5$ is —H and $R^4$ is —O-alkynylene-cycloalkyl.
In another embodiment, $R^1$ is alkyl, $R^5$ is —H and $R^4$ is haloalkyl.
In still another embodiment, $R^1$ is alkyl, $R^5$ is —H and $R^4$ is —O—N=C(R$^7$)$_2$.
In one embodiment, $R^1$ is haloalkyl, $R^5$ is —H and $R^4$ is —O-alkynyl.
In another embodiment, $R^1$ is haloalkyl, $R^5$ is —H and $R^4$ is —O-alkynylene-cycloalkyl.
In another embodiment, $R^1$ is haloalkyl, $R^5$ is —H and $R^4$ is haloalkyl.
In still another embodiment, $R^1$ is haloalkyl, $R^5$ is —H and $R^4$ is —O—N=C(R$^7$)$_2$.
In one embodiment, $R^1$ is -alkylene-cycloalkyl, $R^5$ is —H and $R^4$ is —O-alkynyl.
In another embodiment, $R^1$ is -alkylene-cycloalkyl, $R^5$ is —H and $R^4$ is —O-alkynylene-cycloalkyl.
In yet another embodiment, $R^1$ is -alkylene-cycloalkyl, $R^5$ is —H and $R^4$ is haloalkyl.
In still another embodiment, $R^1$ is -alkylene-cycloalkyl, $R^5$ is —H and $R^4$ is —O—N=C(R$^7$)$_2$.

The following embodiments refer to the compounds of formula (II), wherein Q is:

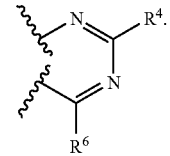

In one embodiment, $R^1$ is alkyl.
In another embodiment, $R^1$ is haloalkyl.
In another embodiment, $R^1$ is arylalkyl.
In still another embodiment, $R^1$ is -alkylene-S-alkyl.
In yet another embodiment, $R^1$ is -alkylene-cycloalkyl.
In another embodiment, $R^1$ is -alkylene-cyclopropyl, -alkylene-cyclobutyl, -alkylene-cyclopentyl or -alkylene-cyclohexyl.
In a further embodiment, $R^1$ is -alkylene-cycloalkenyl.
In another embodiment, $R^1$ is a straight chain alkyl having from 1 to 6 carbon atoms.
In one embodiment, $R^1$ is methyl.
In another embodiment, $R^1$ is ethyl.
In another embodiment, $R^1$ is n-propyl.
In still another embodiment, $R^1$ is n-butyl.
In one embodiment, $R^1$ is n-pentyl.
In another embodiment, $R^1$ is n-hexyl.
In yet another embodiment, $R^1$ is a branched chain alkyl having from 3 to 6 carbon atoms.
In a further embodiment, $R^1$ is isopropyl.
In one embodiment, $R^1$ is isobutyl.
In another embodiment, $R^1$ is isopentyl.
In another embodiment, $R^1$ is sec-butyl.
In still another embodiment, $R^1$ is tert-butyl.
In yet another embodiment, $R^1$ is haloalkyl, having from 1 to 3 F atoms.
In another embodiment, $R^1$ is —(CH$_2$)$_3$CF$_3$.
In one embodiment, $R^2$ is —H.
In another embodiment, $R^2$ is —CN.
In another embodiment, $R^2$ is —NHC(O)-alkyl.
In still another embodiment, $R^2$ is —NHC(O)CH$_3$.
In one embodiment, $R^4$ is —CF$_3$.
In another embodiment, $R^4$ is —H.

In another embodiment, $R^4$ is —O-cycloalkyl.
In another embodiment, $R^4$—O-alkynyl.
In still another embodiment, $R^4$ is —O-alkynylene-cycloalkyl.
In yet another embodiment, $R^4$ is haloalkyl.
In a further embodiment, $R^4$ is —O—N=C($R^7$)$_2$.
In one embodiment, $R^4$ is is —CH$_2$F.
In another embodiment, $R^4$ is —CH(F)$_2$.
In another embodiment, $R^4$ is —CF$_3$.
In another embodiment, $R^4$ is —OCH$_2$C≡CCH$_2$CH$_3$.
In another embodiment, $R^4$ is —OCH$_2$C≡C(CH$_2$)$_3$CH$_3$.
In still another embodiment, $R^4$ is —OCH$_2$C≡CCH$_2$CH$_3$.
In yet another embodiment, $^4$ is —OCH$_2$C≡C-cyclopropyl.
In a further embodiment, $R^4$ is —OCH$_2$=CCH(OCH$_3$)CH$_3$.
In one embodiment, $R^4$ is —OCH$_2$C≡CCH(OH)CH$_3$.
In another embodiment, $R^4$ is —OCH$_2$C≡CCH(OH)CH$_2$CH$_3$.
In another embodiment, $R^4$ is —OCH$_2$C≡CCH$_2$CH$_2$OCH$_3$.
In still another embodiment, $R^4$ is —OCH$_2$C≡CCH$_2$CH$_2$OH.
In yet another embodiment, $R^4$ is —OCH$_2$C≡C(CH$_2$)$_3$OH.
In a further embodiment, $R^4$ is —OCH(CH$_3$)C≡CCH$_2$CH$_3$.
In another embodiment, $R^4$ is —OCH$_2$C≡C-cyclohexyl.
In one embodiment, $R^4$ is —O-cyclobutyl.
In another embodiment, $R^4$ is:

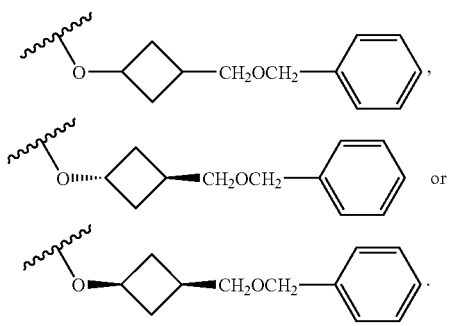

In one embodiment, $R^4$ is:

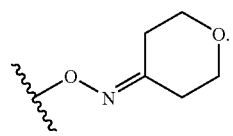

In one embodiment, $R^6$ is alkoxy.
In another embodiment, $R^6$ is —O-alkylene-O-alkyl.
In another embodiment, $R^6$ is —O-arylalkyl.
In still another embodiment, $R^6$ is —O-haloalkyl.
In yet another embodiment, $R^6$ is —OCH$_2$-(4-methoxyphenyl).
In one embodiment, $R^6$ is —OCH$_2$F.
In another embodiment, $R^6$ is —OCH$_2$CH$_2$F.
In another embodiment, $R^6$ is —OCH$_2$CH$_3$.
In still another embodiment, $R^6$ is —OCH$_2$CH$_2$OCH$_3$.
In one embodiment, $R^1$ is alkyl and $R^4$ is —O-alkynyl.

In another embodiment, $R^1$ is alkyl and $R^4$ is —O-alkynylene-cycloalkyl.
In another embodiment, $R^1$ is alkyl and $R^4$ is haloalkyl.
In still another embodiment, $R^1$ is alkyl and $R^4$ is —O—N=C($R^7$)$_2$.
In one embodiment, $R^1$ is haloalkyl and $R^4$ is —O-alkynyl.
In another embodiment, $R^1$ is haloalkyl and $R^4$ is —O-alkynylene-cycloalkyl.
In another embodiment, $R^1$ is haloalkyl and $R^4$ is haloalkyl.
In still another embodiment, $R^1$ is haloalkyl and $R^4$ is —O—N=C($R^7$)$_2$.
In one embodiment, $R^1$ is -alkylene-cycloalkyl and $R^4$ is —O-alkynyl.
In another embodiment, $R^1$ is -alkylene-cycloalkyl and $R^4$ is —O-alkynylene-cycloalkyl.
In yet another embodiment, $R^1$ is -alkylene-cycloalkyl and $R^4$ is haloalkyl.
In still another embodiment, $R^1$ is -alkylene-cycloalkyl and $R^4$ is —O—N=C($R^7$)$_2$.

Non-limiting illustrative examples of the compounds of formula (II), include the following compounds:

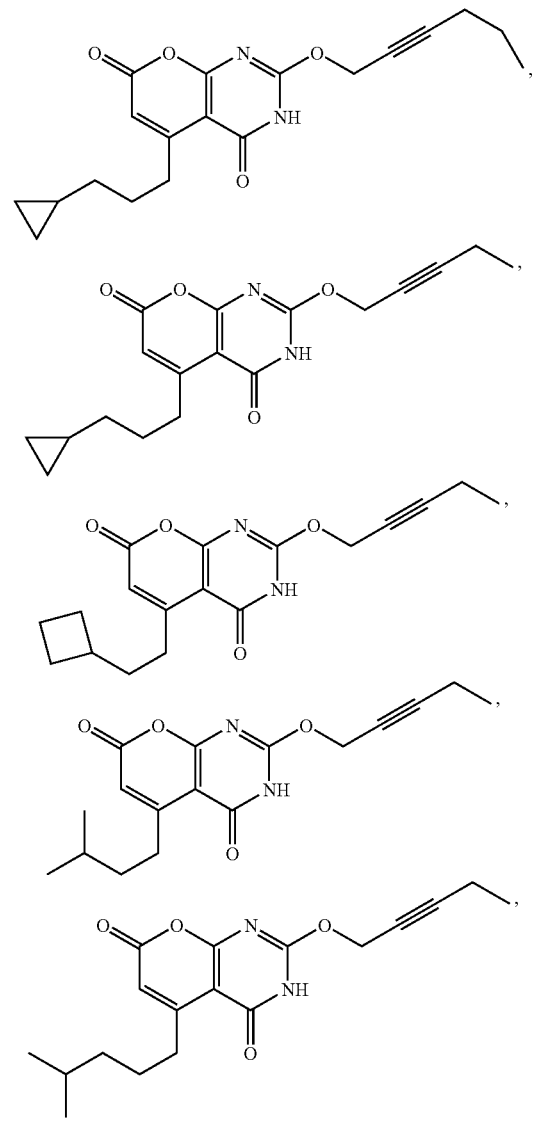

-continued
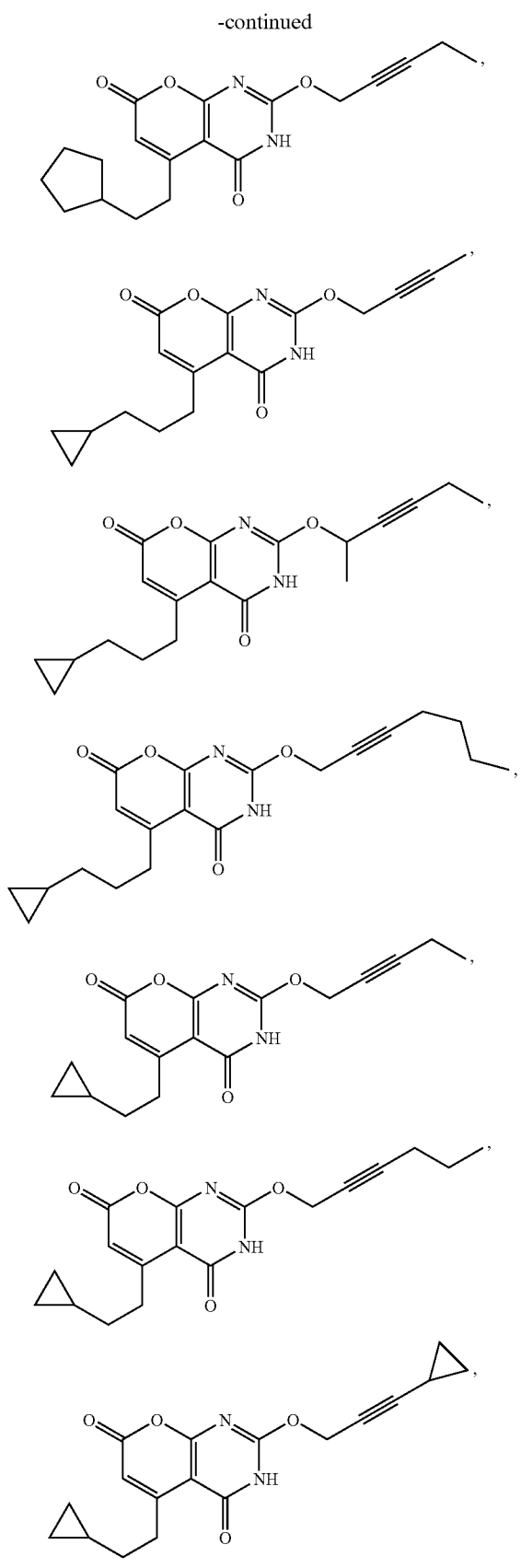
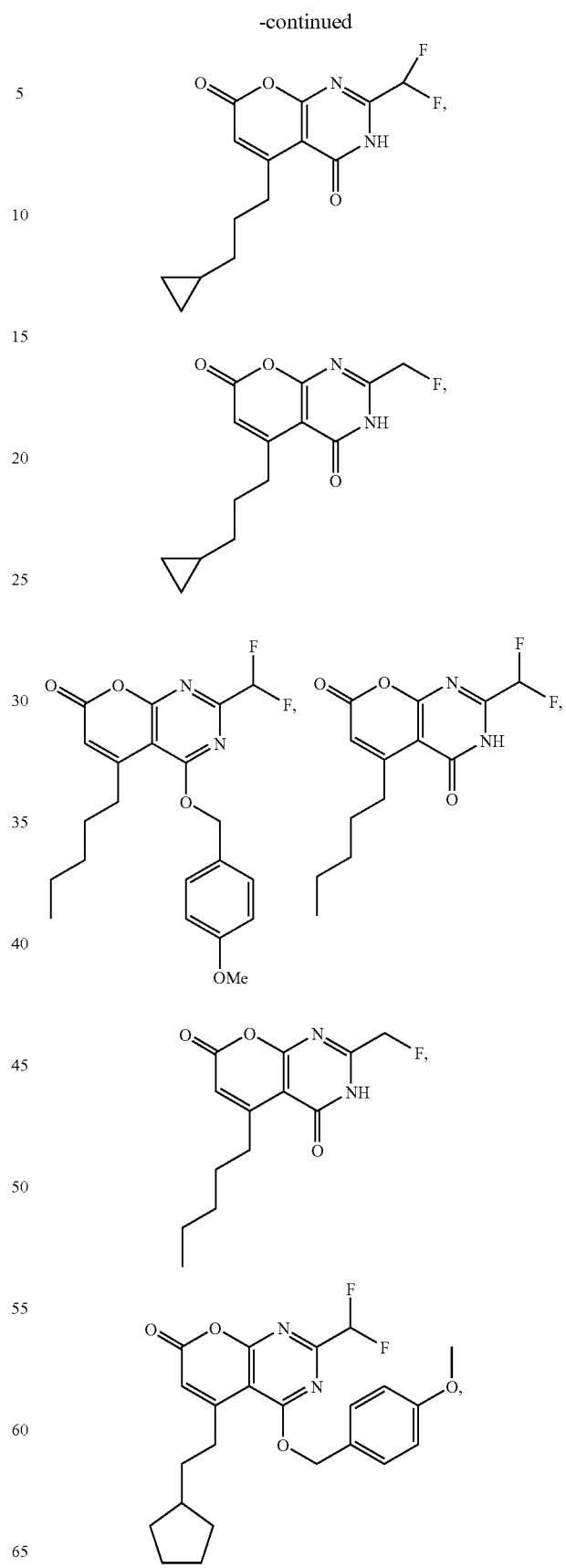

-continued
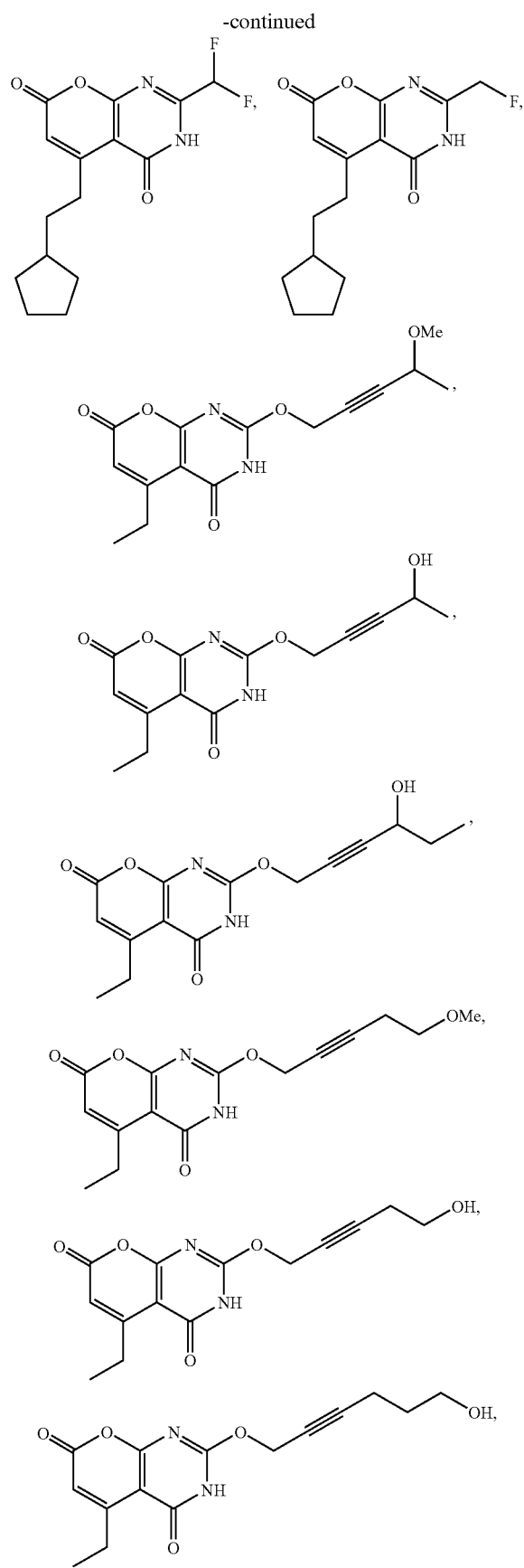
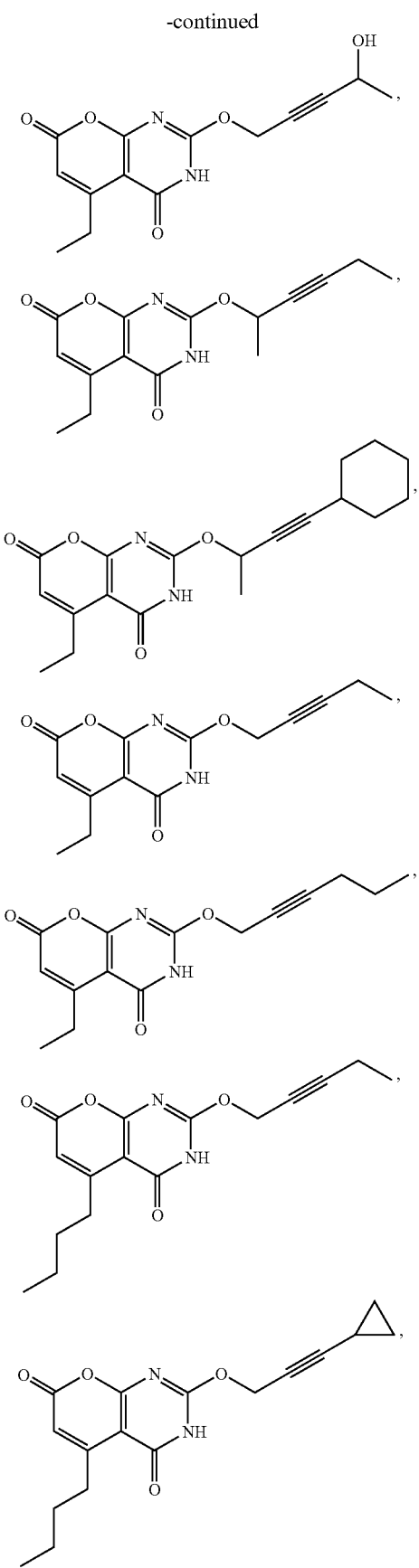

-continued
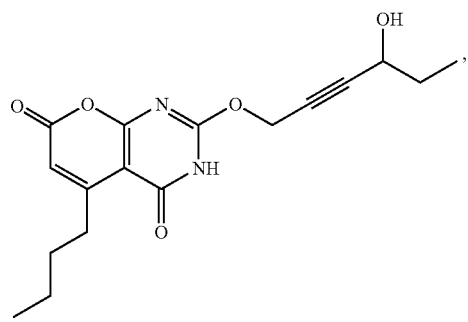
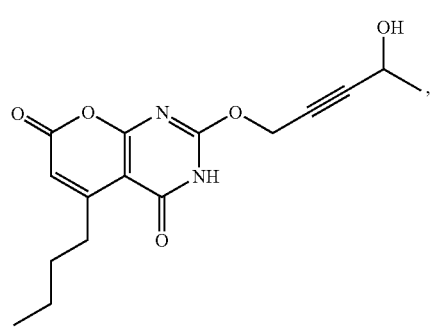
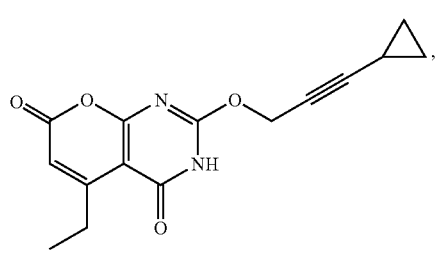
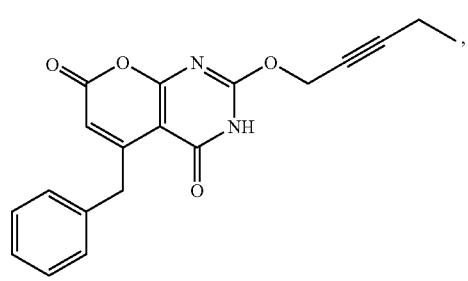
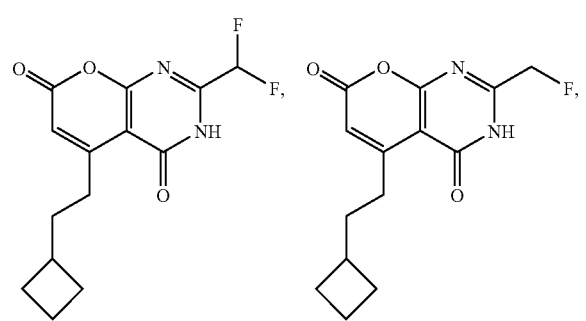
-continued
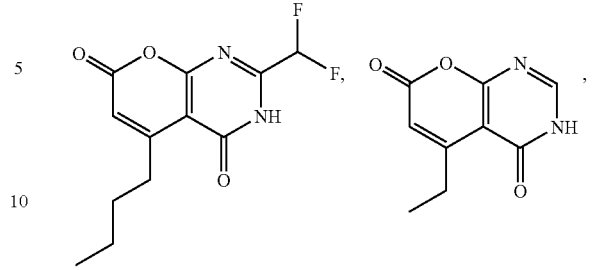
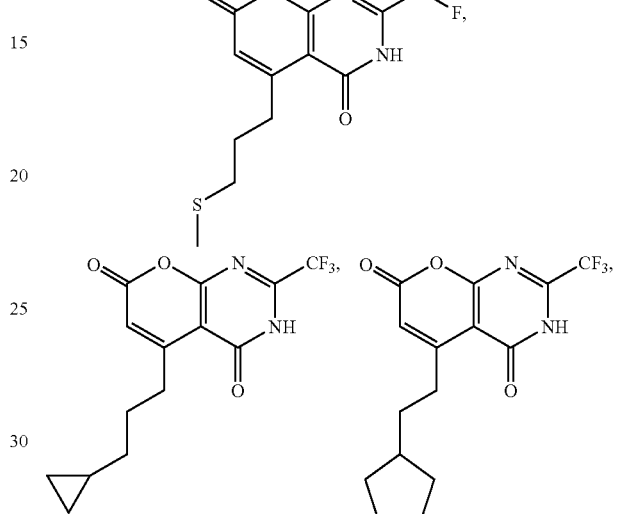
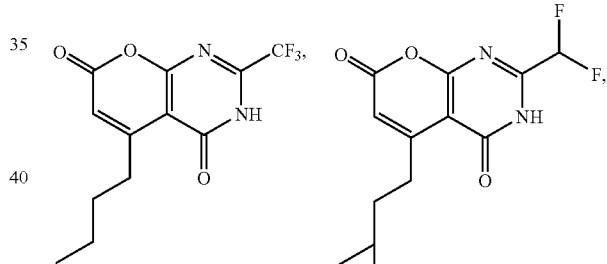
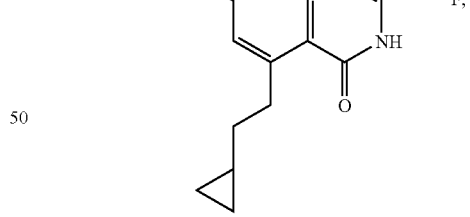
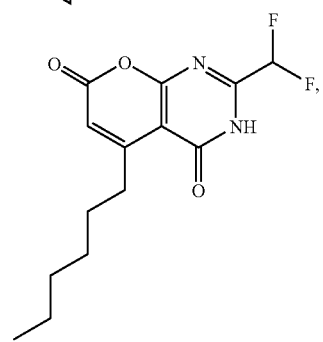

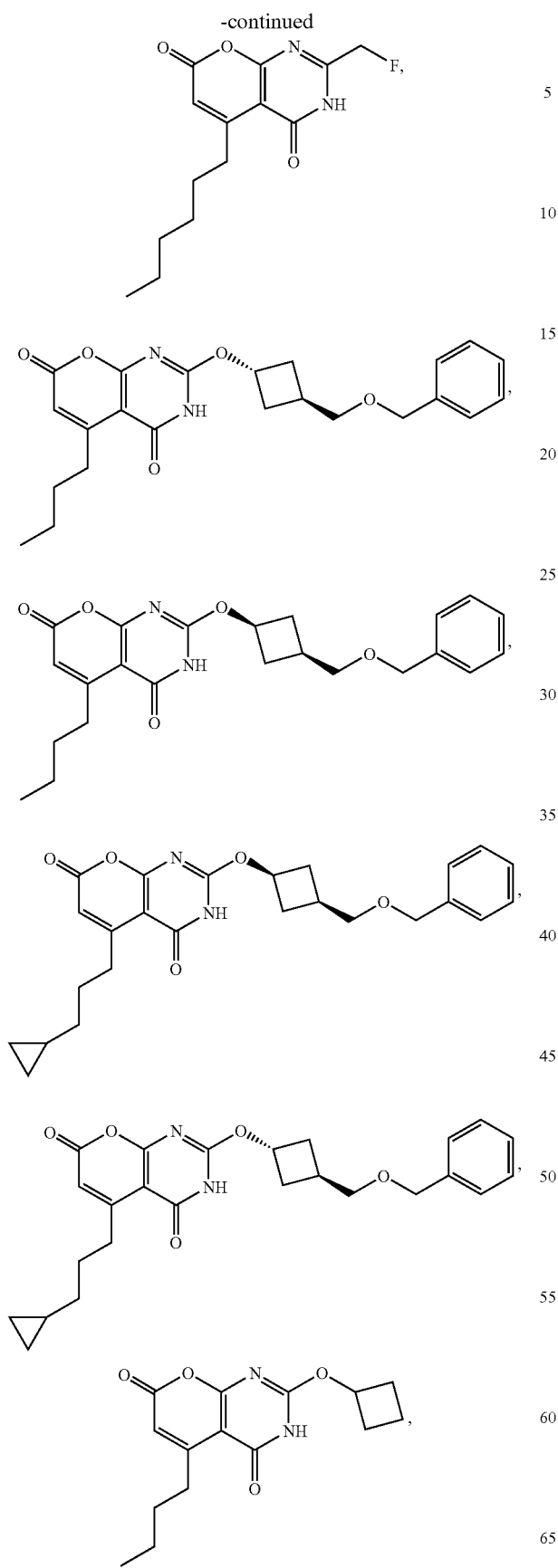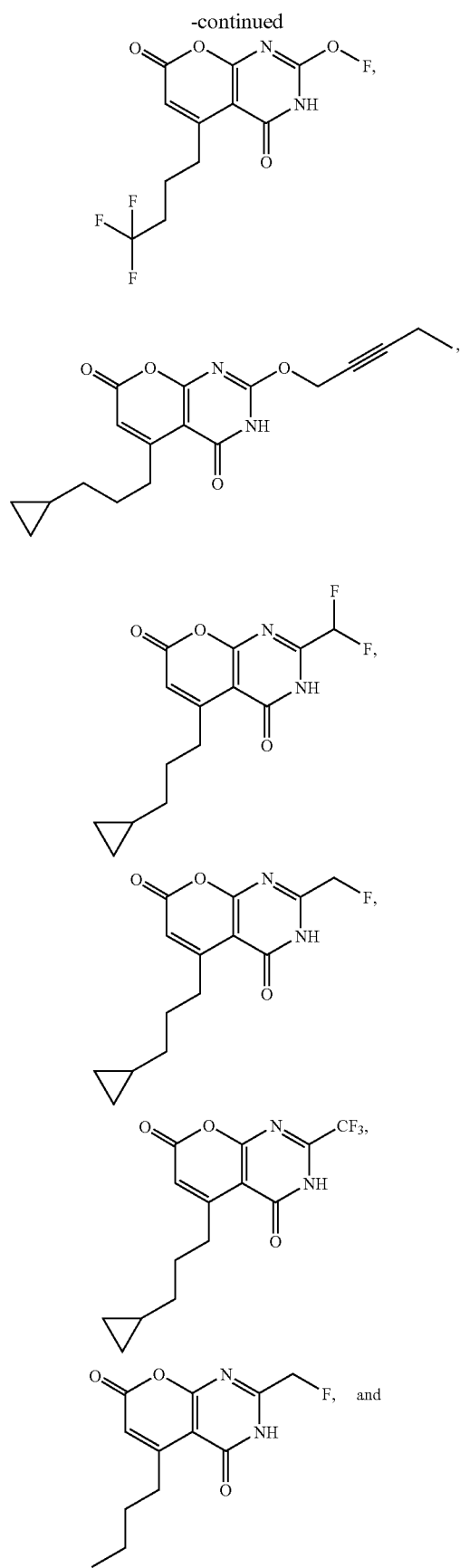

-continued

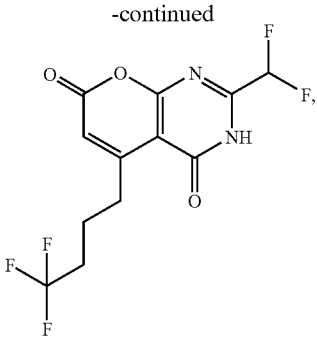

and pharmaceutically acceptable salts, solvates, esters, or tautomers thereof.

In one embodiment, the compounds of formula (I) have the formula (III):

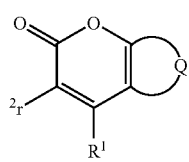

(III)

and pharmaceutically acceptable salts, solvates, esters, or tautomers thereof, wherein:

Q is selected from the group consisting of:

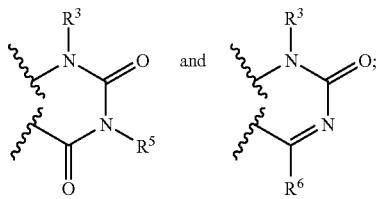

$R^1$ is —H, alkyl, haloalkyl, arylalkyl, -alkylene-S-alkyl or -alkylene-cycloalkyl;

$R^2$ is —H, —CN, or —NHC(O)-alkyl;

$R^3$ is —H, —OH, alkyl, haloalkyl, arylalkyl, —O-alkyl, —O-aryl, cycloalkyl, heterocyclyl, —O-cycloalkyl, —O-heterocyclyl, —O-arylalkyl or -alkylene-O-alkyl;

$R^5$ is —H, —OH, alkyl, haloalkyl, arylalkyl, —O-alkyl, —O-aryl, cycloalkyl, heterocyclyl, —O-cycloalkyl, —O-heterocyclyl, —O-arylalkyl or -alkylene-O-alkyl; and $R^6$ is alkoxy, —O-alkylene-O-alkyl, —O-arylalkyl or —O-haloalkyl.

The following embodiments refer to the compounds of formula (III), wherein Q is:

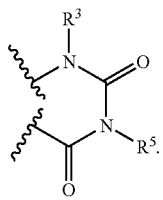

In one embodiment, $R^1$ is alkyl.
In another embodiment, $R^1$ is haloalkyl.
In another embodiment, $R^1$ is -alkylene-S-alkyl.
In still another embodiment, $R^1$ is -arylalkyl.
In yet another embodiment, $R^1$ is -alkylene.

In a further embodiment, $R^1$ is cycloalkyl.
In one embodiment, $R^1$ is -alkylene-cycloalkenyl.
In another embodiment, $R^1$ is a straight chain alkyl having from 1 to 6 carbon atoms.
In one embodiment, $R^1$ is methyl.
In another embodiment, $R^1$ is ethyl.
In another embodiment, $R^1$ is n-propyl.
In still another embodiment, $R^1$ is n-butyl.
In one embodiment, $R^1$ is n-pentyl.
In another embodiment, $R^1$ is n-hexyl.
In yet another embodiment, $R^1$ is a branched chain alkyl having from 3 to 6 carbon atoms.
In a further embodiment, $R^1$ is isopropyl.
In one embodiment, $R^1$ is isobutyl.
In another embodiment, $R^1$ is isopentyl.
In another embodiment, $R^1$ is sec-butyl.
In still another embodiment, $R^1$ is tert-butyl.
In yet another embodiment, $R^1$ is haloalkyl, having from 1 to 3 F atoms.
In another embodiment, $R^1$ is —(CH$_2$)$_3$CF$_3$.
In one embodiment, $R^2$ is —H.
In another embodiment, $R^2$ is —CN.
In another embodiment, $R^2$ is —NHC(O)-alkyl.
In still another embodiment, $R^2$ is —NHC(O)CH$_3$.
In one embodiment, $R^3$ is —H.
In another embodiment, $R^3$ is —OH.
In another embodiment, $R^3$ is alkyl.
In another embodiment, $R^3$ is haloalkyl.
In still another embodiment, $R^3$ is —O-alkyl.
In yet another embodiment, $R^3$ is cycloalkyl.
In a further embodiment, $R^3$ is heterocyclyl.
In one embodiment, $R^3$ is —O-arylalkyl.
In another embodiment, $R^3$ is -alkylene-O-alkyl.
In one embodiment, $R^3$ is —OCH$_3$.
In another embodiment, $R^3$ is cyclobutyl.
In another embodiment, $R^3$ is ethyl.
In still another embodiment, $R^3$ is N-morpholinyl.
In one embodiment, $R^3$ is —O-benzyl.
In another embodiment, $R^3$ is —CH$_2$CH$_2$OCH$_3$.
In yet another embodiment, $R^3$ is —OCH$_2$CH$_3$.
In another embodiment, $R^3$ is —CH$_2$F.
In one embodiment, $R^3$ is —CH$_2$CH$_2$F.
In another embodiment, $R^3$ is —OH.
In one embodiment, $R^5$ is —H.
In another embodiment, $R^5$ is —OH.
In another embodiment, $R^5$ is alkyl.
In another embodiment, $R^5$ is haloalkyl.
In still another embodiment, $R^5$ is —O-alkyl.
In yet another embodiment, $R^5$ is cycloalkyl.
In a further embodiment, $R^5$ is heterocyclyl.
In one embodiment, $R^5$ is —O-arylalkyl.
In another embodiment, $R^5$ is -alkylene-O-alkyl.
In one embodiment, $R^5$ is —OCH$_3$.
In another embodiment, $R^5$ is cyclobutyl.
In another embodiment, $R^5$ is ethyl.
In still another embodiment, $R^5$ is N-morpholinyl.
In one embodiment, $R^5$ is —O-benzyl.
In another embodiment, $R^5$ is —CH$_2$CH$_2$OCH$_3$.
In yet another embodiment, $R^5$ is —OCH$_2$CH$_3$.
In another embodiment, $R^5$ is —CH$_2$F.
In one embodiment, $R^5$ is —CH$_2$CH$_2$F.
In another embodiment, $R^5$ is —OH.
In one embodiment, $R^1$ is alkyl, and each of $R^2$, $R^3$ and $R^5$ is —H.
In another embodiment, $R^1$ is alkyl, $R^2$ is —H, and one, but not both of $R^3$ and $R^5$ is —H.

In another embodiment, $R^1$ is alkyl, $R^2$ is —H, and one of $R^3$ and $R^5$ is —H and the other is alkyl.

In still another embodiment, $R^1$ is alkyl, $R^2$ is —H, and one of $R^3$ and $R^5$ is —H and the other is —O-alkyl.

In yet another embodiment, $R^1$ is alkyl, $R^2$ is —H, and one of $R^3$ and $R^5$ is —H and the other is -cycloalkyl.

In one embodiment, $R^1$ is alkyl, $R^2$ is —H, and one of $R^3$ and $R^5$ is —H and the other is -heterocyclyl.

In one embodiment, $R^1$ is alkyl, $R^2$ is —H, and one of $R^3$ and $R^5$ is —H and the other is -alkylene-O-alkyl.

In one embodiment, $R^1$ is -alkylene-cycloalkyl, and each of $R^2$, $R^3$ and $R^5$ is —H.

In another embodiment, $R^1$ is -alkylene-cycloalkyl, $R^2$ is —H, and one, but not both of $R^3$ and $R^5$ is —H.

In another embodiment, $R^1$ is -alkylene-cycloalkyl, $R^2$ is —H, and one of $R^3$ and $R^5$ is —H and the other is alkyl.

In still another embodiment, $R^1$ is -alkylene-cycloalkyl, $R^2$ is —H, and one of $R^3$ and $R^5$ is —H and the other is —O-alkyl.

In yet another embodiment, $R^1$ is -alkylene-cycloalkyl, $R^2$ is —H, and one of $R^3$ and $R^5$ is —H and the other is -cycloalkyl.

In one embodiment, $R^1$ is -alkylene-cycloalkyl, $R^2$ is —H, and one of $R^3$ and $R^5$ is —H and the other is -heterocyclyl.

In one embodiment, $R^1$ is -alkylene-cycloalkyl, $R^2$ is —H, and one of $R^3$ and $R^5$ is —H and the other is -alkylene-O-alkyl.

The following embodiments refer to the compounds of formula (III), wherein Q is:

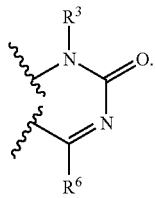

In one embodiment, $R^6$ is alkoxy.
In another embodiment, $R^6$ is —O-alkylene-O-alkyl.
In another embodiment, $R^6$ is —O-arylalkyl.
In still another embodiment, $R^6$ is —O-haloalkyl.
In yet another embodiment, $R^6$ is —OCH$_2$-(4-methoxyphenyl).
In one embodiment, $R^6$ is —OCH$_2$F.
In another embodiment, $R^6$ is —OCH$_2$CH$_2$F.
In another embodiment, $R^6$ is —OCH$_2$CH$_3$.
In still another embodiment, $R^6$ is —OCH$_2$CH$_2$OCH$_3$.
In one embodiment, $R^1$ is alkyl.
In another embodiment, $R^1$ is haloalkyl.
In another embodiment, $R^1$ is -alkylene-S-alkyl.
In still another embodiment, $R^1$ is -arylalkyl.
In yet another embodiment, $R^1$ is -alkylene.
In a further embodiment, $R^1$ is -cycloalkyl.
In one embodiment, $R^1$ is -alkylene-cycloalkenyl.
In another embodiment, $R^1$ is a straight chain alkyl having from 1 to 6 carbon atoms.
In one embodiment, $R^1$ is methyl.
In another embodiment, $R^1$ is ethyl.
In another embodiment $R^1$ is n-propyl.
In still another embodiment, $R^1$ is n-butyl.
In one embodiment, $R^1$ is n-pentyl.
In another embodiment, $R^1$ is n-hexyl.
In yet another embodiment, $R^1$ is a branched chain alkyl having from 3 to 6 carbon atoms.

In a further embodiment, $R^1$ is isopropyl.
In one embodiment, $R^1$ is isobutyl.
In another embodiment, $R^1$ is isopentyl.
In another embodiment, $R^1$ is sec-butyl.
In still another embodiment, $R^1$ is tert-butyl.
In yet another embodiment, $R^1$ is haloalkyl, having from 1 to 3 F atoms.
In another embodiment, $R^1$ is —(CH$_2$)$_3$CF$_3$.
In one embodiment, $R^2$ is —H.
In another embodiment, $R^2$ is —CN.
In another embodiment, $R^2$ is —NHC(O)-alkyl.
In still another embodiment, $R^2$ is —NHC(O)CH$_3$.
In one embodiment, $R^3$ is —H.
In another embodiment, $R^3$ is —OH.
In another embodiment, $R^3$ is alkyl.
In another embodiment, $R^3$ is haloalkyl.
In still another embodiment, $R^3$ is —O-alkyl.
In yet another embodiment, $R^3$ is cycloalkyl.
In a further embodiment, $R^3$ is heterocyclyl.
In one embodiment, $R^3$ is —O-arylalkyl.
In another embodiment, $R^3$ is -alkylene-O-alkyl.
In one embodiment, $R^3$ is —OCH$_3$.
In another embodiment, $R^3$ is cyclobutyl.
In another embodiment, $R^3$ is ethyl.
In still another embodiment, $R^3$ is N-morpholinyl.
In one embodiment, $R^3$ is —O-benzyl.
In another embodiment, $R^3$ is —CH$_2$CH$_2$OCH$_3$.
In yet another embodiment, $R^3$ is —OCH$_2$CH$_3$.
In another embodiment, $R^3$ is —CH$_2$F.
In one embodiment, $R^3$ is —CH$_2$CH$_2$F.
In another embodiment, $R^3$ is —H.
In one embodiment, $R^6$ is alkoxy, $R^1$ is alkyl, and each of $R^2$ and $R^3$ is —H.
In another embodiment, $R^6$ is alkoxy, $R^1$ is alkyl, $R^2$ is —H, and $R^3$ is alkyl.
In still another embodiment, $R^6$ is alkoxy, $R^1$ is alkyl, $R^2$ is —H, and $R^3$ is —O-alkyl.
In yet another embodiment, $R^6$ is alkoxy, $R^1$ is alkyl, $R^2$ is —H, and $R^3$ is -cycloalkyl.
In one embodiment, $R^6$ is alkoxy, $R^1$ is alkyl, $R^2$ is —H, and and $R^3$ is -heterocyclyl.
In one embodiment, $R^6$ is alkoxy, $R^1$ is alkyl, $R^2$ is —H, and $R^3$ is -alkylene-O-alkyl.
In one embodiment, $R^6$ is alkoxy, $R^1$ is -alkylene-cycloalkyl, and each of $R^2$ and $R^3$ is —H.
In another embodiment, $R^6$ is alkoxy, $R^1$ is -alkylene-cycloalkyl, $R^2$ is —H, and $R^3$ is alkyl.
In still another embodiment, $R^6$ is alkoxy, $R^1$ is -alkylene-cycloalkyl, $R^2$ is —H, and $R^3$ is —O-alkyl.
In yet another embodiment, $R^6$ is alkoxy, $R^1$ is -alkylene-cycloalkyl, $R^2$ is —H, and $R^3$ is -cycloalkyl.
In one embodiment, $R^6$ is alkoxy, $R^1$ is -alkylene-cycloalkyl, $R^2$ is —H, and $R^3$ is -heterocyclyl.
In one embodiment, $R^6$ is alkoxy, $R^1$ is -alkylene-cycloalkyl, $R^2$ is —H, and $R^3$ is -alkylene-O-alkyl.
In one embodiment, $R^6$ is —O-alkylene-O-alkyl, $R^1$ is alkyl, and each of $R^2$ and $R^3$ is —H.
In another embodiment, $R^6$ is —O-alkylene-O-alkyl, $R^1$ is alkyl, $R^2$ is —H, and $R^3$ is alkyl.
In still another embodiment, $R^6$ is —O-alkylene-O-alkyl, $R^1$ is alkyl, $R^2$ is —H, and $R^3$ is —O-alkyl.
In yet another embodiment, $R^6$ is —O-alkylene-O-alkyl, $R^1$ is alkyl, $R^2$ is —H, and $R^3$ is -cycloalkyl.
In one embodiment, $R^6$ is —O-alkylene-O-alkyl, $R^1$ is alkyl, $R^2$ is —H, and and $R^3$ is -heterocyclyl.
In one embodiment, $R^6$ is —O-alkylene-O-alkyl, $R^1$ is alkyl, $R^2$ is —H, and $R^3$ is -alkylene-O-alkyl.

In one embodiment, $R^6$ is —O-alkylene-O-alkyl, $R^1$ is -alkylene-cycloalkyl, and each of $R^2$ and $R^3$ is —H.

In another embodiment, $R^6$ is —O-alkylene-O-alkyl, $R^1$ is -alkylene-cycloalkyl, $R^2$ is —H, and $R^3$ is alkyl.

In still another embodiment, $R^6$ is —O-alkylene-O-alkyl, $R^1$ is -alkylene-cycloalkyl, $R^2$ is —H, and $R^3$ is —O-alkyl.

In yet another embodiment, $R^6$ is —O-alkylene-O-alkyl, $R^1$ is -alkylene-cycloalkyl, $R^2$ is —H, and $R^3$ is -cycloalkyl.

In one embodiment, $R^6$ is —O-alkylene-O-alkyl, $R^1$ is -alkylene-cycloalkyl, $R^2$ is —H, and $R^3$ is -heterocyclyl.

In one embodiment, $R^3$ is —O-alkylene-O-alkyl, $R^1$ is -alkylene-cycloalkyl, $R^2$ is —H, and $R^3$ is -alkylene-O-alkyl.

In one embodiment, $R^6$ is —O-arylalkyl, $R^1$ is alkyl, and each of $R^2$ and $R^3$ is —H.

In another embodiment, $R^6$ is —O-arylalkyl, $R^1$ is alkyl, $R^2$ is —H, and $R^3$ is alkyl.

In still another embodiment, $R^6$ is —O-arylalkyl, $R^1$ is alkyl, $R^2$ is —H, and $R^3$ is —O-alkyl.

In yet another embodiment, $R^6$ is —O-arylalkyl, $R^1$ is alkyl, $R^2$ is —H, and $R^3$ is -cycloalkyl.

In one embodiment, $R^6$ is —O-arylalkyl, $R^1$ is alkyl, $R^2$ is —H, and and $R^3$ is -heterocyclyl.

In one embodiment, $R^6$ is —O-arylalkyl, $R^1$ is alkyl, $R^2$ is —H, and $R^3$ is -alkylene-O-alkyl.

In one embodiment, $R^6$ is —O-arylalkyl, $R^1$ is -alkylene-cycloalkyl, and each of $R^2$ and $R^3$ is —H.

In another embodiment, $R^6$ is —O-arylalkyl, $R^1$ is -alkylene-cycloalkyl, $R^2$ is —H, and $R^3$ is alkyl.

In still another embodiment, $R^6$ is —O-arylalkyl, $R^1$ is -alkylene-cycloalkyl, $R^2$ is —H, and $R^3$ is —O-alkyl.

In yet another embodiment, $R^6$ is —O-arylalkyl, $R^1$ is -alkylene-cycloalkyl, $R^2$ is —H, and $R^3$ is -cycloalkyl.

In one embodiment, $R^6$ is —O-arylalkyl, $R^1$ is -alkylene-cycloalkyl, $R^2$ is —H, and $R^3$ is -heterocyclyl.

In one embodiment, $R^6$ is —O-arylalkyl, $R^1$ is -alkylene-cycloalkyl, $R^2$ is —H, and $R^3$ is -alkylene-O-alkyl.

In one embodiment, $R^6$ is —O-haloalkyl, $R^1$ is alkyl, and each of $R^2$ and $R^3$ is —H.

In another embodiment, $R^6$ is —O-haloalkyl, $R^1$ is alkyl, $R^2$ is —H, and $R^3$ is alkyl.

In still another embodiment, $R^6$ is —O-haloalkyl, $R^1$ is alkyl, $R^2$ is —H, and $R^3$ is —O-alkyl.

In yet another embodiment, $R^6$ is —O-haloalkyl, $R^1$ is alkyl, $R^2$ is —H, and $R^3$ is -cycloalkyl.

In one embodiment, $R^6$ is —O-haloalkyl, $R^1$ is alkyl, $R^2$ is —H, and and $R^3$ is -heterocyclyl.

In one embodiment, $R^6$ is —O-haloalkyl, $R^1$ is alkyl, $R^2$ is —H, and $R^3$ is -alkylene-O-alkyl.

In one embodiment, $R^6$ is —O-haloalkyl, $R^1$ is -alkylene-cycloalkyl, and each of $R^2$ and $R^3$ is —H.

In another embodiment, $R^6$ is —O-haloalkyl, $R^1$ is -alkylene-cycloalkyl, $R^2$ is —H, and $R^3$ is alkyl.

In still another embodiment, $R^6$ is —O-haloalkyl, $R^1$ is -alkylene-cycloalkyl, $R^2$ is —H, and $R^3$ is —O-alkyl.

In yet another embodiment, $R^6$ is —O-haloalkyl, $R^1$ is -alkylene-cycloalkyl, $R^2$ is —H, and $R^3$ is cycloalkyl.

Non-limiting illustrative examples of the compounds of formula (III), include the following compounds:

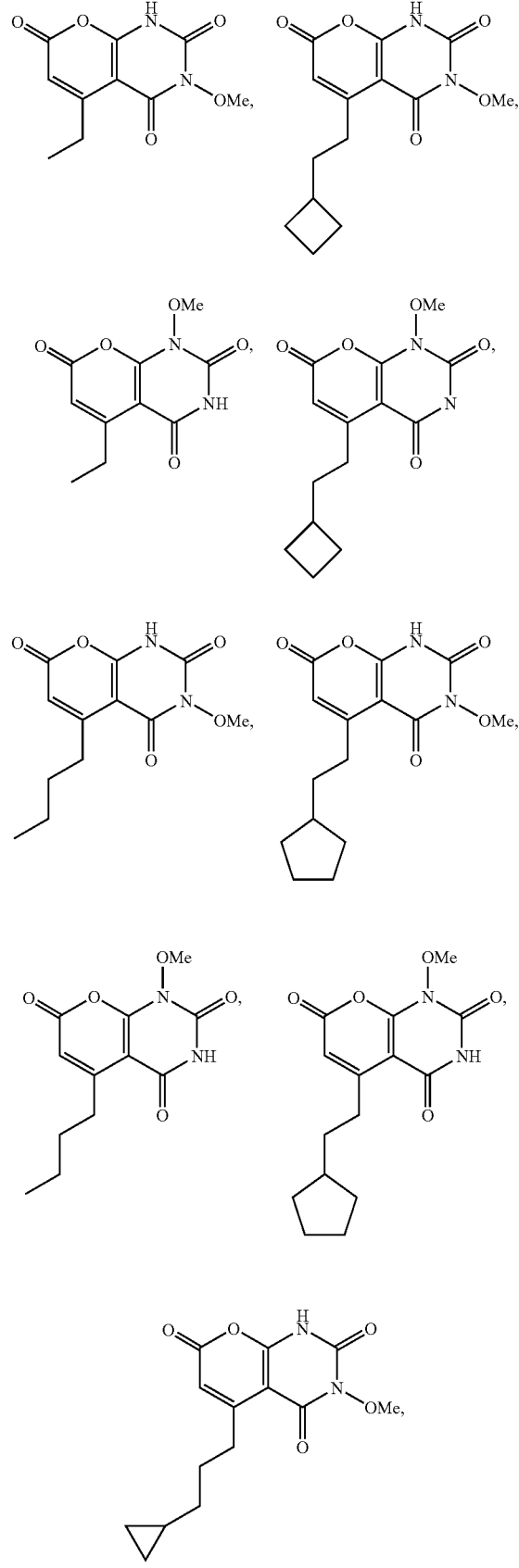

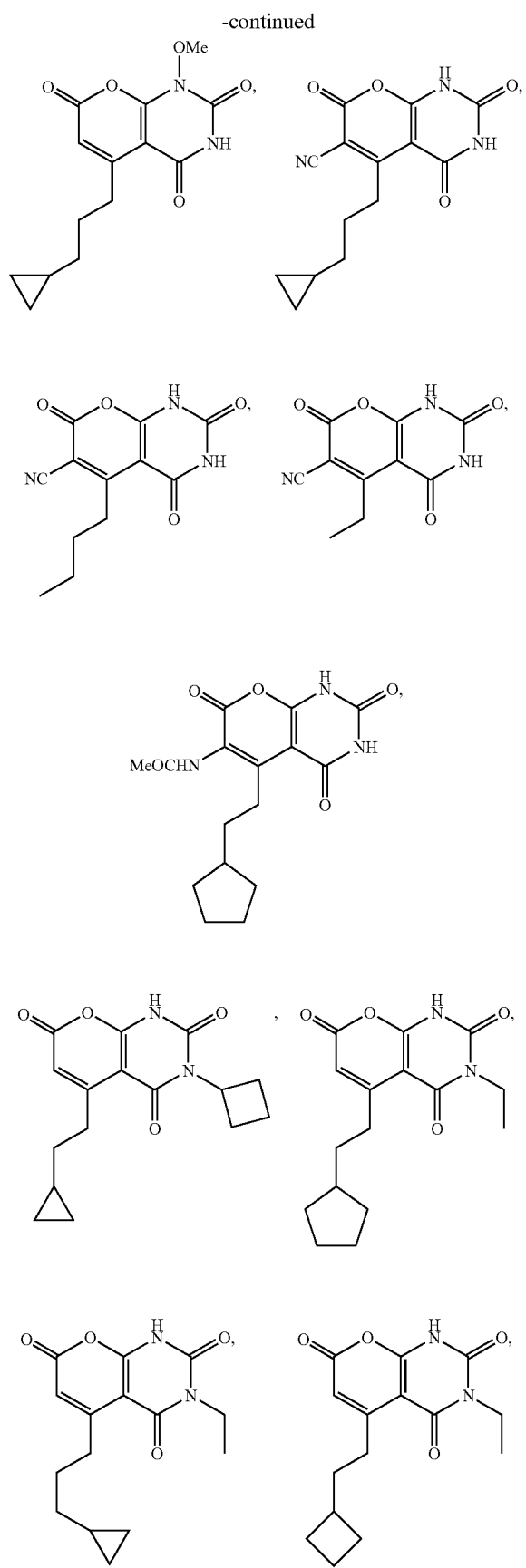
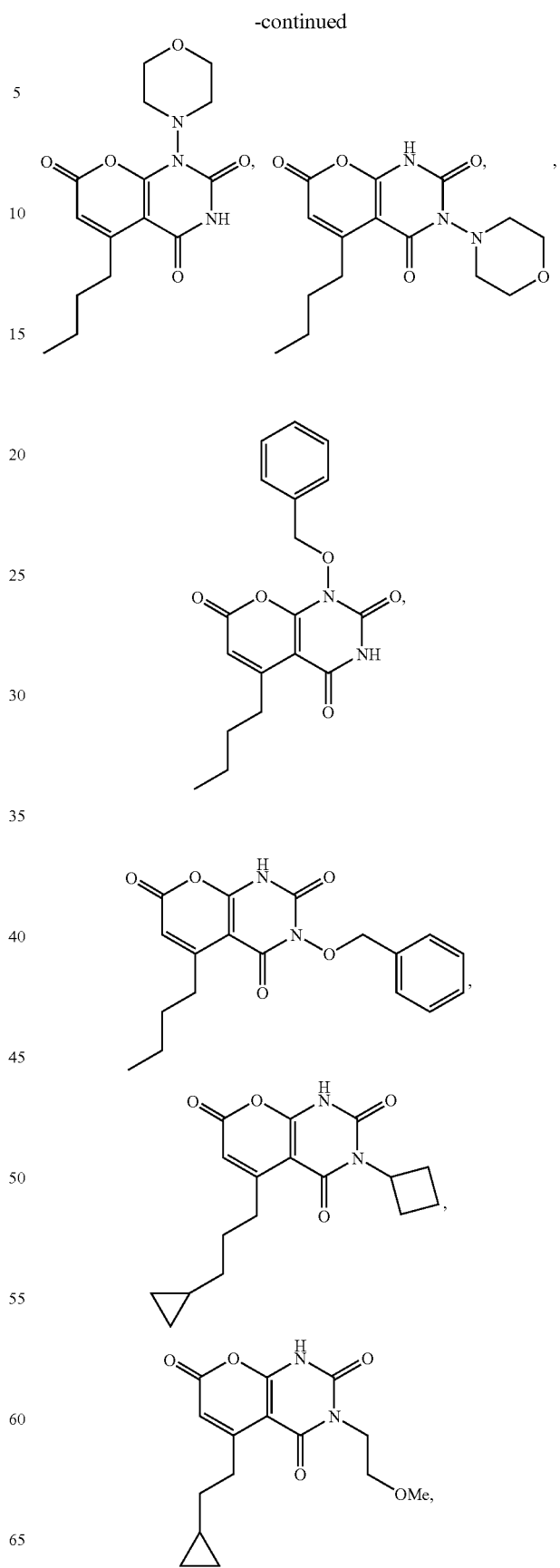

-continued
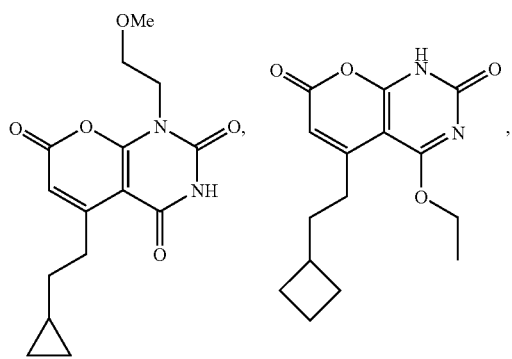
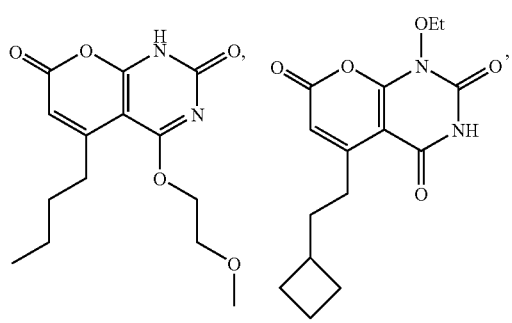
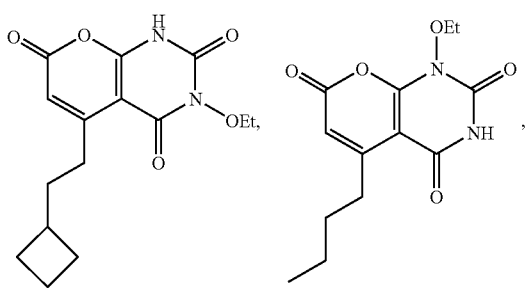
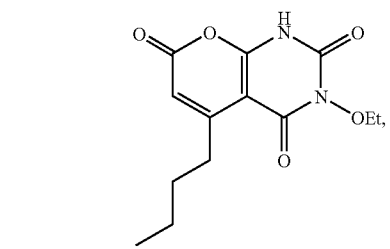
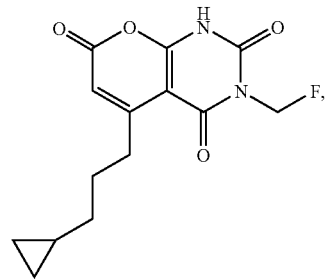
-continued
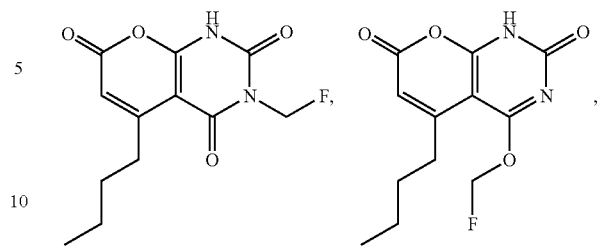
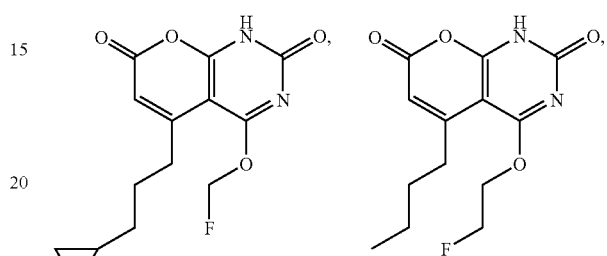
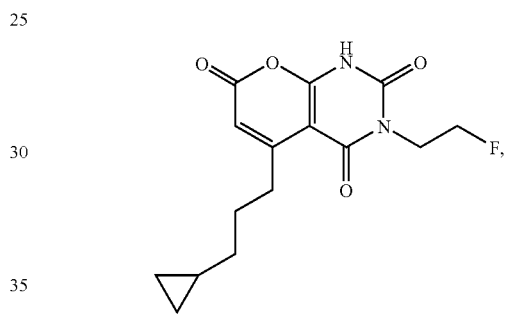
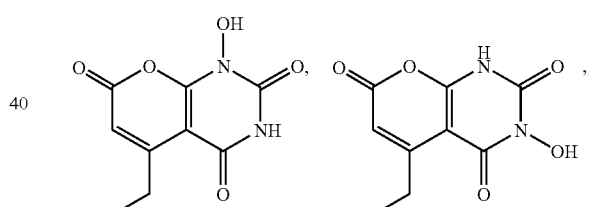
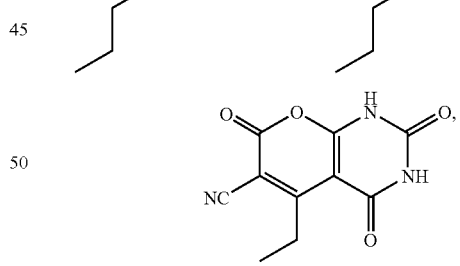
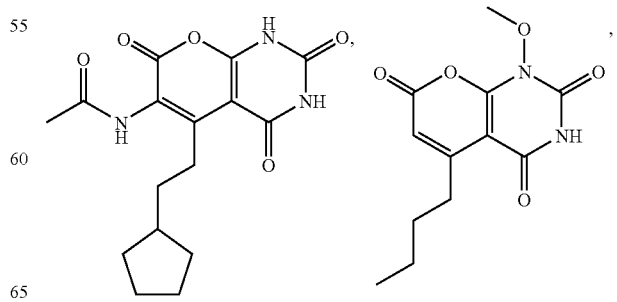

-continued

[Structure: pyrano-pyrimidine dione with butyl and N-OMe substituents]

and

[Structure: pyrano-pyrimidine with cyclopropylpropyl and OCH₂CH₂F substituents]

and pharmaceutically acceptable salts, solvates, esters, or tautomers thereof.

In one embodiment, the compounds of formula (I) are compounds of formula (IV):

[Structure IV: pyrano-pyrimidine dione with R¹ and N-R²]

and and pharmaceutically acceptable salts, solvates, esters, and tautomers thereof, wherein:
$R^1$ is haloalkyl; and
$R^2$ is H or cycloalkyl.

In one embodiment, $R^1$ is fluoroalkyl.
In another embodiment, $R^1$ is -alkylene-F.
In another embodiment, $R^1$ is -alkylene-CF$_2$.
In still another embodiment, $R^1$ is —(CH$_2$)$_2$—CF$_2$.
In another embodiment, $R^1$ is —(CH$_2$)$_3$—CF$_2$.
In another embodiment, $R^1$ is —(CH$_2$)$_4$—CF$_2$.
In yet another embodiment, $R^1$ is —(CH$_2$)$_5$—CF$_2$.
In still another embodiment, $R^1$ is —(CH$_2$)$_3$—F.
In another embodiment, $R^1$ is —(CH$_2$)$_4$—F.
In another embodiment, $R^1$ is —(CH$_2$)$_5$—F.
In yet another embodiment, $R^1$ is —(CH$_2$)$_6$—F.
In one embodiment, $R^2$ is H.
In another embodiment, $R^2$ is cyclopropyl.
In another embodiment, $R^2$ is cyclobutyl.
In still another embodiment, $R^2$ is cyclopentyl.
In another embodiment, $R^2$ is cyclohexyl.
In one embodiment, $R^1$ is fluoroalkyl and $R^2$ is H.
In another embodiment, $R^1$ is fluoroalkyl and $R^2$ is cycloalkyl.
In another embodiment, $R^1$ is -alkylene-CF$_2$ and $R^2$ is H.
In another embodiment, $R^1$ is -alkylene-CF$_2$ and $R^2$ is cycloalkyl.

Non-limiting examples of compounds of formula (IV) include compounds 834, 835 and 837-841 as depicted in the Examples section below, and and pharmaceutically acceptable salts, solvates, esters, and tautomers thereof.

In another embodiment, the compounds of formula (I) are compounds of formula (V):

[Structure V: pyrano-pyrimidine with R¹ and R² substituents]

and and pharmaceutically acceptable salts, solvates, esters, and tautomers thereof, wherein:
$R^1$ and $R^2$ are each, independently, haloalkyl.

In one embodiment, $R^1$ is fluoroalkyl.
In another embodiment, $R^1$ is -alkylene-F.
In another embodiment, $R^1$ is -alkylene-CF$_2$.
In still another embodiment, $R^1$ is —(CH$_2$)$_2$—CF$_2$.
In another embodiment, $R^1$ is —(CH$_2$)$_3$—CF$_2$.
In another embodiment, $R^1$ is —(CH$_2$)$_4$—CF$_2$.
In yet another embodiment, $R^1$ is —(CH$_2$)$_5$—CF$_2$.
In still another embodiment, $R^1$ is —(CH$_2$)$_3$—F.
In another embodiment, $R^1$ is —(CH$_2$)$_4$—F.
In another embodiment, $R^1$ is —(CH$_2$)$_5$—F.
In yet another embodiment, $R^1$ is —(CH$_2$)$_6$—F.
In one embodiment, $R^2$ is fluoroalkyl.
In another embodiment, $R^2$ is —CHF$_2$.
In one embodiment, $R^1$ is fluoroalkyl and $R^2$ is fluoroalkyl.
In another embodiment, $R^1$ is fluoroalkyl and $R^2$ is —CHF$_2$.
In another embodiment, $R^1$ is -alkylene-CF$_2$ and $R^2$ is fluoroalkyl.
In still another embodiment, $R^1$ is -alkylene-CF$_2$ and $R^2$ is —CHF$_2$.

Non-limiting examples of compounds of formula (V) include compounds 836 and 842-844 as depicted in the Examples section below, and and pharmaceutically acceptable salts, solvates, esters, and tautomers thereof.

Additional non-limiting examples of compounds of formula (I) include compounds 845-911 as depicted in the following table:

| Compound No. | Structure |
|---|---|
| 845 | 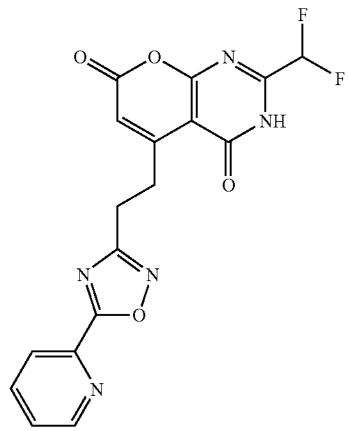 |
| 846 | 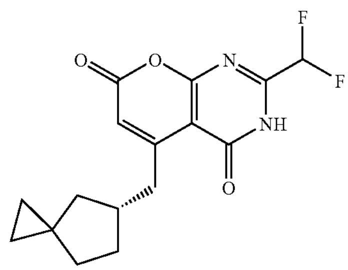 |
| 847 | 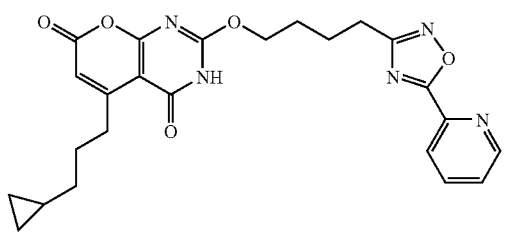 |
| 848 | 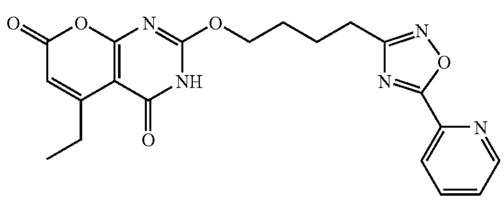 |
| 849 | 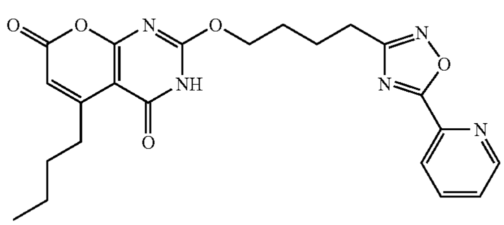 |

-continued

| Compound No. | Structure |
|---|---|
| 850 | 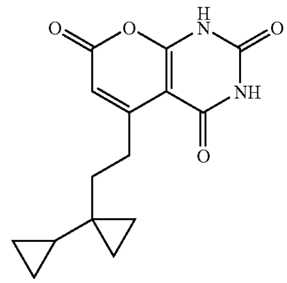 |
| 851 | 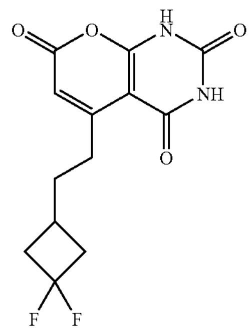 |
| 852 | 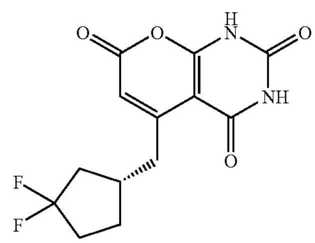 |
| 853 | 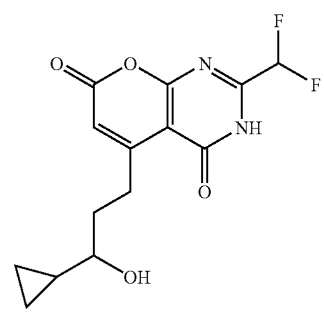 |
| 854 | 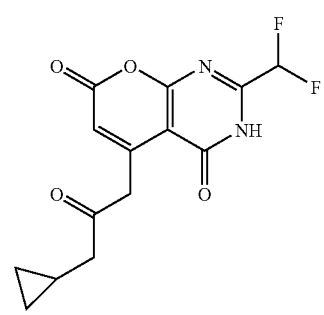 |

-continued
| Compound No. | Structure |
|---|---|
| 855 | 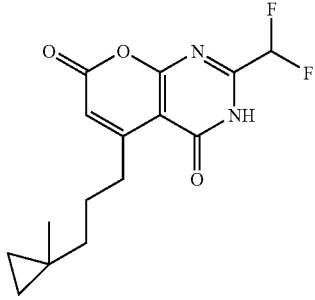 |
| 856 | 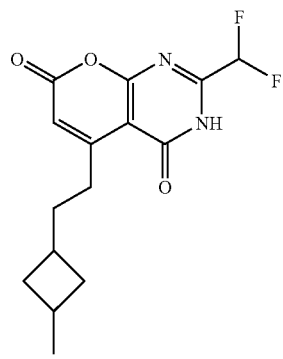 |
| 857 | 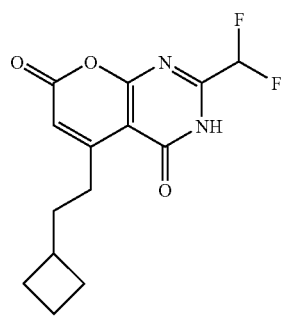 |
| 858 | 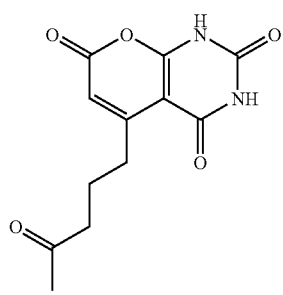 |
| 859 | 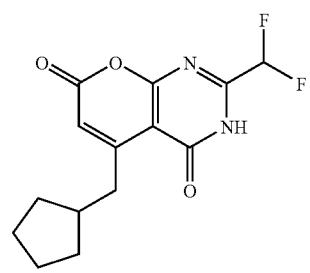 |
-continued
| Compound No. | Structure |
|---|---|
| 860 | 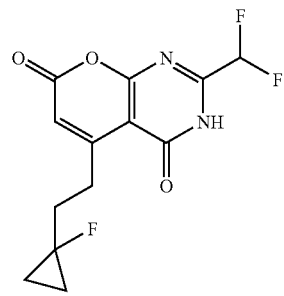 |
| 861 | 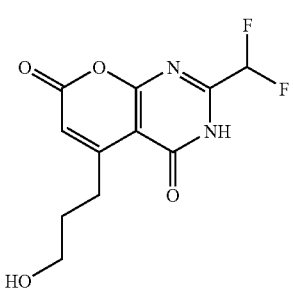 |
| 862 | 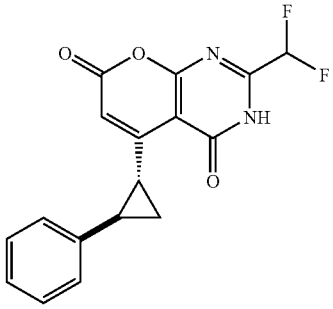 |
| 863 | 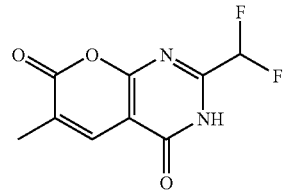 |
| 864 | 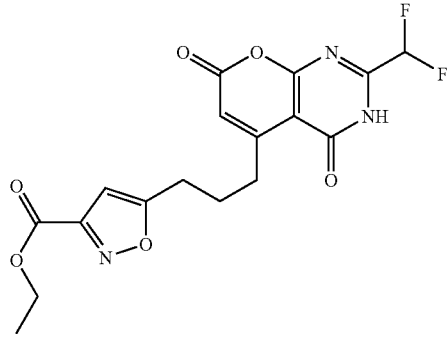 |

-continued
| Compound No. | Structure |
|---|---|
| 865 | 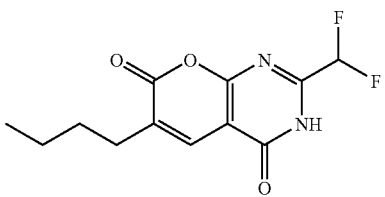 |
| 866 | 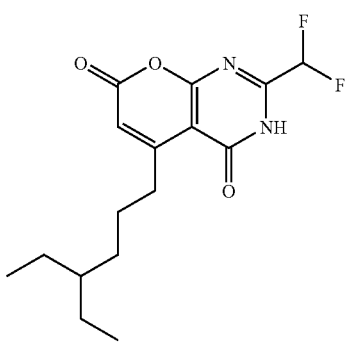 |
| 867 | 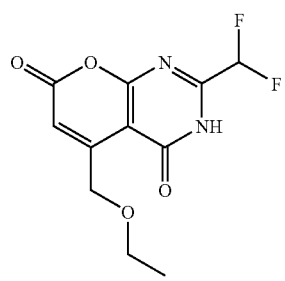 |
| 868 | 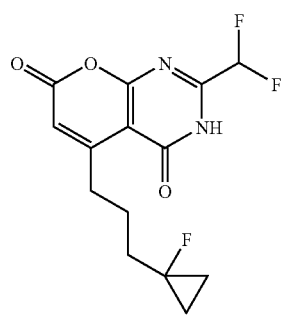 |
| 869 | 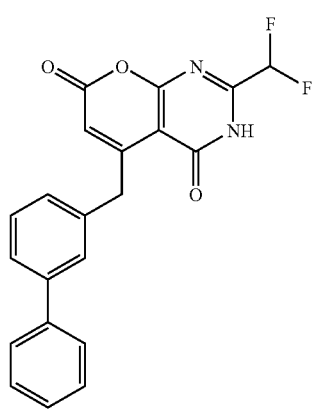 |
-continued
| Compound No. | Structure |
|---|---|
| 870 | 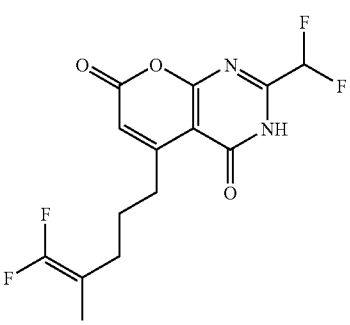 |
| 871 | 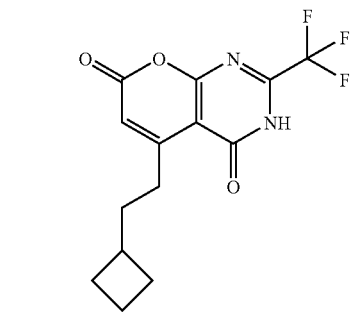 |
| 872 | 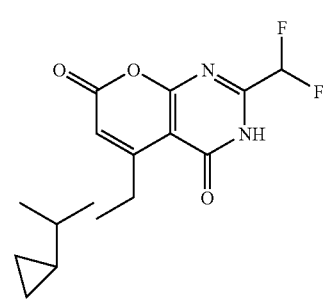 |
| 873 | 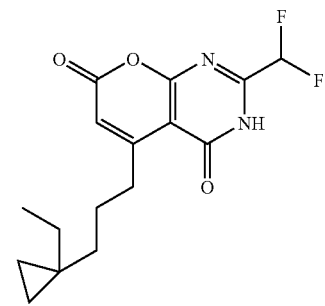 |

| Compound No. | Structure |
|---|---|
| 874 | 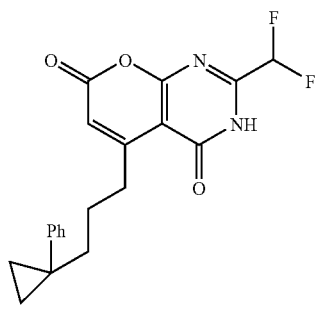 |
| 875 | 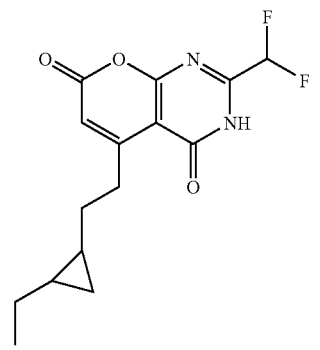 |
| 876 | 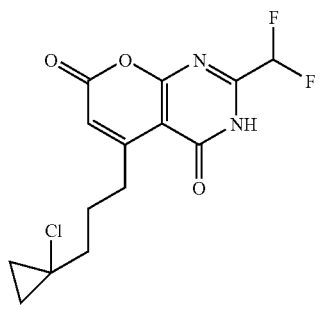 |
| 878 | 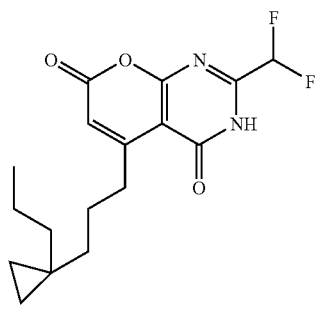 |
| Compound No. | Structure |
|---|---|
| 879 | 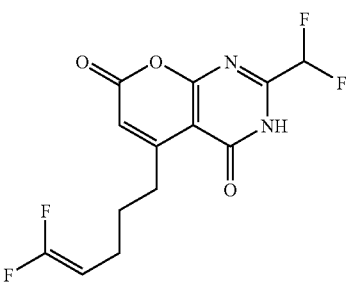 |
| 880 | 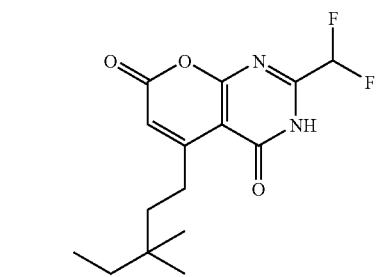 |
| 881 | 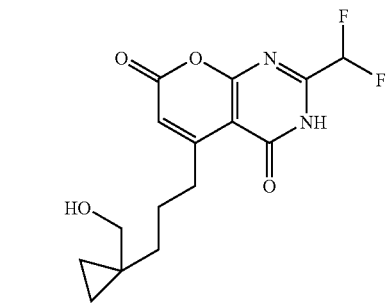 |
| 882 | 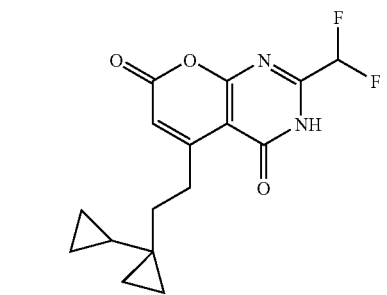 |
| 883 | 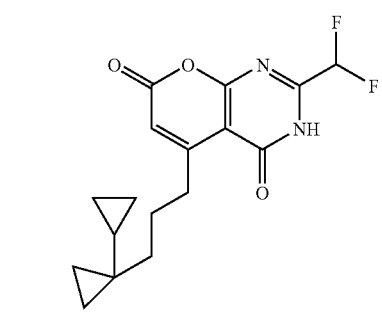 |

-continued
| Compound No. | Structure |
|---|---|
| 884 | 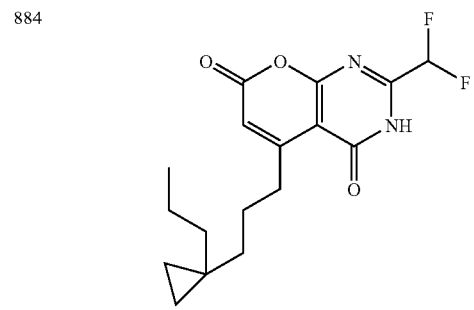 |
| 885 | 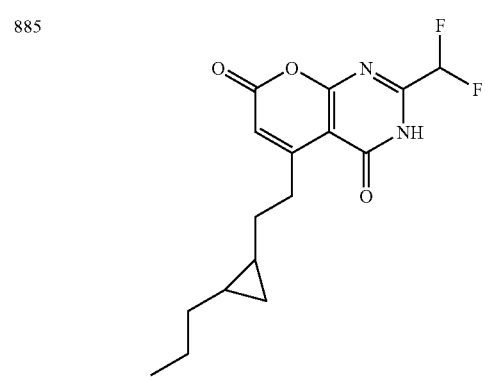 |
| 886 | 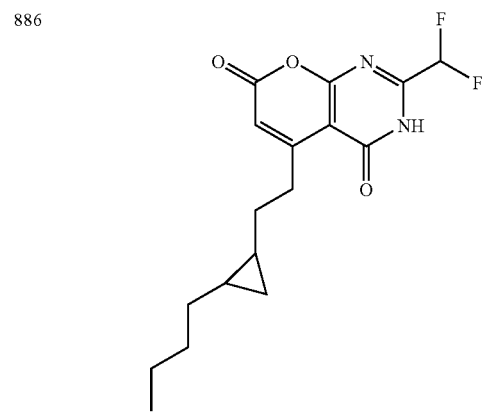 |
| 887 | 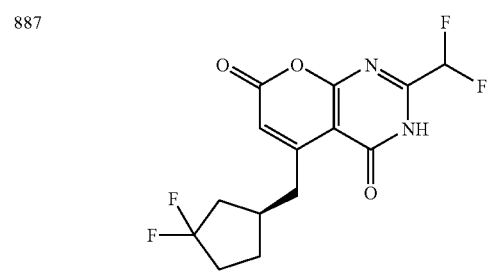 |
-continued
| Compound No. | Structure |
|---|---|
| 888 | 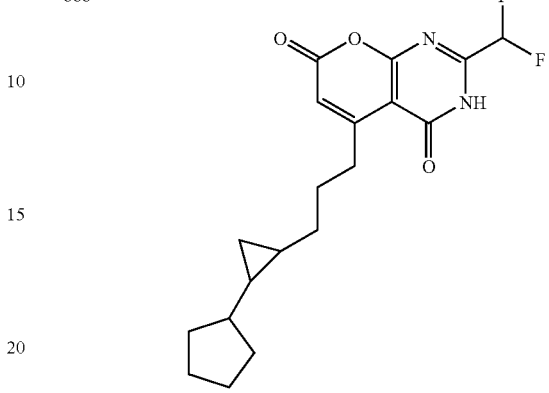 |
| 886 | 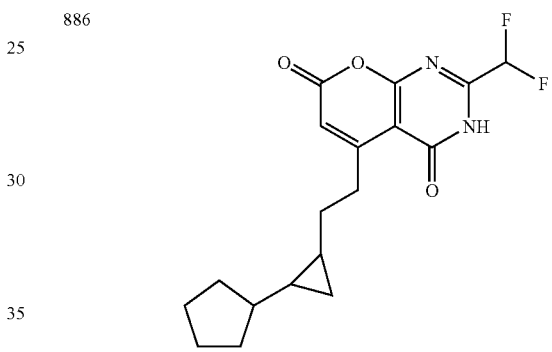 |
| 890 | 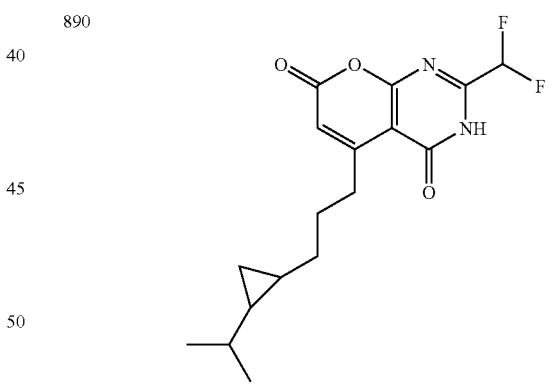 |
| 891 | 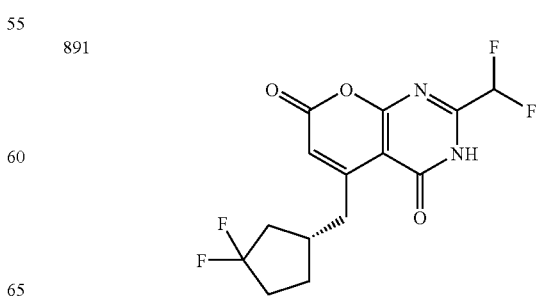 |

-continued

| Compound No. | Structure |
|---|---|
| 892 | 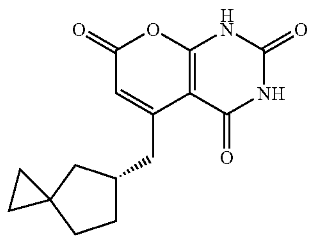 |
| 893 | 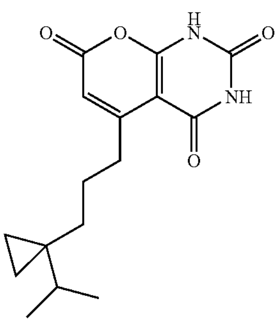 |
| 894 | 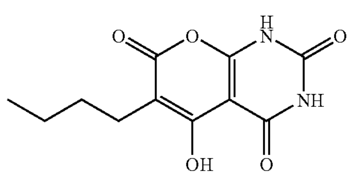 |
| 895 | 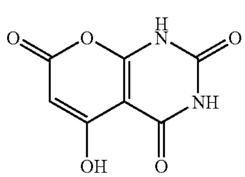 |
| 896 | 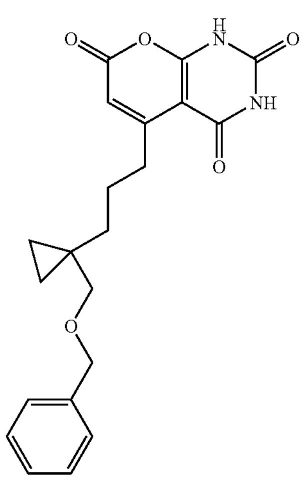 |

-continued

| Compound No. | Structure |
|---|---|
| 897 | 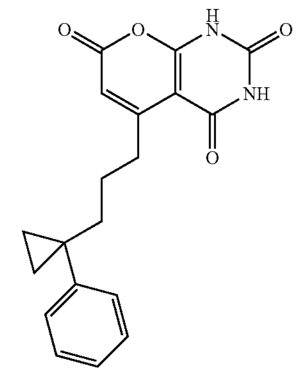 |
| 898 | 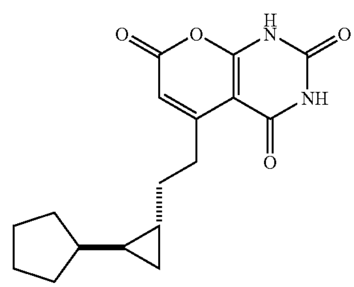 |
| 899 | 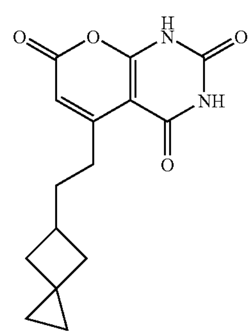 |
| 900 | 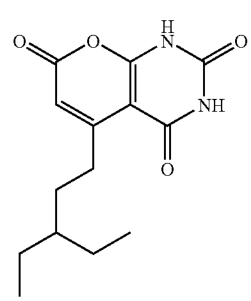 |

-continued

| Compound No. | Structure |
|---|---|
| 901 | 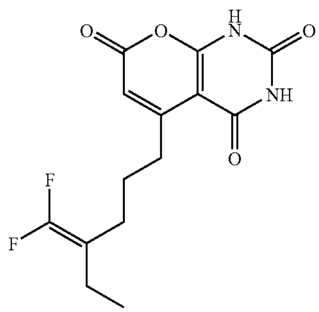 |
| 902 | 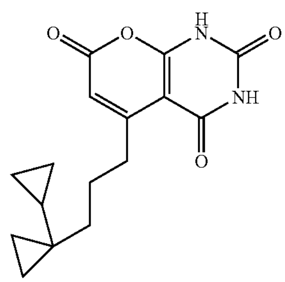 |
| 903 | 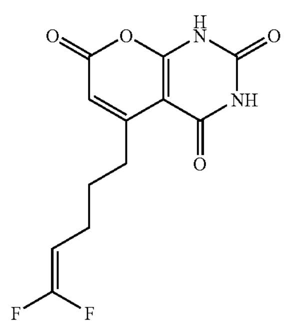 |
| 904 | 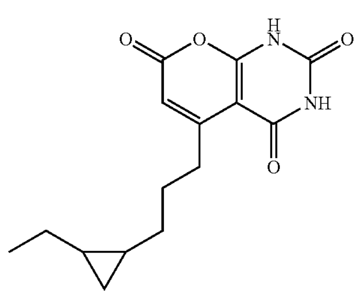 |
| 905 | 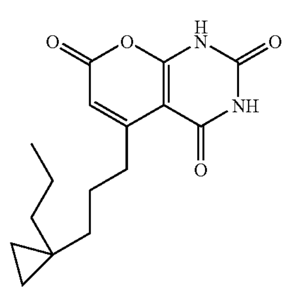 |
| 906 | |
| 907 | |
| 908 | |
| 909 | |
| 910 | |

-continued

| Compound No. | Structure |
|---|---|
| 911 | 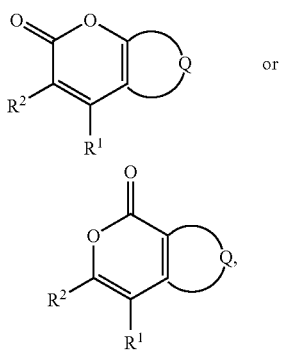 | and and pharmaceutically acceptable salts, solvates, esters, and tautomers thereof.

In all embodiments of the present invention, when L is (f), and $R^2$, $R^3$ and $R^5$ are each H, then $R^1$ is not —$CH_3$. One of skill in the art will recognize that the present invention does not include the following compound, or tautomeric forms thereof:

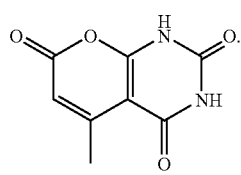

The moiety L of Formula (I) of the present invention can have any chemically stable orientation. That is, when L is (f), the compounds of Formula (I) of the present invention can include the following:

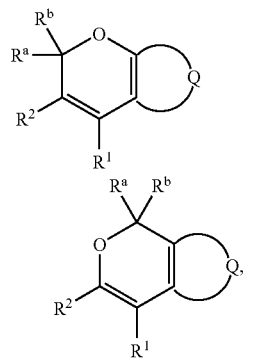

or salts, solvates, esters, or tautomers thereof. When L is (g), the compounds of Formula (I) of the present invention can include the following:

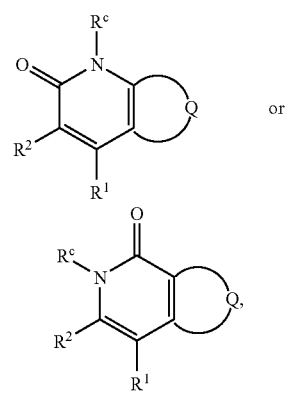

or salts, solvates, esters, or tautomers thereof. When L is (h), the compounds of Formula (I) of the present invention can include the following:

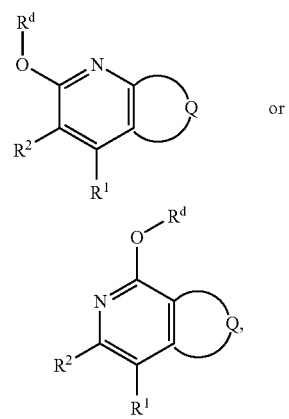

or salts, solvates, esters, or tautomers thereof. When L is (i), the compounds of Formula (I) of the present invention can include the following:

or salts, solvates, esters, or tautomers thereof.

The compounds of Formula (I) can be purified to a degree suitable for use as a pharmaceutically active substance. That is, the compounds of Formula (I) can have a purity of 95 wt % or more (excluding adjuvants such as pharmaceutically acceptable carriers, solvents, etc., which are used in formulating the compound of Formula (I) into a conventional form, such as a pill, capsule, IV solution, etc. suitable for administration into a patient). The purity can be 97 wt % or more, or, 99 wt % or more. A purified compound of Formula (I) includes a single isomer having a purity, as discussed above, of 95 wt % or more, 97 wt % or more, or 99 wt % or more, as discussed above.

Alternatively, the purified compound of Formula (I) can include a mixture of isomers, each having a structure according to Formula (I), where the amount of impurity (i.e., compounds or other contaminants, exclusive of adjuvants as discussed above) is 5 wt % or less, 3 wt % or less, or 1 wt % or less. For example, the purified compound of Formula (I) can be an isomeric mixture of compounds of Structure (I), where the ratio of the amounts of the two isomers is approximately 1:1, and the combined amount of the two isomers is 95 wt % or more, 97 wt % or more, or 99 wt % or more.

Compounds of Formula (I), and salts, solvates, esters and prodrugs thereof, may exist in their tautomeric form (for example, as an amide or imino ether). All such tautomeric forms are contemplated herein as part of the present invention. For example, the compounds of the present invention include tautomeric forms as shown below:

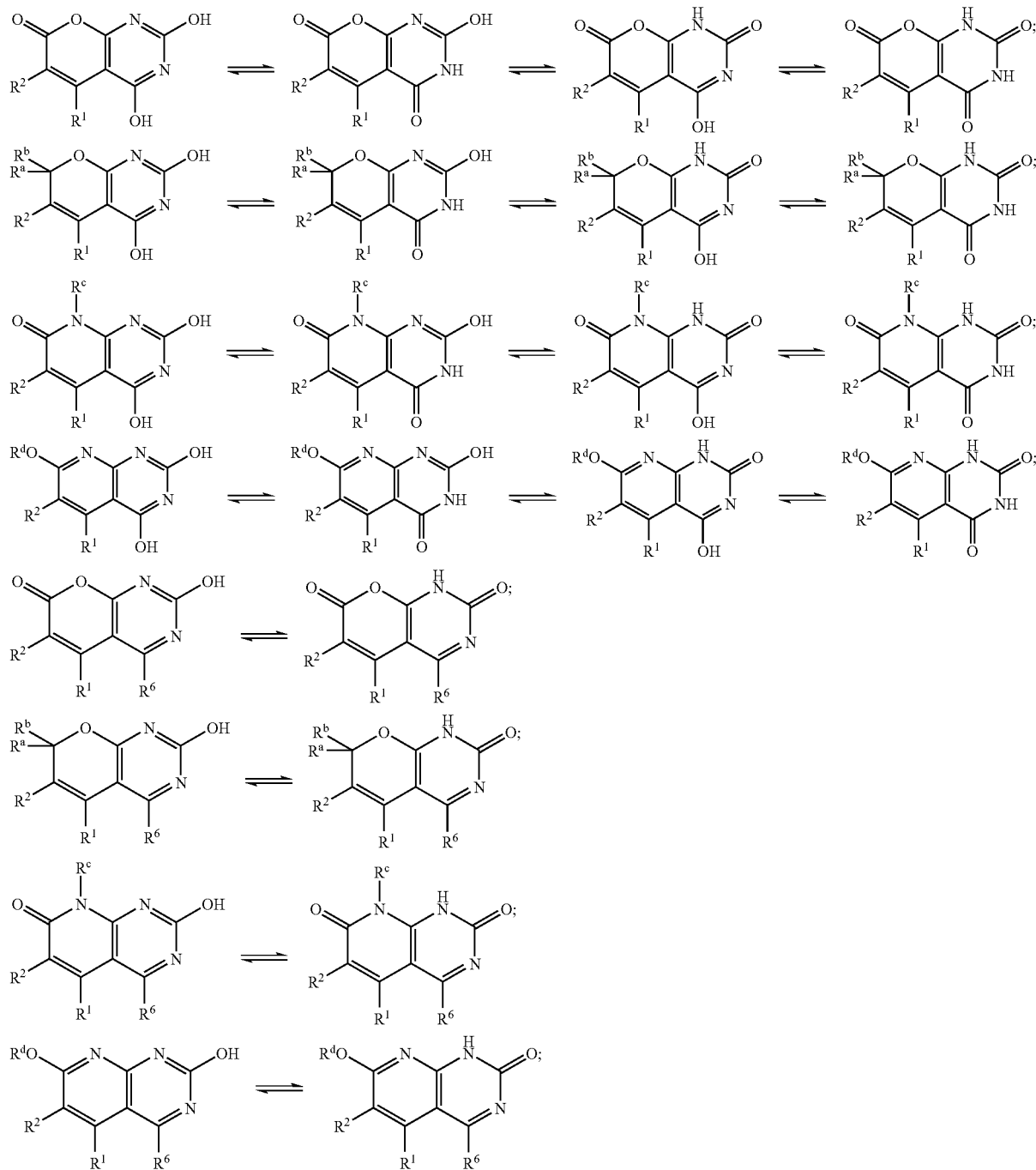

-continued

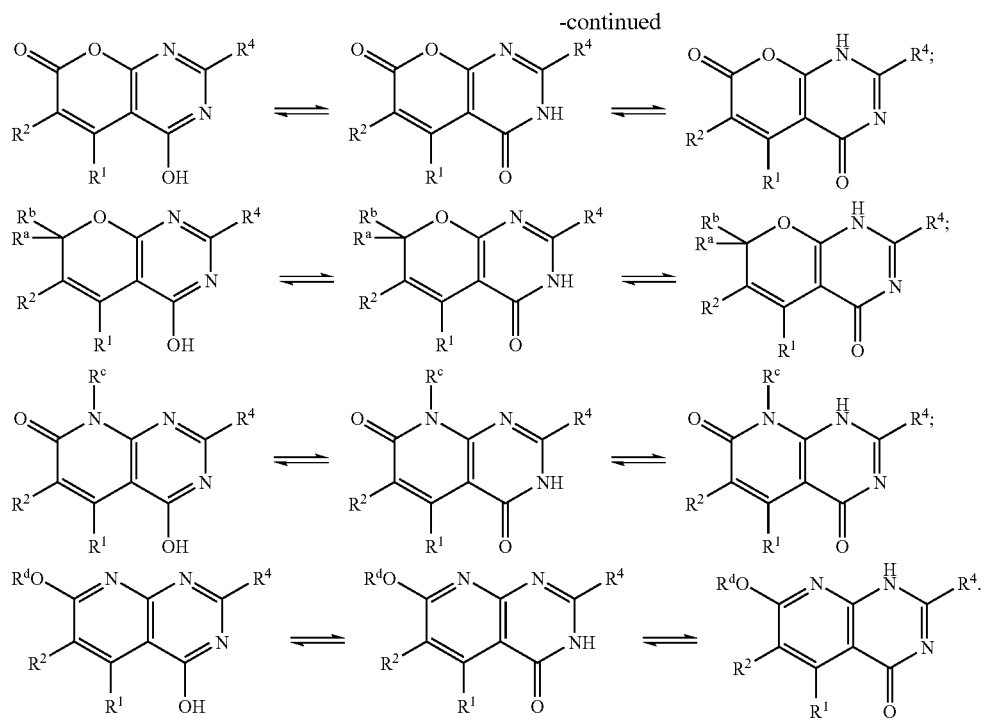

Such tautomeric forms are considered equivalent.

As used above, and throughout this disclosure, the following terms, unless otherwise indicated, shall be understood to have the following meanings:

"AcOH" means acetic acid.
"Bn" means benzyl.
"BnBr" means benzyl bromide.
"BnOH" means benzyl alcohol.
"CDI" means carbodiimide.
"DCM" means dichloromethane ($CH_2Cl_2$).
"DIAD" means diisopropyl azodicarboxylate.
"DIEA" means N,N-diisopropylethylamine.
"DMF" means dimethylformamide.
"Et" means ethyl.
"$EtO_2$" means diethyl ether.
"EtOAc" means ethylacetate.
"HATU" means O-(7-azabenzotriazol-1-yl)-N,N,N',N'-tetramethylammonium hexafluorophosphate.
"HOAc" means acetic acid.
"IBMX" means 3-isobutyl-1-methylxanthine.
"m-CPBA" means m-chloroperoxybenzoic acid.
"Me" means methyl.
"MeCN" means acetonitrile.
"MeI" means iodomethane.
"$Me_2S$" means dimethyl sulfide.
"MeOH" means methanol.
"NaOEt" means sodium ethoxide.
"NaOMe" means sodium methoxide.
"NBS" means N-bromosuccinimide.
"$NEt_3$" means triethylamine.
"NIS" means N-iodosuccinimide.
"t-Bu" means tertiary-butyl.
"t-BuOK" means potassium tertiary-butoxide.
"TFA" means trifluoroacetic acid.
"TfOH" means trifluromethanesulfonic acid.
"THF" means tetrahydrofuran.
"TLC" means thin layer chromatography.
"PMBOH" means 4-methoxybenzyl alcohol.
"PMBCl" means 4-methoxybenzyl chloride.
"Prep TLC" means preparative thin layer chromatography.
"Patient" includes both human and animals.
"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkenylene" means a difunctional group obtained by removal of a hydrogen from an alkenyl group that is defined above. Non-limiting examples of alkenylene include —CH=CH—, —C(CH$_3$)=CH—, and —CH=CHCH$_2$—.

"Alkylene-aryl" (or aryl-alkylene-) means a group in which the aryl and alkylene are as previously described. The bond to the parent moiety is through the alkylene. The alkylene moiety can be bonded to one or more aryl moieties. Alkylene-aryls can comprise a lower alkylene group. Non-limiting examples of suitable alkylene-aryl groups include benzyl, 2-phenethyl, 2,2-diphenylethylene and naphthalenylmethyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

The term "haloalkyl" as used herein refers to an alkyl group, as defined above, wherein one or more of the alkyl group's hydrogen atoms is independently replaced with a halogen. In one embodiment, a haloalkyl group is a "fluoroalkyl group."

The term "fluoroalkyl group" as used herein, refers to an alkyl group, wherein one or more of the alkyl group's hydrogen atoms are replaced with a —F atom. In various embodiments, a fluorooalkyl group contains one F atom, two F atoms or three F atoms. Illustrative example of fluoroalkyl groups include, but are not limited to, —CH$_2$F, —CH(F)$_2$, CH$_2$CH$_2$F, —CF$_3$, and —(CH$_2$)$_3$CF$_3$.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkenyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH₂, —C(=NH)—NH₂, —C(=NH)—NH(alkyl), Y₁Y₂N—, Y₁Y₂N-alkyl-, Y₁Y₂NC(O)—, Y₁Y₂NSO₂— and —SO₂NY₁Y₂, wherein Y₁ and Y₂ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH₃)₂— and the like which form moieties such as, for example:

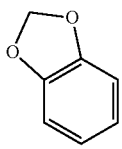 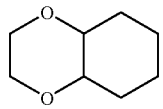 and  .

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

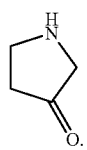

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

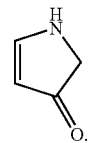

"Heterocyclenylalkyl" means a heterocyclenyl moiety as defined above linked via an alkyl moiety (defined above) to a parent core.

"Cycloalkylene" means a difunctional group obtained by removal of a hydrogen atom from a cycloalkyl group that is defined above. Non-limiting examples of cycloalkylene include

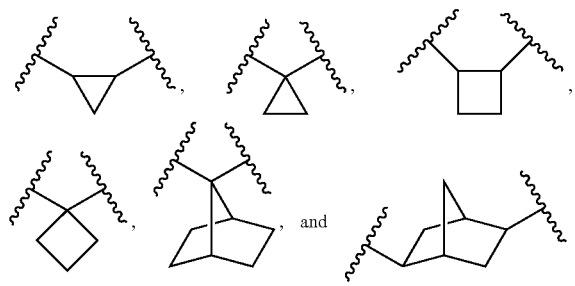

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

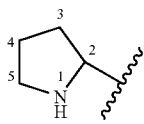

there is no —OH attached directly to carbons marked 2 and 5.

It should also be noted that tautomeric forms such as, for example, the moieties:

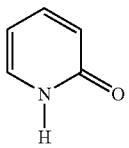 and 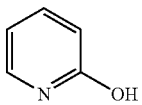

are considered equivalent in certain embodiments of this invention.

"Alkynylalkyl" means an alkynyl-alkyl- group in which the alkynyl and alkyl are as previously described. Alkynylalkyls can contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— groups Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "Purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-(C1-C2)alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy $(C_1-C_6)$alkyl, amino $(C_1-C_4)$alkyl or mono-N— or di-N,N-$(C_1-C_6)$alkylaminoalkyl, —$C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates,. naphthalenesulfonates, nitrates, oxalates, phosphates, propionates, salicylates, succinates, sulfates, tartarates, thiocyanates, toluenesutfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.)

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively.

Certain isotopically-labelled compounds of Formula (I) (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

The compounds of Formula (I), or pharmaceutically acceptable salts, solvates, or esters thereof according to the invention have pharmacological properties; in particular, the compounds of Formula (I) can be nicotinic acid receptor agonists.

The compounds of Formula (I) of the present invention, or pharmaceutically acceptable salts, solvates, or esters thereof are useful in treating diseases or conditions including dyslipidemia and metabolic syndrome.

The compounds of Formula (I), or pharmaceutically acceptable salts, solvates, or esters thereof, can be administered in any suitable form, e.g., alone, or in combination with a pharmaceutically acceptable carrier, excipient or diluent in a pharmaceutical composition, according to standard pharmaceutical practice. The compounds of Formula (I), or pharmaceutically acceptable salts, solvates, or esters thereof, can be administered orally or parenterally, including intravenous, intramuscular, interperitoneal, subcutaneous, rectal, or topical routes of administration, or if so selected, by a combination of one or more of the above-shown methods.

Pharmaceutical compositions comprising at least one compound of Formula (I), or a pharmaceutically acceptable salt, solvate, ester, or tautomer thereof can be in a form suitable for oral administration, e.g., as tablets, troches, capsules, lozenges, aqueous or oily suspensions, dispersible powders or granules, emulsions, syrups, or elixirs. Oral compositions may be prepared by any conventional pharmaceutical method, and may also contain sweetening agents, flavoring agents, coloring agents, and preserving agents.

The amount of compound of Formula (I), or a pharmaceutically acceptable salt, solvate, ester, or tautomer thereof, administered to a patient can be determined by a physician based on the age, weight, and response of the patient, as well as by the severity of the condition treated. For example, the amount of compound of Formula I, or a pharmaceutically acceptable salt, solvate, ester, or tautomer thereof, administered to the patient can range from about 0.1 mg/kg body weight per day to about 60 mg/kg/d. In one embodiment, the amount is from about 0.5 mg/kg/d to about 40 mg/kg/d. In another embodiment, the amount is from about 0.5 mg/kg/d to about 10 mg/kg/d. In another embodiment, the amount is from about 1 mg/kg/d to about 5 mg/kg/d. In still another embodiment, the amount is from about 1 mg/kg/d to about 3 mg/kg/d. In a specific embodiment, the amount is about 1 mg/kg/d. In another specific embodiment, the amount is about 3 mg/kg/d. In another specific embodiment, the amount is about 5 mg/kg/d. In another specific embodiment, the amount is about 7 mg/kg/d. In still another specific embodiment, the amount is about 10 mg/kg/d.

The compounds of Formula (I), or pharmaceutically acceptable salts, solvates, or esters thereof, can also be administered in combination with other therapeutic agents. For example one or more compounds of Formula (I) or pharmaceutically acceptable salts, solvates, or esters thereof, can be administered with one or more additional active ingredients selected from the group consisting of hydroxy-substituted azetidinone compounds, substituted β-lactam compounds, HMG CoA reductase inhibitor compounds, HMG CoA synthetase inhibitors, squalene synthesis inhibitors, squalene epoxidase inhibitors, sterol biosynthesis inhibitors, nicotinic acid derivatives, bile acid sequestrants, inorganic cholesterol sequestrants, AcylCoA:Cholesterol O-acyltransferase inhibitors, cholesteryl ester transfer protein inhibitors, fish oils containing Omega 3 fatty acids, natural water soluble fibers, plant stanols and/or fatty acid esters of plant stanols, anti-oxidants, PPAR α agonists, PPAR γ-agonists, FXR receptor modulators, LXR receptor agonists, lipoprotein synthesis inhibitors, renin angiotensin inhibitors, microsomal triglyceride transport protein inhibitors, bile acid reabsorption inhibitors, PPAR δ agonists, triglyceride synthesis inhibitors, squalene epoxidase inhibitors, low density lipoprotein receptor inducers or activators, platelet aggregation inhibitors, 5-LO or FLAP inhibitors, PPAR δ partial agonists, niacin or niacin receptor agonists, 5HT transporter inhibitors, NE transporter inhibitors, $CB_1$ antagonists/inverse agonists, ghrelin antagonists, $H_3$ antagonists/inverse agonists, MCH1R antagonists, MCH2R agonists/antagonists, NPY1 antagonists, NPY5 antagonists, NPY2 agonists, NPY4 agonists, mGluR5 antagonists, leptins, leptin agonists/modulators, leptin derivatives, opioid antagonists, orexin receptor antagonists, BRS3 agonists, CCK-A agonists, CNTF, CNTF derivatives, CNTF agonists/modulators, 5HT2c agonists, Mc4r agonists, monoamine reuptake inhibitors, serotonin reuptake inhibitors, GLP-1, GLP-1 agonists, GLP-1 mimetics, phentermine, topiramate, phytopharm compound 57, ghrelin antibodies, Mc3r agonists, ACC inhibitors, β3 agonists, DGAT1 inhibitors, DGAT2 inhibitors, FAS inhibitors, PDE inhibitors, thyroid hormone β agonists, UCP-1 activators, UCP-2 activators, UCP-3 activators, acyl-estrogens, glucocorticoid agonists/antagonists, 11β HSD-1 inhibitors, SCD-1 inhibitors, lipase inhibitors, fatty acid transporter inhibitors, dicarboxylate transporter inhibitors, glucose transporter inhibitors, phosphate transporter inhibitors, anti-diabetic agents, anti-hypertensive agents, anti-dyslipidemic agents, DP receptor antagonists, apolipoprotein-B secretion/microsomal triglyceride transfer protein (apo-B/MTP) inhibitors, sympathomimetic agonists, dopamine agonists, melanocyte-stimulating hormone receptor analogs, melanin concentrating hormone antagonists, leptons, galanin receptor antagonists, bombesin agonists, neuropeptide-Y antagonists, thyromimetic agents, dehydroepiandrosterone, analogs of dehydroepiandrosterone, urocortin binding protein antagonists, glucagons-like peptide-1 receptor agonists, human agouti-related proteins (AGRP), neuromedin U receptor agonists, noradrenergic anorectic agents, appetite suppressants, hormone sensitive lipase antagonists, MSH-receptor analogs, α-glucosidase inhibitors, apo A1 milano reverse cholesterol transport inhibitors, fatty acid binding protein inhibitors (FABP), and fatty acid transporter protein inhibitors (FATP).

Non-limiting examples of hydroxy-substituted azetidinone compounds and substituted β-lactam compounds useful in combination with the nicotinic acid receptor agonists of the present invention are those disclosed in U.S. Pat. Nos. 5,767, 115, 5,624,920, 5,668,990, 5,656,624 and 5,688,787, 5,756,470, U.S. Patent Application Nos. 2002/0137690 and 2002/0137689 and PCT Patent Application No. WO 2002/066464, each of which is incorporated herein by reference in their entirety. A preferred azetidinone compound is ezetimibe (for example, ZETIA® which is available from Schering-Plough Corporation).

Non-limiting examples of HMG CoA reductase inhibitor compounds useful in combination with the nicotinic acid receptor agonists of the present invention are lovastatin (for example MEVACOR® which is available from Merck & Co.), simvastatin (for example ZOCOR® which is available from Merck & Co.), pravastatin (for example PRAVACHOL® which is available from Bristol Meyers Squibb), atorvastatin, fluvastatin, cerivastatin, CI-981, rivastatin (sodium 7-(4-fluorophenyl)-2,6-diisopropyl-5-methoxymethylpyridin-3-yl)-3,5-dihydroxy-6-heptanoate), rosuvastatin calcium (CRESTOR® from AstraZeneca Pharmaceuticals), pitavastatin (such as NK-104 of Negma Kowa of Japan).

A non-limiting example of a HMG CoA synthetase inhibitor useful in combination with the nicotinic acid receptor agonists of the present invention is, for example, L-659,699 ((E,E)-11-[3'R-(hydroxy-methyl)-4'-oxo-2'R-oxetanyl]-3,5,7R-trimethyl-2,4-undecadienoic acid).

A non-limiting example of a squalene synthesis inhibitor useful in combination with the nicotinic acid receptor agonists of the present invention is, for example, squalestatin 1.

A non-limiting example of a squalene epoxidase inhibitor useful in combination with the nicotinic acid receptor agonists of the present invention is, for example, NB-598 ((E)-N-ethyl-N-(6,6-dimethyl-2-hepten-4-ynyl)-3-[(3,3'-bithiophen-5-yl)methoxy]benzene-methanamine hydrochloride).

A non-limiting example of a sterol biosynthesis inhibitor useful in combination with the nicotinic acid receptor agonists of the present invention is, for example, DMP-565.

Non-limiting examples of nicotinic acid derivatives (e.g., compounds comprising a pyridine-3-carboxylate structure or a pyrazine-2-carboxylate structure, including acid forms, salts, esters, zwitterions and tautomers) useful in combination with the nicotinic acid receptor agonists of the present invention are niceritrol, nicofuranose and acipimox (5-methyl pyrazine-2-carboxylic acid 4-oxide).

Non-limiting examples of bile acid sequestrants useful in combination with the nicotinic acid receptor agonists of the present invention are cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly (allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl)alkylamines and poliglusam, insoluble quaternized polystyrenes, saponins and mixtures thereof.

Non-limiting examples of inorganic cholesterol sequestrants useful in combination with the nicotinic acid receptor agonists of the present invention are bismuth salicylate plus montmorillonite clay, aluminum hydroxide and calcium carbonate antacids.

Non-limiting examples of AcylCoA:Cholesterol O-acyltransferase ("ACAT") inhibitors useful in combination with the nicotinic acid receptor agonists of the present invention are avasimibe ([[2,4,6-tris(1-methylethyl)phenyl]acetyl]sulfamic acid, 2,6-bis(1-methylethyl)phenyl ester, formerly known as CI-1011), HL-004, lecimibide (DuP-128) and CL-277082 (N-(2,4-difluorophenyl)-N-[[4-(2,2-dimethylpropyl)phenyl]methyl]-N-heptylurea), and the compounds described in P. Chang et al., "Current, New and Future Treatments in Dyslipidaemia and Atherosclerosis", Drugs July 2000; 60(1); 55-93, which is incorporated by reference herein.

Non-limiting examples of cholesteryl ester transfer protein ("CETP") inhibitors useful in combination with the nicotinic acid receptor agonists of the present invention are those disclosed in PCT Patent Application No. WO 00/38721, U.S. Pat. Nos. 6,147,090, 6,958,346, 6,924,313 6,906,082, 6,861,561, 6,803,388, 6,794,396, 6,787,570, 6,753,346, 6,723,752, 6,723,753, 6,710,089, 6,699,898, 6,696,472, 6,696,435, 6,683,113, 5,519,001, 5,512,548, 6,410,022, 6,426,365, 6,448,295, 6,387,929, 6,683,099, 6,677,382, 6,677,380, 6,677,379, 6,677,375, 6,677,353, 6,677,341, 6,605,624, 6,586,433, 6,451,830, 6,451,823, 6,462,092, 6,458,849, 6,458,803, 6,455,519, 6,583,183, 6,562,976, 6,555,113, 6,544,974, 6,521,607, 6,489,366, 6,482,862, 6,479,552, 6,476,075, 6,476,057, and 6,897,317, each of which are incorporated herein by reference; compounds described in Yan Xia et al., "Substituted 1,3,5-Triazines As Cholesteral Ester Transfer Protein Inhibitors", Bioorganic & Medicinal Chemistry Letters, vol. 6, No. 7, 1996, pp. 919-922, herein incorporated by reference; natural products described in S. Coval et al., "Wiedendiol-A and -B, Cholesteryl Ester Transfer Protein Inhibitors From The Marine Sponge Xestosponga Wiedenmayeri", Bioorganic & Medicinal Chemistry Letter, vol. 5, No. 6, pp. 605-610, 1995, herein incorporated by reference; the compounds described in Barrett et al. *J. Am. Chem. Soc.*, 188, 7863-63 (1996), herein incorporated by reference; the compounds described in Kuo et al. *J. Am. Chem. Soc.*, 117, 10629-34 (1995), herein incorporated by reference; the compounds described in Pietzonka et al. *Bioorg, Med. Chem. Lett.* 6, 1951-54 (1996), herein incorporated by reference; the compounds described in Lee et al. *J. Antibiotics*, 49, 693-96 (1996), herein incorporated by reference; the compounds described by Busch et al. *Lipids*, 25, 216-220, (1990), herein incorporated by reference; the compounds described in Morton and Zilversmit *J. Lipid Res.*, 35, 836-47 (1982), herein incorporated by reference; the compounds described in Connolly et al. *Biochem. Biophys. Res. Comm.*, 223, 42-47 (1996), herein incorporated by reference; the compounds described in Bisgaier et al. Lipids, 29, 811-8 (1994), herein incorporated by reference; the compounds described in EP 818448, herein incorporated by reference; the compounds described in JP 10287662, herein incorporated by reference; the compounds described in PCT applications WO 98/35937, WO 9914174, WO 9839299, and WO 9914215, each of which is herein incorporated by reference; the compounds of EP applications EP 796846, EP 801060, 818448, and 818197, each of which is herein incorporated by reference; probucol or derivatives thereof, such as AGI-1067 and other derivatives disclosed in U.S. Pat. Nos. 6,121,319 and 6,147,250, herein incorporated by reference; low-density lipoprotein (LDL) receptor activators such as HOE-402, an imidazolidinyl-pyrimidine derivative that directly stimulates LDL receptor activity, described in M. Huettinger et al., "Hypolipidemic activity of HOE-402 is Mediated by Stimulation of the LDL Receptor Pathway", Arterioscler. Thromb. 1993; 13:1005-12, herein incorporated by reference; 4-carboxyamino-2-substituted-1,2,3,4-tetrahydroquinolines, e.g., torcetrapib, described in WO 00/017164, WO 00/017166, WO 00/140190, WO 00/213797, and WO 2005/033082 (each of which is herein incorporated by reference). Torcetrapib can be combined with HMG-CoA reductase inhibitors such as atorvastatin (WO 00/213797, WO 2004/056358, WO 2004/056359, and WO2005/011634).

A non-limiting example of a fish oil containing Omega 3 fatty acids useful in combination with the nicotinic acid receptor agonists of the present invention is 3-PUFA.

Non-limiting examples of GLP-1 mimetics useful in combination with the nicotinic acid receptor agonists of the present invention include exendin-3, exendin-4, Byetta-Exanatide, Liraglutinide, CJC-1131 (ConjuChem), Exanatide-LAR (Amylin) BIM-51077 (Ipsen/LaRoche), ZP-10 (Zealand Pharmaceuticals), and compounds disclosed in International Publication No. WO 00/07617.

Non-limiting examples of natural water soluble fibers useful in combination with the nicotinic acid receptor agonists of the present invention are psyllium, guar, oat and pectin.

A non-limiting example of a plant stanol and/or fatty acid ester of plant stanols useful in combination with the nicotinic acid receptor agonists of the present invention is the sitostanol ester used in BENECOL® margarine.

A non-limiting example of an anti-oxidant useful in combination with the nicotinic acid receptor agonists of the present invention includes probucol.

Non-limiting examples of PPAR α agonists useful in combination with the nicotinic acid receptor agonists of the present invention include beclofibrate, benzafibrate, ciprofibrate, clofibrate, etofibrate, fenofibrate, and gemfibrozil.

Non-limiting examples of lipoprotein synthesis inhibitors useful in combination with the nicotinic acid receptor agonists of the present invention include niacin or nicotinic acid.

Non-limiting examples of 5HT (serotonin) transport inhibitors useful in combination with the nicotinic acid receptor agonists of the present invention include paroxetine, fluoxetine, fenfluramine, fluvoxamine, sertraline, and imipramine.

Non-limiting examples of NE (norepinephrine) transport inhibitors useful in combination with the nicotinic acid receptor agonists of the present invention include GW 320659, despiramine, talsupram, and nomifensine.

Non-limiting examples of $CB_1$ antagonists/inverse agonists useful in combination with the nicotinic acid receptor agonists of the present invention include rimonabant, SR-147778 (Sanofi Aventis), and the compounds described in U.S. Pat. Nos. 5,532,237, 4,973,587, 5,013,837, 5,081,122, 5,112,820, 5,292,736, 5,624,941, 6,028,084, WO 96/33159, WO 98/33765, WO 98/43636, WO 98/43635, WO 01/09120, WO 98/31227, WO 98/41519, WO 98/37061, WO 00/10967, WO 00110968, WO 97/29079, WO 99/02499, WO 01/58869, WO 02/076949, and EP-658546 (each of the preceding references is herein incorporated by reference).

Non-limiting examples of ghrelin antagonists useful in combination with the nicotinic acid receptor agonists of the present invention include those described in WO 01/87335 and WO 02/08250 (each of the preceding references is herein incorporated by reference). Ghrelin antagonists are also known as GHS (growth hormone secretagogue receptor) antagonists. The pharmaceutical combinations and methods of the present invention therefore comprehend the use GHS antagonists in place of ghrelin antagonists (in combination with the nicotinic acid receptor agonists of the present invention).

Non-limiting examples of $H_3$ antagonists/inverse agonists useful in combination with the nicotinic acid receptor agonists of the present invention include thioperamide, 3-(1H-imidazol-4-yl)propyl N-(4-pentenyl)carbamate, clobenpropit, iodophenpropit, imoproxifan, and GT2394 (Gliatech), those described in: WO 02/15905 (herein incorporated by reference); O-[3-(1H-imidazol-4-yl)propanol]carbamates described in Kiec-Kononowicz, K. et al., Pharmazie, 55:349-55 (2000) (herein incorporated by reference), piperidine-containing histamine $H_3$-receptor antagonists described in Lazewska, D. et al., Pharmazie, 56:927-32 (2001) (herein incorporated by reference), benzophenone derivatives and related compounds described in Sasse, A. et al., Arch. Pharm. (Weinheim) 334:45-52 (2001) (herein incorporated by reference), substituted N-phenylcarbamates described in Reidemeister, S. et al., Pharmazie, 55:83-6 (2000) (herein incorporated by reference), and proxifan derivatives described in Sasse, A. et al., J. Med. Chem. 43:3335-43 (2000) (each of the preceding references is herein incorporated by reference).

Non-limiting examples of MCH1R (melanin-concentrating hormone 1 receptor) antagonists and MCH2R (melanin-concentrating hormone 2 receptor) agonists/antagonists useful in combination with the nicotinic acid receptor agonists of the present invention include those described in WO 01/82925, WO 01/87834, WO 02/06245, WO 02/04433, WO 02/51809, and JP 13226269 (each of the preceding references is herein incorporated by reference), and T-226296 (Takeda).

Non-limiting examples of NPY1 antagonists useful in combination with the nicotinic acid receptor agonists of the present invention include those described in U.S. Pat. No. 6,001,836, WO 96/14307, WO 01/23387, WO 99/51600, WO 01/85690, WO 01/85098, WO 01/85173, and WO 01/89528 (each of the preceding references is herein incorporated by reference); and BIBP3226, J-115814, BIBO 3304, LY-357897, CP-671906, and GI-264879A.

Non-limiting examples of NPY5 antagonists useful in combination with the nicotinic acid receptor agonists of the present invention include those described in U.S. Pat. Nos. 6,140,354, 6,191,160, 6,258,837, 6,313,298, 6,337,332, 6,329,395, 6,340,683, 6,326,375, 6,335,345, EP-01010691, EP-01044970, WO 97/19682, WO 97/20820, WO 97/20821, WO 97/20822, WO 97/20823, WO 98/27063, WO 00/64880, WO 00/68197, WO 00/69849, WO 01/09120, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, WO 02/49648, WO 01/14376, WO 04/110375, WO 05/000217 and Norman et al., J. Med. Chem. 43:4288-4312 (2000) (each of the preceding references is herein incorporated by reference); and 152,804, GW-569180A, GW-594884A, GW-587081X, GW-548118X; FR226928, FR 240662, FR252384; 1229U91, GI-264879A, CGP71683A, LY-377897, PD-160170, SR-120562A, SR-120819A and JCF-104.

Non-limiting examples of NPY2 agonists useful in combination with the nicotinic acid receptor agonists of the present invention include PYY3-36 as described in Batterham, et al., Nature. 418:650-654 (2003), NPY3-36, and other Y2 agonists such as N acetyl [Leu(28,31)] NPY 24-36 (White-Smith and Potter, Neuropeptides 33:526-33 (1999)), TASP-V (Malis et al., Br. J. Pharmacol. 126:989-96 (1999)), cyclo-(28/32)-Ac-[Lys28-Glu32]-(25-36)-pNPY (Cabrele and Beck-Sickinger J-Pept-Sci. 6:97-122 (2000)) (each of the preceding references is herein incorporated by reference).

Non-limiting examples of NPY4 agonists useful in combination with the nicotinic acid receptor agonists of the present invention include pancreatic peptide (PP) as described in Batterham et al., J. Clin. Endocrinol. Metab. 88:3989-3992 (2003), and other Y4 agonists such as 1229U91 (Raposinho et al., Neuroendocrinology. 71:2-7 (2000) (both references are herein incorporated by reference).

Non-limiting examples of mGluR5 (Metabotropic glutamate subtype 5 receptor) antagonists useful in combination with the nicotinic acid receptor agonists of the present invention include 2-methyl-6-(phenylethynyl)-pyridine (MPEP) and (3-[(2-methyl-1,3-thiazol-4-yl)ethynyl]pyridine) (MTEP) and those compounds described in Anderson J. et al., J, Eur J Pharmacol. Jul. 18, 2003;473(1):35-40; Cosford N. et al., Bioorg Med Chem Lett. Feb. 10, 2003;13(3): 351-4; and Anderson J. et al., J Pharmacol Exp Ther. December 2002:303(3):1044-51 (each of the preceding references is herein incorporated by reference).

Non-limiting examples of leptins, leptin derivatives, and leptin agonists/modulators useful in combination with the nicotinic acid receptor agonists of the present invention include recombinant human leptin (PEG-OB, Hoffman La Roche) and recombinant methionyl human leptin (Amgen). Leptin derivatives (e.g., truncated forms of leptin) useful in the present invention include those described in U.S. Pat. Nos. 5,552,524, 5,552,523, 5,552,522, 5,521,283, WO 96/23513, WO 96/23514, WO 96/23515, WO 96/23516, WO 96/23517, WO 96/23518, WO 96/23519, and WO 96/23520 (each of the preceding references is herein incorporated by reference).

Non-limiting examples of opioid antagonists useful in combination with the nicotinic acid receptor agonists of the present invention include nalmefene (Revex™), 3-methoxynaltrexone, naloxone, and naltrexone, as well as opioid antagonists described in WO 00/21509 (herein incorporated by reference).

Non-limiting examples of orexin receptor antagonists useful in combination with the nicotinic acid receptor agonists of the present invention include SB-334867-A, as well as those described in WO 01/96302, WO 01/68609, WO 02/51232, and WO 02/51838 (each of the preceding references is herein incorporated by reference).

Non-limiting examples of CNTF (specific ciliary neurotrophic factors) useful in combination with the nicotinic acid receptor agonists of the present invention include GI-181771 (Glaxo-SmithKline); SR146131 (Sanofi Aventis); butabindide; PD170,292, PD 149164 (Pfizer).

Non-limiting examples of CNTF derivatives and CNTF agonists/modulators useful in combination with the nicotinic acid receptor agonists of the present invention include axokine (Regeneron) and those described in WO 94/09134, WO 98/22128, and WO 99/43813 (each of which is herein incorporated by reference).

Non-limiting examples of 5HT2c agonists useful in combination with the nicotinic acid receptor agonists of the present invention include BVT933, DPCA37215, WAY161503, and R-1065, as well as those described in U.S. Pat. No. 3,914,250, WO 02/6596, WO 02/48124, WO 02/10169, WO 01/66548, WO 02/44152, WO 02/51844, WO 02/40456, and WO 02/40457 (each of which is herein incorporated by reference).

Non-limiting examples of Mc4r agonists useful in combination with the nicotinic acid receptor agonists of the present invention include CHIR86036 (Chiron); ME-10142, and ME-10145 (Melacure), as well as those described in WO 01/991752, WO 01/74844, WO 02/12166, WO 02/11715, and WO 02/12178 (each of which is herein incorporated by reference).

Non-limiting examples of monoamine reuptake inhibitors useful in combination with the nicotinic acid receptor agonists of the present invention include sibutramine (Meridia™/Reductil™), as well as those described in WO 01/27068, WO 01/62341, U.S. Pat. No. 4,746,680, 4,806,570, 5,436,272, and US 2002/0006964 (each of which is herein incorporated by reference).

Non-limiting examples of serotonin reuptake inhibitors useful in combination with the nicotinic acid receptor agonists of the present invention include dexfenfluramine, fluoxetine, and those described in U.S. Pat. No. 6,365,633, WO 01/27060, and WO 01/162341 (each of which is herein incorporated by reference).

A non-limiting example of an acyl-estrogen useful in combination with the nicotinic acid receptor agonists of the present invention includes oleoyl-estrone.

Non-limiting examples of 11β HSD-1 inhibitors useful in combination with the nicotinic acid receptor agonists of the present invention include those described in WO 03/065983 and WO 03/104207 (both of which are herein incorporated by reference).

A non-limiting example of a lipase inhibitor useful in combination with the nicotinic acid receptor agonists of the present invention include orlistat.

Anti-diabetic agents useful in combination with the nicotinic acid receptor agonists of the present invention include sulfonylureas, meglitinides, α-amylase inhibitors, α-glucoside hydrolase inhibitors, PPAR-γ agonists, PPARα/γ agonists, biguanides, PTP-1B inhibitors, DP-IV inhibitors, DPP-IV inhibitors, insulin secretagogues, fatty acid oxidation inhibitors, A2 antagonists, c-jun amino-terminal kinase inhibitors, insulin, insulin mimetics, glycogen phosphorylase inhibitors, VPAC2 receptor agonists, glucokinase activators, and non-thiazolidinedione PPAR ligands. Non-limiting examples of sulfonylureas useful in combination with the nicotinic acid receptor agonists of the present invention include acetohexamide, chlorpropamide, diabinese, glibenclamide, glipizide, glyburide, glimepiride, gliclazide, glipentide, gliquidone, glisolamide, tolazamide, and tolbutamide.

Non-limiting examples of meglitinides useful in combination with the nicotinic acid receptor agonists of the present invention include repaglinide, mitiglinide and nateglinide.

Non-limiting examples of α-amylase inhibitors useful in combination with the nicotinic acid receptor agonists of the present invention include tendamistat, trestatin, and AI-3688.

Non-limiting examples of α-glucoside hydrolase inhibitors useful in combination with the nicotinic acid receptor agonists of the present invention include acarbose, adipose, camiglibose, emiglitate, miglitol, voglibose, pradimicin-Q, salbostatin, CDK-711, MDL-25,637, MDL-73,945, and MOR 14.

Non-limiting examples of PPAR-γ agonists useful in combination with the nicotinic acid receptor agonists of the present invention include balaglitazone, ciglitazone, darglitazone, englitazone, isaglitazone (MCC-555), pioglitazone, rosiglitazone, troglitazone, tesaglitazar, netoglitazone, GW-409544, GW-501516, CLX-0921, 5-BTZD, GW-0207, LG-100641, LY-300512, LY-519818, R483 (Roche), and T131 (Tularik).

Non-limiting examples of PPARα/γ agonists useful in combination with the nicotinic acid receptor agonists of the present invention include CLX-0940, GW-1536, GW-1929, GW-2433, KRP-297, L-796449, LR-90, MK-0767, and SB 219994.

Non-limiting examples of biguanides useful in combination with the nicotinic acid receptor agonists of the present invention include buformin, metformin, and phenformin.

Non-limiting examples of PTP-1B inhibitors (protein tyrosine phosphatase-1B inhibitors) useful in combination with the nicotinic acid receptor agonists of the present invention include A-401,674, KR 61639, OC-060062, OC-83839, OC-297962, MC52445, and MC52453.

Non-limiting examples of DPP-IV inhibitors (dipeptidyl peptidase IVi inhibitors) useful in combination with the nicotinic acid receptor agonists of the present invention include sitagliptin, saxagliptin, denagliptin, vildagliptin, alogliptin, alogliptin benzoate, Galvus (Novartis), ABT-279 and ABT-341 (Abbott), ALS-2-0426 (Alantos), ARI-2243 (Arisaph), BI-A and BI-B (Boehringer Ingelheim), SYR-322 (Takeda), MP-513 (Mitsubishi), DP-893 (Pfizer) and RO-0730699 (Roche), isoleucine thiazolidide, NVP-DPP728, P32/98, LAF 237, TSL 225, valine pyrrolidide, TMC-2A/2B/2C, CD-26 inhibitors, and SDZ 274-444.

Non-limiting examples of insulin secretagogues useful in combination with the nicotinic acid receptor agonists of the present invention include linogliride and A-4166.

Non-limiting examples of fatty acid oxidation inhibitors useful in combination with the nicotinic acid receptor agonists of the present invention include clomoxir and etomoxir.

Non-limiting examples of A2 antagonists useful in combination with the nicotinic acid receptor agonists of the present invention include midaglizole, isaglidole, deriglidole, idazoxan, earoxan, and fluparoxan.

Non-limiting examples of insulin mimetics useful in combination with the nicotinic acid receptor agonists of the present invention include biota, LP-100, novarapid, insulin detemir, insulin lispro, insulin glargine, insulin zinc suspension (lente and ultralente), Lys-Pro insulin, GLP-1 (73-7) (insulintropin), and GLP-1 (7-36)-$NH_2$).

Non-limiting examples of glycogen phosphorylase inhibitors useful in combination with the nicotinic acid receptor agonists of the present invention include CP-368,296, CP-316,819, and BAYR3401.

Non-limiting examples of non-thiazolidinedione PPAR ligands useful in combination with the nicotinic acid receptor agonists of the present invention include JT-501 and farglitazar (GW-2570/GI-262579).

Anti-hypertensive agents useful in combination with the nicotinic acid receptor agonists of the present invention include diuretics, β-adrendergic blockers, α-adrenergic blockers, aldosterone inhibitors, alpha 1 blockers, calcium channel blockers, angiotensin converting enzyme inhibitors, neutral endopeptidase inhibitors. angiotensin II receptor antagonists, endothelin antagonists, vasodilators, alpha 2a agonists, and α/β adrenergic blockers.

Non-limiting examples of diuretics useful in combination with the nicotinic acid receptor agonists of the present invention include chlorthalidone, chlorthiazide, dichlorophenamide, hydroflumethiazide, indapamide, hydrochlorothiazide, bumetanide, ethacrynic acid, furosemide, torsemide, amiloride, triamterene, spironolactone, and epirenone.

Non-limiting examples of β-adrendergic blockers useful in combination with the nicotinic acid receptor agonists of the present invention include acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol.

Non-limiting examples of alpha 1 blockers useful in combination with the nicotinic acid receptor agonists of the present invention include terazosin, urapidil, prazosin, bunazosin, trimazosin, doxazosin, naftopidil, indoramin, WHIP 164, and XEN010.

Non-limiting examples of calcium channel blockers useful in combination with the nicotinic acid receptor agonists of the present invention include amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil.

Non-limiting examples of angiotensin converting enzyme inhibitors useful in combination with the nicotinic acid receptor agonists of the present invention include alacepril, benazepril, ceronapril, captopril, cilazapril, delapril, enalapril, fosinopril, imidapril, losinopril, moveltopril, moexipril, quinapril, quinaprilat, ramipril, perindopril, peridropril, quanipril, spirapril, temocapril, trandolapril, and zofenopril.

Non-limiting examples of neutral endopeptidase inhibitors useful in combination with the nicotinic acid receptor agonists of the present invention include omapatrilat, cadoxatril, ecadotril, fosidotril, sampatrilat, AVE7688, and ER4030.

Non-limiting examples of angiotensin II receptor antagonists useful in combination with the nicotinic acid receptor agonists of the present invention include candesartan, eprosartan, irbesartan, losartan, pratosartan, tasosartan, telisartan, valsartan, EXP-3137, F16828K, RNH6270, losartan monopotassium, and losartan potassium-hydrochlorothiazide.

Non-limiting examples of endothelin antagonists useful in combination with the nicotinic acid receptor agonists of the present invention include tezosentan, A308165, and YM62899.

Non-limiting examples of vasodilators useful in combination with the nicotinic acid receptor agonists of the present invention include hydralazine (apresoline), clonidine (catapres), minoxidil (loniten), and nicotinyl alcohol (roniacol).

Non-limiting examples of alpha 2a agonists useful in combination with the nicotinic acid receptor agonists of the present invention include lofexidine, tiamenidine, moxonidine, rilmenidine, and guanobenz.

Non-limiting examples of α/β adrenergic blockers useful in combination with the nicotinic acid receptor agonists of the present invention include nipradilol, arotinolol, and amosulalol.

DP receptor antagonists useful in combination with the nicotinic acid receptor agonists of the present invention include those described in US 2004/0229844 (herein incorporated by reference).

Non-limiting examples of additional agents that can be combined with the nicotinic acid receptor agonists of the present invention include aspirin, Niaspan, Norvsac® (amlodipine), NSAIDS agents (e.g., Celecoxib (Celebrex®), Diclofenac (Cataflam®, Voltaren®, Arthrotec®,) Diflunisal (Dolobid®), Etodolac (Lodine®), Fenoprofen (Nalfon®), Flurbirofen (Ansaid®), Ibuprofen (Motrin®, ADVIL®, NUPRIN®, Tab-Profen®, Vicoprofen®, Combunox®) Indornethacin (Indocin®, Indo-Lemmon®, Indornethagan®) Ketoprofen (Oruvail®), Ketorolac (Toradol®), Mefenamic acid (Ponstel®, commercially available from First Horizon Pharmaceutical), flufenamic acid ([N-(3-trifluoromethylphenyl)anthranilic acid]), Meloxicam (Mobic®), Naburnetone (Relafen®), Naproxen (Naprosyn®, ALEVE®, Anaprox®, Naprelan®, Naprapac®), Oxaprozin (Daypro®), Piroxicam (Feldene®), Sulindac (Clinoril®) and Tolmetin (Tolectin®)), antihypertensive agents (Prazosin®, Propranolol, nadolol, timolol, metoprolol, pindolol, labetalol, guanethidine, reserpine, clonidine, methyldopa, guanabenz, captopril, enalapril, lisinopril, losartan, verapamil, diltiazem, nifedipine, hydrochlorothiazide, chlorothalidone, furosemide, triamterene, hydralazine, minoxidil), PGE2 receptor antagonists (e.g., EP2 and EP4).

Non-limiting examples of additional agents that can be combined with the nicotinic acid receptor agonists of the present invention include homocysteinase, orphan GPCR modulator, HRE-based gene therapy, gene therapy, dual PPARα/γ agonists, recombinant FGF-1, VRI-1, CRx-150, VEGF-114 based therapy, CT-500, regadenosan, CK-1827452, JAK2 tyrosine kinase inhibitors, adipose-derived regenerative cells, STARBURST dendrimer-based MRI contrast agents, TBC-11299, HEMOxygenation, heparin, GO-EPO, IDN-6734, ISIS-301012, HIF-alpha gene therapy, α2b adrenoceptor antagonists, KI-0002, adenosine modulators, Ki-23095, PR-5 (Melacure), L-364373, histone deacetylase inhibitors, adenylate cyclase inhibitors (E.g., HI-30435 from Millennium), MITO-0139 (from MitoKor), NV-04 (from Novogen), M-118 (Momenta), hypoxia response element, PI-99 (from progen), NEXVAS (from Resverlogix), CS-207) from Shenzhen Chipscreen Biosciences), estrogen-regulated gene therapy, SLV-327 (from SolvaY), TNX-832 (from Sunol Molecular Corp), SLx-2101 (from Surface Logix), recombinant human annexin (from SurroMed), Chymase inhibitors (e.g, from Toa Eiyo), VM-202 (from ViroMed), liver x receptor modulators (erg., from Exelixis/ Bristol Myers Squibb), Heberkinasa (from Y. M. Biosciences), atorvastatin-amlodipine combination, AGN-195795 (Allergan), angiotensisn (1-7) agonists (erg., from Arena), Toprol XL/hydrochlorothiazide (from AstraZeneca), Teczem (Aventis), sGC stimulators, calcium channel blockers, CYT-006-AngQb (CytosBiotechnology), renin inhibitors (e.g., from Roche/Speedel), Coxagen (from geneRx+ Inc), MC-4262 (from Medicure), VNP-489 (from Novartis), felodipine (from Pierre Fabre SA), 2-methoxyestradiol (from PR Pharmaceuticals), α1 adrenoreceptor antagonists (erg., from Recordati SpA), lercanidipine-enalapril combination (from Recordati SpA). NO donors 9 e.g., from Renopharm), CR-3834 (from Rottapharm Gr), iloprost (from Schering AG), SPP-1100 (from The Speedel Group), angiotensinogen, MC-4232 (from Medicure), ACE inhibitor (from Servier), LCP-Feno/Stat. (from LifeCycle Pharma), APA-01statin combination (from Phosphagenics Ltd), KH-01502 (from Kos), KS-01019 (from Kos), niacin-lovastatin combination (from Kos/Merck KGaA), MK-0524/extended release niacin/simvastatin combination (from Merck), MK-0524/extended release combination (from Merck), Pro-NAD (from Niadyne Inc), beraprost, perindopril erbumine, barnidipine, irbesartan, valsartan, valsartan-HCTZ combination, meclinertant, TAK-536, SR-121463, irbesatran+HCTZ combination, darusentan, PMD-2850, CR-2991, SLV-306, bisoprolol fumarate+HCTZ combination, NV-04, FG-3019, TRC-4149, AVE-7688, PV-903, diltiazem, QC-BT16, cardiotherpay (from Cytopia), treprostinil sodium, enalapril+ diltiazem combination, eprosartan mesylate+HCTZ combination, renin inhibitor (from Vitae), LG-105 inhibitors (from Lexicon(, LG-844 inhibitors (from Lexicon), NO-enhancing PDE inhibitors, hyaluronidase, propranolol hydrochloride, BIO-236, RWJ-351647, metoprolol, YM-222546, bLN-5, olmesartan+azelnidipine combination (from Sanyo), moxonidine+HCTZ combination, NS-304, BIO-123, aldosterone antagonists, clonidine, BIO-003 and CR-3834.

In addition, the nicotinic acid receptor agonists of the present invention can also be used in combination with two or more therapeutic agents. A non-limiting example of two or more therapeutic agents useful in combination with the nicotinic acid receptor agonists of the present invention is the combination of a compound of the present invention with VYTORIN® (a combination of simvastatin and ezetimibe).

The invention disclosed herein is exemplified by the following preparations and examples which should not be construed to limit the scope of the disclosure. Alternative mechanistic pathways and analogous structures will be apparent to those skilled in the art.

EXAMPLES

In the examples and tables that follow, the exemplary compounds of the invention are referred to by number. In some instances, the compounds of the invention are referred to as "Example X," wherein "X" would be the representative number of that particular compound. In other instances, the compounds of the invention are referred to as "compound X," wherein "X" would be the representative number of that particular compound. In other instances, a compound of the invention may simply be referred to by it's number. It is to be understood that these terms are used interchangeably. For example, the compound labeled "Example 1" can also be referred to as "compound 1" and vice versa.

Preparative Example 1

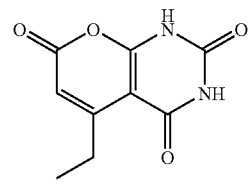

Example 1

Step A:

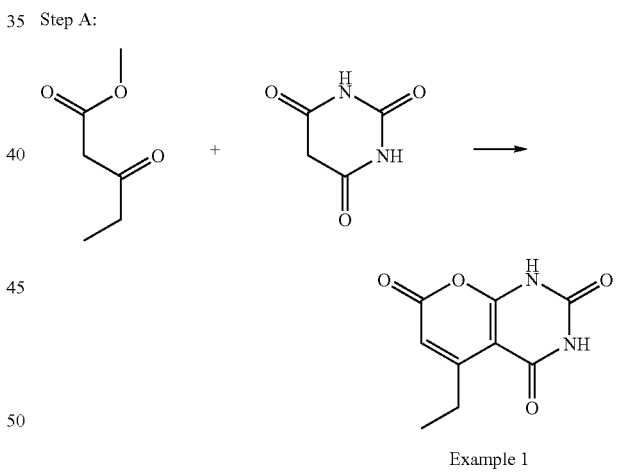

Example 1

Methyl propionylacetate (12.5 g, 96.1 mmol, 1.23 eq.) and barbituric acid (10 g, 78.1 mmol, 1 eq.) were mixed together and without solvent, the mixture was heated to 195° C. in air for 2 hr., at which time all of the liquids had evaporated. The solid was washed with boiling distilled water twice. The remaining solid was recrystallized with 2-methoxyethanol/ water to give 4 g of Example 1 as a yellow solid (20% yield).

$^1$H NMR (CD$_3$OD): δ 1.20 (t, 3 H, J=7.3 Hz), 3.00 (q, 2 H, J=7.3 Hz), 580 (s, 1 H)

$^{13}$C NMR (CD$_3$OD): δ 12.6, 27.4, 92.0, 104.2, 149.5, 158.4, 161.8, 162.1, 164.1

Mass for C$_9$H$_9$N$_2$O$_4$ (MH)$^+$: 209. Found: 209.

Preparative Example 2

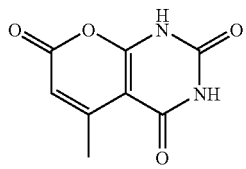

Example 2

Example 2 was prepared by a method analogous to the method used to prepare Example 1, except that methyl acetonylacetate was used instead of methyl propionylacetate.

$^1$H NMR (CD$_3$OD): δ 2.41 (s, 3 H) 5.75 (s, 1 H)

Mass for C$_8$H$_7$N$_2$O$_4$ (MH)$^+$: 195. Found: 195.

Preparative Example 3

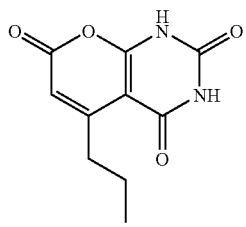

Example 3

Example 3 was prepared by a method analogous to the method used to prepare Example 1, except that methyl butanoylacetate was used instead of methyl propionylacetate.

$^1$H NMR (CD$_3$OD): δ 0.96 (t, 3 H, J=7.6 Hz), 1.57 (m, 2 H), 2.86 (m, 2 H), 5.75 (s, 1 H)

Mass for C$_{10}$H$_{11}$N$_2$O$_4$ (MH)$^+$: 223. Found: 223.

Preparative Example 4

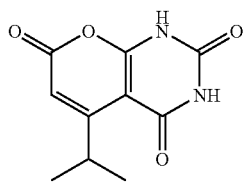

Example 4

Example 4 was prepared by a method analogous to the method used to prepare Example 1, except that ethyl isobutylacetate was used instead of methyl propionylacetate, and Example 4 was purified by HPLC (5% acetonitrile in water to 95% acetonitrile in 10 min).

$^1$H NMR (CD$_3$OD): δ 1.14 (d, 6 H, J=6.8 Hz), 4.03 (m, 1 H), 5.86 (s, 1 H)

Mass for C$_{10}$H$_{11}$N$_2$O$_4$ (MH)$^+$: 223. Found: 223.

Preparative Example 5

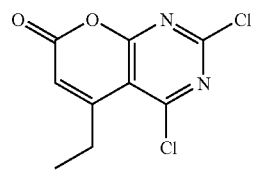

Example 5

Step A:

[Example 1]  +  POCl$_3$  →  [Example 5]

Example 1 (5 g, 24.04 mmol, 1 eq), POCl$_3$ (36.86 g, 240 mmol, 10 eq.) and pyridine (0.95 g, 12 mmol, 0.5 eq) were mixed and heated to 115° C. for 8 hours. After cooling to room temperature, the solvent was removed and the brownish residue was purified using flash chromatography with 20% EtOAc/hexane as the eluting solvent. The desired product (4 g) was obtained in 68% yield.

$^1$H NMR (CD$_3$OD): δ 1.29 (t, 3 H, J=7.2 Hz), 3.12 (m, 2 H), 6.39 (s, 1 H)

Mass for C$_9$H$_7$Cl$_2$N$_2$O$_2$ (MH)$^+$: 245. Found: 245.

Preparative Example 6

Example 6

Step A:

[Example 5]  +  PhNH$_2$  →

-continued

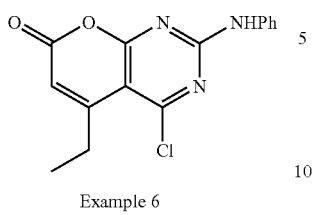

Example 6

Compound 1 (0.15 g, 0.61 mmol, 1 eq.) and aniline (0.06 g, 0.64 mmol, 1.05 eq) were mixed in 3 mL of anhydrous THF and stirred for 12 hours. Solvent was removed and the residue was purified by prep TLC with 25% EtOAc/hexane as the eluting solvent to give desired product as first fraction (7 mg, 4% yield).

$^1$H NMR (CD$_3$OD): δ 1.27 (t, 3 H, J=7.2 Hz), 3.05 (m, 2 H), 6.11 (s, 1 H), 7.11 (t, 1 H, J=7.6 Hz), 7.34 (m, 2 H), 7.48 (br s, 1 H), 7.60 (d, 2 H, J=8.0 Hz)

Mass for C$_{15}$H$_{13}$ClN$_3$O$_2$ (MH)$^+$: 302. Found: 302.

Preparative Example 7

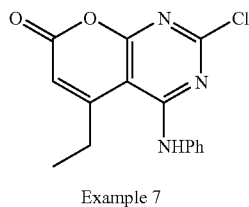

Example 7

Step A:

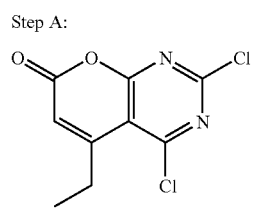

Example 5

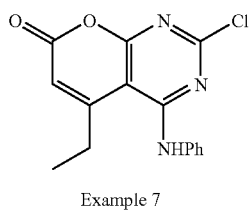

Example 7

Example 7 was prepared using the method used to prepare Example 6, except that Example 7 was obtained as the second fraction by prep TLC (8 mg, 4% yield).

$^1$H NMR (CD$_3$OD): δ 1.43 (t, 3 H, J=7.2 Hz), 2.96 (m, 2 H), 6.22 (s, 1 H), 7.37-7.48 (m, 5H)

Mass for C$_{15}$H$_{13}$ClN$_3$O$_2$ (MH)$^+$: 302. Found: 302.

Preparative Example 8

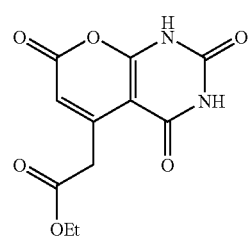

Example 8

Step A:

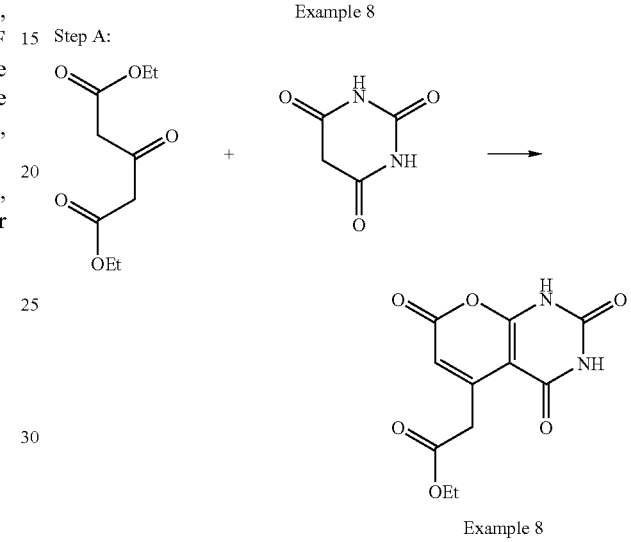

Example 8

Example 8 was prepared using a method analogous to the method used to prepare Example 1, except that diethyl 1,3-acetonedicarboxylate was used instead of methyl propionylacetate.

$^1$H NMR (CD$_3$OD): δ 1.20 (t, 3 H, J=7.3 Hz), 3.88 (s, 2 H), 4.10 (q, 2 H, J=7.3 Hz), 5.81 (s, 1 H)

$^{13}$C NMR (CD$_3$OD): δ 13,4, 39.6, 61.2, 92.2, 108.1, 149.7, 153.1, 157.8, 161.7, 162.0, 170.3

Mass for HRMS for C$_{11}$H$_{11}$N$_2$O$_6$ (MH)$^+$: calcd 267.0617, found 267.0623.

Preparative Example 9

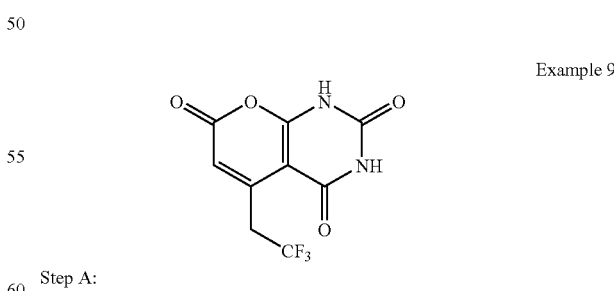

Example 9

Step A:

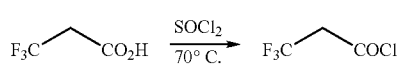

A mixture of 3,3,3,-trifluoropropionic acid (16 g, 125 mmol), thionyl chloride (29.75 g, 250 mmol), and DMF (0.5 mL) was heated to 70° C. for 4 hours. The reaction mixture was distilled under reduced pressure to give 3,3,3,-trifluoropropionyl chloride (11.5 g, 72%).

Step B:

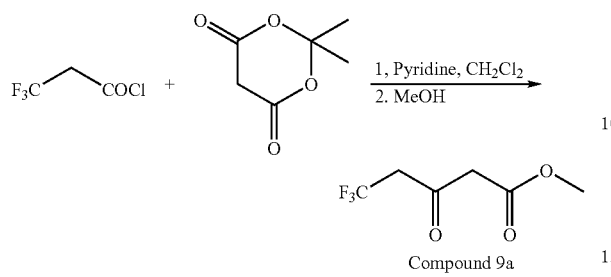

Compound 9a

Into a solution of Meldrum's acid (2,2-dimethyl-4,6-dioxo-1,3-dioxane; 9 g, 62 mmol) and pyridine (9.8 g, 68 mmol) in anhydrous $CH_2Cl_2$ (10 mL), which cooled to 0° C., was added 3,3,3,-trifluoropropionyl chloride (10 g, 68 mmol). The resulting reaction mixture was stirred under $N_2$ at 0° C. for 1 hour then at room temperature for 2 hours. The reaction mixture was then concentrated under reduced pressure. The resulting paste was mixed with MeOH (20 mL), and heated to 80° C. for 5 hours. The solvent was removed and the resulting mixture was distilled under reduced pressure to give Compound 9a (6.2 g, 54%).

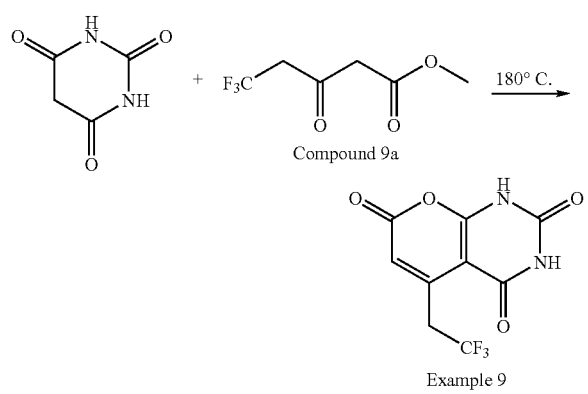

Example 9

A mixture of Compound 9a (2.2 g, 12 mmol) and barbituric acid was heated to 180° C. for 1 hour to provide a black solid. After cooling to room temperature, the black solid was dissolved into hot water (70 mL). The resulting mixture was extracted with ethyl acetate (4×50 mL). The organic solution was dried ($Na_2SO_4$) and concentrated under reduced pressure. The crude product was purified by reverse phase HPLC eluting with formic acid (0.1%)/acetonitrile to give Example 9 (0.17 g, 5%). Electrospray MS $[M+1]^+$ 263.

Preparative Example 10

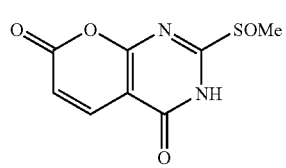

Example 10

Step A:

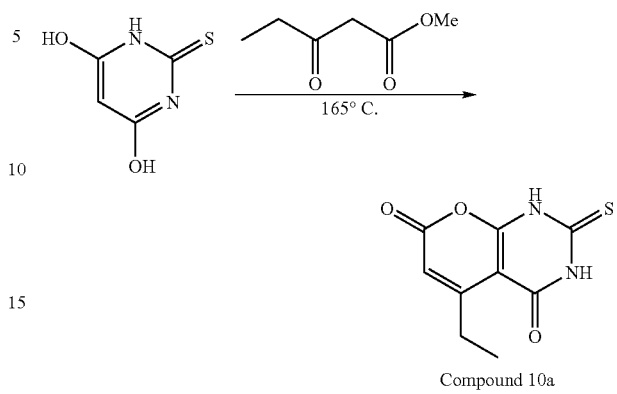

Compound 10a

A mixture of 4,6-dihydroxy-2-mercapto-pyrimidine (20.0 g, 138.7 mmol) and methyl propionylacetate (21.8 mL, 173.4 mmol) was heated at 165° C. until the ester was completely reacted. The reaction mixture was cooled down and poured into water (75 mL) and then filtered through a sintered funnel. The solid residue was washed with water (2×20 mL) and dried under vacuum to yield Compound 10a (11.6 g, 37%).

Step B:

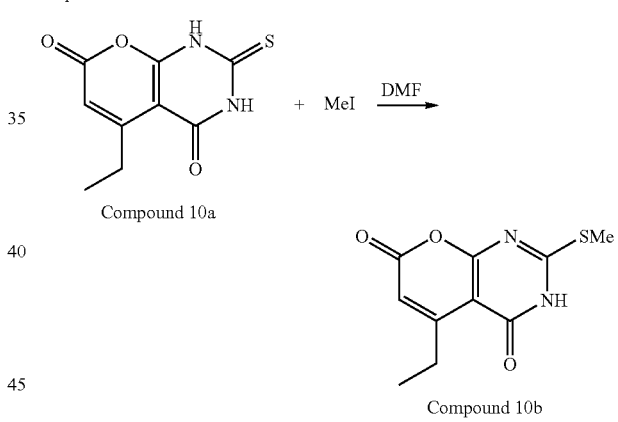

Compound 10b

MeI (2.23 mL, 35.72 mmol) was added to a suspension of Compound 10a (4.0 g, 17.86 mmol) in DMF (40 mL) at room temperature. The reaction mixture was stirred at room temperature overnight. The reaction mixture was then poured into water (250 mL) and filtered through a sintered funnel. The solid residue was washed with water (2×50 mL) and dried under vacuum to give Compound 10b (4.1 g, 96%).

Step C:

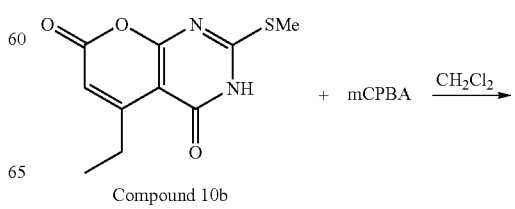

Compound 10b

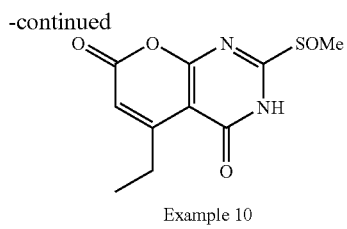

Example 10 m-CPBA (3.1 g, 70%, 12.6 mmol) was added to a suspension of Compound 10b (2.0 g, 8.4 mmol) in CH$_2$Cl$_2$ (150 mL) at room temperature, The solvent was removed from the suspension after 3 hours and the crude product was purified using silica gel flash column chromatography, eluting first with hexane/EtOAc (v/v=1/1) then CH$_2$Cl$_2$/MeOH (v/v=2/1) to give Example 10 (2.09 g, 94%). Electrospray MS [M+1]$^+$ 255.1.

Preparative Example 11

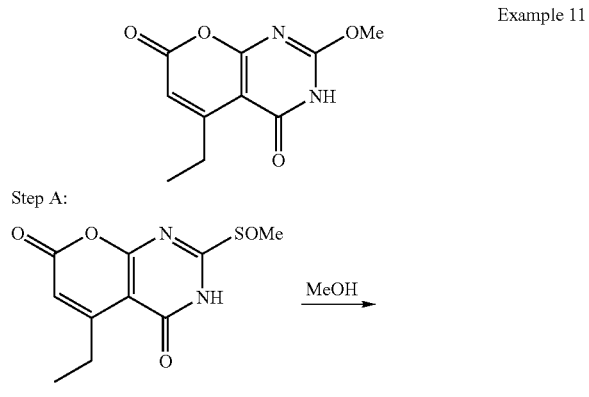

Example 10 (0.35 g, 1.37 mmol) in MeOH (40 mL) was heated at reflux overnight. After cooling to room temperature, the solvent was removed under reduced pressure and the crude product was purified using silica gel flash column chromatography eluting with CH$_2$Cl$_2$/MeOH (v/v=50/1) to give Example 11 (0.23 g, 76%). Electrospray MS [M+1]$^+$ 223.1.

Preparative Example 12

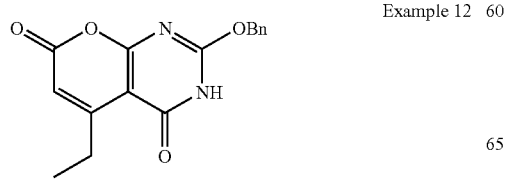

Example 12

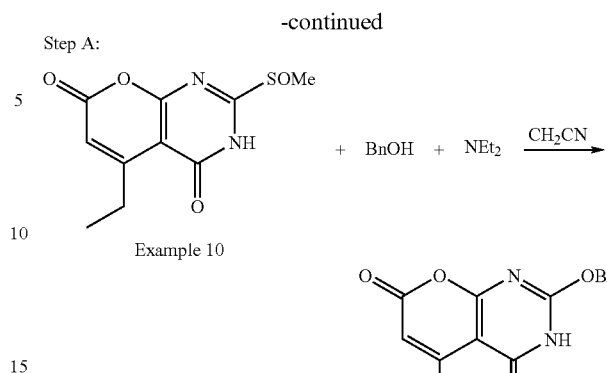

Example 12

BnOH (2.46 mL, 23.76 mmol) was added to a solution of Example 10 (0.404 g, 1.58 mmol) and NEt$_3$ (0.22 mL, 1.58 mmol) in CH$_3$CN (12.0 mL) at room temperature. The reaction mixture was heated at 85° C. overnight. After cooling to room temperature, HOAc (0.09 mL, 1.58 mmol) was added and the solvent was removed under reduced pressure. The crude product was purified using silica gel flash column chromatography eluting with CH$_2$Cl$_2$/MeOH (v/v=50/1) to give Example 12 (0.20 g. 42%). Electrospray MS [M+1]$^+$ 299.1.

Preparative Example 13

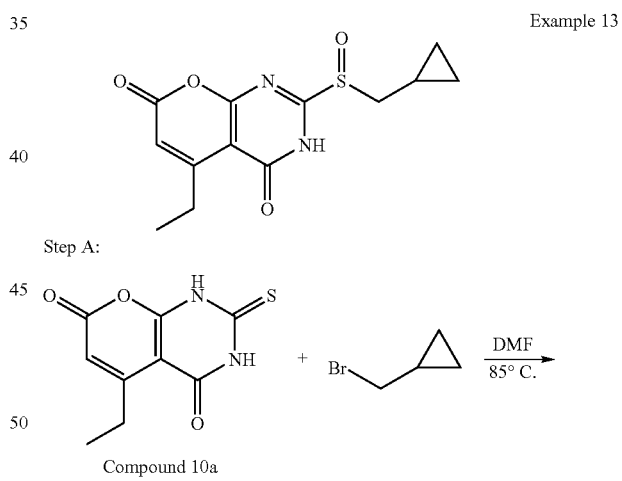

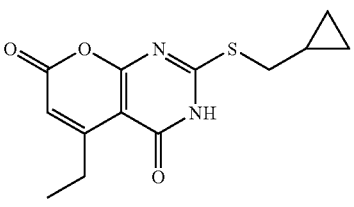

Cyclopropyl methyl bromide (1.30 mL, 13.4 mmol) was added to a suspension of Compound 10a (0.5 g, 2.24 mmol) in DMF (5.0 mL) at room temperature. The reaction mixture was stirred at 85° C. for two days. The reaction mixture was cooled down and poured into water (75 mL) and then filtered through a sintered funnel. The solid residue was washed with water (2×20 mL) and dried under vacuum to give Compound 13a (0.55 g, 88%).

Step B:

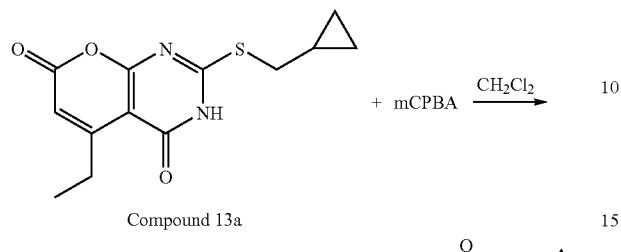

Compound 13a

Example 13 m-CPBA (0.33 g, 70%, 1.35 mmol) was added to a suspension of Compound 13a (0.25 g, 0.9 mmol) in CH$_2$Cl$_2$ (30 mL) at room temperature. Solvent was removed after 3 hours, and the crude product was purified using silica gel flash column chromatography eluting with EtOAc/CH$_2$Cl$_2$/MeOH (v/v=4/1/2) to give Example 13 (0.15 g, 57%). Electrospray MS [M+1]$^+$ 295.1.

Preparative Example 14

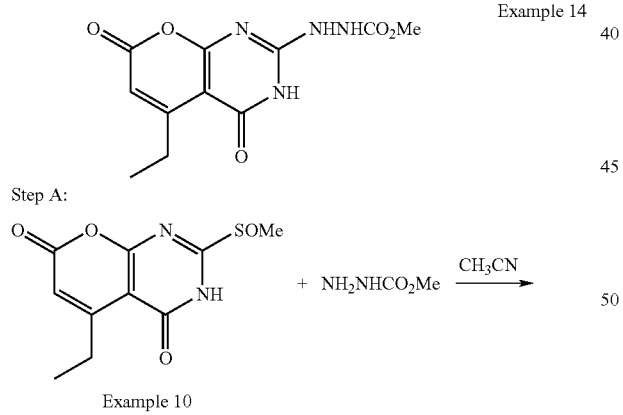

Example 14

Step A:

Example 10

Example 14

A mixture of Example 10 (0.205 g, 0.804 mmol) and NH$_2$NHCO$_2$Me (0.145 g, 1.608 mmol) in MeCN (4.0 mL) was heated at reflux for 3 hours. After cooling to room temperature, the solvent was removed under reduced pressure and the crude product was washed with water (3×25 mL) with filtration. The solid was dried under vacuum to give Example 14 (0.2 g, 89%).

Electrospray MS [M+1]$^+$ 281.1.

Preparative Example 15

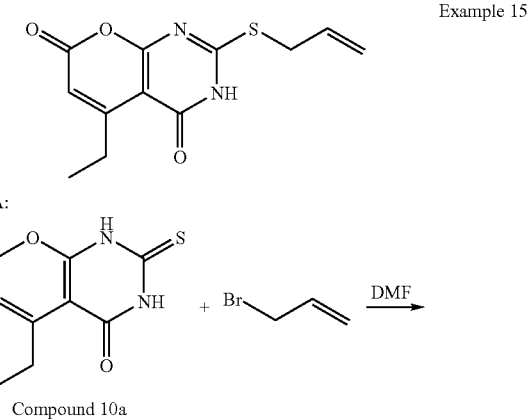

Example 15

Step A:

Compound 10a

Example 15

Allyl bromide (1.74 mL, 20.1 mmol) was added to a suspension of Compound 10a (1.5 g, 6.7 mmol) in DMF (15.0 mL) at room temperature. The reaction mixture was stirred at 45° C. overnight. The reaction mixture was cooled down and poured into water (200 mL) and then filtered through a sintered funnel. The solid residue was washed with water (2×40 mL) and dried under vacuum to give Example 15 (1.55 g, 92%). Electrospray MS [M+1]$^+$ 265.1.

Preparative Example 16

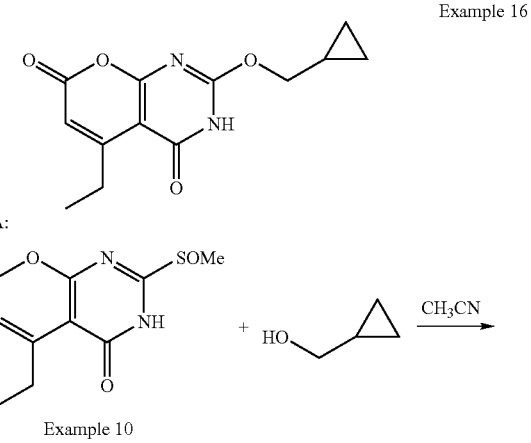

Example 16

Step A:

Example 10

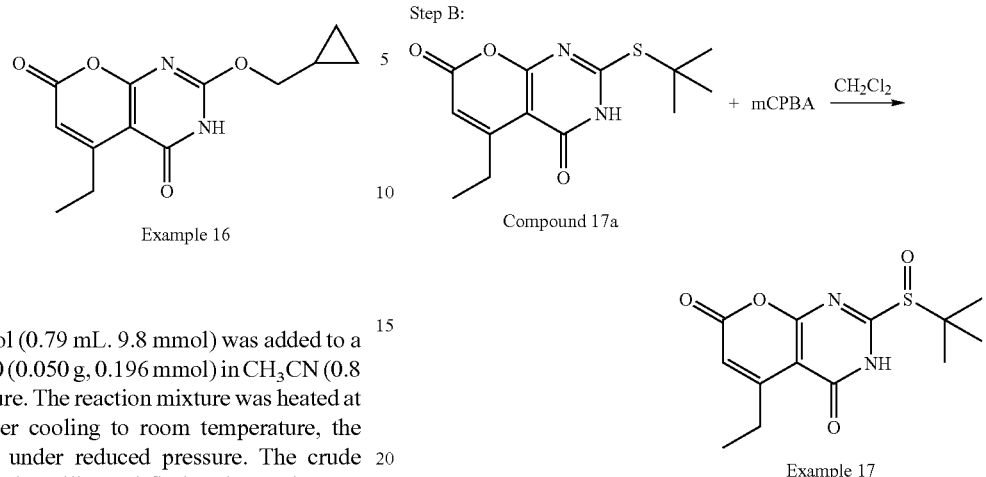

Example 16

Cyclopropyl carbinol (0.79 mL. 9.8 mmol) was added to a solution of Example 10 (0.050 g, 0.196 mmol) in CH₃CN (0.8 mL) at room temperature. The reaction mixture was heated at 85° C. overnight. After cooling to room temperature, the solvent was removed under reduced pressure. The crude product was purified using silica gel flash column chromatography eluting with hexane/EtOAc (v/v=1/1) to give Example 16 (0.027 g, 52%). Electrospray MS [M+1]⁺ 263.1.

Preparative Example 17

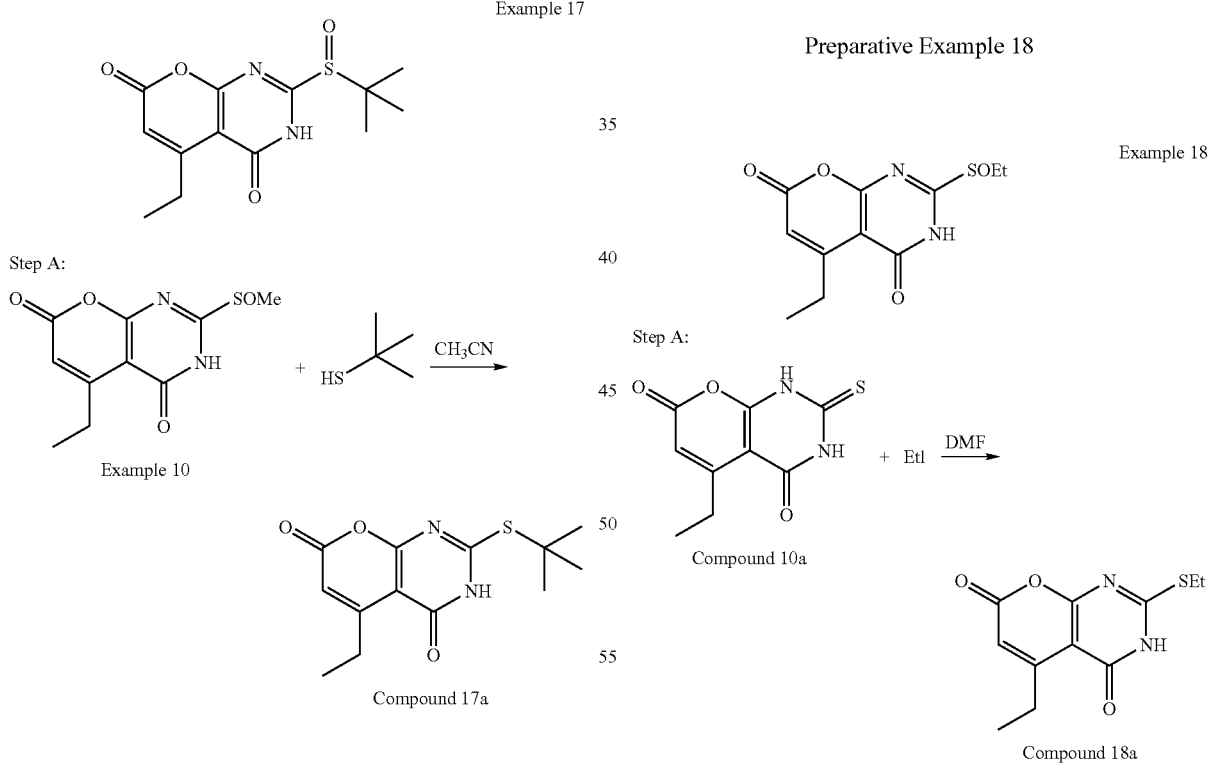

A mixture of Example 10 (0.10 g, 0.392 mmol) and t-BuSH (0.66 mL, 5.88 mmol) in 1,4-dioxane (2.0 mL) was heated at reflux overnight. After cooling to room temperature, the solvent was removed under reduced pressure. The crude product was purified using silica gel flash column chromatography eluting with hexane/EtOAc (v/v=1/1) to give Compound 17a (0.045 g, 41%).

m-CPBA (0.049 g, 70%, 0.20 mmol) was added to a suspension of Compound 17a (0.040 g, 0.143 mmol) in CH₂Cl₂ (2.5 mL) at room temperature. Solvent was removed after 3 hours and the crude product was purified using silica gel flash column chromatography eluting first with hexane/EtOAc (v/v=1/1) then with CH₂Cl₂/MeOH (v/v=5/1) to give Example 17 (0.030 g, 71%). Electrospray MS [M+1]⁺ 297.1.

Preparative Example 18

EtI (2.1 g, 13.4 mmol) was added to a suspension of Compound 10a (1.5 g, 6.7 mmol) in DMF (20 mL). After stirring at room temperature overnight, the reaction mixture was poured into water (50 mL) and filtered through a Buchner funnel. The solid residue was washed with water (2×50 mL) and dried under vacuum to give Compound 18a (1.3 g, 76%).

Step B:

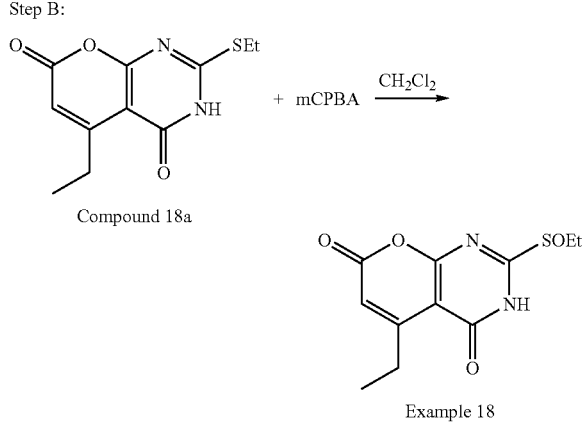

Example 18 m-CPBA (74 mg, 70%, 3 mmol) was added to a suspension of Compound 18a (0.5 g, 2 mmol) in CH$_2$Cl$_2$ (50 mL) at room temperature. After stirring at room temperature 3 hours, the solvent was removed, and the crude product was purified using silica gel flash column chromatography eluting with AcOH/MeOH/CH$_2$Cl$_2$ (v/v/v=0.1/4.9/95) to give Example 18 (0.4 g, 74%).

Electrospray MS [M+1]$^+$ 269.

Preparative Example 19

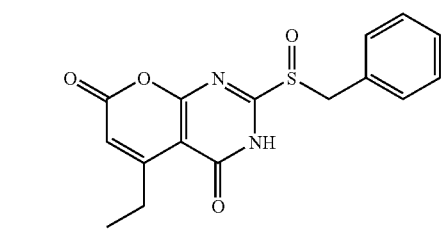

Example 19

Step A:

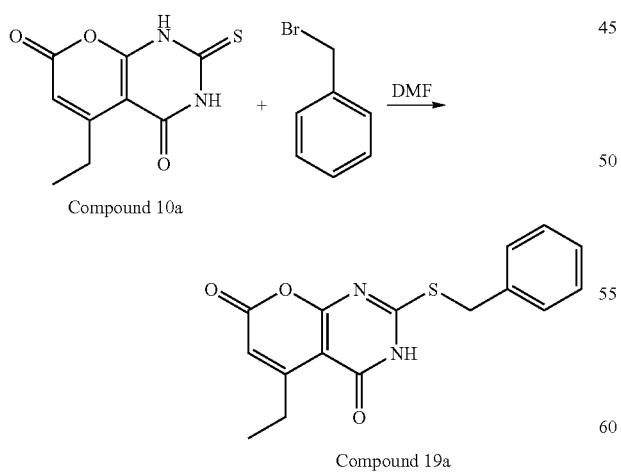

Benzyl bromide (1.54 g, 9 mmol) was added to a suspension of Compound 10a (1 g, 4.5 mmol) in DMF (20 mL). After stirring at room temperature overnight, the reaction mixture was poured into water (50 mL) and filtered through a Buchner funnel. The solid residue was washed with water (2×50 mL) and dried under vacuum to give Compound 19a (1.3 g, 92%).

Step B:

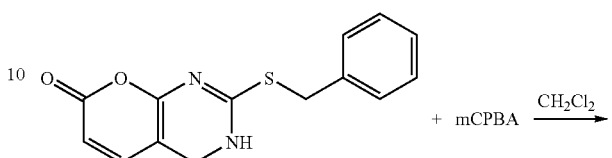

Compound 19a

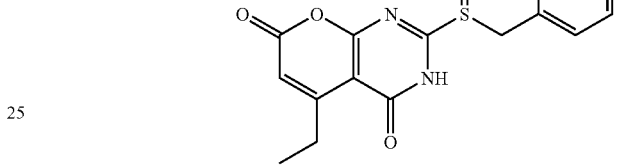

Example 19 m-CPBA (72 mg, 70%, 3 mmol) was added to a suspension of Compound 19a (0.5 g, 2 mmol) in CH$_2$Cl$_2$ (50 mL) at room temperature. After stirring at room temperature 3 hours, the solvent was removed, and the crude product was purified using silica gel flash column chromatography eluting with AcOH/MeOH/CH$_2$Cl$_2$ (v/v/v=0.1/2.9/97) to give Example 19 (0.5 g, 76%).

Electrospray MS [M+1]$^+$ 331.

Preparative Example 20

Example 20

Step A:

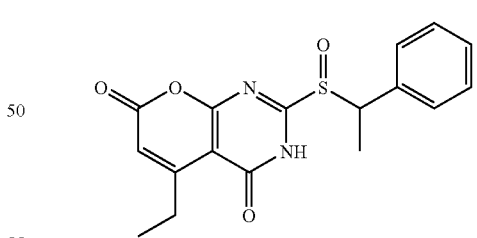

Compound 10a

-continued

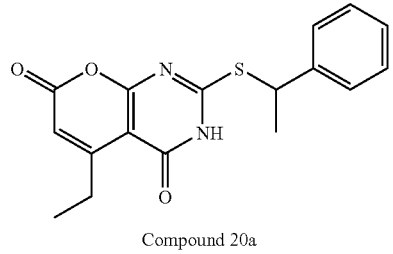

Compound 20a (1-Bromoethyl)benzene (3.4 g, 18 mmol) was added to a suspension of Compound 10a (1 g, 4.5 mmol) in DMF (20.0 mL) at room temperature The reaction mixture was stirred at 70° C. for one day. The reaction mixture was cooled down and poured into water (50 mL) and then filtered through a Buchner funnel. The solid residue was washed with water (2×20 mL) and dried under vacuum to Compound 20a (1.3 g, 87%). Electrospray MS [M+1]$^+$ 329.

Step B:

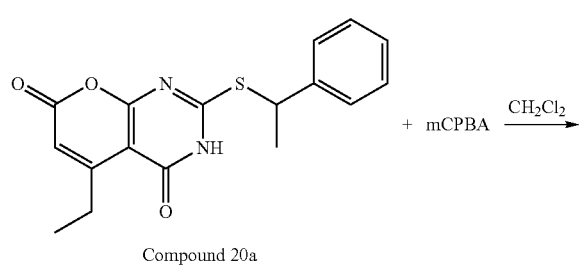

Compound 20a

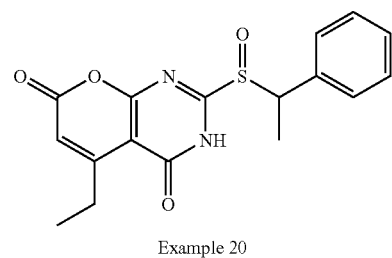

Example 20 m-CPBA (0.3 g, 70%, 1.2 mmol) was added to a suspension of Compound 20a (0.33 g, 1 mmol) in CH$_2$Cl$_2$ (30 mL) at room temperature. Solvent was removed after 3 hours and the crude product was purified using silica gel flash column chromatography eluting with 5% EtOH in EtOAc/hexanes (v/v=1:1) to give Example 20 (0.1 g, 50%). Electrospray MS [M+1]$^+$ 345.

Preparative Example 21

Example 21

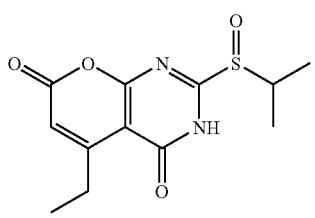

-continued

Step A:

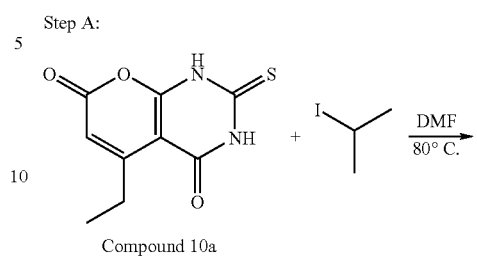

Compound 10a

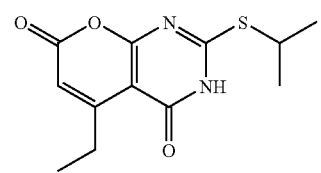

Compound 21a

2-Iodopropane (1.53 g, 9 mmol) was added to a suspension of Compound 10a (1 g, 4.5 mmol) in DMF (20 mL). The reaction mixture was stirred at 80° C. for one day. The reaction mixture was cooled down and poured into water (50 mL) and then filtered through a Buchner funnel. The solid residue was washed with water (2×20 mL) and dried under vacuum to give Compound 21a (1.05 g, 88%).

Step B:

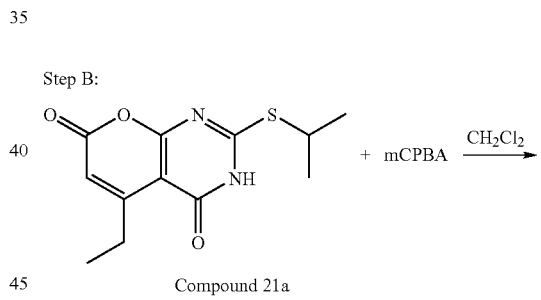

Compound 21a

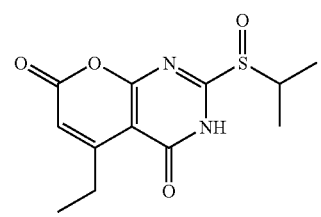

Example 21 m-CPBA (0.74 g, 70%, 3 mmol) was added to a suspension of Compound 21a (0.53 g, 2 mmol) in CH$_2$Cl$_2$ (30 mL) at room temperature. Solvent was removed after 3 hours, the crude product was purified using a silica gel flash column chromatography eluting with 0.1% AcOH in MeOH/CH$_2$Cl$_2$ (v/v=2:98) to give Example 21 (0.45 g, 80%). Electrospray MS [M+1]$^+$ 283.

Preparative Examples 22 and 23

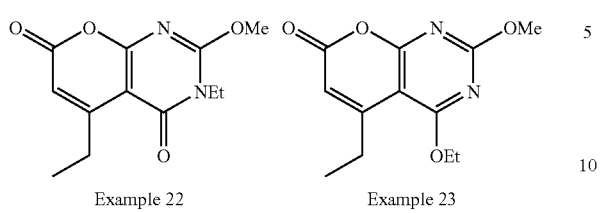

Example 22            Example 23

Step A:

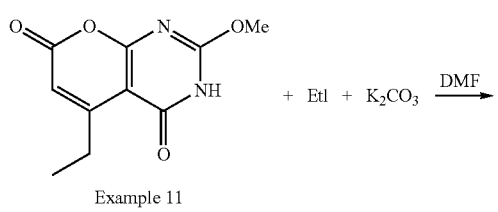

Example 11

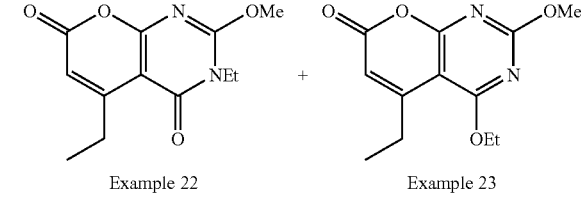

Example 22            Example 23

K$_2$CO$_3$ (36.7 mg, 0.266 mmol) was added to a mixture of Example 11 (29.6 mg, 0.133 mmol) and EtI (0.064 mL, 0.8 mmol) in DMF (1.0 mL) at room temperature. The reaction was stirred over night before it was diluted with by the addition of EtOAc (50 mL) and water (10 mL). The organic phase was washed with water (3×15 mL), brine (15 mL), and dried over MgSO$_4$. After filtration and concentration, the crude product was purified using preparative TLC with hexane/CH$_2$Cl$_2$/EtOAc (v/v/v=7/3/1) as eluent to give Example 22 (7.0 mg, 21%) and Example 23 (20 mg, 60%). Electrospray MS [M+1]$^+$ 251.1.

Preparative Example 24

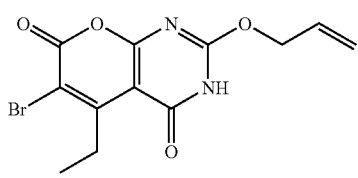

Example 24

Step A:

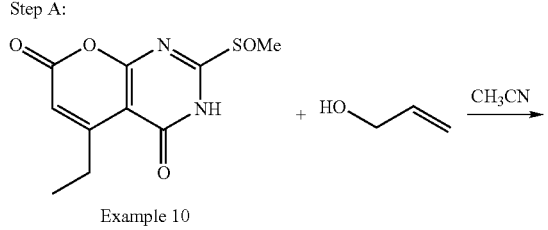

Example 10

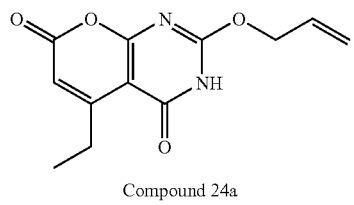

Compound 24a

Example 10 (0.216 g, 0.847 mmol) in allyl alcohol (3.0 mL) was heated at reflux overnight. After cooling to room temperature, the solvent was removed under reduced pressure and the crude product was purified using silica gel flash column chromatography eluting with EtOAc/MeOH (v/v=5/1) to give Compound 24a (0.1 g, 48%).

Step B:

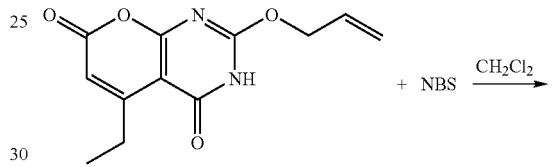

Compound 24a

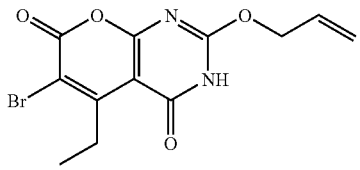

Example 24

NBS (36 mg, 0.202 mmol) was added to a solution of Compound 24a (0.040 g, 0.161 mmol) in CH$_2$Cl$_2$ (2.0 mL) at room temperature. Solvent was removed over 1 hour and the crude product was purified using silica gel flash column chromatography eluting with hexane/EA (v/v=1/1) to give Example 24 (0.025 g, 48%). Electrospray MS [M+1]$^+$ 327.1.

Preparative Example 25

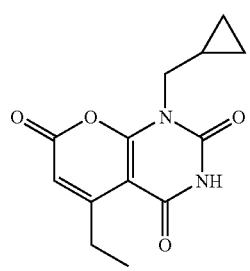

Example 25

Step A:

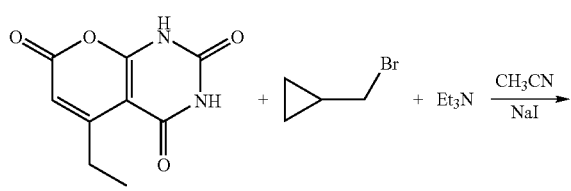

Example 1

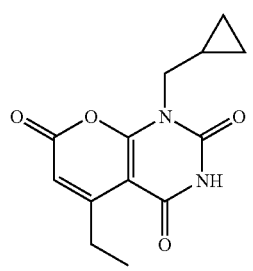

Example 25

Example 1 (0.5 g, 2.4 mmol) was taken up in CH₃CN (10 mL). Triethylamine (0.33 mL, 2.4 mmol) was added to the suspension followed by cyclopropyl methyl bromide (0.26 mL, 2.64 mmol) and NaI (0.36 g, 2.4 mmol). The reaction mixture was heated to reflux overnight. After cooling to room temperature, the solvent was evaporated in vacuo. The crude product was purified by crystallization from EtOAc/hexanes to give Example 25 (0.25 g, 40%).

Preparative Example 26

Example 26

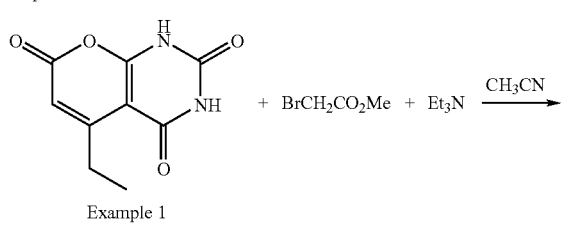

Step A:

Example 26

Example 1 (0.1 g, 0.48 mmol) was taken up in CH₃CN (3.0 mL). Triethylamine (0.067 mL. 0.48 mmol) was added to the suspension followed by methyl bromoacetate (0.046 mL, 0.48 mmol). The reaction mixture was allowed to stir overnight at room temperature. The solvent was removed under reduced pressure and the crude mixture was purified by column chromatography eluting with EtOAc/hexanes (2/3:v/v) to yield Example 26 (0.06 g, 45%).

Preparative Example 27

Example 27

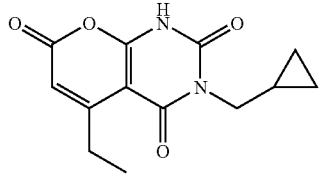

Step A:

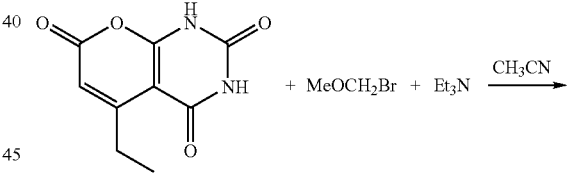

Example 1

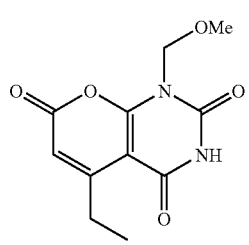

Compound 27a

Example 1 (1.0 g, 4.8 mmol) was taken up in CH₃CN (20 mL). Triethylamine (0.67 mL, 4.8 mmol) was added to the suspension followed by bromomethyl methyl ether (0.44 mL, 4.8 mmol). The reaction mixture was allowed to stir at room temperature for 10 min after which it was concentrated. The crude mixture was purified by column chromatography eluting with EtOAc/hexanes (2/3:v/v) to yield Compound 27a (0.6 g, 50%).

Step B:

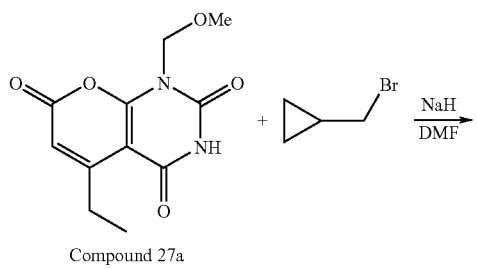

Compound 27a

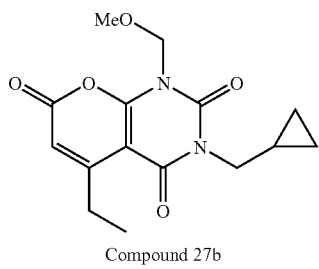

Compound 27b

Sodium hydride (0.058 g, 1.46 mmol) was added to a mixture of Compound 27a (0.335 g, 1.33 mmol) in 8 mL DMF at 0° C. followed by cyclopropyl methyl bromide (0.142 mL, 1.46 mmol). The suspension was allowed to stir at room temperature overnight before being diluted with EtOAc (10 mL) and quenched by the addition of water (5 mL). The aqueous phase was extracted with EtOAc (2×5 mL). The organic layers were combined, dried over MgSO$_4$, and concentrated to give the crude product. The crude mixture was purified by column chromatography eluting with EtOAc/hexanes (2/3:v/v) to yield Compound 27b (0.175 g, 43%).

Step C:

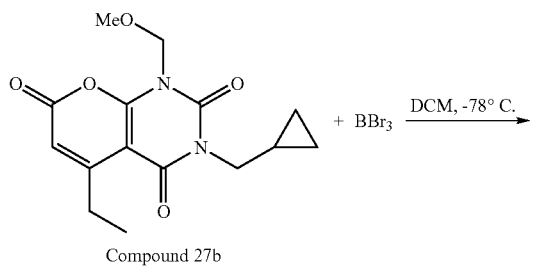

Compound 27b

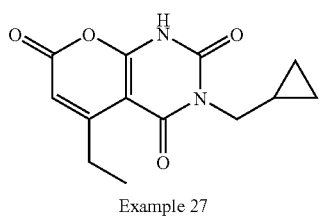

Example 27

Boron tribromide (2.85 mL, 2.85 mmol, 1.0 M solution in DCM) was added to a solution of Compound 27b (0.175 g, 0.57 mmol) in CH$_2$Cl$_2$ (8.0 mL) at −78° C. The reaction was allowed to stir for 2 h before being quenched with water (5.0 mL). The reaction mixture was extracted with EtOAc (2×5 mL). The organic layers were combined, dried over MgSO$_4$, and concentrated to give the crude product. The crude mixture was purified by column chromatography eluting with EtOAc/hexanes (2/3:v/v) to yield Example 27 (0.1 g, 67%).

Preparative Example 28

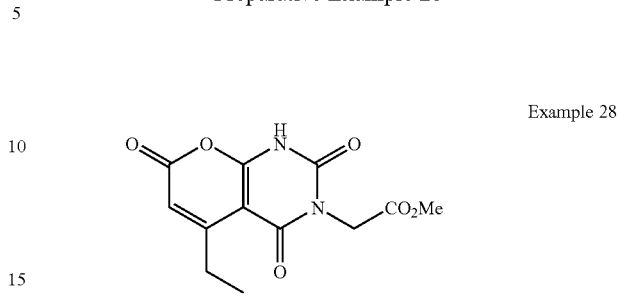

Example 28

Step A:

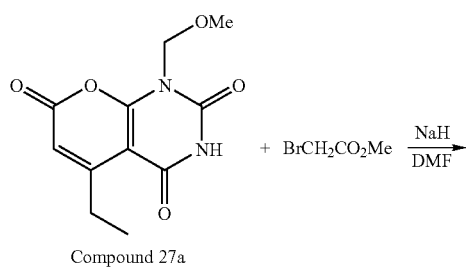

Compound 27a

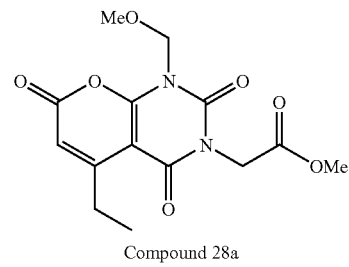

Compound 28a

Sodium hydride (0.016 g, 0.396 mmol) was added to a mixture of Compound 27a (0.100 g, 0.396 mmol) in 2 mL DMF at 0° C. followed by methyl bromoacetate (0.041 mL, 0.44 mmol). The suspension was allowed to stir at room temperature overnight before being diluted with EtOAc (5 mL) and quenched by the addition of water (5 mL). The aqueous phase was extracted with EtOAc (2×5 mL). The organic layers were combined, dried over MgSO$_4$, and concentrated to give the crude product. The crude mixture was purified by column chromatography eluting with EtOAc/hexanes (2/3:v/v) to yield Compound 28a (0.07 g, 54%).

Step B:

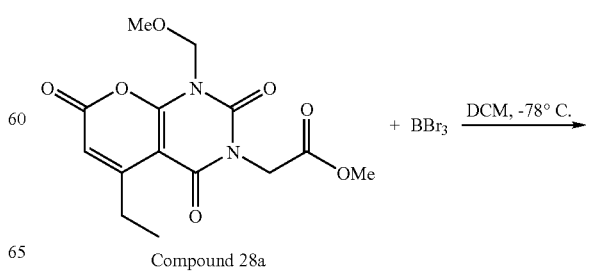

Compound 28a

-continued

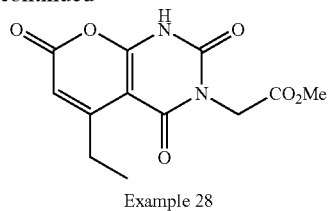

Example 28

Boron tribromide (1.1 mL, 1.1 mmol, 1.0 M solution in DCM) was added to a solution of Compound 28a (0.07 g, 0.22 mmol) in CH₂Cl₂ (3.0 mL) at −78° C. The reaction was allowed to stir for 2 h before being quenched with water (5.0 mL). The reaction mixture was extracted with EtOAc (2×5 mL). The organic layers were combined, dried over MgSO₄, and concentrated to give the crude product. The crude mixture was purified by column chromatography eluting with EtOAc/hexanes (2/3:v/v) to yield Example 28 (0.02 g, 33%).

Preparative Example 29

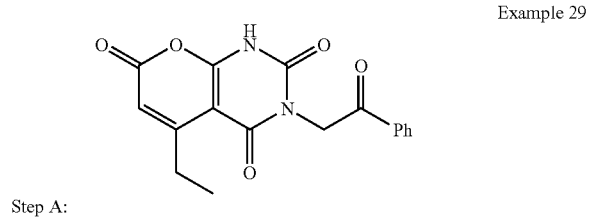

Example 29

Step A:

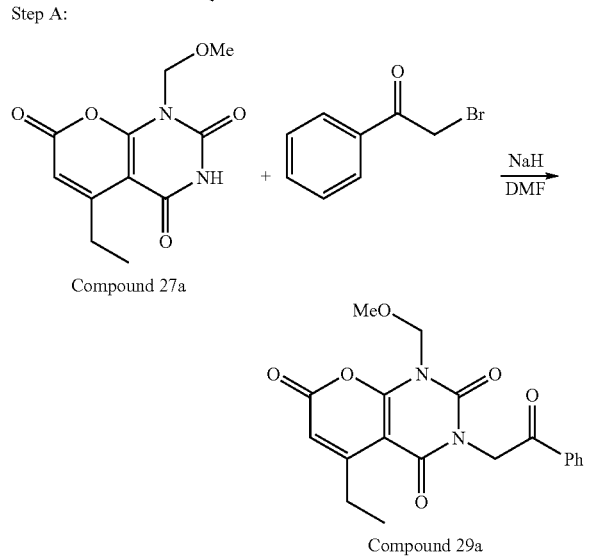

Sodium hydride (0.080 g, 1.98 mmol) was added to a mixture of Compound 27a (0.500 g, 1.98 mmol) in 8 mL DMF at 0° C. followed by 2-bromoacetophenone (0.434 g, 1.98 mmol). The suspension was allowed to stir at room temperature overnight before being diluted with EtOAc (5 mL) and quenched by the addition of water (5 mL). The aqueous phase was extracted with EtOAc (2×5 mL). The organic layers were combined, dried over MgSO₄, and concentrated to give the crude product. The crude mixture was purified by column chromatography eluting with EtOAc/hexanes (2/3:v/v) to yield Compound 29a (0.37 g, 50%).

Step B:

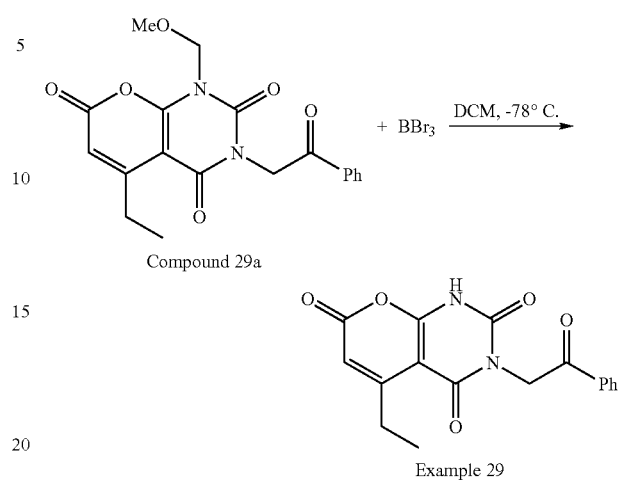

Boron tribromide (4.7 mL, 4.7 mmol, 1.0 M solution in DCM) was added to a solution of Compound 29a (0.350 g, 0.95 mmol) in CH₂Cl₂ (10.0 mL) at −78° C. The reaction was allowed to stir for 2 h before being quenched with water (5.0 mL). The reaction mixture was extracted with EtOAc (2×15 mL). The organic layers were combined, dried over MgSO₄, and concentrated to give the crude product. The crude mixture was purified by column chromatography eluting with EtOAc/hexanes (2/3:v/v) to yield Example 29 (0.175 g, 56%).

Preparative Example 30 and 31

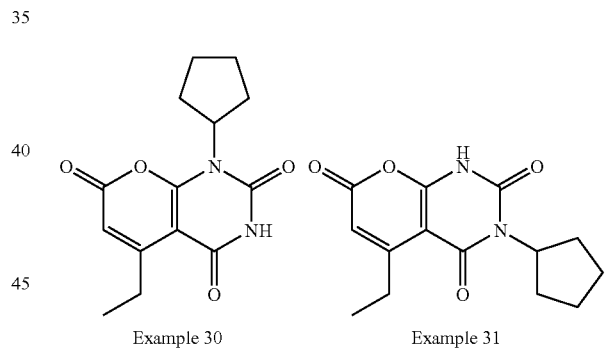

Step A:

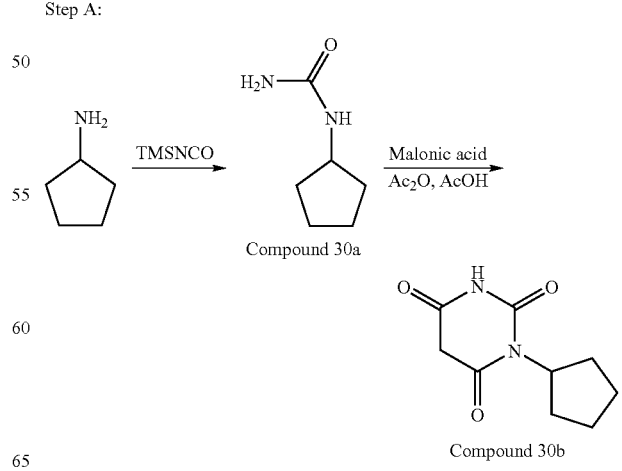

To a CH$_2$Cl$_2$ solution of cyclopentylamine was added trimethylsilyl isocyanate. The reaction mixture was stirred overnight. To this was added 200 ml of CH$_3$OH, and the mixture was stirred for another 2 hrs. The reaction mixture was concentrated and was titrated using diethyl ether to give an off-white precipitate. The precipitate was filtered through a Buchner funnel to give cyclopentyl urea Compound 30a as a white crystalline solid compound (13.0 g, 86%). To this urea Compound 30a (5.0 g, 38.7 mmol) in acetic acid (11 mL), was added malonic acid (4.0 g, 38.7 mmol) followed by acetic anhydride (18 mL) and the reaction was stirred at 70° C. for 12 hrs. The reaction mixture was concentrated, cooled in an ice bath and titrated using 4/1 EtO$_2$/EtOAc. A pale yellow crystalline solid precipitated out. The precipitate was filtered and washed 2-3 times using cold diethyl ether to obtain a pale yellow solid Compound 30b (2.5 g, 33%).

Step B:

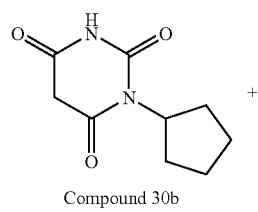

Compound 30b

+

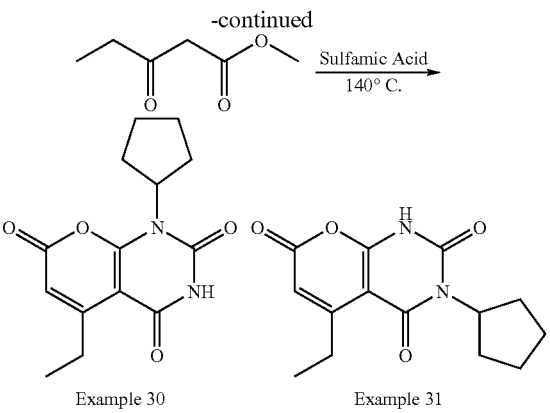

Example 30   Example 31

Compound 30b (0.75 g, 1.0 equiv., 3.82 mmol) was condensed with methyl propional acetate (0.48 mL, 3.82 mmol) in the presence of sulfamic acid and heated to 140° C. for 6 hrs, forming a dark brown solid. The reaction mixture was diluted with EtOAc, washed with H$_2$O, dried using Na$_2$SO$_4$ and concentrated to give a crude mixture. Prep TLC purification of the crude mixture in 95/5 CH$_2$Cl$_2$/CH$_3$OH yielded both the N$_1$ and N$_3$ isomers, Example 30 LCMS: (M+1) 277.1 and Example 31 LCMS: (M+1). 277.1

A similar two-step procedure was used to synthesize Examples 32-43.

| substituents | N-1 products | LCMS: (M + 1) of N-1 products | N-3 products | LCMS: (M + 1) of N-3 products |
|---|---|---|---|---|
| cyclopropyl | 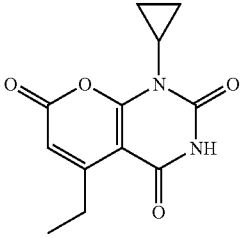 Example 32 | 249.1 | 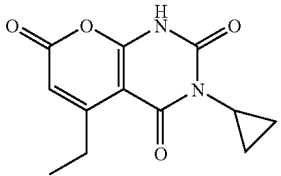 Example 33 | 249.1 |
| cyclobutyl | 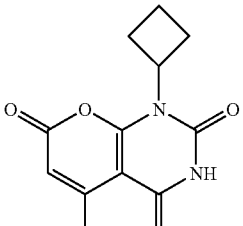 Example 34 | 263.1 | 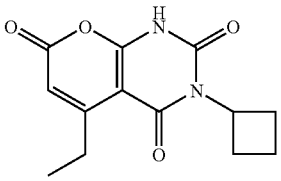 Example 35 | 263.1 |

-continued

| substituents | N-1 products | LCMS: (M + 1) of N-1 products | N-3 products | LCMS: (M + 1) of N-3 products |
|---|---|---|---|---|
| Pr | Example 36 | 251.1 | Example 37 | 251.1 |
| Et | Example 38 | 237.1 | Example 38 | 237.1 |
| Me | Example 40 | | Example 41 | 223.0 |
| allyl | Example 42 | 249.1 | Example 43 | 249.1 |

151

Using the procedure set forth above for making the compound of Example 30, and substituting the appropriate reagents and intermediates, compounds 780-785 were prepared:

| Compound No. | Structure | Electrospray LCMS [M + 1]+ |
|---|---|---|
| 780 | 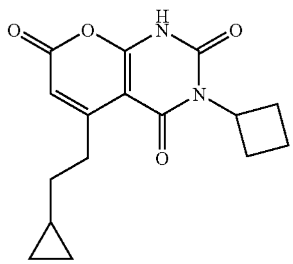 | 303.1 |
| 781 | 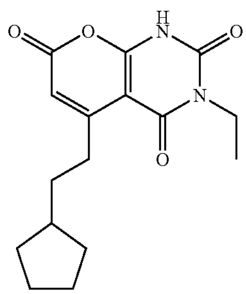 | 305.2 |
| 782 | 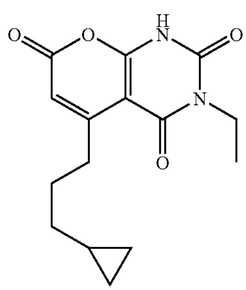 | 291.2 |
| 783 | 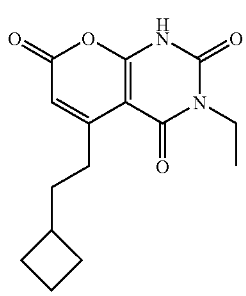 | 291.2 |
| 784 | 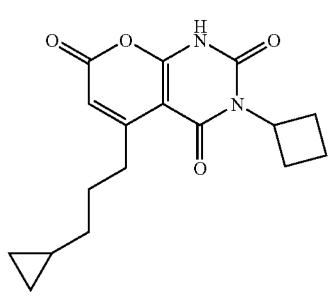 | 317.2 |

152

Preparative Example 44

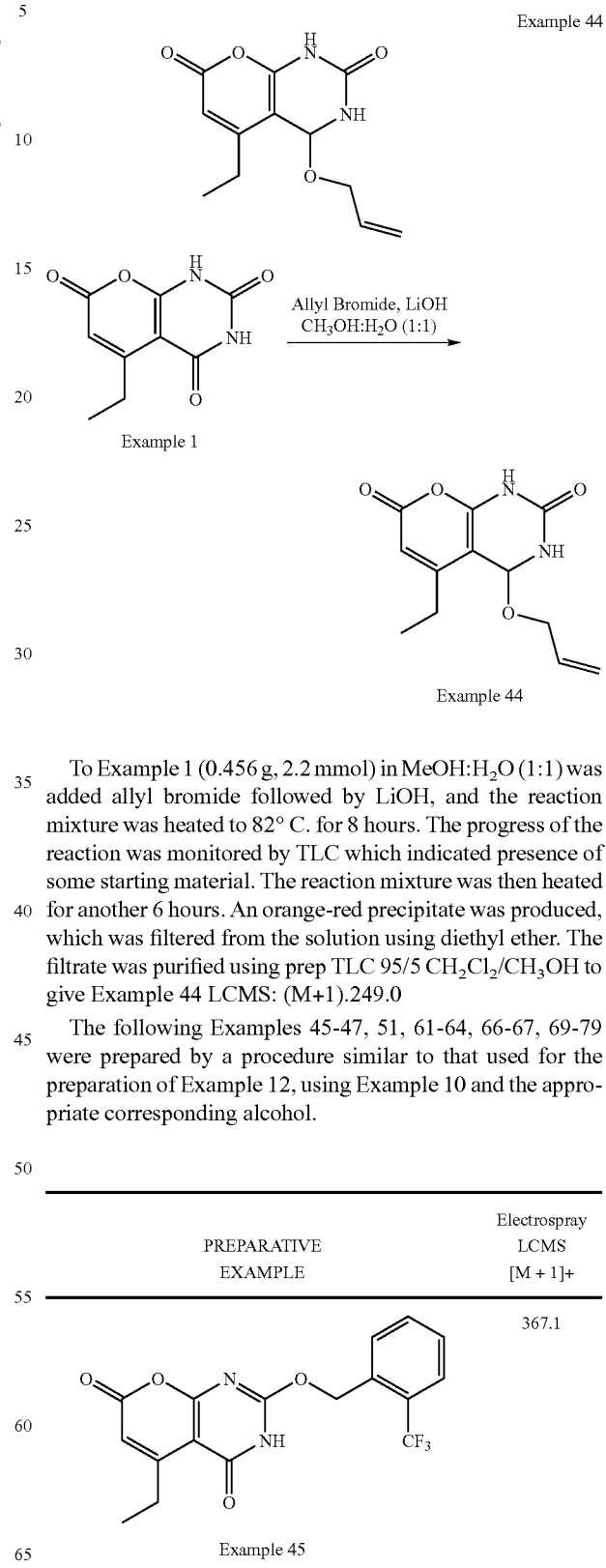

Example 44

Example 1

Example 44

To Example 1 (0.456 g, 2.2 mmol) in MeOH:H$_2$O (1:1) was added allyl bromide followed by LiOH, and the reaction mixture was heated to 82° C. for 8 hours. The progress of the reaction was monitored by TLC which indicated presence of some starting material. The reaction mixture was then heated for another 6 hours. An orange-red precipitate was produced, which was filtered from the solution using diethyl ether. The filtrate was purified using prep TLC 95/5 CH$_2$Cl$_2$/CH$_3$OH to give Example 44 LCMS: (M+1).249.0

The following Examples 45-47, 51, 61-64, 66-67, 69-79 were prepared by a procedure similar to that used for the preparation of Example 12, using Example 10 and the appropriate corresponding alcohol.

| PREPARATIVE EXAMPLE | Electrospray LCMS [M + 1]+ |
|---|---|
| | 367.1 |

Example 45

| PREPARATIVE EXAMPLE | Electrospray LCMS [M + 1]+ |
|---|---|
| 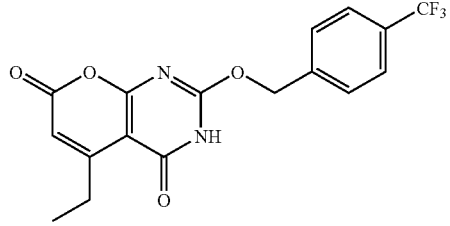<br>Example 46 | 367.1 |
| 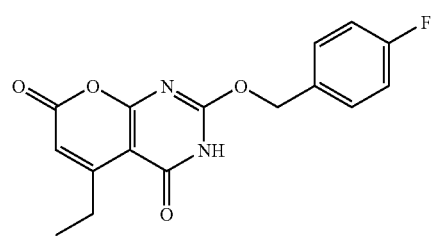<br>Example 47 | 317.1 |
| 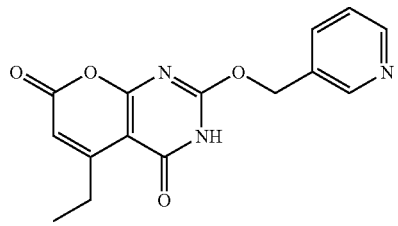<br>Example 51 | 300.1 |
| 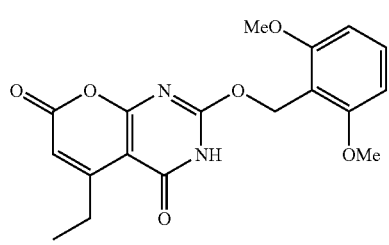<br>Example 61 | 359.1 |
| 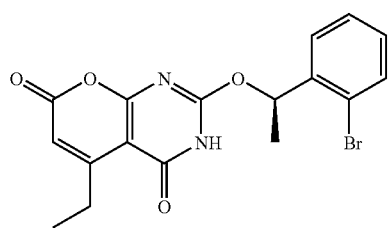<br>Example 62 | 391.1 |
| PREPARATIVE EXAMPLE | Electrospray LCMS [M + 1]+ |
|---|---|
| 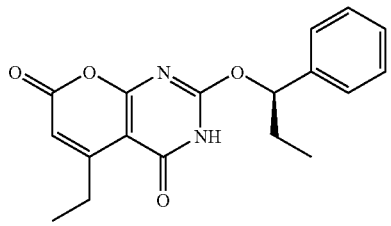<br>Example 63 | 327.1 |
| 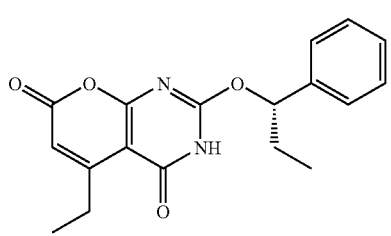<br>Example 64 | 327.1 |
| 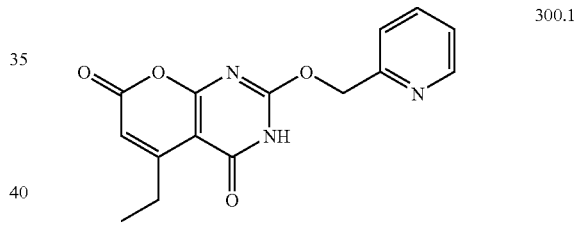<br>Example 66 | 300.1 |
| 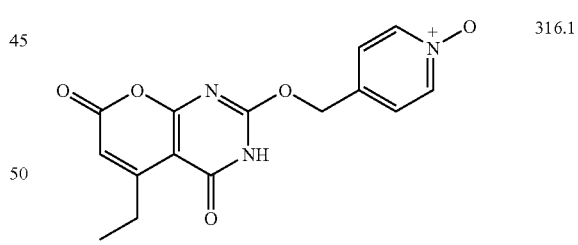<br>Example 67 | 316.1 |
| 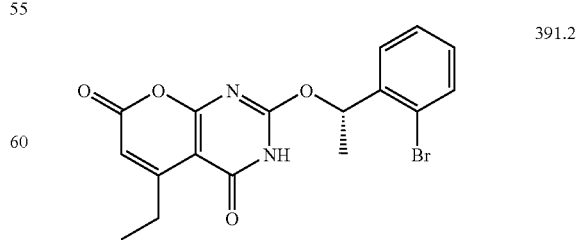<br>Example 69 | 391.2 |

| PREPARATIVE EXAMPLE | Electrospray LCMS [M + 1]+ |
|---|---|
| 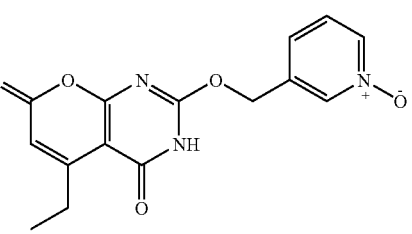 Example 70 | 314.1 |
| 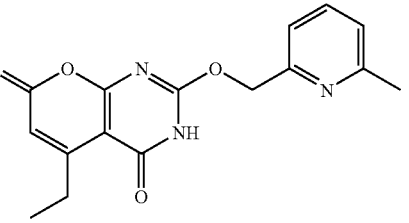 Example 71 | 316.1 |
| 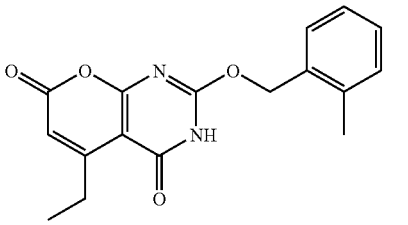 Example 72 | 314.1 |
| 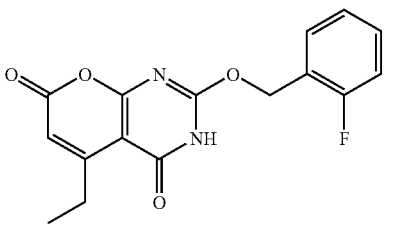 Example 73 | 313.1 |
| 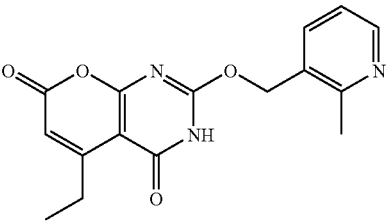 Example 74 | 317.1 |
| PREPARATIVE EXAMPLE | Electrospray LCMS [M + 1]+ |
|---|---|
| 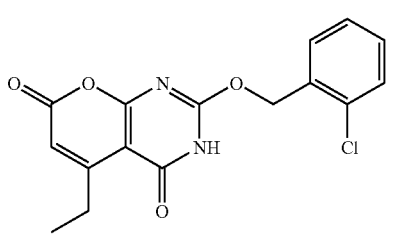 Example 75 | 383.1 |
| 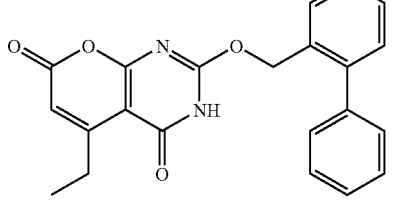 Example 76 | 333.1 |
| 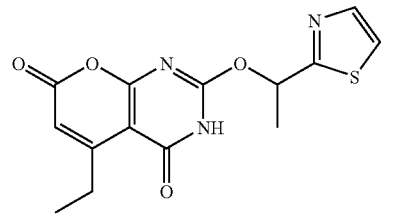 Example 77 | 375.1 |
| 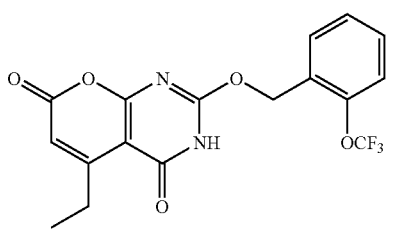 Example 78 | 320.1 |
| 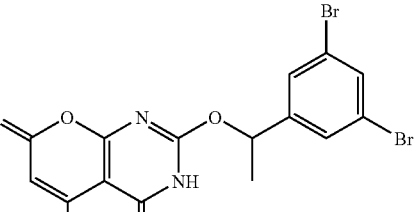 Example 79 | 469.1 |

Preparative Example 48

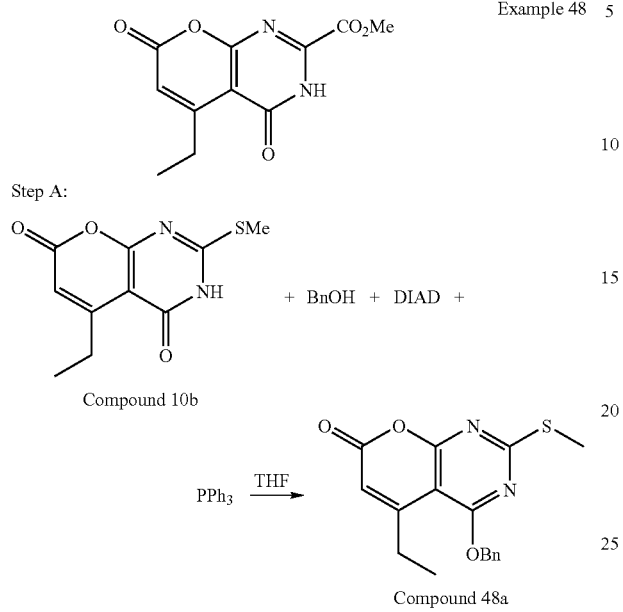

Example 48

Step A:

Compound 10b + BnOH + DIAD + PPh₃ —THF→ Compound 48a

DIAD (0.488 mL, 2.52 mmol) was added drop wise to a solution of Compound 10b (0.5 g, 2.10 mmol), BnOH (0.261 mL, 2.52 mmol) and PPh₃ (0.661 g, 2.52 mmol) in THF (6.0 mL) at room temperature. The resulting reaction mixture was stirred for 5 hours before it was worked up by silica gel flash column chromatography using a solid sample loading method, eluting with hexane/EtOAc (v/v=5/1) to give Compound 48a (0.25 g, 36%).

Step B:

Compound 48a + m-CPBA —CH₂Cl₂→ Compound 48b m-CPBA (0.384 g, 1.55 mmol, 60-70%) was added at room temperature to a solution of Compound 48a (0.17 g, 0.518 mmol) in CH₂Cl₂ (5 mL). The reaction mixture was stirred for 5 hours before it was quenched with addition of Me₂S (76 uL, 1.55 mmol). The mixture was then diluted with EtOAc and washed with NaHCO₃ solution. The organic phase was washed with water, brine, and dried (Na₂SO₄). Solvent was removed under reduced pressure, and the crude product was purified by silica gel flash column chromatography eluting with hexane/CH₂Cl₂/EtOAc (v/v/v=7/3/2) to give Compound 48b (0.15 g, 80%).

Step C:

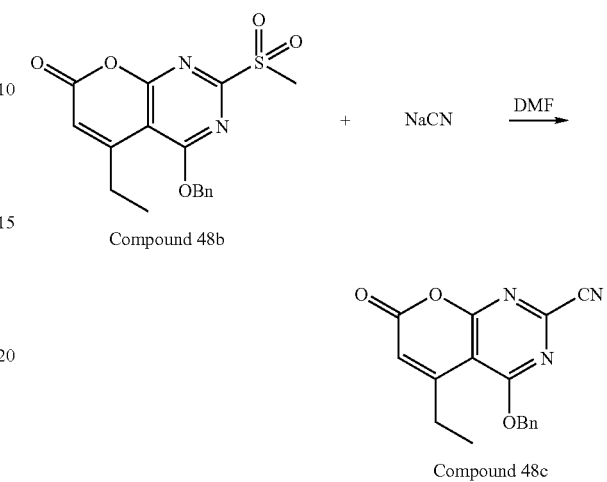

Compound 48b + NaCN —DMF→ Compound 48c

NaCN (14.0 mg, 0.286 mmol) was added to a solution of Compound 48b (85.8 mg, 0.238 mmol) in DMF (1.5 mL) at room temperature. The reaction mixture was stirred at room temperature for 2 hours before it was worked up by dilution with EtOAc and water. The organic phase was washed with water (2×), brine, and dried (MgSO₄). Solvent was removed under reduced pressure, and the crude product was purified by silica gel flash column chromatography, eluting with hexane/CH₂Cl₂/EtOAc (v/v/v=5/1/1) to give Compound 48c (37 mg, 50%).

Step D:

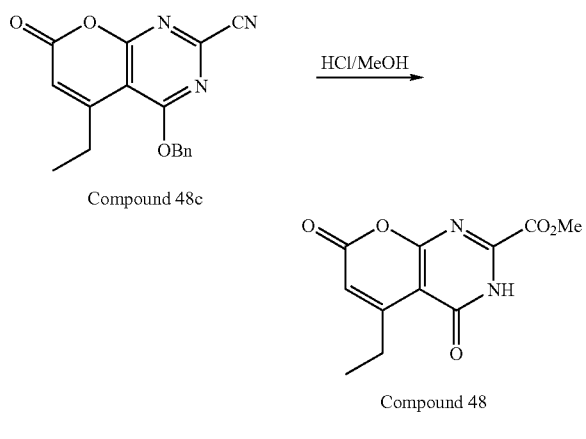

Compound 48c —HCl/MeOH→ Compound 48

A solution of Compound 48c (10 mg, 0.0326 mmol) in 4.0 M HCl in dioxane (0.7 mL) and MeOH (0.7 mL) in a sealed tube was heated at 70° C. for 7 hours. The mixture was cooled to room temperature and solvent was removed under reduced pressure to give crude product. The crude product was purified with preparative thin layer silica gel chromatography eluting with hexane/CH₂Cl₂/MeOH (v/v/v=6/4/1) to give Example 48 (5 mg, 61%).

Electrospray MS [M+1]⁺ 251.1.

Preparative Example 49

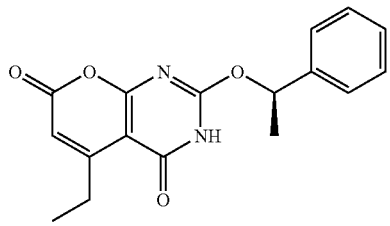

Example 49

Step A:

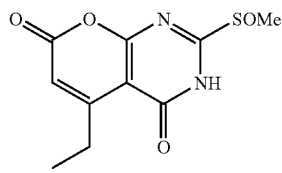

Example 10

+

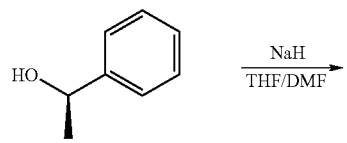

→ NaH / THF/DMF

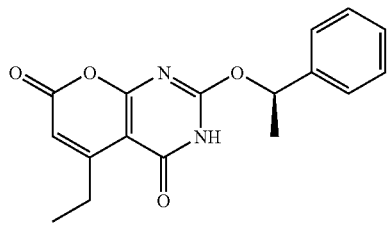

Example 49

(R)-Phenethanol (0.24 mL, 2.0 mmol) was added drop wise to a suspension of NaH (87.4 mg, 2.0 mmol, 55% in mineral oil) in THF (3.0 mL) at room temperature. The mixture was stirred for 2 hours until the solution was clear. The alkoxide thus formed was then added drop wise to a solution of the Compound 10 (0.27 g, 1.0 mmol) in DMF (3.0 mL) at room temperature. The reaction mixture was stirred for 2 hours before it was quenched by the addition of HOAc (0.11 mL, 2.0 mmol). The reaction mixture was taken up in EtOAc/CH$_2$Cl$_2$ (8/2), washed with diluted HCl (0.1 M), water and brine, then dried (MgSO$_4$). The solvent was removed under reduced pressure. The crude product was purified using silica get flash column chromatography eluting with hexane/CH$_2$Cl$_2$/EtOAc (v/v/v=7/3/2) to give Compound 49 (0.25 g, 80%).

Electrospray MS [M+1]$^+$ 313.1.

Using the method set forth above and substituting the appropriate reagents and intermediates, compounds 791-795 were prepared:

| Compound No. | Structure | Electrospray LCMS [M + 1]+ |
|---|---|---|
| 791 | 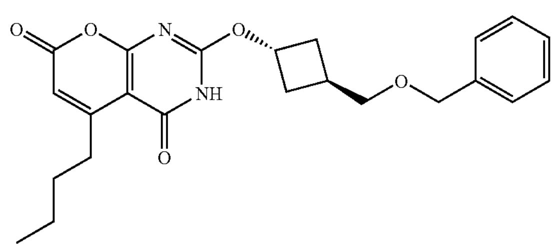 | 411.2 |
| 792 | 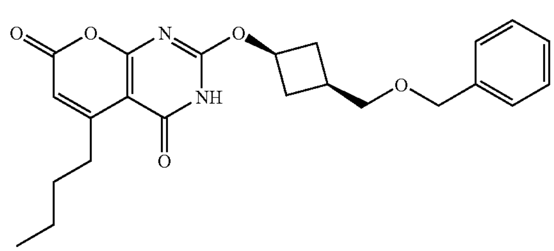 | 411.2 |

| Compound No. | Structure | Electrospray LCMS [M + 1]+ |
|---|---|---|
| 793 | ![structure] | 437.2 |
| 794 | ![structure] | 437.2 |
| 795 | ![structure] | 291.2 |

Preparative Example 50

Example 50

Example 50 was prepared by a procedure similar to that used to prepare Example 29, using Compound 27a and the appropriate corresponding bromide Electrospray MS [M+1]+ 345.1.

Preparative Example 52

Example 52

Example 52 was prepared by a procedure similar to that used to prepare Example 49, using Example 10 and (S)-phenethanol. Electrospray MS [M+1]+ 313.1.

Preparative Example 53

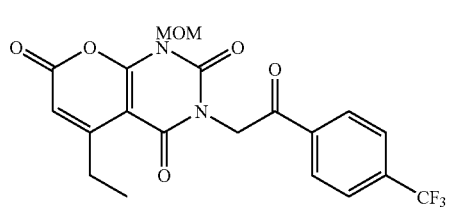

Example 53

Example 53 prepared by a procedure similar to that used in Step A of the preparation of Example 29, using Compound 27a and the appropriate corresponding bromide. Electrospray MS [M+1]$^+$ 439.4.

Preparative Example 54

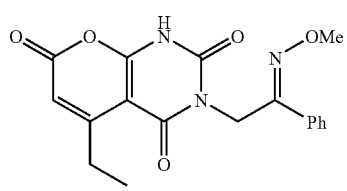

Example 54

Step A:

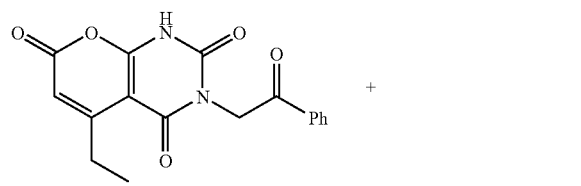

Example 29

NH$_2$OMe·HCl $\xrightarrow{\text{NaOAc, EtOH}}$

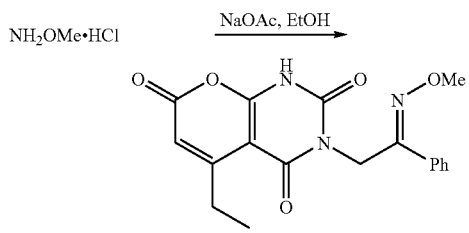

Example 54

Example 29 (0.05 g, 0.153 mmol) was taken up in ethanol (3.0 mL), Methoxylamine hydrochloride (0.051 g, 0.61 mmol) was added to the mixture followed by sodium acetate (0.038 g, 0.46 mmol). The reaction mixture was stirred at 60° C. overnight. After being cooled to room temperature, the solvent was removed under reduced pressure, diluted with CH$_2$Cl$_2$ (5 mL) and water (5 mL). The product was extracted from CH$_2$Cl$_2$ (2×5 mL), dried over MgSO$_4$, concentrated. The crude product was dissolved in minimum CH$_2$Cl$_2$, diluted with hexanes and filtered to give Example 54. Electrospray MS [M+1]$^+$ 356.1.

Preparative Example 55

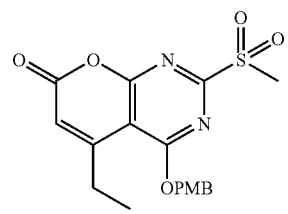

Example 55

Step A:

Compound 10b

PPh$_3$ $\xrightarrow{\text{THF}}$

Compound 55a

Di-t-butyl diazodicarboxylate (2.32 g, 10.08 mmol) was added to a solution of Compound 10b (2.0 g, 8.4 mmol), 4-methoxybenzyl alcohol (1.39 g, 10.08 mmol) and PPh$_3$ (2.64 g, 10.08 mmol) in THF (20.0 mL) at room temperature. The resulting reaction mixture was stirred for 4 hours before it was worked up by direct silica gel flash column chromatography using a solid sample loading method, eluting with hexane/CH$_2$Cl$_2$/EtOAc (v/v/v=9/1/1) to give Compound 55a (1.6 g, 53%).

Step B:

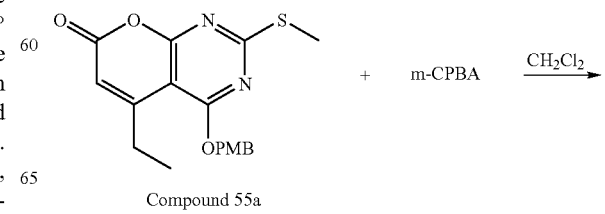

Compound 55a

165

-continued

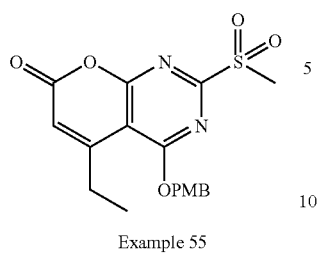

Example 55 m-CPBA (0.47 g, 1.92 mmol, 60-70%) was added at room temperature to a solution of Compound 55a (0.287 g, 0.80 mmol) in CH₂Cl₂ (8 mL). The reaction mixture was stirred for 5 hours before it was quenched by the addition of Me₂S (124 μL, 1.92 mmol). The mixture was then diluted with EtOAc and washed with NaHCO₃ solution. The organic phase was washed with water, brine, and dried (Na₂SO₄). Solvent was removed under reduced pressure, crude product was purified with silica gel flash column chromatography eluting with hexane/CH₂Cl₂/EtOAc (v/v/v=7/3/2) to give Example 55 (0.15 g, 80%). Electrospray MS [M+1]⁺ 391.1.

Preparative Example 56

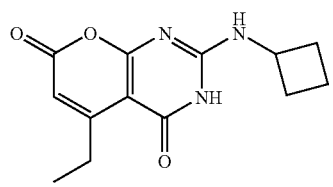

Example 56

Step A:

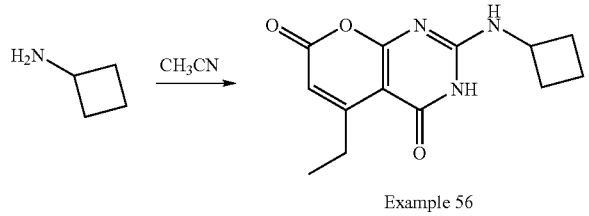

Cyclobutylamine (0.14 g, 2 mmol) was added to a suspension of Example 10 (0.25 g, 1 mmol) in CH₃CN (15 mL). The reaction mixture was stirred at room temperature for 16 hours. Solvent was removed and the crude product was purified using silica gel flash column chromatography eluting with 10% NH₄OH in MeOH/CH₂Cl₂ (v/v=3:97) to give Example 56 (0.045 g, 17%). Electrospray MS [M+1]⁺ 262.1

166

Preparative Example 57

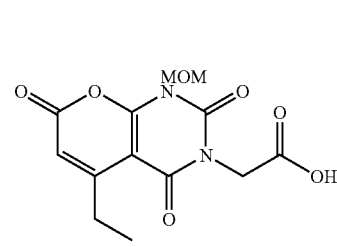

Example 57

Step A:

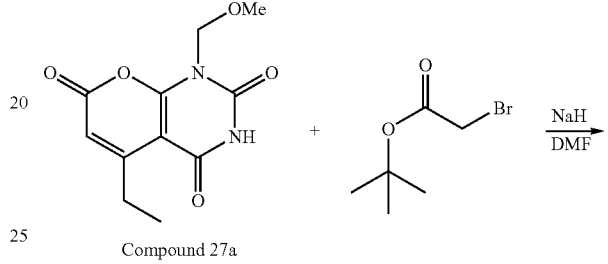

Compound 27a

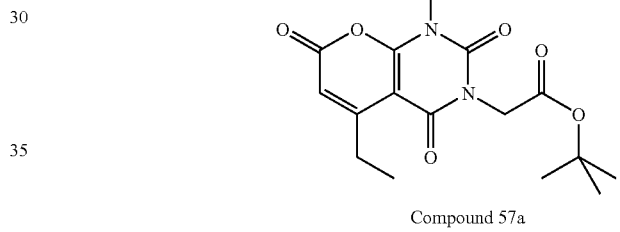

Compound 57a

A mixture of Compound 27a (2 g, 7.9 mmol) in DMF (100 mL), t-butyl bromoacetate (1.7 g, 8.7 mmol), and diisopropyl ethyl amine (1.1 g, 8.7 mmol) was stirred at 40° C. for 4 hours, then at room temperature for 16 hours. The reaction mixture was mixed with water (200 mL), and then extracted with ethyl acetate (100 mL×3). The organic solution was dried (Na₂SO₄) and concentrated. The crude product was purified using silica gel flash column chromatography eluting with MeOH/CH₂Cl₂ (v/v=2:98) to give Compound 57a (1.8 g, 62%). Electrospray MS [M+1]⁺ 367.2.

Step B:

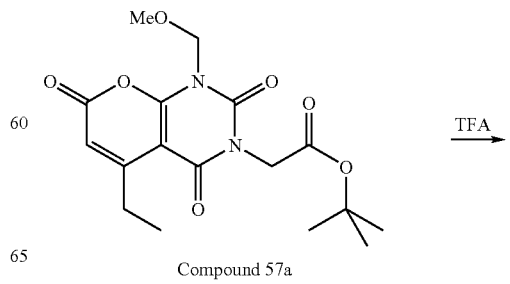

Compound 57a

-continued

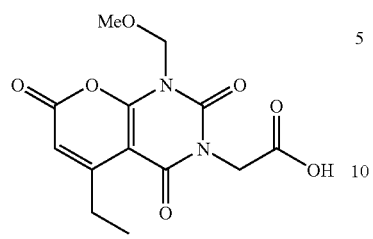

Example 57

A mixture of Compound 57a (0.95 g, 2.6 mmol) in CH$_2$Cl$_2$ (5 mL) and trifluoroacetic acid (1.5 g, 13 mmol) was stirred at room temperature for 4 hours. Removal of solvent and excess trifluoroacetic acid gave Example 57 (0.89 g, 100%). Electrospray MS [M+1]$^+$ 311.2

Preparative Example 58

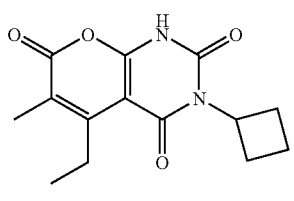

Example 58

Step A:

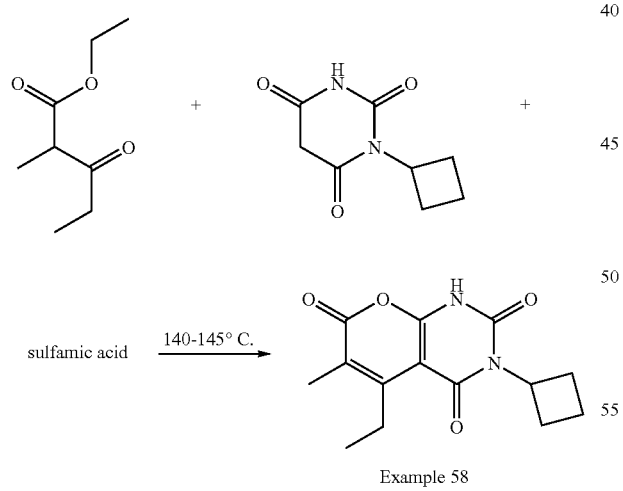

Example 58

To a mixture of mono-cyclobutylbarbituric acid (300 mg, 1.6 mmol) and 2-Methyl-3-oxo-pentanoic acid ethyl ester (1.041 g, 6.59 mmol) was added sulfamic acid (77 mg, 0.8 mmol). The mixture was heated at 140-145° C. for 48 h. The residue was loaded onto preparative silica gel plates and eluted with 5% MeOH/CH$_2$Cl$_2$ to afford Example 58 (42 mg, 9%). LCMS: M+1: 277.1

Preparative Example 59

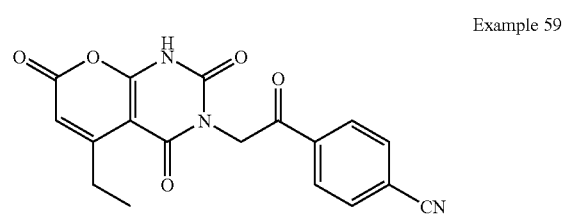

Example 59

EXAMPLE 59 was prepared using a two step procedure similar to that used for the preparation of Example 29, using Compound 27a and the appropriate corresponding bromide. Electrospray MS [M+1]$^+$ 252.1.

Preparative Example 60

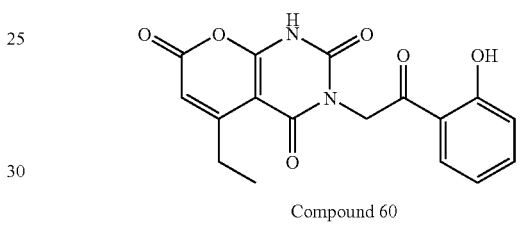

Compound 60

Step A:

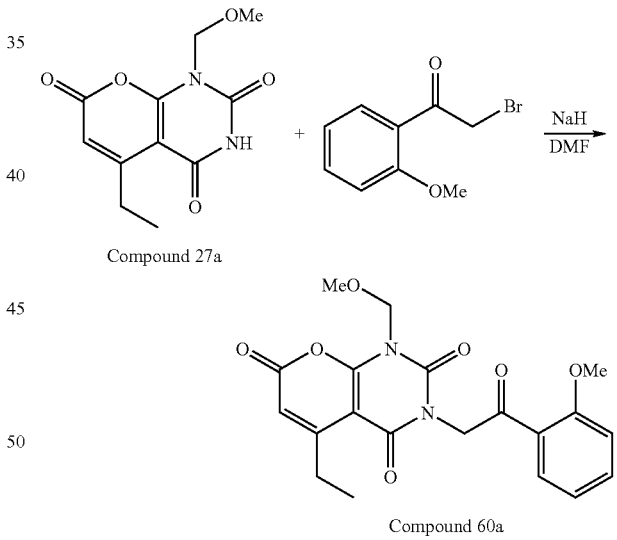

Compound 60a

Sodium hydride (0.035 g, 0.869 mmol) was added to a mixture of Compound 27a (0.200 g, 0.79 mmol) in 3 mL DMF at 0° C. followed by 2-methoxyphenacyl bromide (0.2 g, 0.87 mmol). The suspension was allowed to stir at room temperature overnight before being diluted with EtOAc (10 mL) and quenched by the addition of water (5 mL). The aqueous phase was extracted with EtOAc (2×5 mL). The organic layers were combined, dried over MgSO$_4$, and concentrated to give the crude product. The crude mixture was purified by column chromatography eluting with EtOAc/hexanes (2/3:v/v) to yield Compound 60a.

Step B:

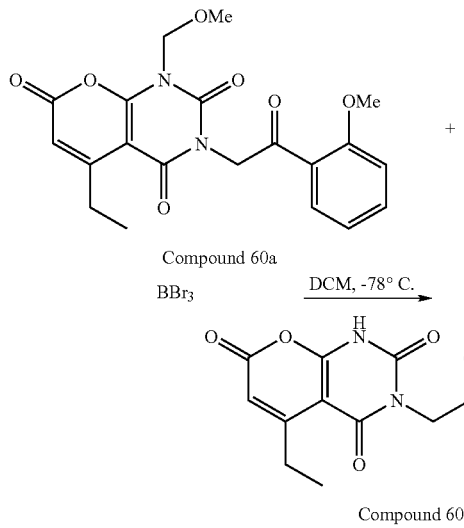

Compound 60a

BBr₃, DCM, -78° C.

Compound 60

Boron tribromide (1.3 mL, 1.31 mmol, 1.0 M solution in DCM) was added to a solution of Compound 60a (0.105 g, 0.262 mmol) in CH₂Cl₂ (5.0 mL) at −78° C. The reaction mixture was allowed to stir for 2 h before being quenched with water (5.0 mL). The reaction mixture was extracted with EtOAc (2×5 mL). The organic layers were combined, dried over MgSO₄, and concentrated to give the crude product. The crude mixture was purified by column chromatography eluting with EtOAc/hexanes (2/3:v/v) to yield Compound 60. Electrospray MS [M+1]⁺ 343.1.

Preparative Example 65

Example 65

Step A:

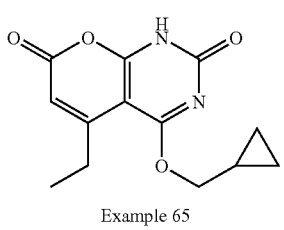

Compound 12

K₂CO₃, DMF

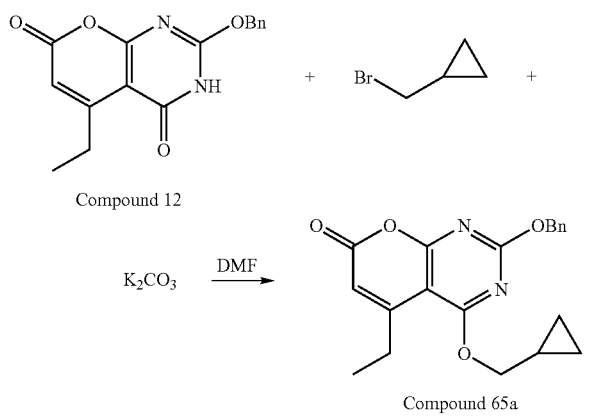

Compound 65a

K₂CO₃ (64.7 mg, 0.47 mmol) was added to a mixture of Example 12 (70 mg, 0.235 mmol) and cyclopropyl methyl bromide (0.068 mL, 0.705 mmol) in DMF (2.0 mL) at room temperature. The reaction mixture was stirred overnight before it was diluted by the addition of EtOAc (50 mL) and water (10 mL). The organic phase was washed with water (3×15 mL), brine (15 mL), and dried over MgSO₄. After filtration and concentration, the crude product was purified using preparative TLC with hexane/CH₂Cl₂/EtOAc (v/v/v=7/3/1) as eluent to give Compound 65a (26 mg, 31%)

Step B:

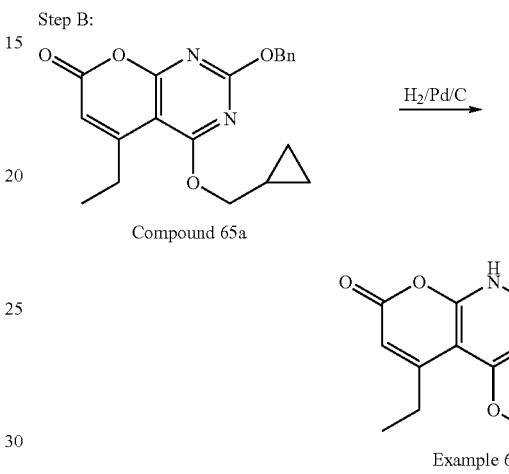

Compound 65a

H₂/Pd/C

Example 65

Compound 65a (26 mg, 0.074 mmol) in EtOH (5.0 mL) was treated at room temperature with Pd/C (7.8 mg, 10 wt %) and was hydrogenated with a H₂ balloon for 30 minutes. The reaction mixture was filtered through a short pad of Celite and the residue was washed with EtOH (15 mL). Solvent was removed under reduced pressure and the crude product was purified using preparative TLC with hexane/CH₂Cl₂/MeOH (v/v/v=3/7/1) as eluent to give Example 65 (6 mg, 30%). Electrospray MS [M+1]⁺ 263.1.

Using the method set forth above and substituting the appropriate reagents and intermediates, compounds 786-790 were prepared:

| Compound No. | Structure | Electrospray LCMS [M+]+ |
|---|---|---|
| 786 | 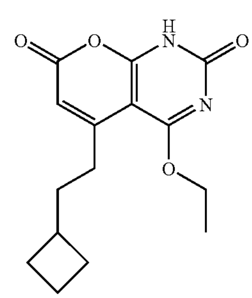 | 291.2 |

| Compound No. | Structure | Electrospray LCMS [M + ]+ |
|---|---|---|
| 787 | 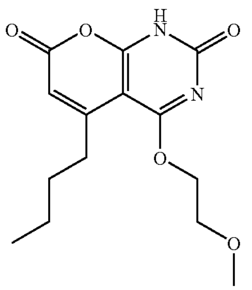 | 295.2 |
| 788 | 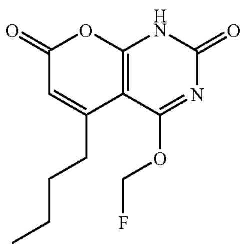 | 269.1 |
| 789 | 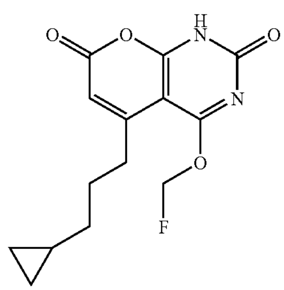 | 295.2 |
| 790 | 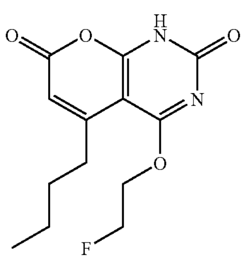 | 283.2 |

Preparative Example 68

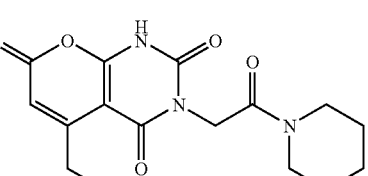

Example 68

-continued

Step A:

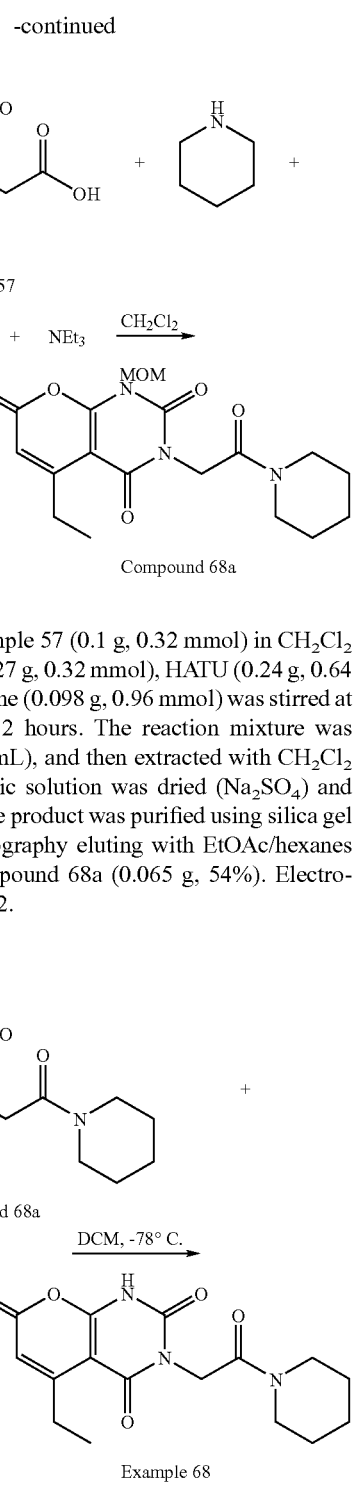

Example 57

Compound 68a

The mixture of Example 57 (0.1 g, 0.32 mmol) in CH$_2$Cl$_2$ (5 mL), piperidine (0.027 g, 0.32 mmol), HATU (0.24 g, 0.64 mmol), and triethylamine (0.098 g, 0.96 mmol) was stirred at room temperature for 2 hours. The reaction mixture was mixed with water (20 mL), and then extracted with CH$_2$Cl$_2$ (10 mL×2). The organic solution was dried (Na$_2$SO$_4$) and concentrated. The crude product was purified using silica gel flash column chromatography eluting with EtOAc/hexanes (v/v=1:1) to give Compound 68a (0.065 g, 54%). Electrospray MS [M+1]$^+$ 378.2.

Step B:

Compound 68a

Example 68

1M BBr$_3$ solution in CH$_2$Cl$_2$ (0.75 mL, 0.75 mmol) was added to a solution of Compound 68a (0.056 g, 0.15 mmol) at −78° C. After the reaction mixture was stirred at −78° C. for 2 hours, water (5 mL) was added. The organic solution was dried (Na$_2$SO$_4$) and concentrated. The crude product was purified using silica gel flash column chromatography eluting with 10% NH$_4$OH in MeOH/CH$_2$Cl$_2$ (v/v=3:97) to give Example 68 (0.01 g, 20%). Electrospray MS [M+1]$^+$ 334.2.

Preparative Example 80

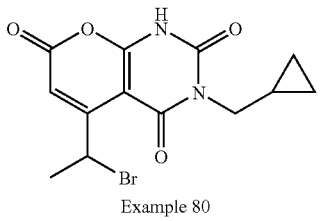
Example 80

Step A:

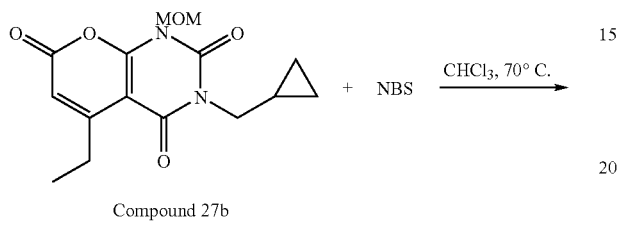
Compound 27b

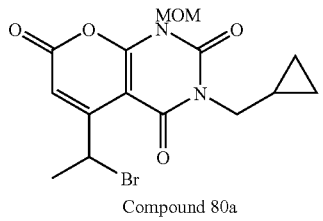
Compound 80a

Compound 27a (0.1 g, 0.33 mmol) was taken up in CH$_2$Cl$_2$ at room temperature. NBS was then added and the reaction was stirred for 4 hours. After no progress in the reaction was observed, a mixture of NBS (0.061 g, 0.34 mmol) in chloroform (4 mL) was added. The reaction mixture was heated for 12 hrs at 70° C. Both the TLC (30/70 EtOAc/Hexane) and mass spectrogram indicated that the reaction was complete. The reaction mixture was cooled to room temperature and diluted with CH$_2$Cl$_2$ and washed with H$_2$O. The organic phase was dried with Na$_2$SO$_4$ and solvent was removed to give the crude product. Preparative silica gel chromatography purification in EtOAc/Hexane (v/v=30/70) yielded Compound 80a (0.075 g, 60%).

Step B:

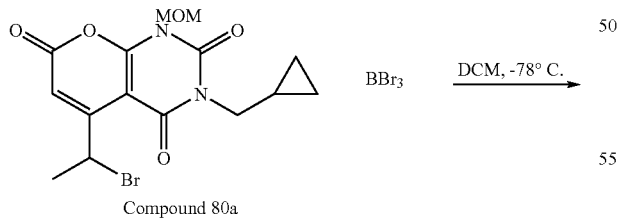
Compound 80a

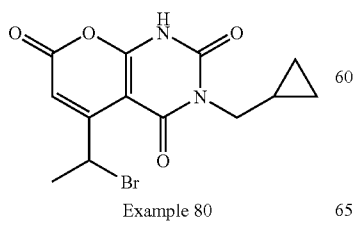
Example 80

Compound 80a (0.070 g, 0.18 mmol) was taken up in CH$_2$Cl$_2$ and the mixture was cooled to −78° C. 1M BBr$_3$ (0.909 mL, 0.9 mmol) was added. The reaction mixture was stirred for 4 hours. Upon completion of the reaction, the mixture was diluted with CH$_2$Cl$_2$, washed with H$_2$O, dried with Na$_2$SO$_4$, and then solvent was removed to give crude product. The crude product was purified by preparative silica gel chromatography using 30/70 EtOAc/Hexane, to give Example 80. Electrospray MS [M+1]$^+$ 341.2.

Preparative Example 81

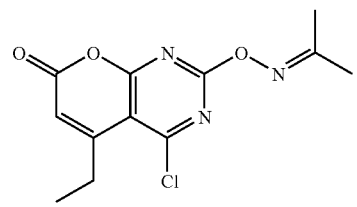
Example 81

Step A:

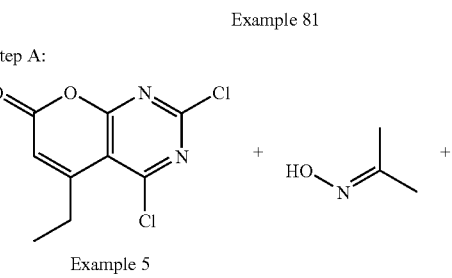
Example 5

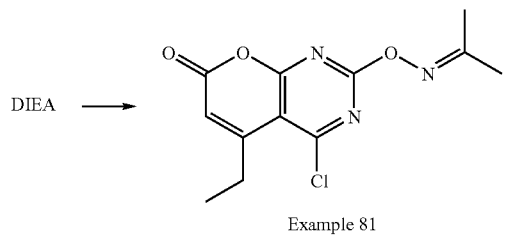
Example 81

To a mixture of Example 5 (84 mg, 0.34 mmol) and acetone oxime (27.5 mg, 0.37 mmol) was added DIEA (0.09 ml, 0.52 mmol) and the mixture was stirred for 3 days. The mixture was concentrated and was subjected to silica gel column chromatography to give Example 81 (30 mg, 31%) LCMS: M+1: 282.1

Preparative Example 92

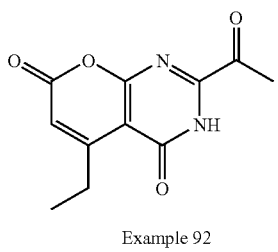
Example 92

Step A:

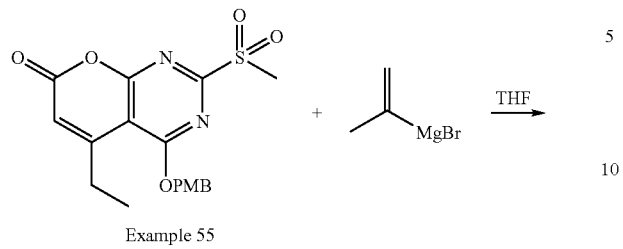

Example 55

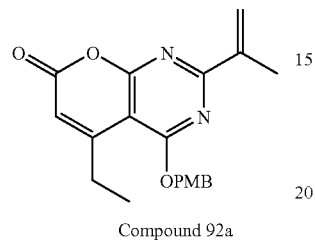

Compound 92a

Isopropenyl magnesium bromide (0.95 mL, 0.475 mmol, 0.5 M in THF) was added drop wise to a solution of Example 55 (0.133 g, 0.341 mmol) in THF (4.0 mL) at 0° C. The mixture was stirred at 0° C. for 2 hours before it was quenched with HCl (0.2 M). The mixture was taken up in EtOAc and washed with water and brine. The organic phase was dried over MgSO$_4$. Solvent was removed under reduced pressure and the crude product was purified with silica gel flash column chromatography eluting with hexane/CH$_2$Cl$_2$/EtOAc (v/v/v=4/1/1) to give Compound 92a (59 mg, 49%).

Step B:

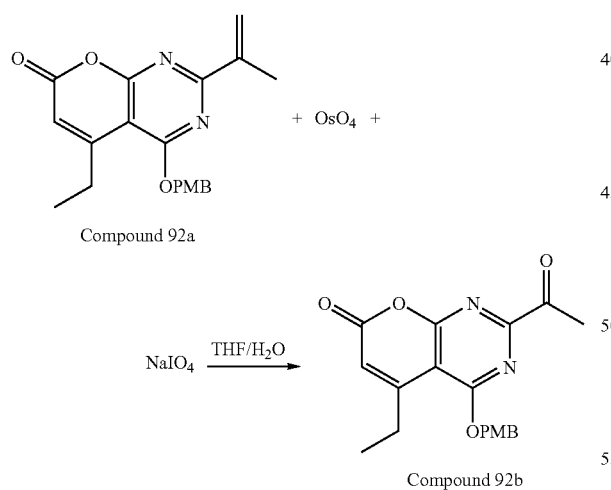

NaIO$_4$ (70.1 mg, 0.328 mmol) was added to a solution of Compound 92a (46.2 mg, 0.131 mmol) and OsO4 (22.2 μL, 4 wt % in water) in THF (5.0 mL) and water (5.0 mL) at room temperature. The reaction mixture was stirred overnight before it was quenched by the addition of Me$_2$S (20 μL, 0.328 mmol). The mixture was diluted with EtOAc and washed with HCl (0.5 M), water and brine. The organic phase was dried over MgSO$_4$. Solvent was removed under reduced pressure and the crude product was purified by silica gel flash column chromatography eluting with hexane/CH$_2$Cl$_2$/EtOAc (v/v/v=2/1/1) to give Compound 92b (39 mg, 84%).

Step C:

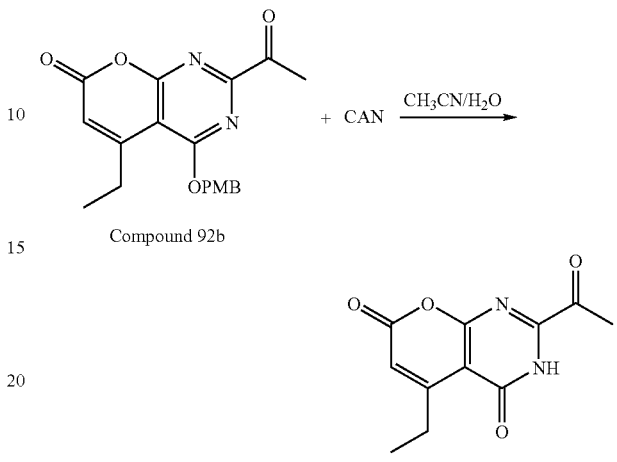

Example 92

Ceric ammonium nitrate (70.9 mg, 0.129 mmol) was added to a solution of Compound 92b (20.8 mg, 0.059 mmol) in MeCN (3.0 mL) and water (0.3 mL) at room temperature. The reaction mixture was stirred for 2 hours before it was diluted with EtOAc. The organic phase was washed with HCl (0.5 M), water, brine and dried over MgSO$_4$. Solvent was removed under reduced pressure and crude product was purified using preparative TLC with hexane/CH$_2$Cl$_2$/MeOH (v/v/v=2/8/1) as eluent to give Example 92 (8 mg, 58%).Electrospray MS [M+1]$^+$ 235.1.

Examples 82-91 were prepared by procedures similar to those used for the preparation of Example 49, using Example 10 and the appropriate corresponding alcohols.

| PREPARATIVE EXAMPLE | Electrospray LCMS [M + 1]+ |
|---|---|
| 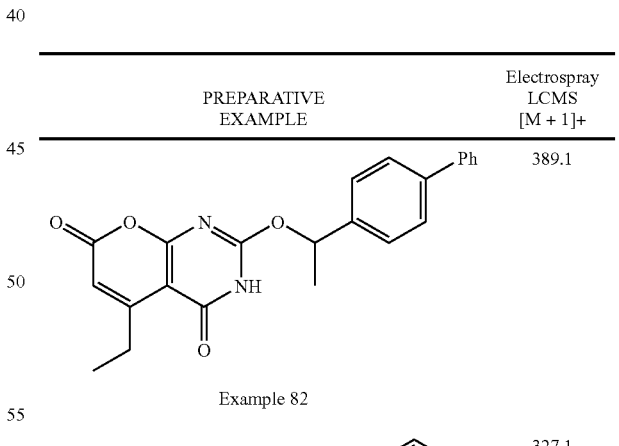<br>Example 82 | 389.1 |
| 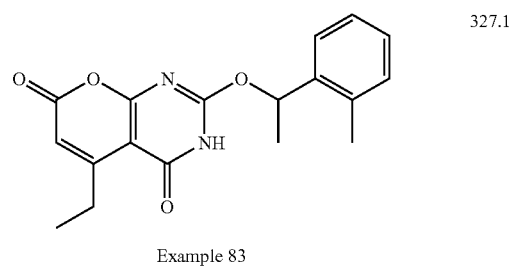<br>Example 83 | 327.1 |

-continued
| PREPARATIVE EXAMPLE | Electrospray LCMS [M + 1]+ |
|---|---|
| 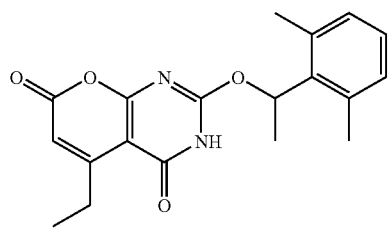<br>Example 84 | 341.1 |
| 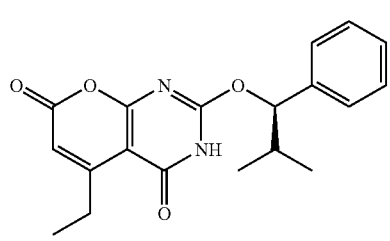<br>Example 85 | 341.1 |
| 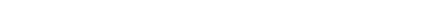<br>Example 86 | 391.1 |
| 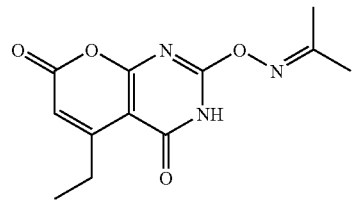<br>Example 87 | 264.1 |
| 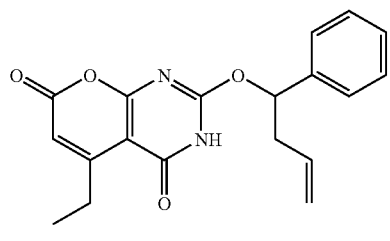<br>Example 88 | 339.1 |
-continued
| PREPARATIVE EXAMPLE | Electrospray LCMS [M + 1]+ |
|---|---|
| 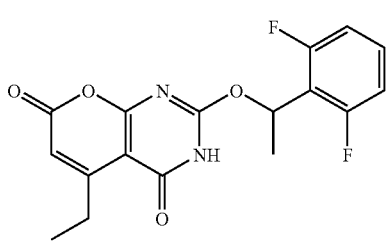<br>Example 89 | 349.1 |
| Example 90 | 331.1 |
| Example 91 | 341.1 |
Preparative Example 92
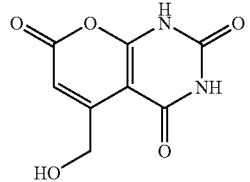
Example 92
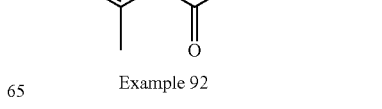
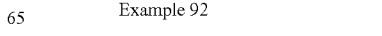
Example 92

-continued

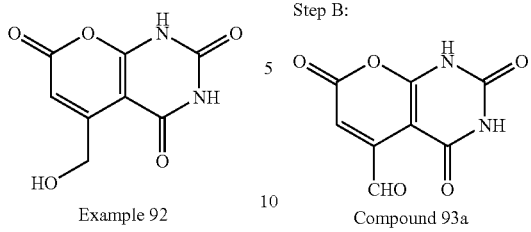
Example 92

Example 2 (0.71 g, 3.66 mmol, 1 eq) and SeO$_2$ (0.46 g, 1.1 eq) were mixed together in 1,4-dioxane (10.5 mL) and THF (1.5 mL) and the mixture was heated to 90° C. in air for 24 hr. 5% of the resulting crude product was purified by directly loading it onto a reverse-phase HPLC column to afford the desired product Example 92 (7.4 mg) as a white solid.

$^1$H NMR (CD$_3$OD): δ 4.80 (s, 2 H) 6.20 (s, 1 H)

Mass of C$_8$H$_7$N$_2$O$_5$ (MH)$^+$: 211. Found: 211.

Preparative Example 93

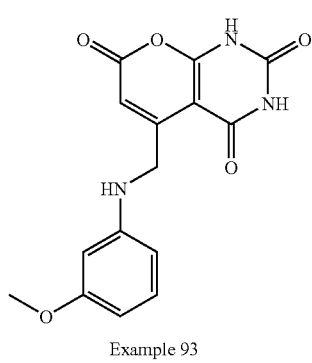
Example 93

Step A:

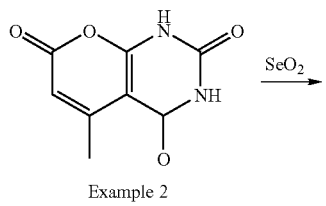

Compound 93a was prepared by a procedure similar to that used to prepare alcohol Example 92, except that the alcohol was allowed to oxidize further to the corresponding aldehyde. After purification several times using reverse-phase HPLC, Compound 93a (90 mg) was obtained.

Mass of C$_8$H$_5$N$_2$O$_5$ (MH)$^+$: 209. Found: 209.

Step B:

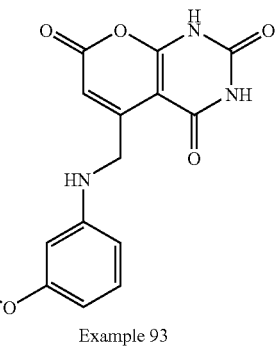
Compound 93a

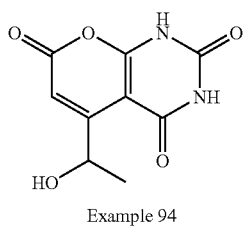
Example 93

Compound 93b (90 mg, 0.43 mmol, 1 eq)) was mixed with 3-methoxyaniline (109 mg, 2 equiv.) and sodium triacetoxyborohydride (185 mg, 2 equiv.) in 2 mL of THF. After stirring overnight, the reaction mixture was quenched with methanol. Preparative TLC afforded 15.3 mg of the desired product Example 93.

$^1$H NMR (CD$_3$OD): δ 3.60 (s, 3 H) 4.60 (s, 2 H) 5.75 (s, 1 H) 6.20 (m, 3 H) 6.95 (m, 1 H)

Mass of C$_{15}$H$_{14}$N$_3$O$_5$ (MH)$^+$: 316. Found: 316.

Preparative Example 94

Example 94

Example 1

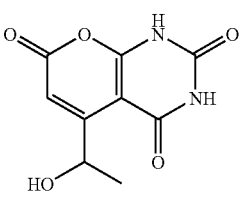
Example 94

Example 94 was prepared by a procedure similar to that used to prepare Example 92, except that Example 1 was oxidized instead of Example 2.

$^1$H NMR (CD$_3$OD): δ 1.38 (d, 2 H, J=6.8 Hz) 5.50 (q, 1 H, J=6.8 Hz) 6.20 (s, 1 H)

Mass of C$_9$H$_9$N$_2$O$_5$ (MH)$^+$: 225. Found: 225.

Preparative Example 95

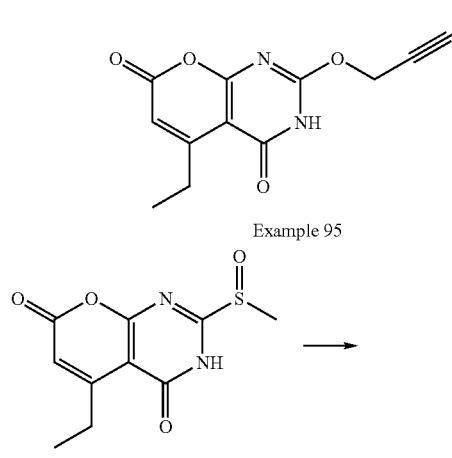

Example 95

Example 10

Example 95

2-butyn-1-ol (140 mg, 2 mmol, 2 equiv.) in 4 mL of THF was treated with 1.6 M n-BuLi (1.2 mL, 2 equiv.) at 0° C. for 5 min to provide an alkoxide solution. Example 10 (0.25 g, 1 mmol, 1 equiv.) was then added to the alkoxide solution. After stirring 1.5 hr, 0.12 g of acetic acid (2 equiv.) was added to the solution. The solvent was removed and extraction with diethyl ether and water provided a white solid. The solid was washed with cold diethyl ether and dried under vacuum. 80 mg of the desired product Example 95 was obtained.

$^1$H NMR (CDCl$_3$): δ 1.20 (t, 2 H, J=6.8 Hz) 1.83 (s, 3 H) 3.00 (q, 2 H, J=6.98 Hz) 5.00 (s, 2 H) 6.00 (s, 1 H)

Mass of C$_{13}$H$_{13}$N$_2$O$_4$ (MH)$^+$: 261. Found: 261.

Preparative Example 96

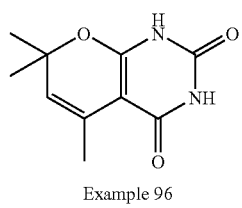

Example 96

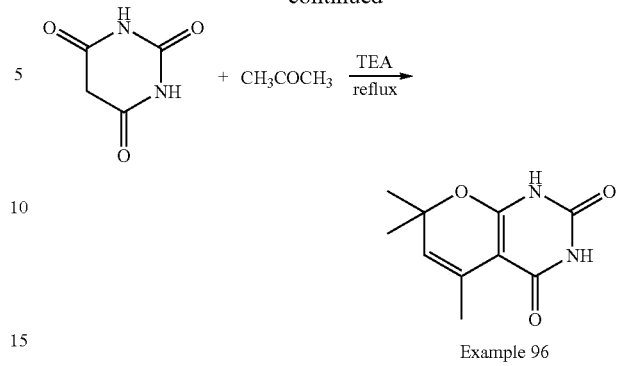

Example 96

Barbituric acid (1.0 g, 7.81 mmol) was taken up in excess acetone. Triethylamine (2 mL) was added, and the reaction mixture was refluxed overnight after which it was cooled and filtered. The crude solid was purified by preparative TLC (8:1:1/EtOAc:DCM:MeOH) to yield the desired product, Example 96.

Electrospray MS [M+1]$^+$ for Example 96 is 209.0

Preparative Examples 97 and 98

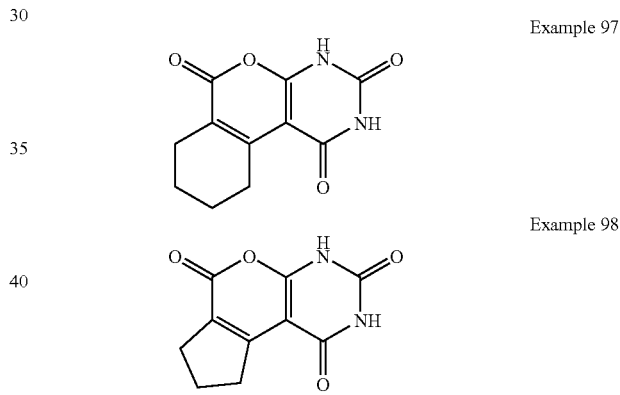

Example 97

Example 98

Examples 97 and 98 were prepared by methods analogous to the method used to prepare Example 1, except that 2-oxo-cyclohexanecarboxylic acid methyl ester and 2-oxo-cyclo-pentanecarboxylic acid methyl ester, respectively, were used instead of methylpropionylacetate.

Electrospray MS [M+1]$^{+ for}$ 96 and 97 are 235.1.

Preparative Example 99

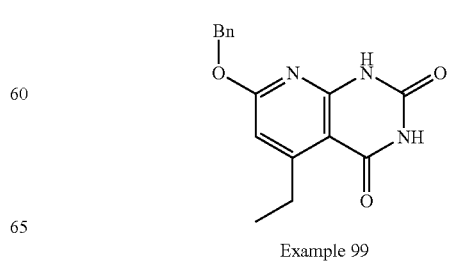

Example 99

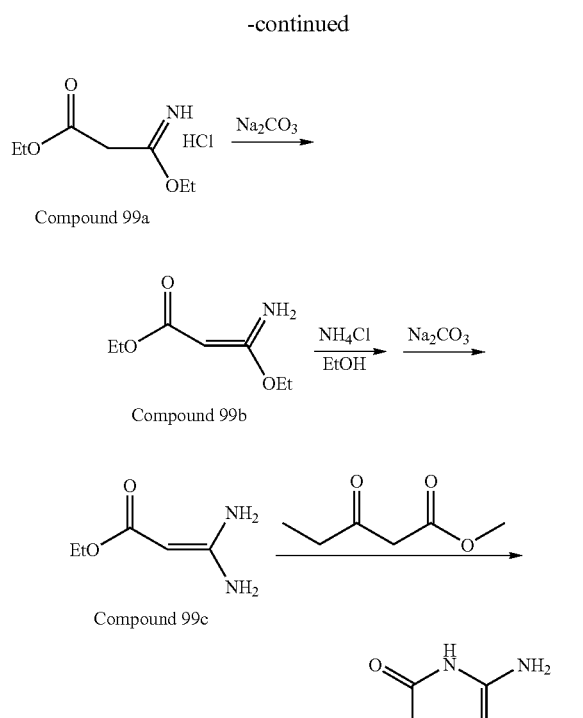

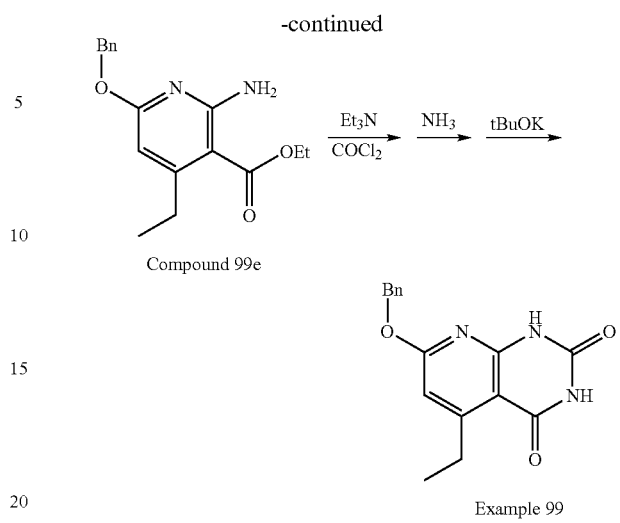

Compound 99d (3.0 g, 14.28 mmol) was treated with BnBr (2.44 g, 1 eq) and K$_2$CO$_3$ (3.94 g, 2 eq) in 100 mL acetone at 70° C. for 17 h. The solvent was removed and chromatographic purification (5% EtOAc in hexane) provided 2.53 g pure Compound 99e in 58% yield.

Compound 99e (0.3 g, 1 mmol) was treated with Et$_3$N (0.22 g, 2.2 eq), COCl$_2$ (1.9 M in toluene, 0.53 mL, 1 equiv) in 5 mL DCM at −78° C. for 45 min. The reaction mixture was warmed to room temperature in 1 h. NH$_3$ (0.5 M in 1,4-dioxane, 2 mL, 1 eq) was added and the reaction mixture was stirred overnight. The solvent was then removed, 3 mL anhydrous THF was added along with t-BuOK (1 M in THF, 1 mL, 1 equiv), and the mixture was stirred overnight. The solvent was removed, hexane and a small amount of MeOH were added and the resulting white solid was collected. The solid was further washed with anhydrous diethyl ether to give 3.8 mg of Example 99 as a white solid.

$^1$H NMR (CDCl$_3$): δ 1.20 (t, 3 H, J=7.3 Hz) 3.10 (q, 2 H, J=7.3 Hz) 5.40 (s, 2 H) 6.40 (s, 1 H) 7.20-7.40 (m, 4 H) 8.30 (m, 2 H)

Mass of C$_{16}$H$_{16}$N$_3$O$_3$ (MH)$^+$: 298. Found: 298.

Commercially available (Aldrich) Compound 99a (75 g, 383 mmol) was stirred with cold aqueous Na$_2$CO$_3$ (15%, 450 mL) for 2 h. Extraction with EtOAc and drying over Na$_2$CO$_3$ provided Compound 99b as a colorless oil, which was immediately treated with NH$_4$Cl (19.5 g, 364 mmol) in 200 mL of dry EtOH at 50° C. for 60 h. The crude product mixture was cooled and the solvent was removed. The resulting light yellow solid was treated with cold K$_2$CO$_3$ (30%, 300 mL H$_2$O) for 0.5 h. Extraction with EtOAc gave Compound 99c as a light yellow solid (37.92 g). This solid was reacted with methyl propionylacetate (38.0 g, 292 mmol), 2 mL pyridine, in 400 mL of dry EtOH at 100° C. for 24 h. After cooling and filtration, the solid was washed with EtOH and 18 g of Compound 99d as a white solid was obtained (22% yield from Compound 99a).

$^1$H NMR (CDCl$_3$): δ 1.20 (t, 3 H, J=7.3 Hz) 1.40 (t, 3 H, J=7.1 Hz) 2.90 (q, 2 H, J=7.3 Hz) 4.30 (q, 2 H, J=7.1 Hz) 5.75 (s, 1 H)

Mass of C$_{10}$H$_{15}$N$_2$O$_3$ (MH)$^+$: 211. Found: 211.

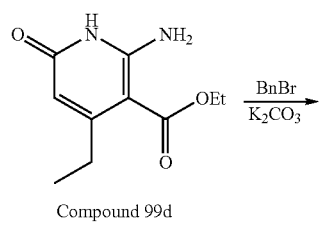

Preparative Example 100

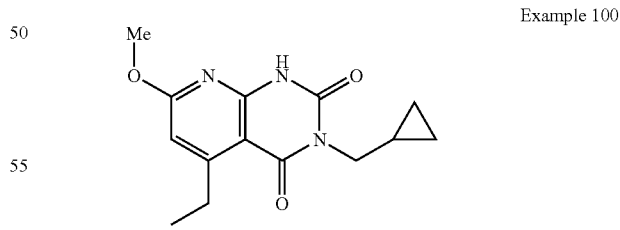

Example 100 was prepared following procedures similar to those used to prepare Example 99, except that methyl iodide was used instead of BnBr, and cyclopropylmethylamine was used instead of ammonia.

$^1$H NMR (CDCl$_3$): δ 0.40 (m, 4 H) 1.18-1.25 (m, 4 H) 3.10 (q, 2 H, J=7.2 Hz) (3.82 (d, 2 H, J=7.4 Hz) 3.90 (s, 3 H) 6.38 (s, 1 H) 8.10 (br s, 1 H)

Mass of C$_{14}$H$_{18}$N$_3$O$_3$ (MH)$^+$: 276. Found: 276.

Preparative Example 101

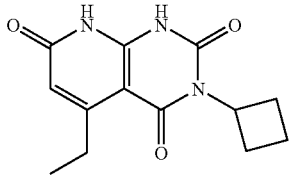
Example 101

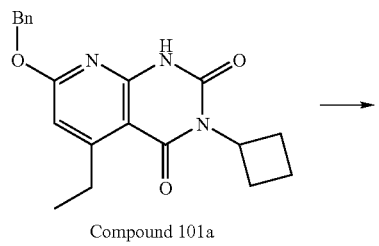
Compound 101a

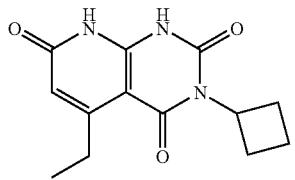
Example 101

Intermediate Compound 101a was prepared using procedures similar to those used to prepare Example 99, except that cyclobutylamine was used instead of ammonia.

$^1$H NMR (CDCl$_3$): δ 1.20 (t, 2 H, J=7.3 Hz) 1.60-1.80 (m, 2 H) 2.10 (m, 2 H) 3.00 (m, 2 H) 3.10 (q, 2 H, J=7.3 Hz) 5.30 (m, 1 H) 5.40 (s, 2 H) 6.40 (s, 1 H) 7.20-7.40 (m, 5 H) 8.20 (br s, 1 H)

Mass of C$_{20}$H$_{22}$N$_3$O$_3$ (MH)$^+$: 352. Found: 352.

Compound 101a (70 mg) was treated with 3% Pd/C (50 mg), 10 mL MeOH under a hydrogen atmosphere (hydrogen balloon) overnight. After filtration, prep HPLC purification provided 1.2 mg of Example 101.

$^1$H NMR (CDCl$_3$): δ 1.20 (t, 2 H, J=7.3 Hz) 1.60-1.80 (m, 2 H) 2.10 (m, 2 H) 2.95 (m, 2 H) 3.20 (q, 2 H, J=7.3 Hz) 5.30 (m, 1 H) 6.40 (s, 1 H) 8.00 (br s, 1 H).

Mass of C$_{14}$H$_{17}$N$_3$O$_3$ (MH)$^+$: 276. Found: 276.

Preparative Example 102

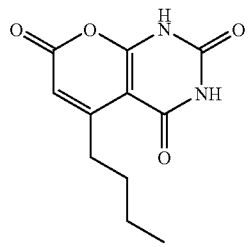
Example 102

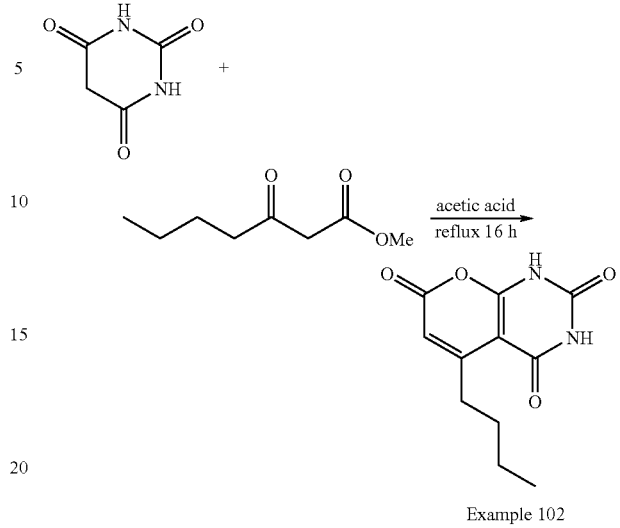
Example 102

In a 25 mL round bottomed flask equipped with a magnetic stirring bar and a nitrogen balloon was placed 1.0 g of barbituric acid (7.8 mmol) and 1.52 mL of 3-oxoheptanoic acid methyl ester (9.6 mmol, 1.23 equiv.). 8 mL of acetic acid was added to the reaction mixture and was refluxed for 16 h after which the reaction was cooled to room temperature. The excess acetic acid was concentrated and dried in vacuo to give crude product Example 102 along with unreacted starting materials. The crude product was stirred with 20 mL of boiling water for a few minutes and filtered. The precipitate was washed with boiling water (2×10 mL) and dried to yield 0.65 g (35% yield) of Example 102.

$^1$H NMR (DMSO): δ 0.9 (t, 3 H, J=7.5 Hz) 1.32-1.40 (m, 2 H) 1.45-1.51 (m, 2 H) 2.84-2.87 (t, 2 H, J=7.5 Hz) 5.82 (s, 1 H) 11.34 (s, 1 H) 12.72 (br s, 1 H)

Mass of C$_{11}$H$_{12}$N$_2$O$_4$ (MH)$^+$: 236.22. Found: 237.1.

Examples 103-135

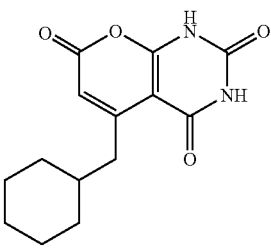
Example 103

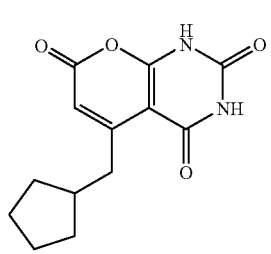
Example 104

-continued
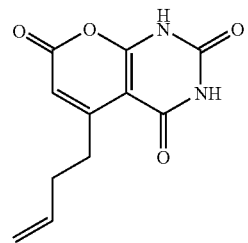
Example 105
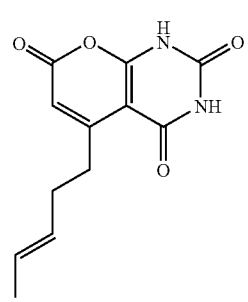
Example 106
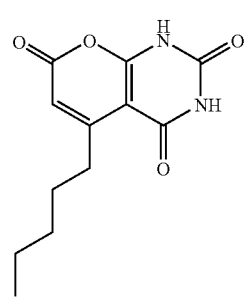
Example 107
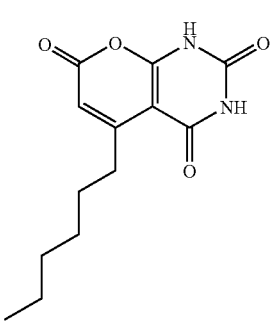
Example 108
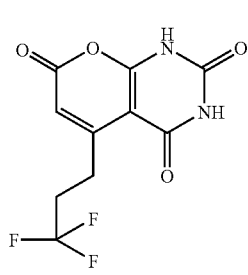
Example 109
-continued
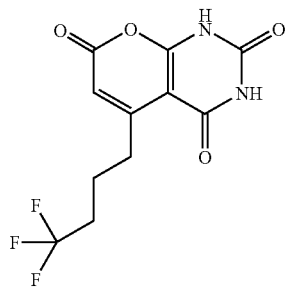
Example 110
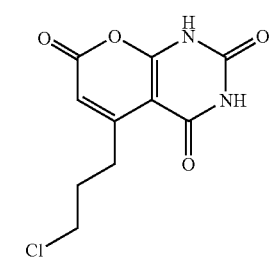
Example 111
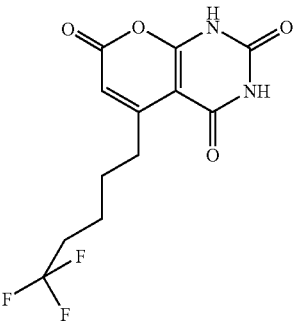
Example 112
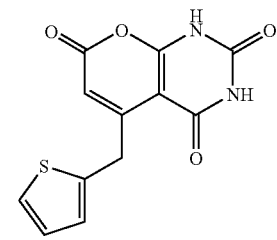
Example 113
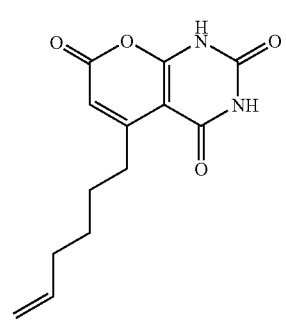
Example 114

-continued
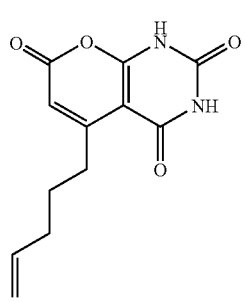
Example 115
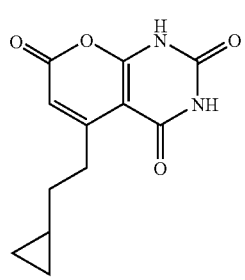
Example 116
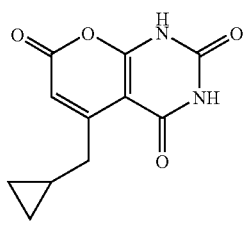
Example 117
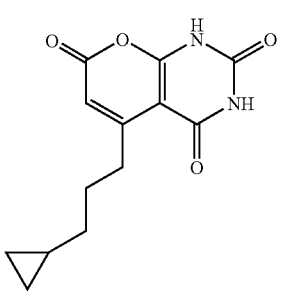
Example 118
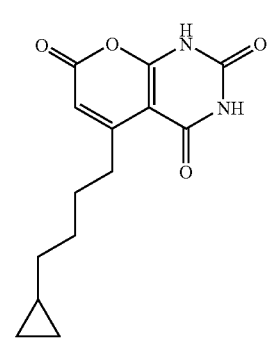
Example 119
-continued
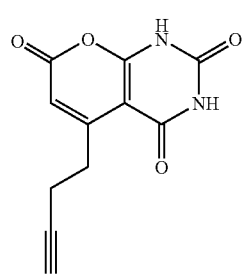
Example 120
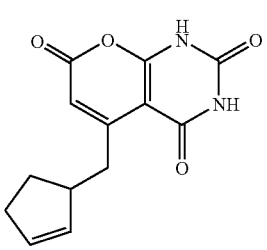
Example 121
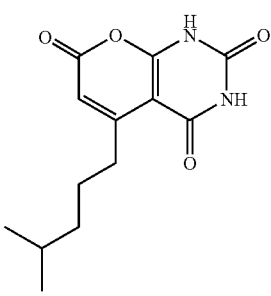
Example 122
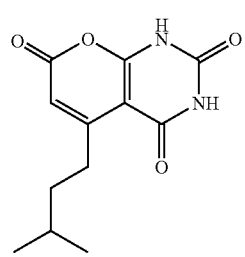
Example 123
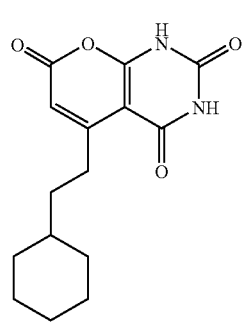
Example 124

-continued
Example 125
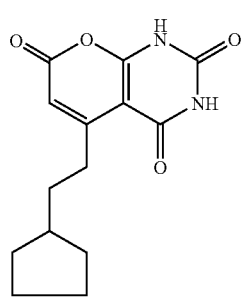
Example 126
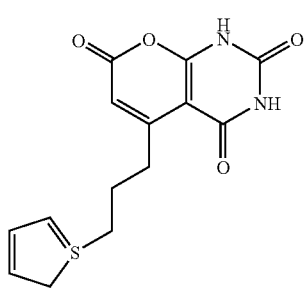
Example 127
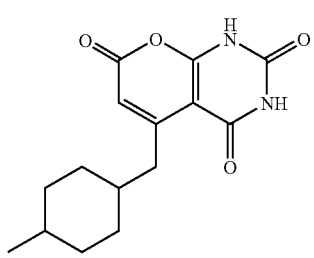
Example 128
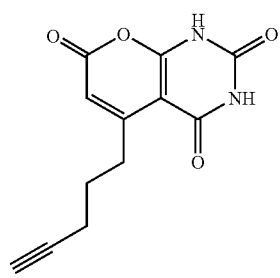
Example 129
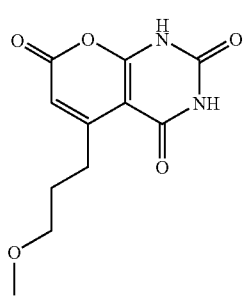
-continued
Example 130
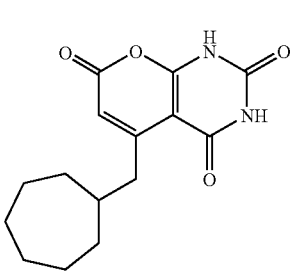
Example 131
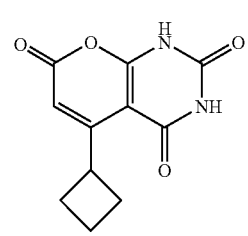
Example 132
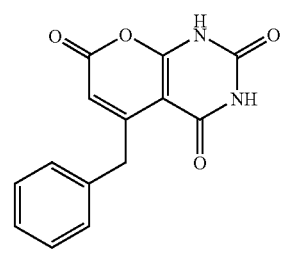
Example 133
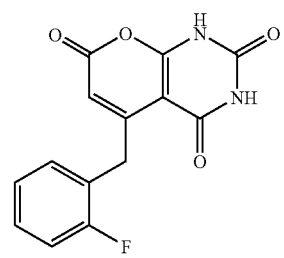
Example 134
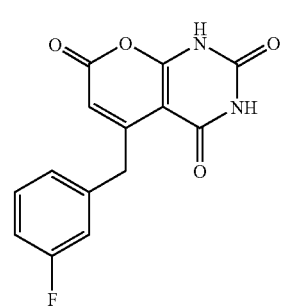

Example 135

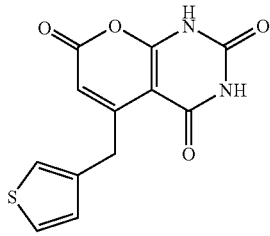

Examples 103-135 where prepared using procedures similar to those used to prepare Example 102, except that an appropriately substituted keto-ester was used instead of 3-oxoheptanoic acid methyl ester. The examples 200, 210, 241, 242, 245, 246, 252-260, 274-278, 280, 281, 282, 284, 285, 291 were prepared by a procedure similar to that used for the preparation of Example 30 and 31.

The examples 201, 202, 204-209, 211-218, 224-240, 243, 244, 247-251, 261-273, 279, 283, 286-290, 293, 294-297 were prepared by a procedure similar to that used for the preparation of example 102, using barbituric acid and the corresponding keto ester.

The preparation of ketoesters starting material where appropriate is shown below.

The preparation of keto ester starting material for examples 247 is as follows

Preparative Example 247a

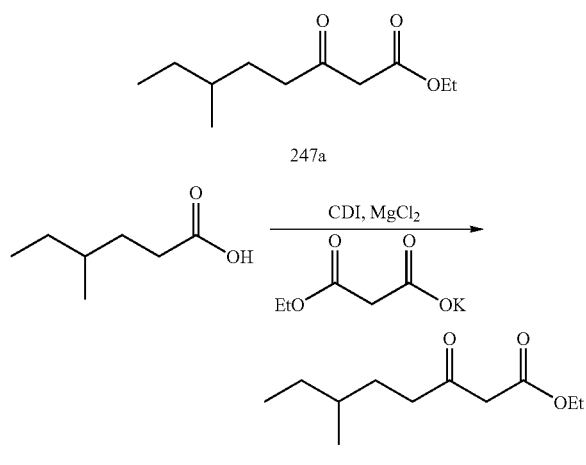

4-Methylhexanoic acid (3.0 g, 23.08 mmol) was taken in 40 mL THF. 1,1'-Carbonyldiimidazole (4.49 g, 27.69 mmol) was added and the reaction was stirred at room temperature for 1 h after which MgCl$_2$ (2.2 g, 23.08 mmol) and ethyl potassium malonate (5.89 g, 34.62 mmol) was added. The reaction was allowed to run at room temperature overnight. The crude reaction mixture was filtered through a short pad of silica gel and eluted with EtOAc/hexanes (1:3) to yield compound 247a.

Preparative Example 223a

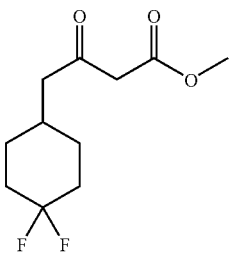

The starting material for the preparation of example 223 is as follows.

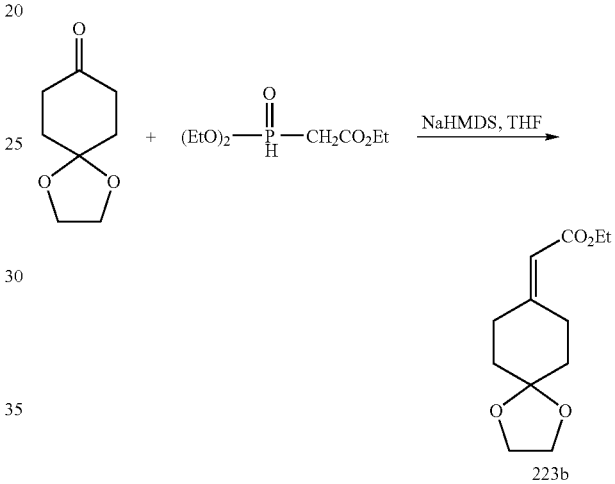

Step A: A solution of triethyl phosphonate (44.8 g, 200 mmol) in THF (30 ml) at 0° C. was treated with a 1M solution (200 ml) of sodium bis(trimethylsilylamide) in THF. The resulting mixture was stirred at room temperature for 0.5 hour, and then cooled to 0° C. A solution of 1,4-cyclohexanedione mono ethylene ketal (15.6 g, 200 mmol) in THF (50 ml) was added drop wise, and the resulting solution was stirred at room temperature for 18 hours. The reaction mixture was then cooled to 0° C., treated with cold aqueous citric acid, and the mixture was extracted with EtOAc. The extract was washed with satd. aqueous NaHCO$_3$, brine, dried over Na$_2$SO$_4$, filtered, and the filtrate was concentrated.

The residue was chromatographed on silica gel, eluting with a gradient of CH$_2$Cl$_2$/EtOAc to afford 223b (21 g, 91%),

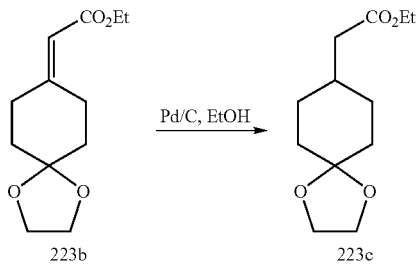

Step 8: The compound 223b (20 g) was dissolved in EtOH (150 ml) and treated with 10% Pd/C under 1 atm of hydrogen for 3 days. The mixture was filtered and the filtrate was evaporated to 223c (20.3 g, 100%).

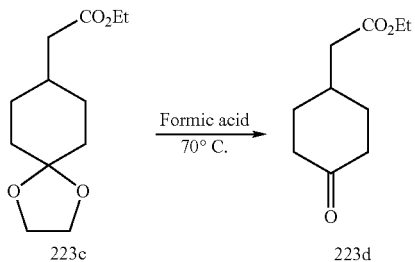

Step C: The compound 223c (7 g) was dissolved in formic acid (50 ml) and heated at 70° C. for 1 h. The solution was concentrated and the residue was taken up in EtOAc and washed with satd. aqueous NaHCO$_3$, brine, dried over Na$_2$SO$_4$ and concentrated. The residue was chromatographed on silica gel to afford 223d (5 g).

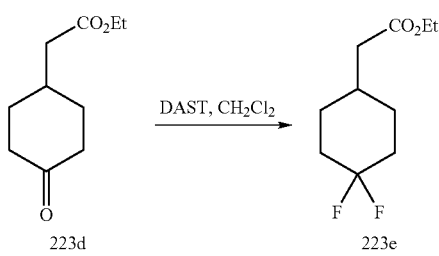

Step D: The compound 223d (4.6 g) was dissolved in CH$_2$Cl$_2$ (10 ml) and treated with diethylaminosulfur trifluoride (DAST, 5 ml) at room temperature for 3 hours. The reaction mixture was poured into ice/water (30 ml) and extracted with CH$_2$Cl$_2$. The extract was washed with satd. aqueous NaHCO$_3$, brine, dried over Na$_2$SO$_4$ and concentrated to afford 223e as brown oil (3.2 g, 62%).

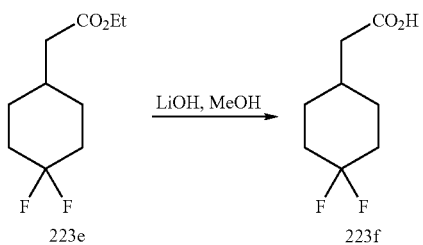

Step E: The compound 223e (3.2 g, 15.5 mmol) was dissolved in MeOH (5 ml) and treated with LiOH (559 mg, 23.3 mmol) overnight. The reaction mixture was acidified by 3 N HCl to pH 4 and extracted with CH$_2$Cl$_2$. The extract was dried over Na$_2$SO$_4$ and concentrated to afford 223f as brown oil (3 g, 100%).

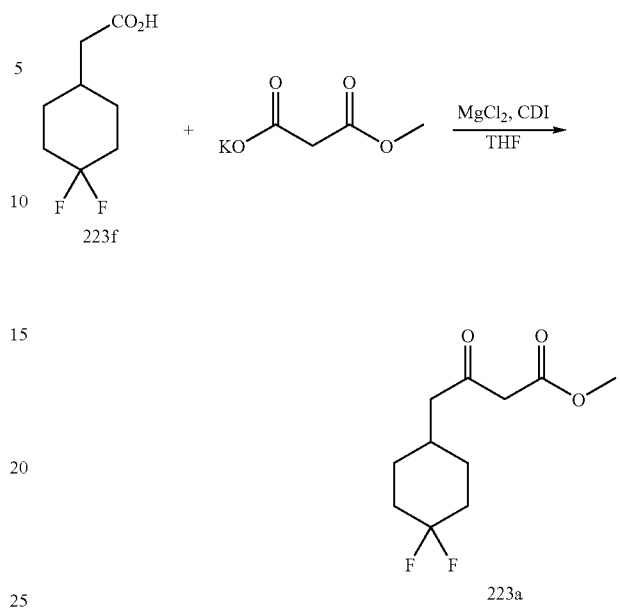

Step F: The compound 223f (900 mg, 5.0 mmol) was dissolved in THF (15 ml), added with CDI (972 mg, 6.0 mmol) and stirred for 45 min. Then methyl malonate potassium salt (1.02 g, 6.0 mmol) and MgCl$_2$ (570 mg, 6.0 mmol) were added into the above solution. The resulting mixture was stirred overnight and filtered through a short pad of silica gel and washed with EtOAc. The filtrate was concentrated and chromatographed on silica gel to afford 223a as colorless oil (400 mg, 34%).

The starting materials for structures 262, 263 were prepared in a manner similar to 218a.

Preparative Example 262a

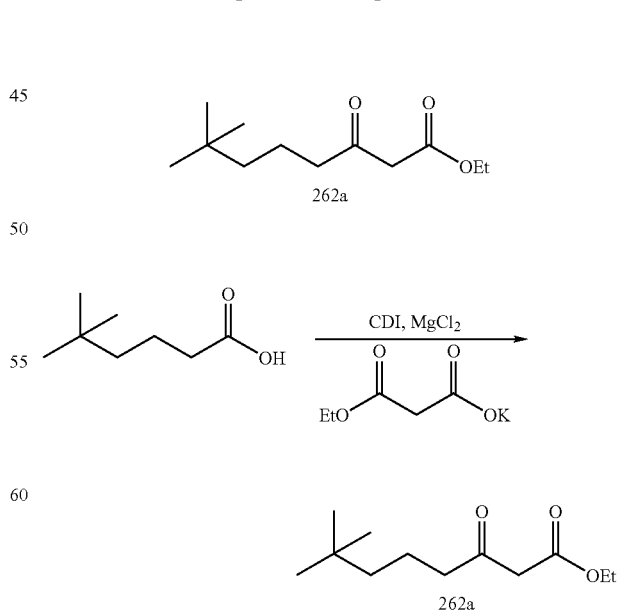

Prepared in the same manner as in example 218a.

Preparative Example 263a

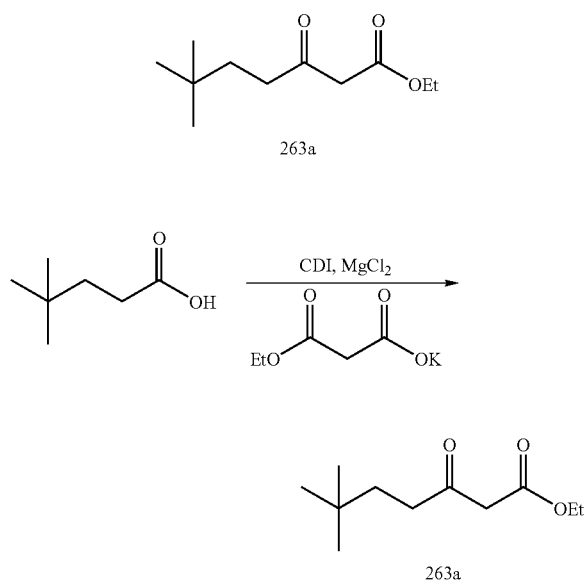

Prepared in the same manner as in example 218a.

Preparative Example 266a

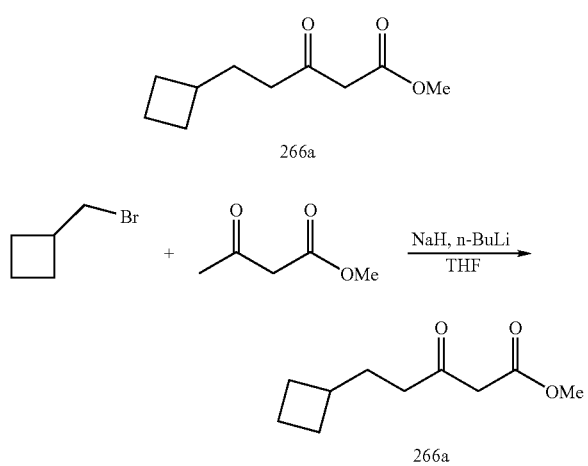

Sodium hydride (1.42 g, 35.56 mmol) was taken in THF (20 mL) in a round bottomed flask equipped with a stirring bar and nitrogen balloon. It was cooled to 0° C. and methyl acetoacetate (3.84 mL, 35.56 mmol) dissolved in 10 mL THF was added drop wise. The reaction mixture was stirred at 0° C. for 30 min after which n-BuLi (2.5 M solution in hexanes, 14.2 mL, 35.56 mmol) was added drop wise. The reaction was allowed to run for 30 min at 0° C. and then cooled to −25° C. Bromomethylcyclobutane (4.82 g, 32.32 mmol) dissolved in 20 mL THF was added drop wise and the reaction was stirred at −25° C. for 4 h followed by room temperature overnight. It was quenched with the addition of sat. NH$_4$Cl, extracted with EtOAc (2×30 mL), dried over MgSO$_4$, concentrated in vacuo. The crude product was purified by biotage (5% EtOAc/hexanes) to yield compound 266a.

Preparative Example 267a

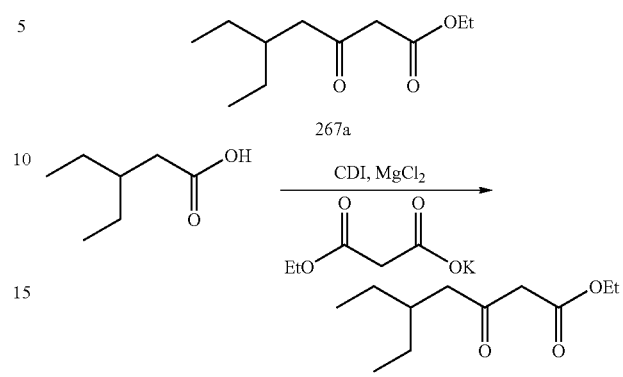

Prepared in the same manner as in example 218a.

Preparative Example 268a

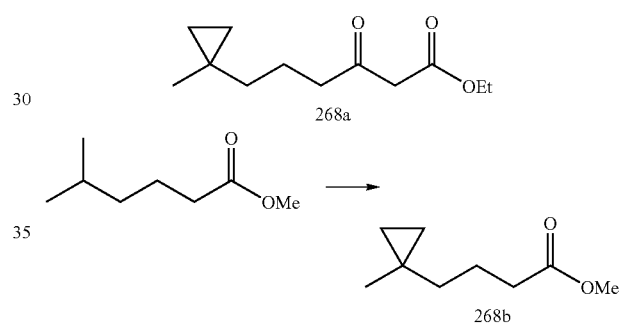

Trifluoroacetic acid (7.84 mL, 105.48 mmol) and diiodomethane (8.5 mL, 105.48 mmol) in 50 mL DCM was cooled to 0° C. Diethylzinc (1.0 M solution in hexanes, 105.5 mL, 105.48 mmol) was added drop wise. The reaction was allowed to stir at 0° C. for 20 min after which 5-Methyl-5-hexenoic acid methyl ester (5.0 g, 35.16 mmol) in 20 mL DCM was added drop wise.

The reaction was allowed to stir at room temperature overnight. The reaction was quenched by the addition of sat. NH$_4$Cl, extracted with DCM (2×30 mL), dried over MgSO$_4$, concentrated in vacuo to yield compound 268b which was carried over to the next step without further purification.

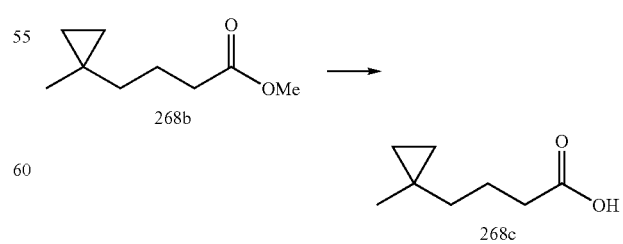

Ester 268b (5.0 g, 32 mmol) was taken in MeOH (50 mL) and NaOH (3.2 g, 80 mmol) was added to it. The reaction was allowed to stir at room temperature overnight. The reaction was diluted with water (50 mL) and acidified with conc HCl. It was extracted with Et$_2$O (2×30 mL), washed with brine, dried over MgSO$_4$, and concentrated in vacuo. The crude product 268c was used as such without any further purification.

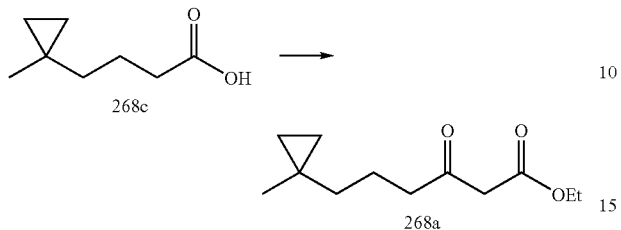

Prepared in the same manner as in example 262a.

Preparative Example 269a

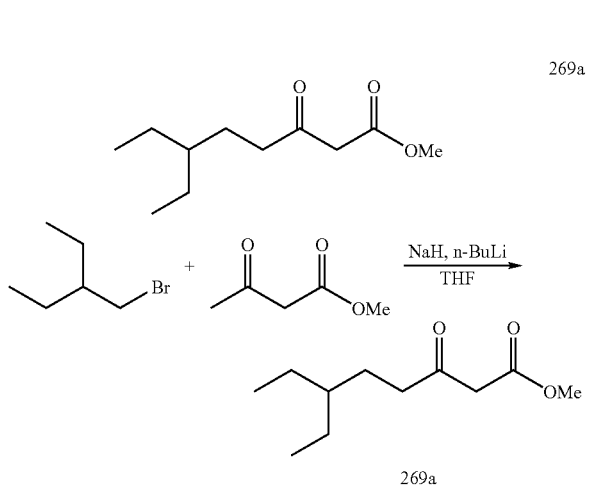

Prepared in the same manner as in example 266a.

Preparative Example 279a

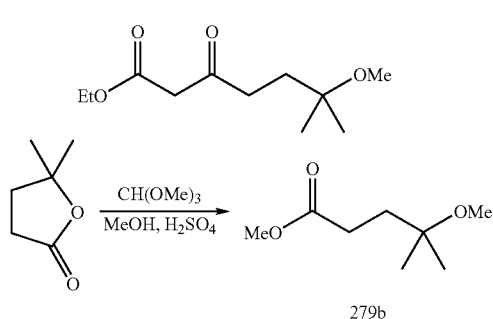

5,5-Dimethyl-dihydro-furan-2-one (5.0 g, 43.8 mmol), trimethyl orthoformate (11.5 mL, 105.12 mmol), and sulfuric acid (0.43 g, 4.38 mmol) were taken in MeOH (50 mL). The reaction mixture was heated to 50° C. overnight. After cooling, the solvent was removed in vacuo, quenched with sat. NaHCO$_3$ and extracted with EtOAc (2×30 mL). The organic layer was washed with brine, dried over MgSO$_4$ and concentrated in vacuo to yield compound 279b which was used without any further purification.

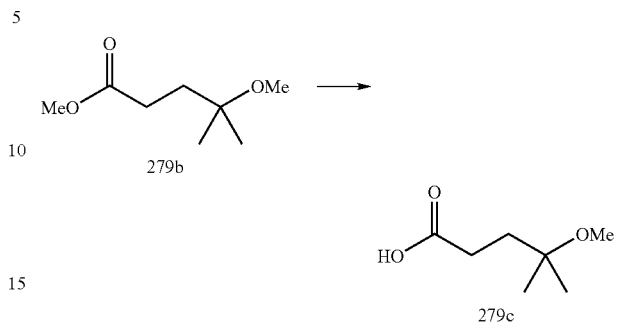

Prepared in the same manner as in example 268c.

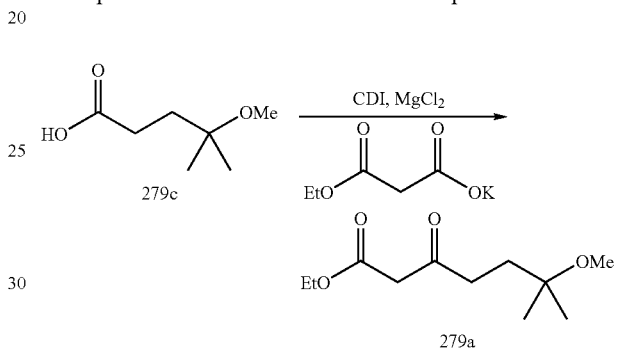

Prepared in the same manner as in example 262a.

Preparative Example 288a

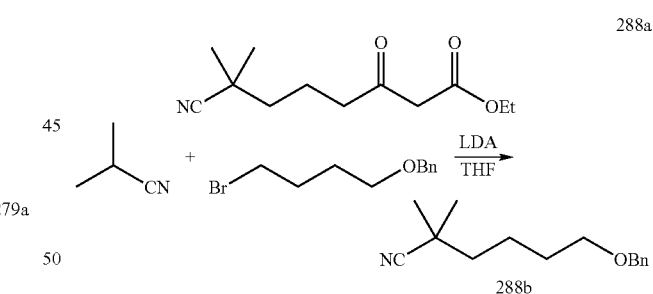

Lithium diisopropylamide (2.0 M solution in THF/heptane/ethyl benzene, 43.4 mL, 86.82 mmol) was taken in THF (30 mL) and cooled to −78° C. Isobutyronitrile (6 g, 86.82 mmol) in THF (10 mL) was added drop wise and the reaction was stirred at −78° C. for 1 h and 0° C. for 2 h. Benzyl 4-bromobutyl ether (21.1 g, 86.82 mmol) in THF (10 mL) was added drop wise and the reaction mixture was allowed to warm to room temperature overnight. The reaction was quenched by the addition of saturated NH$_4$Cl and extracted with Et$_2$O. The organic layer was washed with brine, dried over MgSO$_4$ and concentrated in vacuo. The crude compound obtained was purified by biotage (5% EtOAc/hexanes) to yield compound 288b.

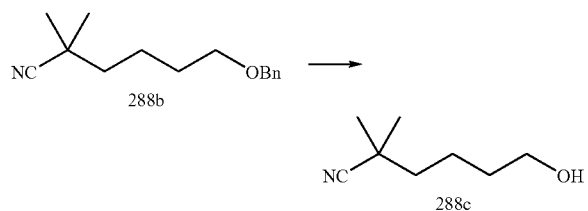

Compound 288b was taken up in CH$_2$Cl$_2$ (25 mL) in a 100 mL round bottomed flask equipped with a stirring bar and nitrogen balloon and cooled to −78° C. Boron trichloride (1.0 M solution in hexanes, 43.2 mL, 43.2 mmol) was added drop wise and the reaction was allowed to gradually warm to 0° C. After 1 h the reaction was quenched by the addition of sat. NaHCO$_3$, extracted with CH$_2$Cl$_2$. The organic layer was washed with brine, dried over MgSO$_4$, and concentrated in vacuo to yield the crude compound which was purified by filtering through a short pad of silica gel eluting with 50% EtOAc/hexanes to yield compound 288c.

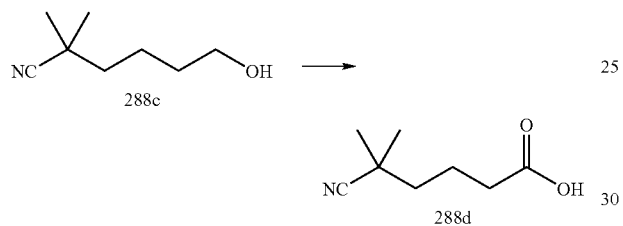

Compound 288c (3.0 g, 21.2 mmol) was taken in acetone (20 mL) and cooled to 0° C. Jones reagent was added drop wise until there was no change in color to green upon addition of the reagent The excess reagent was quenched by the addition of i-PrOH, and water (20 mL) extracted with Et$_2$O. The organic layer was washed with brine, dried over MgSO$_4$, and concentrated in vacuo to yield compound 288d which was used without further purification.

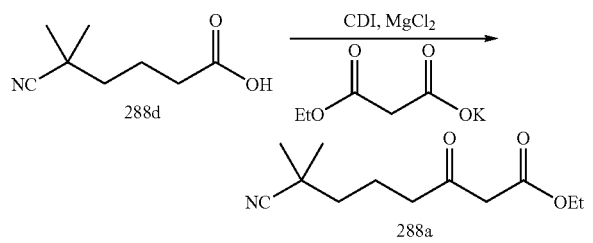

Prepared in the same manner as in example 262a.

Preparative Example 293a

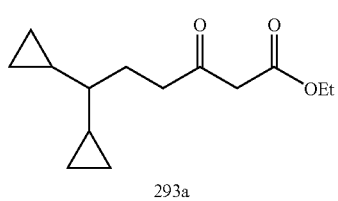

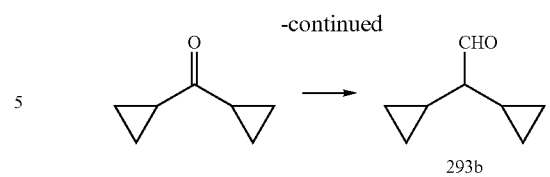

Lithium bis(trimethylsilyl)amide (1.0 M solution in THF, 108.9 mL, 108.9 mmol) was taken up in 100 mL THF in a 500 mL round bottomed flask equipped with a stirring bar and nitrogen balloon. The solution was cooled to 0° C. and (methoxymethyl)triphenylphosphonium chloride (37.3 g, 108.9 mmol) was added portionwise and the dark red solution was stirred at 0° C. for 45 min. Dicyclopropyl ketone (10 g, 90.78 mmol) in THF (10 mL) was added drop wise and the reaction was stirred at 0° C. for 3 h after which the reaction mixture was poured into hexane. The mixture was filtered through silica gel eluting with hexane. Solvent removal gave the crude enol ether.

The crude enol ether was taken up in THF (100 mL) and 10% HCl (100 mL) was added. The reaction was refluxed overnight. Upon cooling, diluted with water and extracted with Et$_2$O (2×50 mL), washed with brine, dried over MgSO$_4$, concentrated in vacuo. The crude mixture 293b was used as such without further purification.

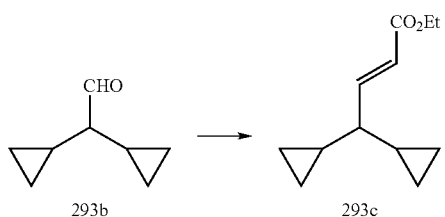

Sodium hydride (6.44 g, 161 mmol) was taken in THF (30 mL) in a 250 mL round bottomed flask equipped with a magnetic stirring bar and nitrogen balloon. The mixture was cooled to 0° C. Triethylphosphonoacetate (36.1 g, 161 mmol) in 20 mL THF was added drop wise and the mixture was stirred at room temperature for 1 h after which it was cooled back to 0° C. and compound 293b (10 g, 80.5 mmol) in 20 mL THF was added drop wise and the reaction was allowed to stir at room temperature for 2 h. The reaction was quenched by the addition of water and was extracted with Et$_2$O. The organic layer was washed with brine, dried over MgSO$_4$, and concentrated in vacuo. The crude was purified by biotage (2% EtOAc/haxanes) to yield compound 293c.

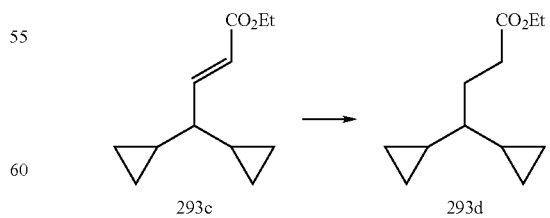

Compound 293c was taken up in 100 mL EtOH in a 200 mL round bottomed flask. To the solution was added Pd/C (10 wt %, 7.0 g, 5.7 mmol) and the mixture was hydrogenated using a hydrogen balloon under ambient temperature for 12 h. The

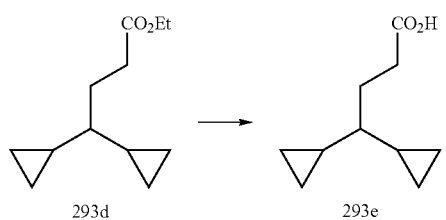

Prepared in the same manner as in example 268c.

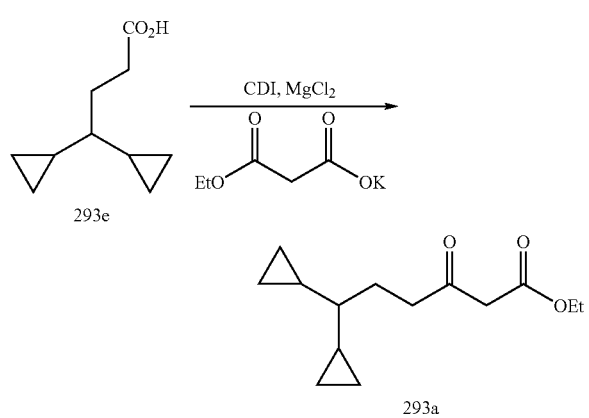

Prepared in the same manner as in example 262a.

Preparative Example 294a

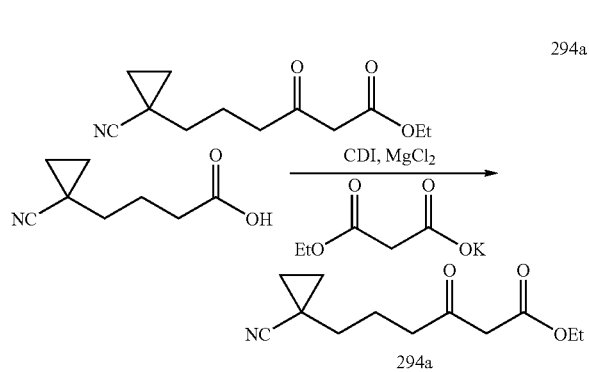

Prepared in the same manner as in example 288a.

Preparative Example 295a

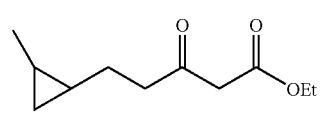

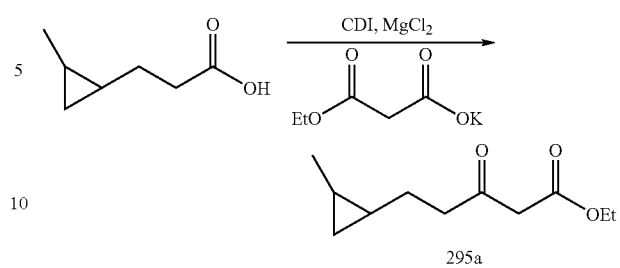

Prepared in the same manner as in example 262a.

Preparative Example 292a

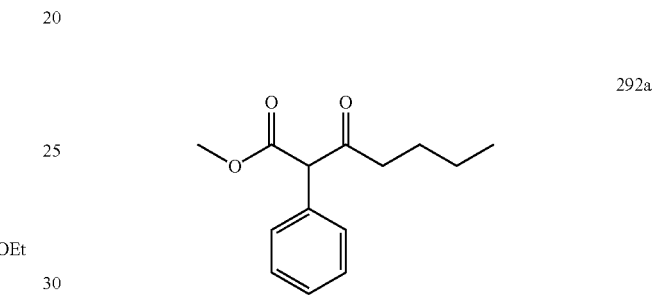

The starting material for the preparation of example 292 is as follows.

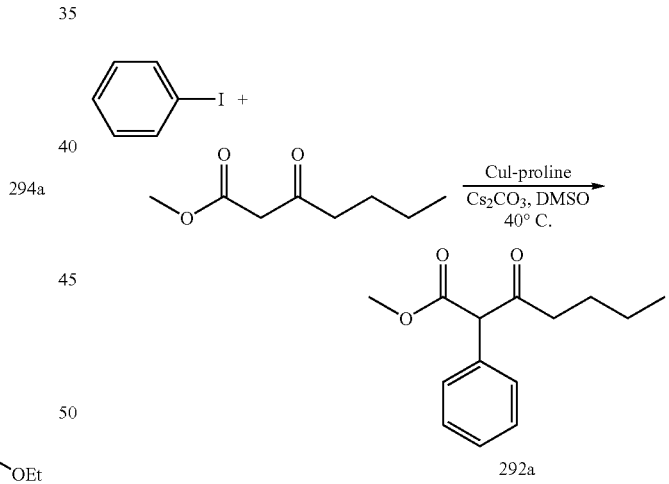

Into the solution of iodobenzene (10.2 g, 50 mmol) in anhydrous DMSO (150 mL) and 3-oxoenanthic acid methyl ester (15.8 g, 100 mmol) was added copper(I) iodide (1.9 g, 10 mmol), L-proline (2.3 g, 20 mmol), and cesium carbonate (65.2 g, 200 mmol). After stirred under $N_2$ at 40° C. for 18 hours, the reaction mixture was dissolved into ethyl acetate (250 mL), washed with water (4×150 ml). The organic solution was dried with sodium sulfate, and concentrated under reduced pressure. The resulting crude product was purified using silica gel flash column chromatography eluting with ethyl acetate/hexanes (v/v=5/95) to give compound 292a (4.5 g, 38%).

Preparative Example 297a

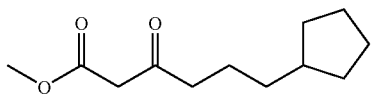

The starting material for the preparation of example 297 is as follows.

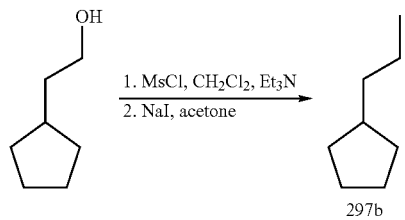

To a solution of 2-cyclopentyl ethanol (11.4 g, 100 mmol), anhydrous $CH_2Cl_2$ (80 mL), and triethyl amine (12 g, 120 mmol), which cooled to 0° C., was added via syringe MsCl (13.7 g, 120 mmol). After stirring under $N_2$ at 0° C. for 1 hour then at room temperature for 18 hours, the reaction mixture was washed with water (2×100 mL), dried with sodium sulfate, and concentrated under reduced pressure to give a clear oil (19 g, 100%). The oil was dissolved into anhydrous $CH_2Cl_2$ (250 mL) and mixed with NaI (20 g, 200 mmol). After stirring at room temperature for 18 hours, the reaction mixture was filtered from solid. The resulting filtrate was concentrated under reduced pressure to give a brown paste. The paste was dissolved into diethyl ether (300 mL), washed with water (2×150 mL), dried with sodium sulfate, concentrated under reduced pressure to give compound 297b (20 g, 89%).

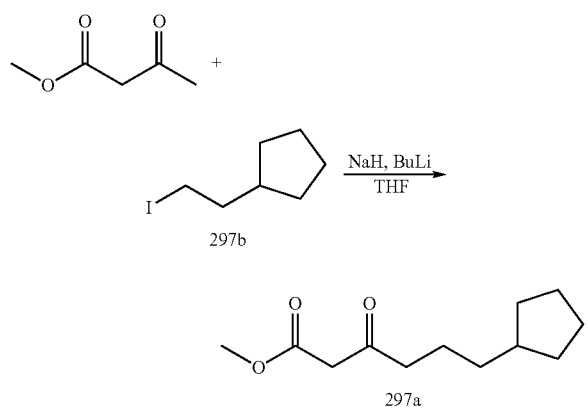

To a solution of methyl acetoacetate (5.8 g, 50 mmol) and anhydrous THF (100 mL), which cooled to 0° C., was added NaH (60%, 2.4 g, 60 mmol). After stirring under $N_2$ at 0° C. for 0.5 hour, n-BuLi (2.5 M in hexanes, 20 mL) was added via syringe. After stirring at 0° C. for 0.5 hour, the reaction mixtures was cooled to −25° C., the compound 297b was added via syringe. The reaction mixture was stirred at 0° C. for 0.5 hour, then room temperature for 18 hours. The reaction mixture was quenched with saturated ammonium chloride (200 mL) and extracted with ethyl acetate (2×200 mL) washed with water (2×100 mL). The organic solution was dried with sodium sulfate, and concentrated under reduced pressure to give a brown oil, which purified using silica gel flash column chromatography eluting with ethyl acetate/hexanes (v/v=7/93) to give compound 297a (3.2 g, 32%).

Preparative Example 214

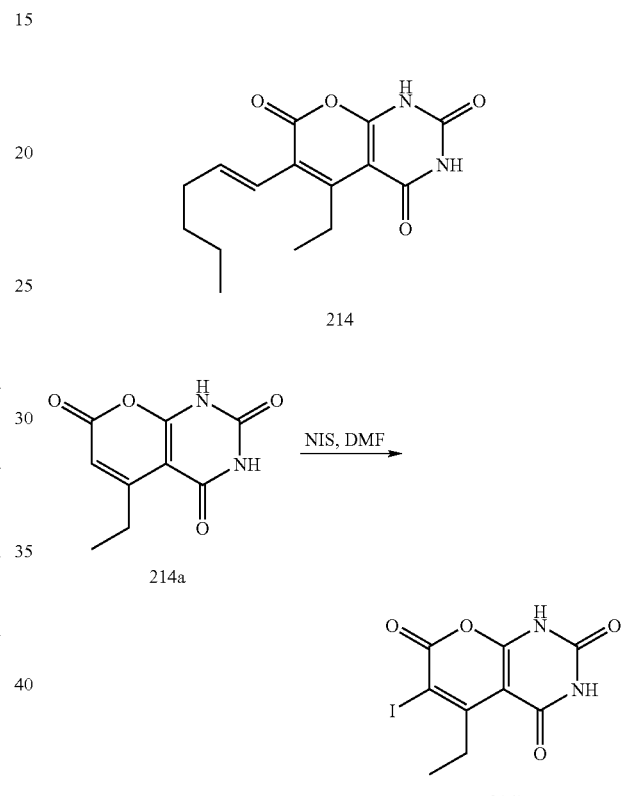

Compound 214a (10 y, 48.04 mmol) was taken in DMF (50 mL) in a round bottomed flask equipped with a magnetic stirring bar. N-Iodosuccinimide (22 g, 97.79 mmol) was added portionwise and the reaction mixture was heated to 50° C. overnight. After cooling to ambient temperature, $H_2O$ (100 mL) was added. The product was filtered, washed with water followed by ether to give a white powdery mixture (>95% yield). The product 214b was used as such for the next step without any further purification.

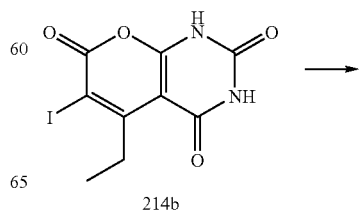

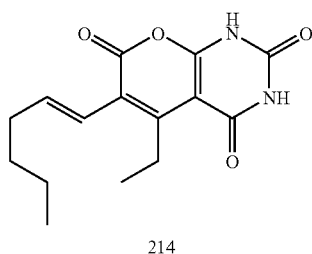

214

Compound 214b (0.1 g, 0.3 mmol) was taken in C$_6$H$_6$ (1 mL) in a 10 mL round bottomed flask. Pd(OAc)$_2$ (0.004 g, 0.018 mmol), PPh$_3$ (0.014 g, 0.054 mmol), and Na$_2$CO$_3$ (0.5 mL, 2M solution) was added and the reaction mixture was allowed to stir at room temperature for 30 min. trans-1-Hexen-1-ylboronic acid (0.042 g, 0.33 mmol) in EtOH (0.5 mL) was added and the reaction mixture was allowed to reflux (80° C.) overnight. After cooling, the mixture was diluted with H$_2$O (2 mL), extracted with EtOAc (2×10 mL), dried over MgSO$_4$, concentrated and dried to yield the crude compound 214. Purification by preparative TLC (10% MeOH/DCM) to yield compound 214.

Preparative Example 219

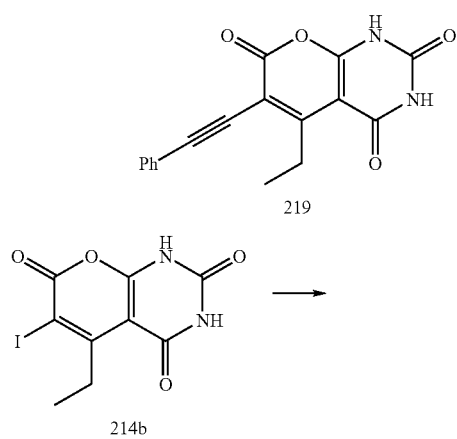

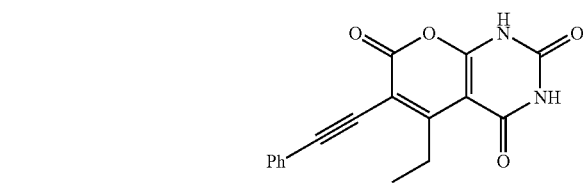

Compound 214b (0.1 g, 0.3 mmol) was taken in DMF (3.0 mL) in a 10 mL round bottomed flask. PdCl$_2$(PPh$_3$)$_2$ (0.011 g, 0.015 mmol), phenylacetylene (0.061 g, 0.6 mmol), CuI (0.006 g, 0.03 mmol), and triethylamine (0.091 g, 0.9 mmol) was added and the reaction mixture was stirred at room temperature overnight. The reaction mixture was diluted with EtOAc (5 mL), neutralized with 1N HCl, and extracted with EtOAc (2×10 mL), dried over MgSO$_4$, concentrated and dried to yield crude 219. The crude product was taken in ether and filtered to yield pure compound 219.

Preparative Example 220

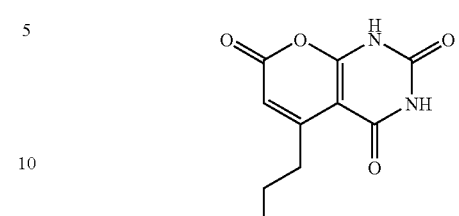

220

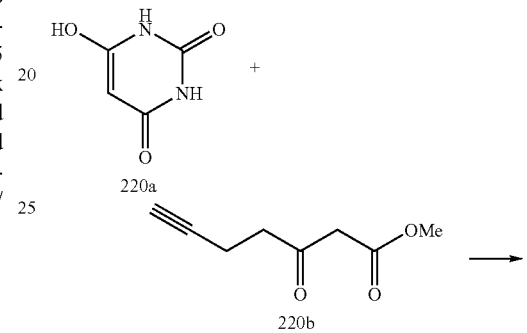

Barbituric acid 220a (1.0 g, 7.81 mmol) and keto ester 220b (1.45 g, 9.4 mmol) was taken in glacial acetic acid (8 mL) and the reaction mixture was heated to reflux overnight. After cooling to room temperature, the acetic acid was removed in vacuo and hot water was added to remove excess barbituric acid. The procedure was repeated a few times until no starting material was left. It was followed by washing with ether. The product 220c was dried and needed no further purification.

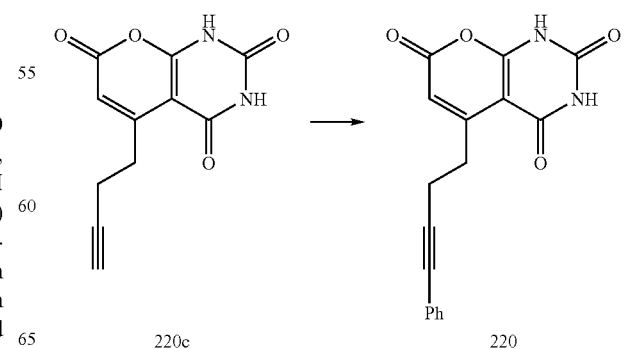

Compound 220c (0.1 g, 0.431 mmol) was taken in DMF (1 mL) in a 10 mL round bottomed flask. Iodobenzene (0.053 g, 0.258 mmol), PdCl$_2$(PPh$_3$)$_2$ (0.003 g, 0,0043 mmol), CuI (0.002 g, 0.0086 mmol), and Et$_2$NH (0.157 g, 2.15 mmol) was added and the reaction mixture was stirred at room temperature overnight. The reaction was diluted with EtOAc (2 mL), neutralized with 1N HCl and extracted with EtOAc (2×10 mL). It was dried over MgSO$_4$, concentrated in vacuo. The crude product was purified by preparative TLC (20% MeOH/DCM) to yield compound 220.

Preparative Example 216

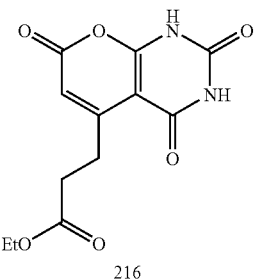
216

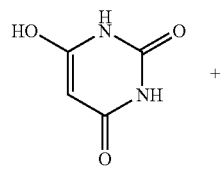
+

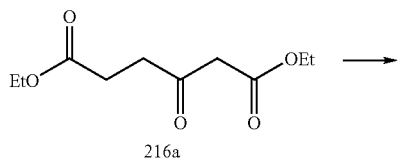
216a

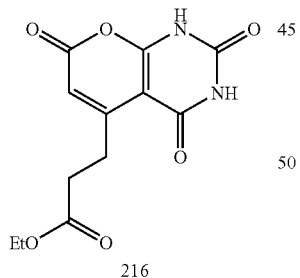
216

Barbituric acid (1.0 g, 7.81 mmol) and Diethyl β-ketoadipate 216a (2.03 g, 9.4 mmol) was taken in glacial acetic acid (8 mL) and the reaction mixture was heated to reflux overnight. After cooling to room temperature, the acetic acid was removed in vacuo and hot water was added to remove excess barbituric acid. The procedure was repeated a few times until no starting material was left. It was followed by washing with ether. The product 216 was dried and needed no further purification.

The starting material for the preparation of example 203 is as follows.

Preparative Example 203

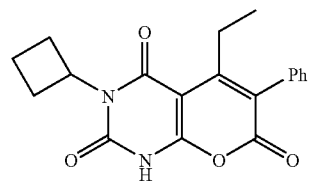
203

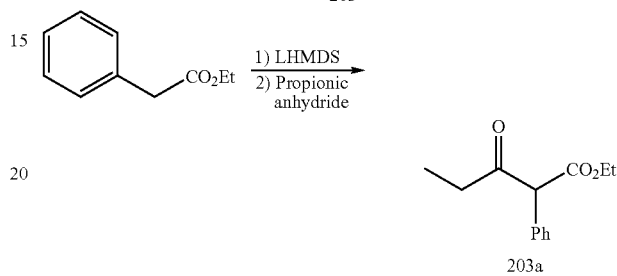
203a

To a solution of ethylphenylacetate (8.2 g, 0.05 mol) in THF at −78° C. was added LHMDS (1M in THF, 100 ml, 0.10 mol) and stirred for 20 min. Propionic anhydride (6.5 ml, 0.05 mol) was added rapidly. The mixture was allowed to warm up to 0° C. and stirred for 30 min. It was quenched with NH$_4$Cl (aq.) and extracted with EtOAc. Usual work up afforded the crude material which was chromatographed on silica gel to obtain product.

Step B:

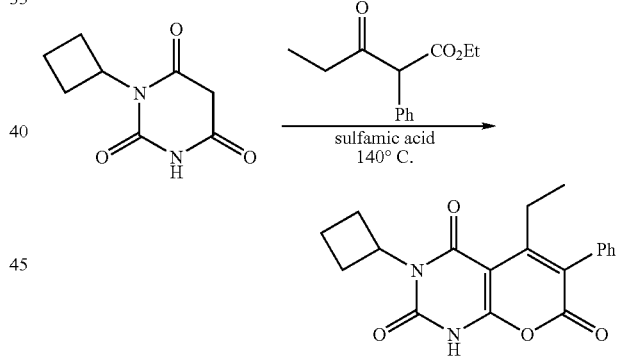

Compound 203 was obtained by normal condensation procedure with cyclobutylbarbituric acid.

Preparative Example 209

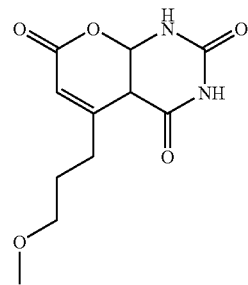
209

Step A:

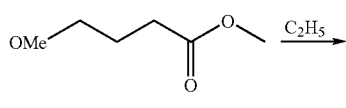

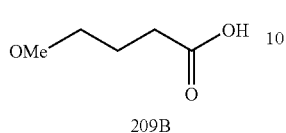

Starting material 209a (9.9 g, 75 mmol) was dissolved in THF (100 mL) and water (25 mL). LiOH (3.4 g, 80.9 mmol), the resulting mixture was stirred at room temperature overnight. 1 N HCl (100 mL) was added and extracted with EtOAc. The organic extracts were combined, washed with brine, dried (MgSO$_4$) to give compound 209b (8.8 g, 93%).

Step B:

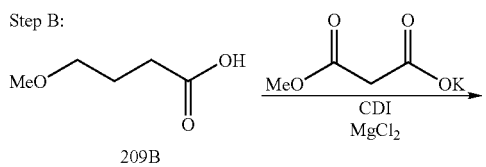

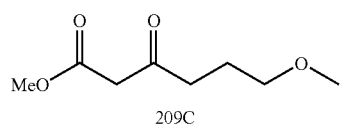

Compound 209c (1.9 g, 16.1 mmol) was dissolved in THF (50 mL), CDI (12.3 mmol) was added. The resulting mixture was stirred at room temperature for 1 h. MgCl$_2$ (1.5 g, 16.1 mmol) and KOCOCH$_2$CO$_2$Me (3.8 g, 24.2 mmol) were added, the resulting mixture was stirred at room temperature overnight. EtOAc (100 mL), water (50 mL) were added. The aqueous layer was separated and extracted with EtOAc. The aqueous layer was extracted with EtOAc. The organic extracts were combined, washed with brine, dried (MgSO$_4$), filtered and concentrated. The residue was separated by silica gel chromatography, with Biotage 40S+ column, eluted with EtOAc: hexanes, 1:10, to give 2.1 g (74%) yellow liquid as Compound 209d.

Step B:

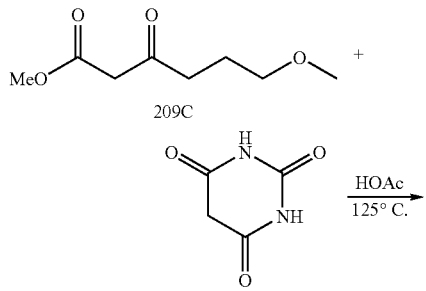

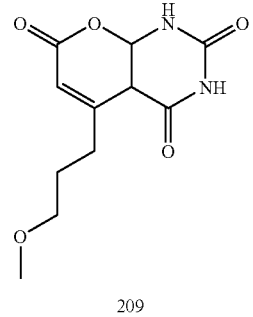

Compound 209c (1.13 g, 6.49 mmol) and barbituric acid (0.5 g, 3.90 mmol) was mixed with HOAc (2 mL) in a sealed tube, and heated in an oil bath at 125° C. overnight. The mixture was cooled to room temperature, HOAc was removed and the residue was taken up in MeOH, and filtered. The volume of the mother liquid was reduced until solid started to come out, the beige solid was collected to give Compound 209 (153 mg, 10%).

Electrospray MS [M+1]: 253.1.

Compound 208 was prepared in a similar fashion as in Compound 209, from the commercially available Compound 208a.

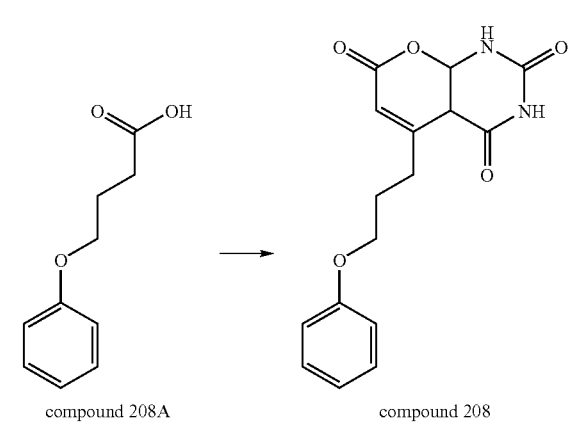

Preparative Example 270

Step A:

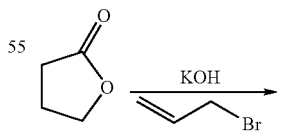

Starting lactone (10 g, 116 mmol) was mixed with allyl-bromide (30 mL, 346 mmol), toluene (75 mL), and KOH (19.5 g, 348 mmol). The mixture was heated 110° C. overnight. The mixture was cooled to room temperature; water (100 mL) was added. The aqueous layer was extracted with EtOAc. The organic extracts were combined, washed with brine, dried (MgSO$_4$), filtered and concentrated to give a yellow liquid as the desired Compound 270a (11.8 g, 55.2%).

Step B:

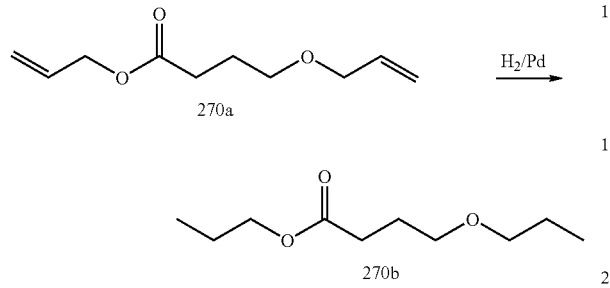

Compound 270a (3.0 g, 16.3 mmol) was dissolve in EtOH (20 mL), 10% Pd/C (300 mg) was added. The slurry was stirred under H$_2$ overnight. The mixture was filtered through Celite, and the filtrate was concentrated to give a yellow liquid as the desired Compound 270b (2.5 g, 81%).

Step C:

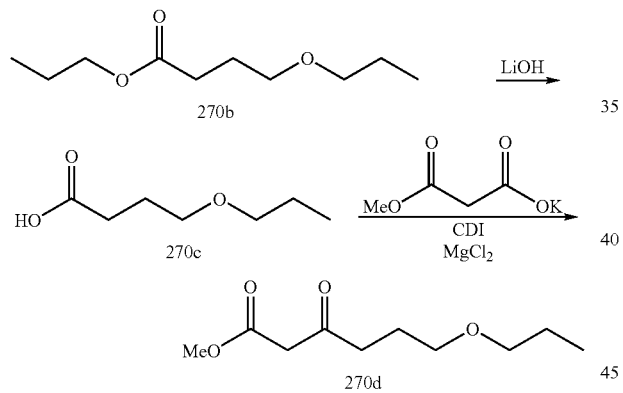

Compound 270b (3.0 g, 16.3 mmol) was dissolve in THF (20 mL)-H$_2$O (7 mL), LiOH (1.66 g, 39.5 mmol) was added. The resulting mixture was stirred at room temperature overnight. 1 N HCl (75 mL) was added, and extracted with Et$_2$O. The organic extracts were combined, dried (MgSO$_4$) filtered and concentrated. The residue was dissolved in THF (50 mL), CDI (12.3 mmol) was added. The resulting mixture was stirred at room temperature for 1 h. MgCl2 (1.3 g, 13.6 mmol) and KOCOCH$_2$CO$_2$Me (2.9 g, 18.5 mmol) were added, the resulting mixture was stirred at room temperature overnight. EtOAc (100 mL), water (50 mL) were added. The aqueous layer was separated and extracted with EtOAc. The aqueous layer was extracted with EtOAc. The organic extracts were combined, washed with brine, dried (MgSO$_4$), filtered and concentrated. The residue was separated by silica gel chromatography, with Biotage 40S+ column, eluted with EtOAc: hexanes, 1:10, to give 1.5 g (46%) yellow liquid as Compound 270d.

Step D:

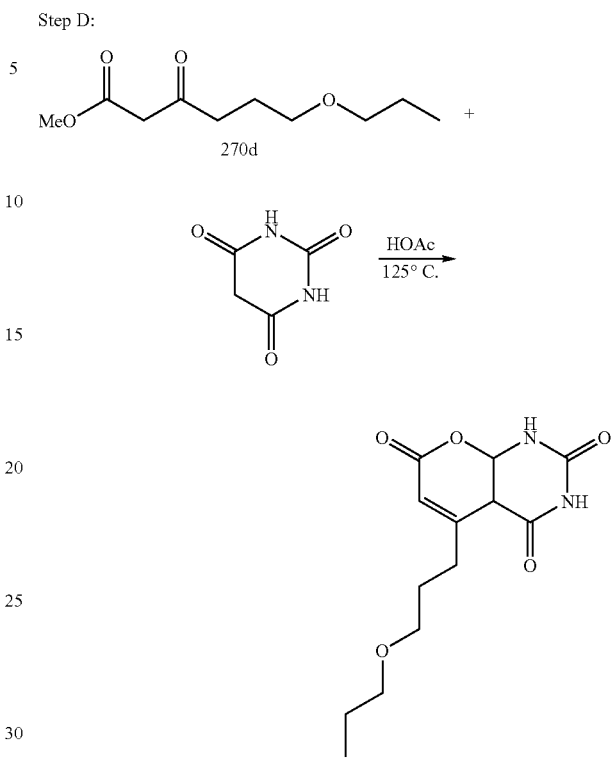

Compound 270d (448 mg, 2.22 mmol) and barbituric acid (340 mg, 2.65 mmol) was mixed with HOAc (2 mL) in a sealed tube, and heated in an oil bath at 125° C. overnight. The mixture was cooled to room temperature, HOAc was removed and the residue was taken up in MeOH, and filtered. The mother liquid was concentrated and separated by preparative TLC, eluted with 1:10:10, HOAc:DCM:EtOAc, to give desired Compound 270 (72 mg, 11.4%) as a white solid. Electrospray MS [M+1]: 281.2.

Preparative Example 271

Step A:

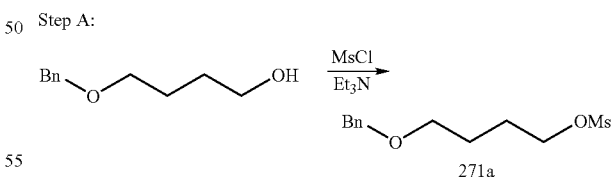

Starting alcohol (5.2 g,. 28.0 mmol) was dissolved in DCM (100 mL), triethylamine (6 mL, 42.7 mmol) and MsCl (2.6 mL, 33.6 mmol) was added. The resulting solution was stirred at room temperature for 1 h. The mixture was diluted with EtOAc and washed with 1 N HCl (50 mL×2). The aqueous layers were combined, extracted with EtOAc. The organic layers were combined, washed with brine, dried (MgSO4), filtered, and concentrated to give Compound 271a (7.26 g, 100%).

Step B:

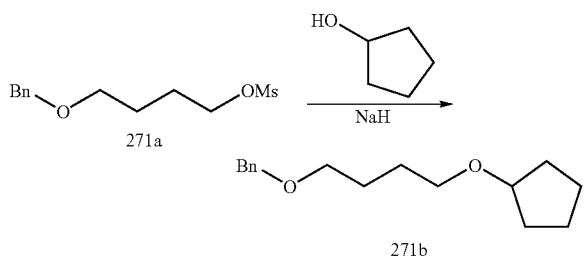

Cyclopentanol (3.8 mL, 42 mmol) was dissolved in THF (50 mL) under nitrogen. NaH (0.85 g, 95% oil dispersion, 33.7 mmol) was added. The resulting slurry was stirred at room temperature for 1 h. A solution of mesylate 271a (7.26 g, 28 mmol) in DMF (30 mL) was added via syringe. The resulting mixture was heated at 85° C. overnight. The mixture was cooled to room temperature, and diluted with EtOAc, and washed with water (50 mL×3). The aqueous layers were combined and extracted with EtOAc. The organic extracts were combined, washed with brine, dried ($MgSO_4$), filtered and concentrated in vacuo. The residue was purified over silica gel column, eluted with EtOAc-hexanes (1:10) to give 4.95 g (71%) of Compound 271b as an amber liquid.

Step B:

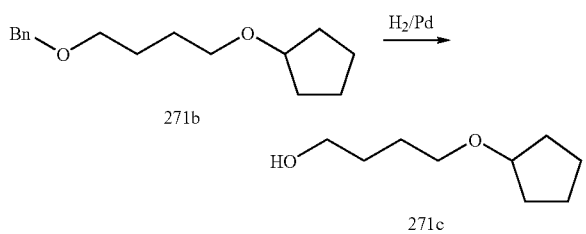

Compound 271b (4.95 g, 20 mmol) was dissolved in EtOH (100 mL), 10% Pd/C (0.55 g) was added and stirred under 1 atm of hydrogen balloon overnight. Filtered through Celite, the filtrate was concentrated in vacuo. The residue was purified over silica gel column, eluted with EtOAc-hexanes (1:3) to give 3.1 g (98%) of Compound 271c as a colorless liquid.

Step C:

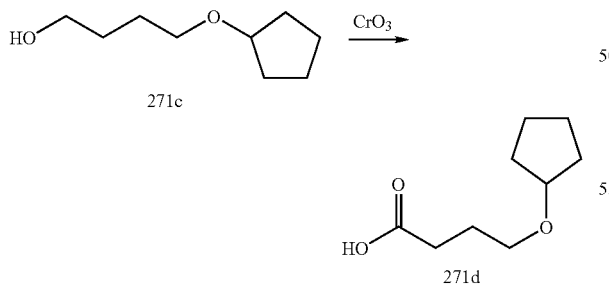

$CrO_3$ was mixed with 4.7 mL of conc. $H_2SO_4$. The mixture was diluted with water to 36 mL. Compound 271c was dissolved in acetone (30 mL), and Jones reagent was added. The mixture was stirred at room temperature for 1 h, diluted with water and extracted with DCM. The organic extracts were combined, washed with brine, dried ($MgSO_4$), filtered and concentrated to give 1.99 9 (71%).

Step D:

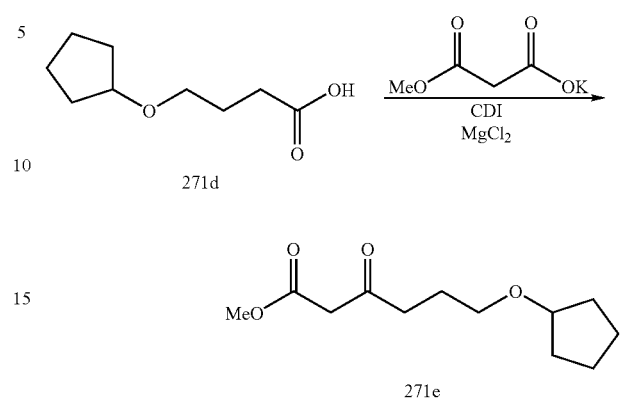

Compound 271d (2.40 g, 14.0 mmol) dissolved in THF (50 mL), CDI (2.48 g, 15.3 mmol) was added. The resulting mixture was stirred at room temperature for 1 h. $MgCl_2$ (1.5 g, 15.3 mmol) and $KOCOCH_2CO_2Me$ (3.3 A, 20.9 mmol) were added, the resulting mixture was stirred at room temperature overnight. EtOAc (100 mL), water (50 mL) were added. The aqueous layer was separated and extracted with EtOAc. The aqueous layer was extracted with EtOAc. The organic extracts were combined, washed with brine, dried ($MgSO_4$), filtered and concentrated. The residue was filtered through a pad of silica gel, eluted with EtOAc: hexanes, 1:3, to give 2.2 g (69%) yellow liquid as Compound 270e.

Step D:

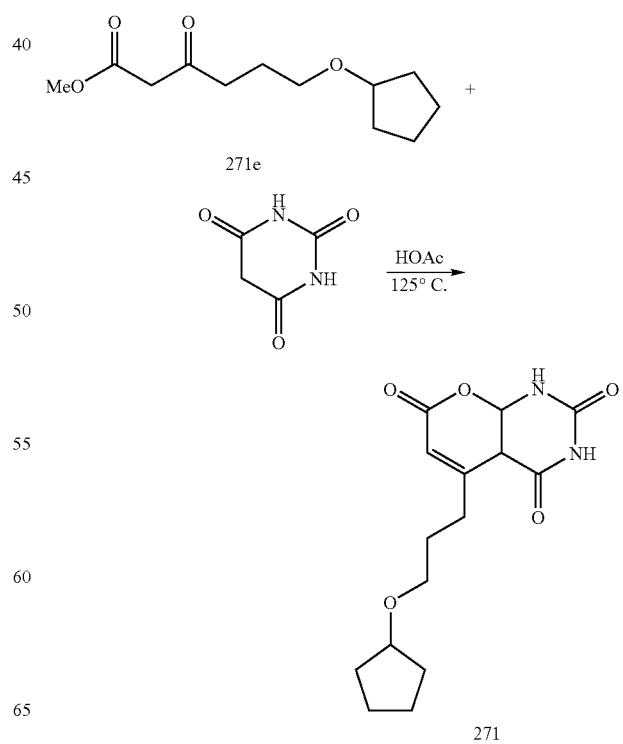

Compound 271e (448 mg, 2.22 mmol) and barbituric acid (340 mg, 2.65 mmol) was mixed with HOAc (2 mL) in a sealed tube, and heated in an oil bath at 125° C. overnight. The mixture was cooled to room temperature, HOAc was removed and the residue was taken up in MeOH, and filtered. The mother liquid was concentrated and separated by preparative TLC, eluted with 1:10:10, HOAc:DCM:EtOAc, to give desired Compound 271 (55 mg, 4%) as a white solid. Electrospray MS [M+1]: 307.2.

Compound 273, Compound 287 and Compound 290 are prepared in a similar fashion as Compound 271 from the corresponding alcohols.

Preparative Example 205

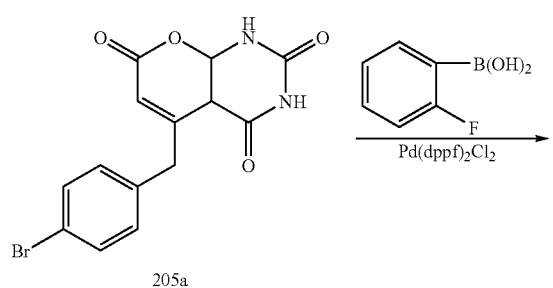

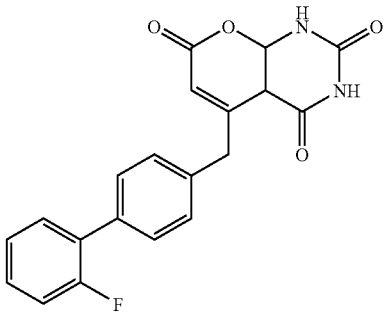

205

Compound 205a (50 mg, 0.14 mmol) was dissolved in DMF (2 mL) and H$_2$O (2 mL), Pd(dppf)$_2$Cl$_2$ and K$_2$CO$_3$ were added. The resulting mixture was heated at 85° C. under nitrogen for 5 h. The mixture was cooled to room temperature and filtered through Celite. The filtrated was concentrated. The residue was dissolved in MeOH, and DCM was added until precipitation persisted. The solid was collected as the desired Compound 205 (21 mg, 40%). Electrospray MS [M+1]: 481.5.

Compound 207 was prepared in a similar fashion as Compound 205, using the corresponding boronic acid.

Several compounds of the invention are shown in the Table below as well as in the Tables presented later in this specification. The LCMS data is also shown wherever available. The activity (EC50) data is also shown, wherever measured and available, and is designated A, B or C, where A=0.001 nM to 100 nM; B is >100<1000 nM and C is >1000 nM.

| Compound No. | STRUCTURE | NA EC50 camp (nM) | Electrospray LCMS [M + 1]+ |
|---|---|---|---|
| 200 | 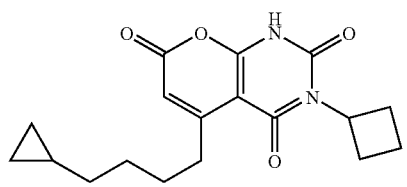 | B | 331.2 |
| 201 | 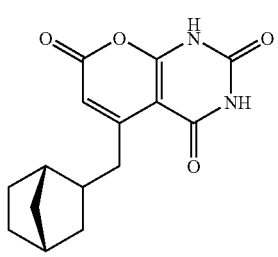 | C | 289.2 |

| Compound No. | STRUCTURE | NA EC50 camp (nM) | Electrospray LCMS [M + 1]+ |
|---|---|---|---|
| 202 | 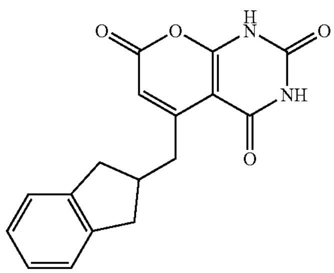 | B | 311.2 |
| 203 | 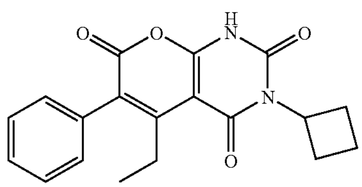 | C | 339.1 |
| 204 | 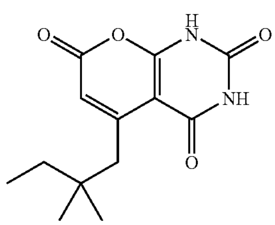 | C | 265.1 |
| 205 | 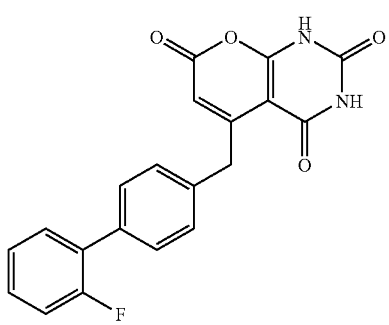 | B | 365.2 |
| 206 | 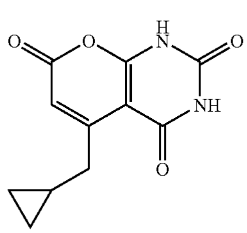 | B | 235.1 |

-continued

| Compound No. | STRUCTURE | NA EC50 camp (nM) | Electrospray LCMS [M + 1]+ |
|---|---|---|---|
| 207 | 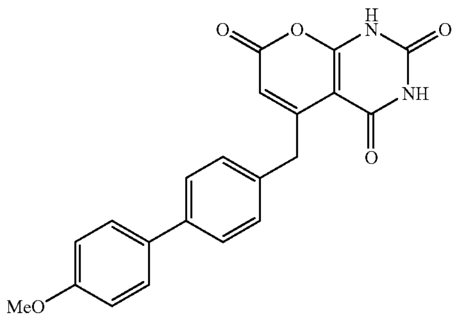 | C | 377.2 |
| 208 | 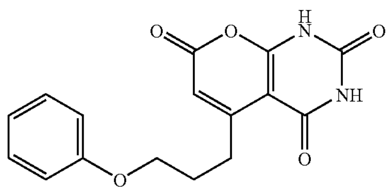 | C | 316.2 |
| 209 | 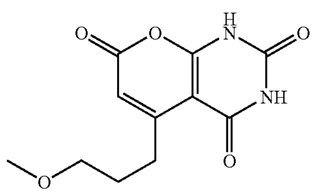 | B | 253.1 |
| 210 | 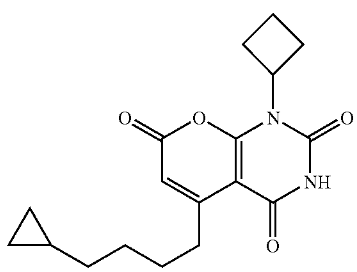 | B | 331.2 |
| 211 | 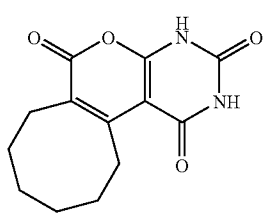 | C | 263.1 |
| 212 | 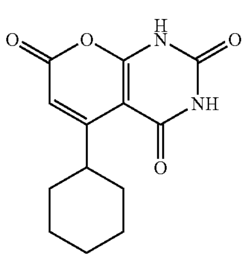 | B | 263.1 |

| Compound No. | STRUCTURE | NA EC50 camp (nM) | Electrospray LCMS [M + 1]+ |
|---|---|---|---|
| 213 | 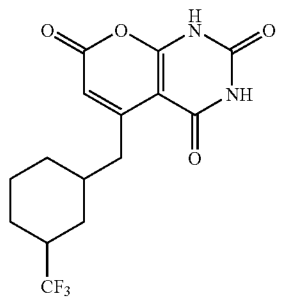 | B | 345.2 |
| 214 | 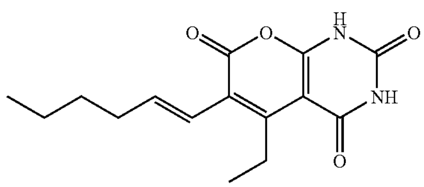 | C | 291.2 |
| 215 | 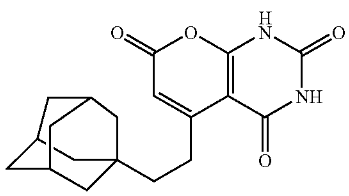 | C | 343.2 |
| 216 | 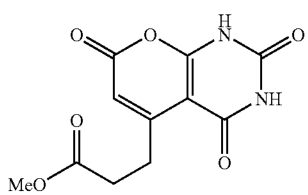 | B | 267.1 |
| 217 | 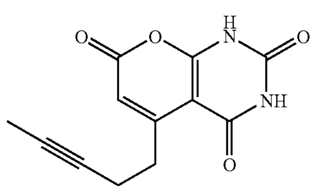 | C | 247.1 |
| 218 | 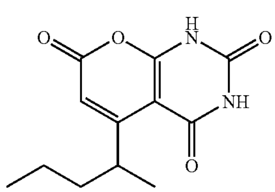 | B | 951.1 |
| 219 | 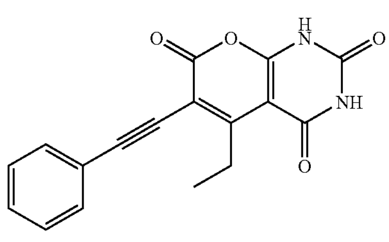 | C | 309.2 |

-continued

| Compound No. | STRUCTURE | NA EC50 camp (nM) | Electrospray LCMS [M + 1]+ |
|---|---|---|---|
| 220 | 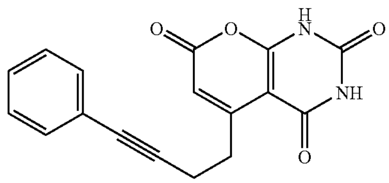 | C | 309.2 |
| 221 | 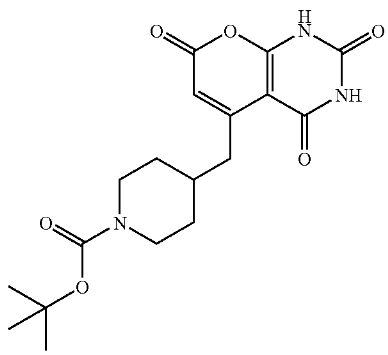 | C | 378.2 |
| 222 | 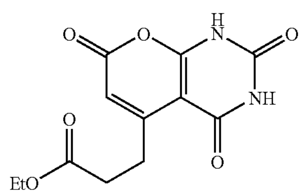 | C | 281.2 |
| 223 | 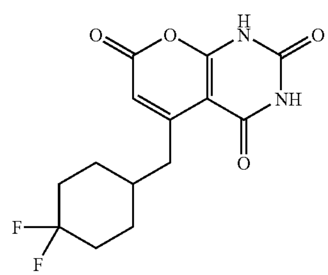 | A | 313 |
| 224 | 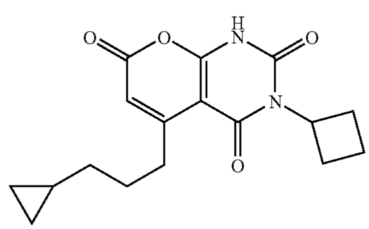 | A | 317.2 |
| 225 | 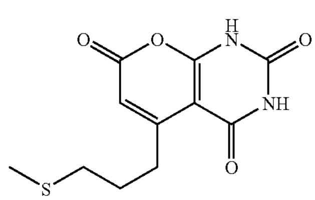 | A | 269.1 |

-continued

| Compound No. | STRUCTURE | NA EC50 camp (nM) | Electrospray LCMS [M + 1]+ |
|---|---|---|---|
| 226 | 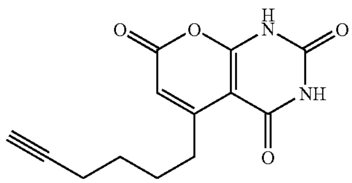 | A | 261.1 |
| 227 | 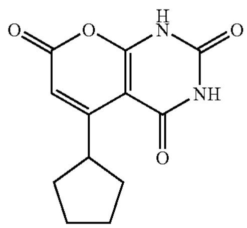 | C | 249.1 |
| 228 | 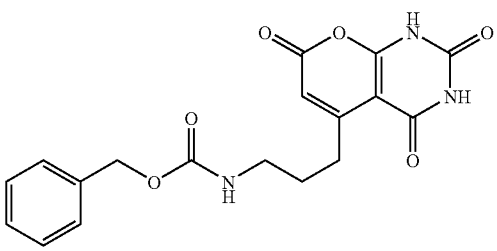 | C | 372.2 |
| 229 | 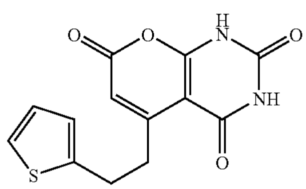 | A | 391.2 |
| 230 | 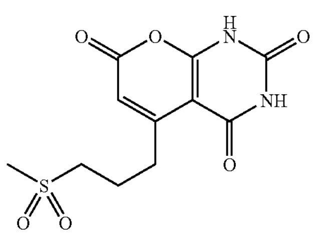 | 8 | 301.2 |
| 231 | 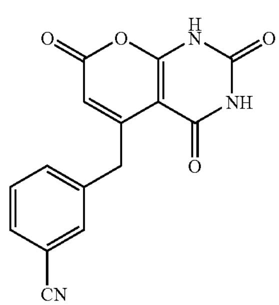 | C | 318.2 (M + Na) |

-continued

| Compound No. | STRUCTURE | NA EC50 camp (nM) | Electrospray LCMS [M + 1]+ |
|---|---|---|---|
| 232 | 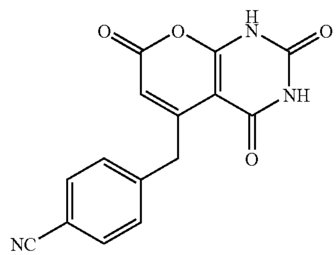 | C | 368.2 (M + Na) |
| 233 | 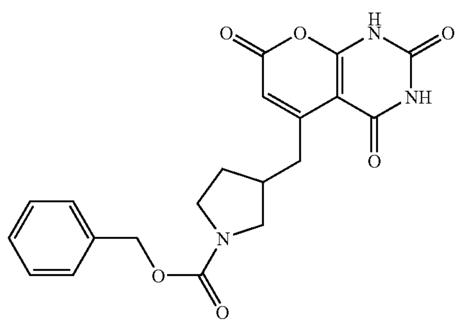 | C | 398 |
| 234 | 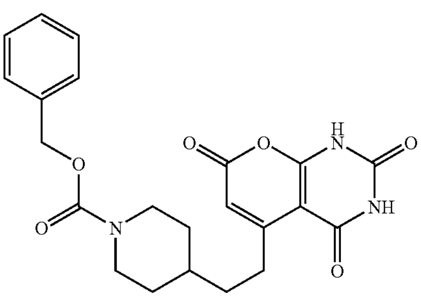 | C | 426 |
| 235 | 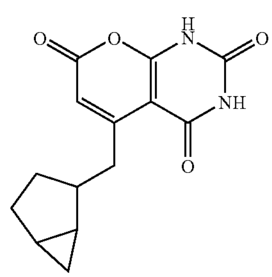 | A | 275.2 |
| 236 | 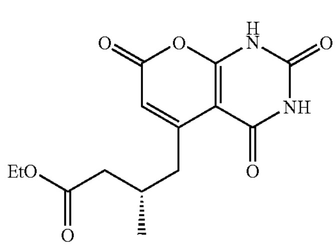 | C | 309.2 |

-continued

| Compound No. | STRUCTURE | NA EC50 camp (nM) | Electrospray LCMS [M + 1]+ |
|---|---|---|---|
| 237 | 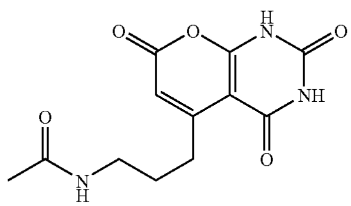 | C | 280.2 |
| 236 | 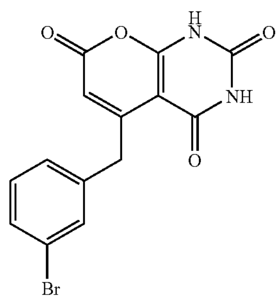 | B | 349.2 |
| 239 | 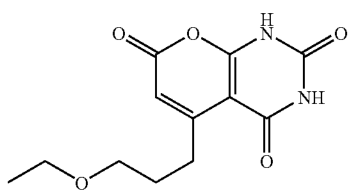 | A | 267.1 |
| 240 | 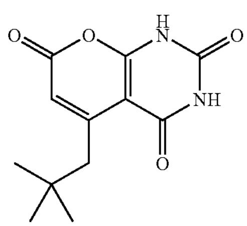 | C | 251 |
| 241 | 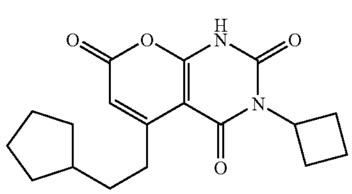 | A | 331.2 |
| 242 | 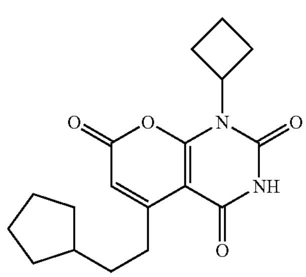 | C | 331.2 |

-continued

| Compound No. | STRUCTURE | NA EC50 camp (nM) | Electrospray LCMS [M + 1]+ |
|---|---|---|---|
| 243 | 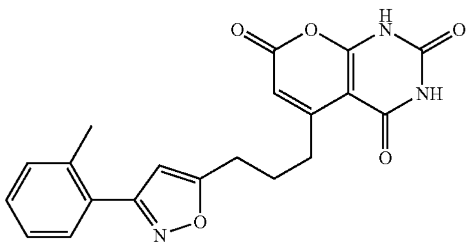 | B | 380 |
| 244 | 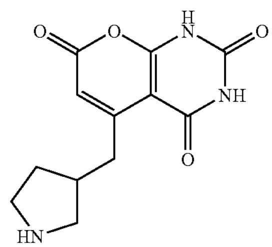 | C | 264 |
| 245 | 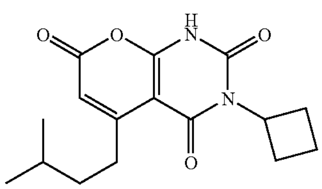 | A | 305.2 |
| 246 | 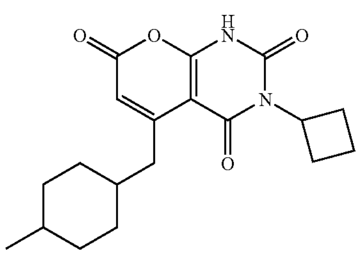 | C | 345.2 |
| 247 | 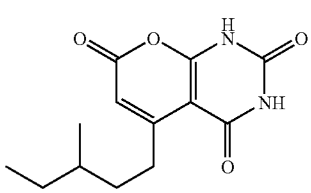 | A | 265.1 |
| 248 | 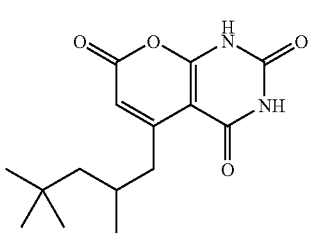 | C | 293.2 |

-continued

| Compound No. | STRUCTURE | NA EC50 camp (nM) | Electrospray LCMS [M + 1]+ |
|---|---|---|---|
| 249 | 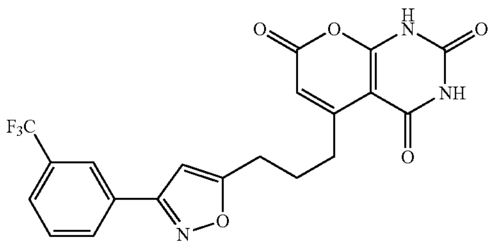 | B | 434 |
| 250 | 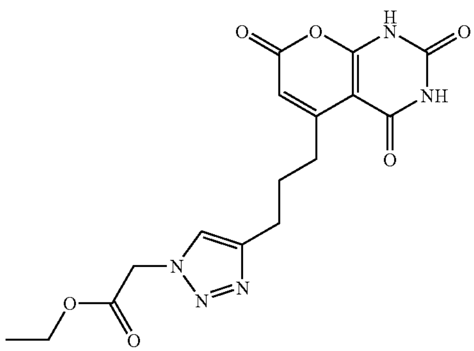 | C | 376 |
| 251 | 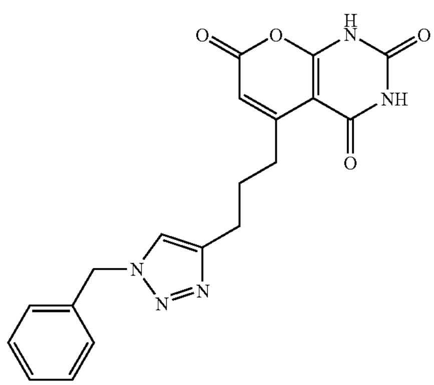 | B | 380 |
| 252 | 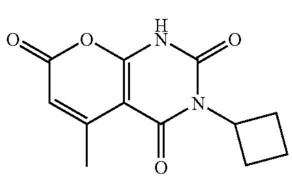 | A | 249.1 |
| 253 | 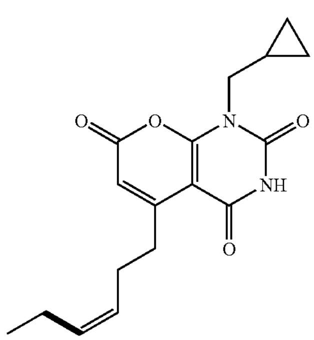 | C | 317.2 |

-continued

| Compound No. | STRUCTURE | NA EC50 camp (nM) | Electrospray LCMS [M + 1]+ |
|---|---|---|---|
| 254 | 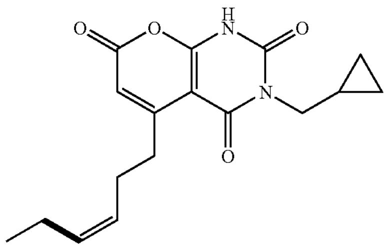 | C | 317.2 |
| 255 | 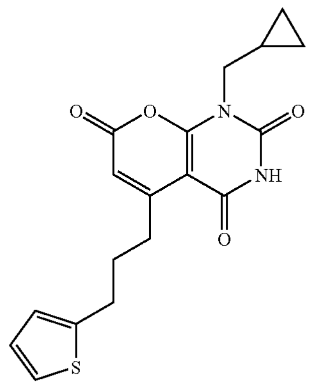 | C | 359.2 |
| 256 | 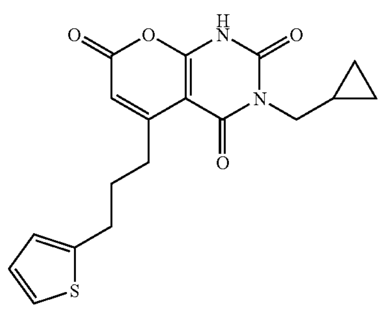 | C | 359.2 |
| 257 | 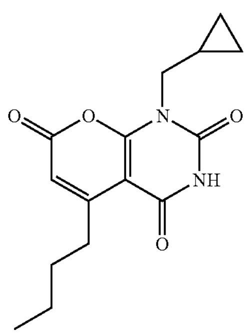 | C | 291.2 |
| 258 | 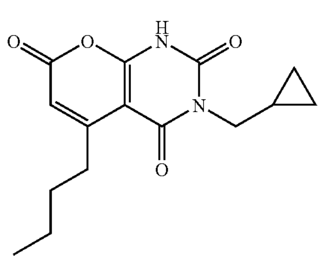 | B | 291.2 |

-continued

| Compound No. | STRUCTURE | NA EC50 camp (nM) | Electrospray LCMS [M + 1]+ |
|---|---|---|---|
| 259 | 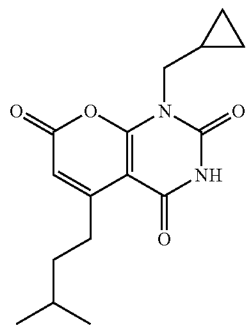 | C | 305.2 |
| 260 | 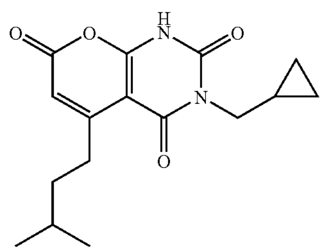 | C | 305.2 |
| 261 | 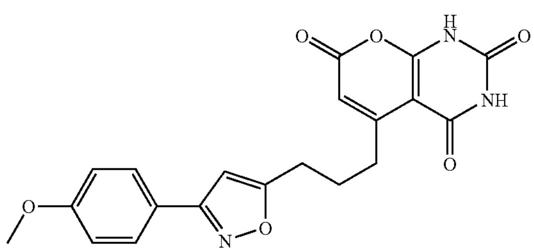 | B | 396 |
| 262 | 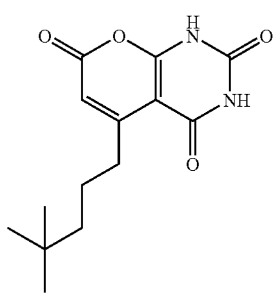 | A | 279.2 |
| 263 | 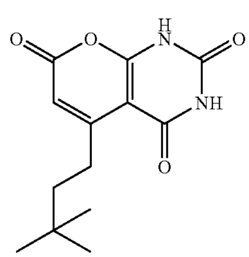 | C | 265.1 |

-continued
| Compound No. | STRUCTURE | NA EC50 camp (nM) | Electrospray LCMS [M + 1]+ |
|---|---|---|---|
| 264 | 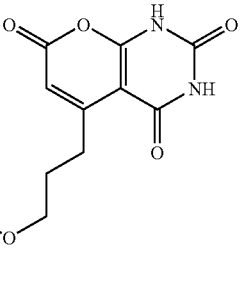 | C | 329.2 |
| 265 | 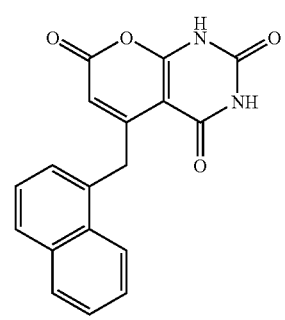 | C | 321.2 |
| 266 | 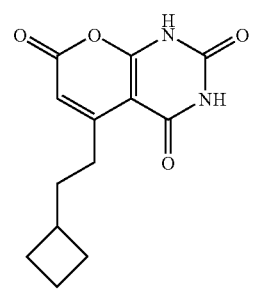 | A | 263.1 |
| 267 | 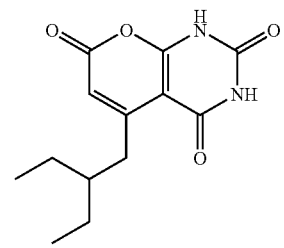 | C | 265.1 |
| 268 | 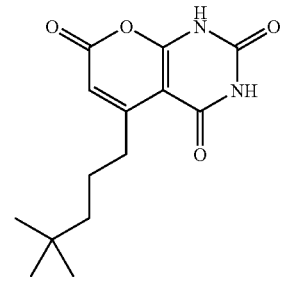 | A | 277.2 |

-continued

| Compound No. | STRUCTURE | NA EC50 camp (nM) | Electrospray LCMS [M + 1]+ |
|---|---|---|---|
| 269 | 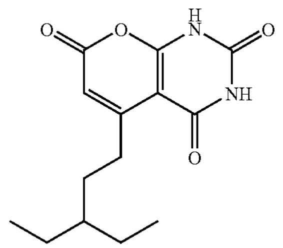 | B | 279.2 |
| 270 | 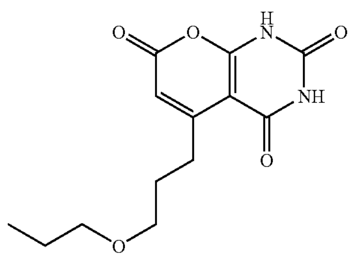 | A | 281.2 |
| 271 | 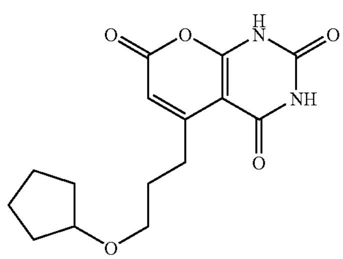 | B | 307.2 |
| 272 | 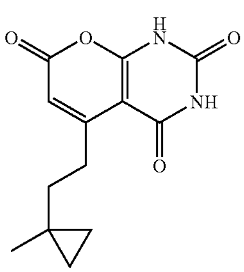 | B | 263.1 |
| 273 | 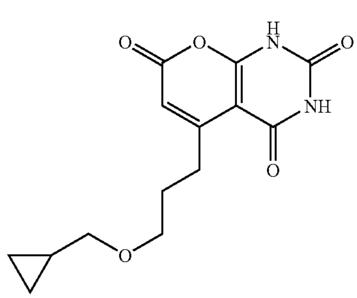 | B | 293.2 |

| Compound No. | STRUCTURE | NA EC50 camp (nM) | Electrospray LCMS [M + 1]+ |
|---|---|---|---|
| 274 | (cyclobutyl-N, pyrano-pyrimidine-dione, cyclopropyl-ethyl) | B | 303.2 |
| 275 | (N-methyl, pyrano-pyrimidine-dione, cyclopropyl-ethyl) | B | 263.1 |
| 276 | (N-H, N-methyl, pyrano-pyrimidine-dione, cyclopropyl-ethyl) | B | 263.1 |
| 277 | (N-ethyl, pyrano-pyrimidine-dione, cyclopropyl-ethyl) | C | 277.2 |
| 278 | (N-H, N-ethyl, pyrano-pyrimidine-dione, cyclopropyl-ethyl) | B | 277.2 |

-continued

| Compound No. | STRUCTURE | NA EC50 camp (nM) | Electrospray LCMS [M + 1]+ |
|---|---|---|---|
| 279 | 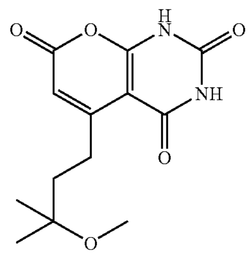 | C | 281.2 |
| 280 | 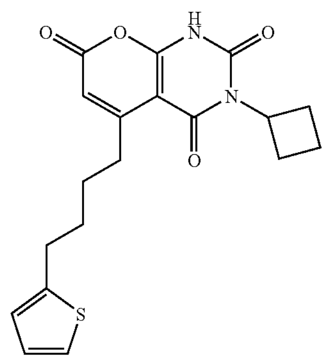 | C | 373.2 |
| 281 | 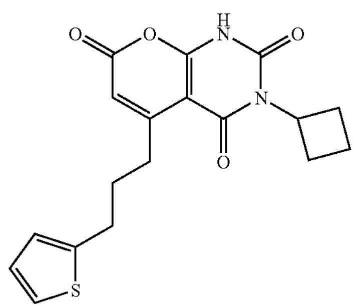 | B | 359.2 |
| 282 | 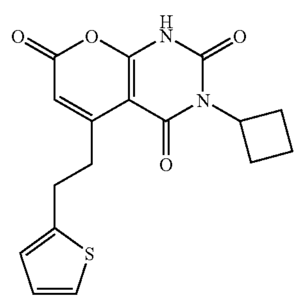 | B | 345.2 |
| 283 | 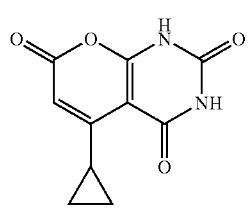 | B | 221.1 |

| Compound No. | STRUCTURE | NA EC50 camp (nM) | Electrospray LCMS [M + 1]+ |
|---|---|---|---|
| 284 | 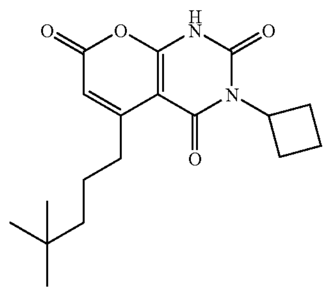 | B | 333.1 |
| 285 | 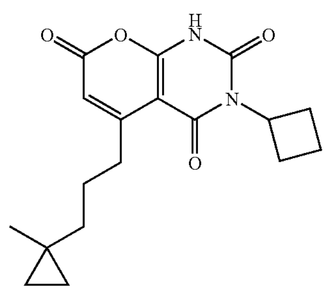 | B | 331.2 |
| 286 | 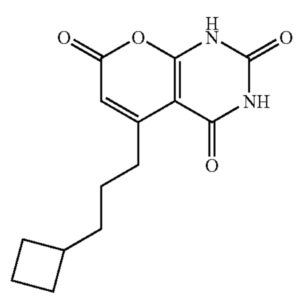 | A | 277.2 |
| 287 | 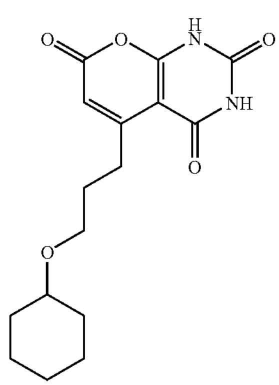 | C | 321.2 |

-continued

| Compound No. | STRUCTURE | NA EC50 camp (nM) | Electrospray LCMS [M + 1]+ |
|---|---|---|---|
| 288 | 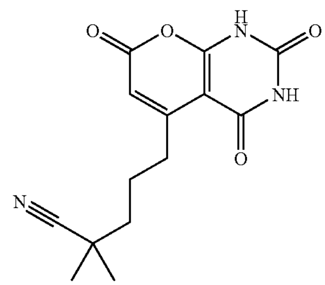 | C | 290.2 |
| 289 | 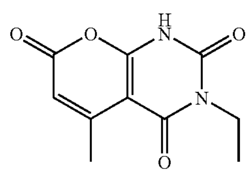 | C | 223.1 |
| 290 | 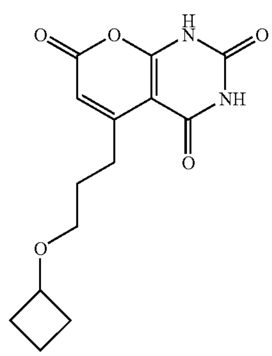 | B | 315.2 (M + Na) |
| 291 | 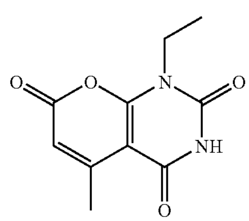 | C | 223.1 |
| 292 | 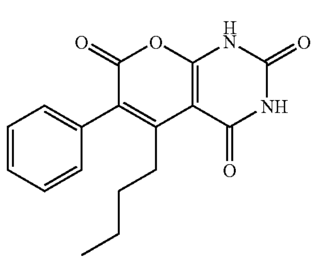 | B | 313.2 |

| Compound No. | STRUCTURE | NA EC50 camp (nM) | Electrospray LCMS [M + 1]+ |
|---|---|---|---|
| 293 | 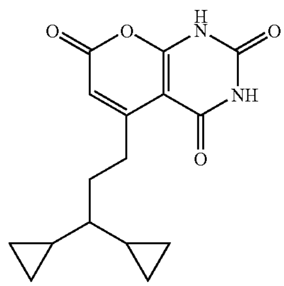 | B | 303.2 |
| 294 | 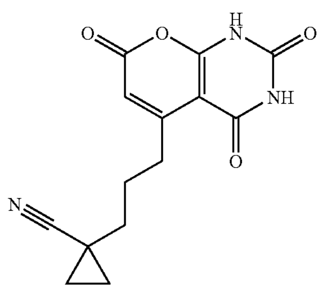 | B | 288.2 |
| 295 | 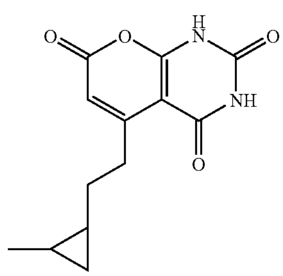 | B | 263.1 |
| 296 | 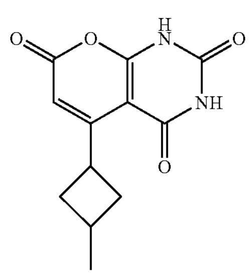 | B | 249.1 |
| 297 | 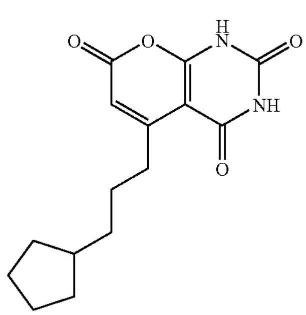 | A | 291.2 |

The compounds 500 to 690 were prepared by a procedure similar to that used for the preparation of Example 49, using Example 10, and the appropriate corresponding alcohol.

Compounds 691 and 698 were prepared by a procedure similar to Example 49, using appropriate oxyaminocarbamate and sulfoxide which was prepared using Example 10.

| Compound No. | Structure | NA EC50 camp (nM) | Electrospray LCMS [M + 1]+ |
|---|---|---|---|
| 500 | 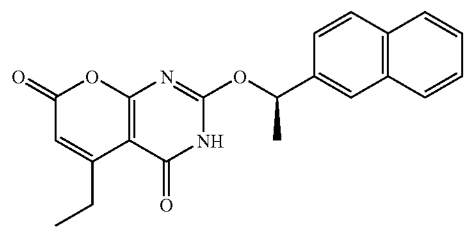 | B | 363.1 |
| 501 | 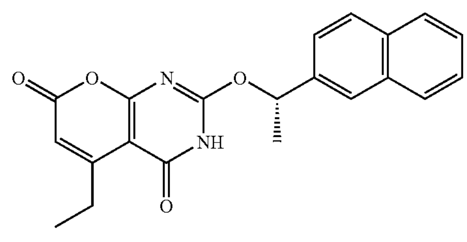 | A | 363.1 |
| 502 | 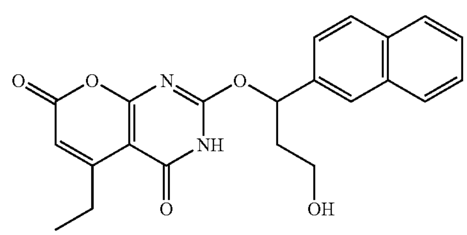 | B | 343 |
| 503 | 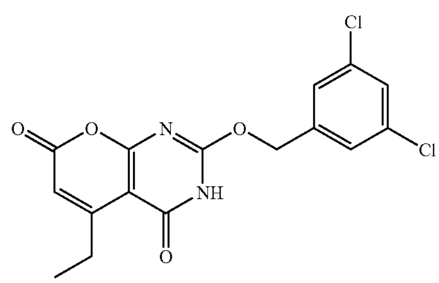 | B | 368 |
| 504 | 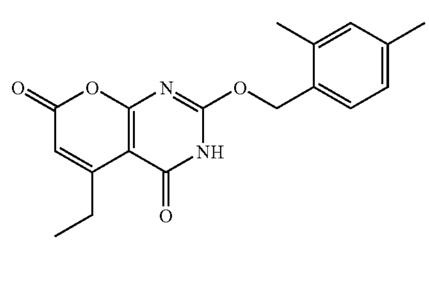 | B | 327 |

| Compound No. | Structure | NA EC50 camp (nM) | Electrospray LCMS [M + 1]+ |
|---|---|---|---|
| 505 | 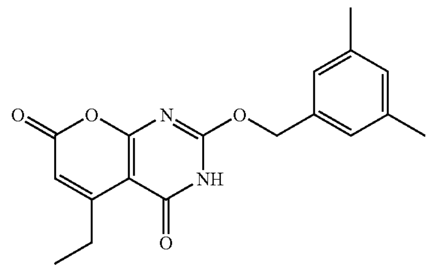 | B | 327 |
| 506 | 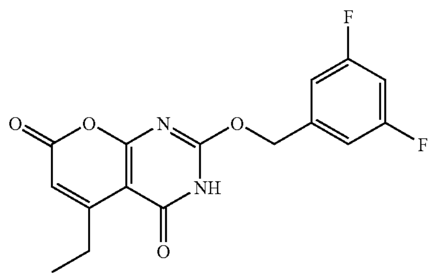 | C | 335 |
| 507 | 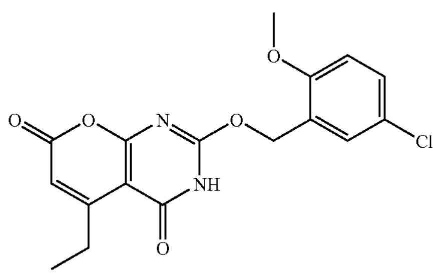 | A | 363 |
| 508 | 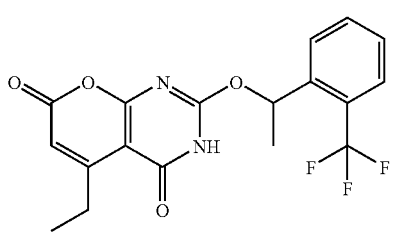 | C | 381.1 |
| 509 | 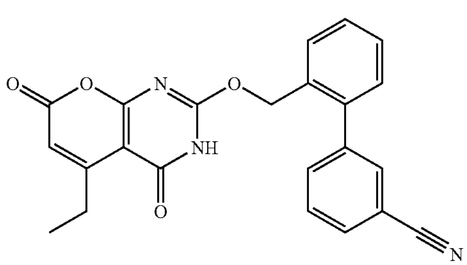 | B | 400 |

-continued

| Compound No. | Structure | NA EC50 camp (nM) | Electrospray LCMS [M + 1]+ |
|---|---|---|---|
| 510 | 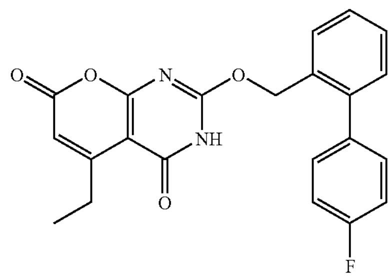 | C | 393 |
| 511 | 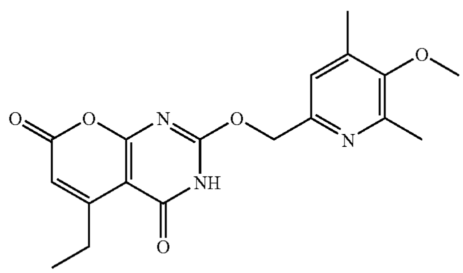 | C | 358.2 |
| 512 | 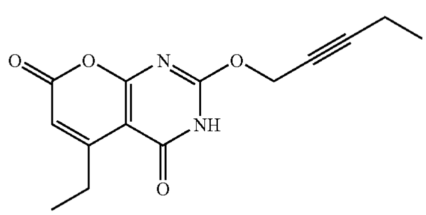 | A | 275 |
| 513 | 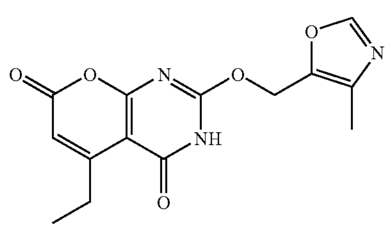 | B | 304 |
| 514 | 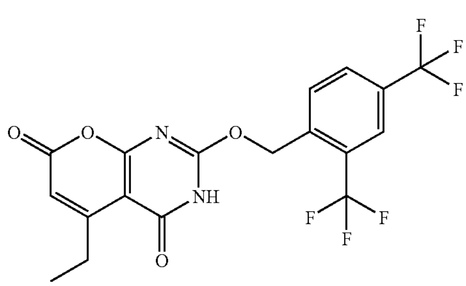 | C | 435 |

-continued

| Compound No. | Structure | NA EC50 camp (nM) | Electrospray LCMS [M + 1]+ |
|---|---|---|---|
| 515 | 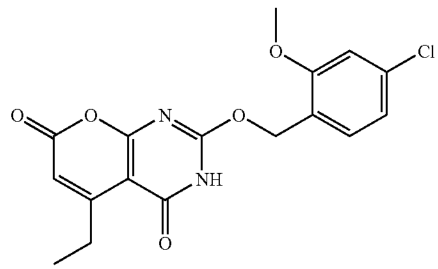 | B | 363 |
| 516 | 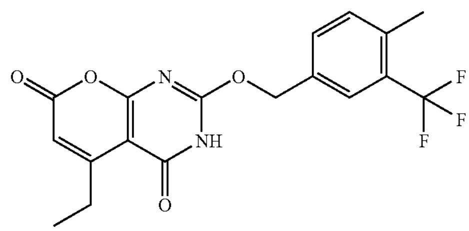 | C | 381 |
| 517 | 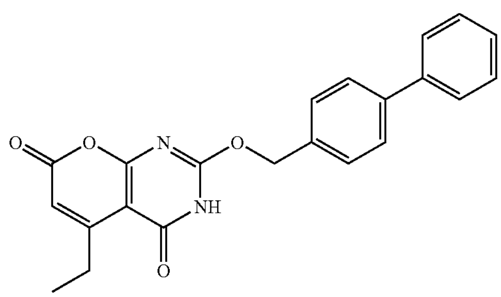 | C | 375.2 |
| 518 | 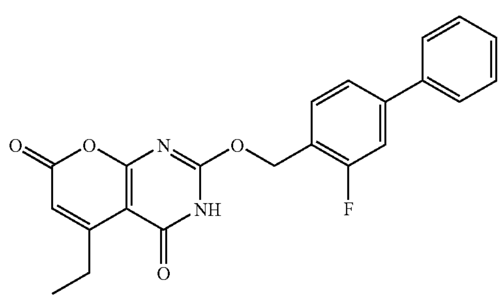 | B | 393.2 |
| 519 | 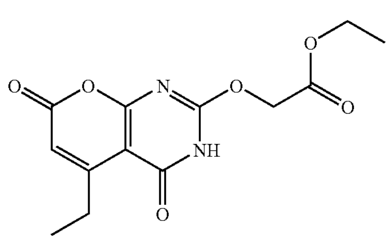 | C | 295.1 |

-continued

| Compound No. | Structure | NA EC50 camp (nM) | Electrospray LCMS [M + 1]+ |
|---|---|---|---|
| 520 | 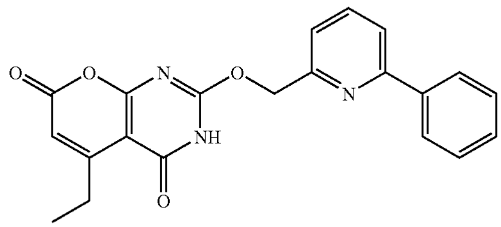 | C | 376.2 |
| 521 | 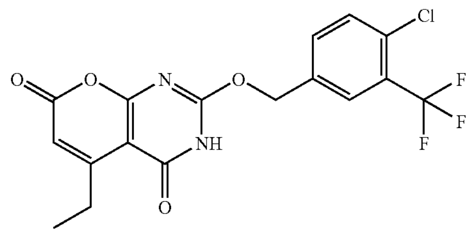 | B | 401.2 |
| 522 | 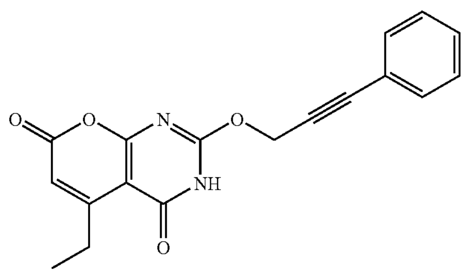 | B | 323 |
| 523 | 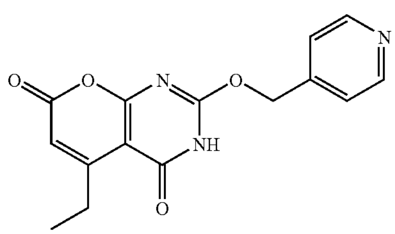 | A | 300.2 |
| 524 | 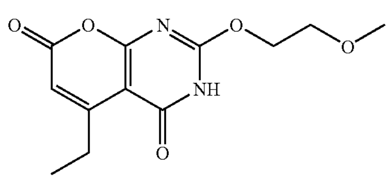 | B | 267.1 |
| 525 | 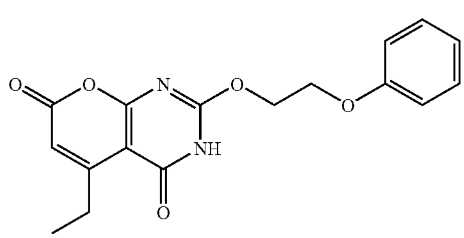 | B | 329.2 |

-continued

| Compound No. | Structure | NA EC50 camp (nM) | Electrospray LCMS [M + 1]+ |
|---|---|---|---|
| 526 | 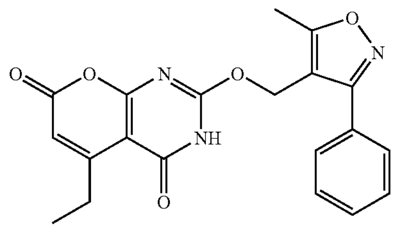 | B | 380 |
| 527 | 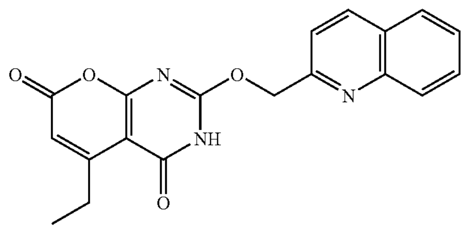 | B | 350 |
| 528 | 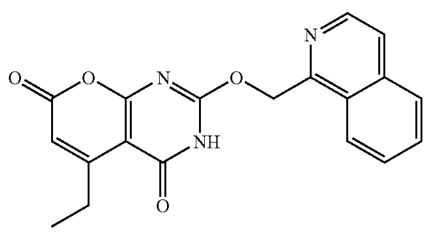 | B | 350 |
| 529 | 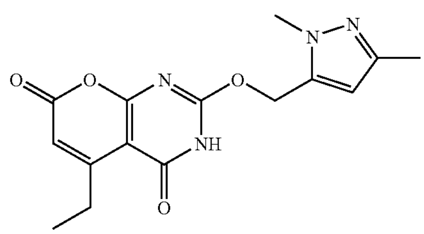 | B | 317 |
| 530 | 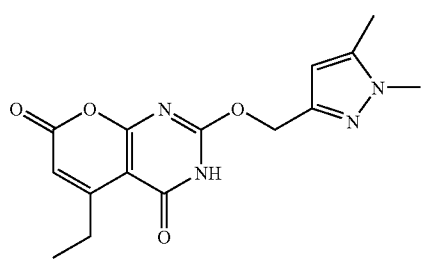 | B | 317 |
| 531 | 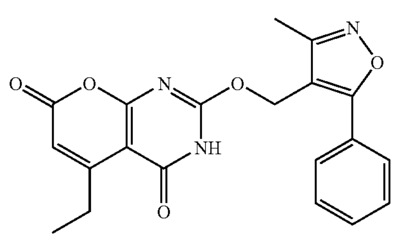 | B | 380 |

-continued
| Compound No. | Structure | NA EC50 camp (nM) | Electrospray LCMS [M + 1]+ |
|---|---|---|---|
| 532 | 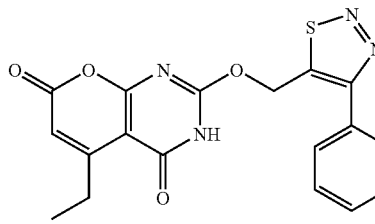 | B | 383 |
| 533 | 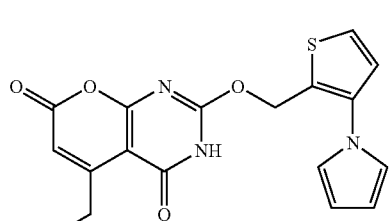 | C | 370 |
| 534 | 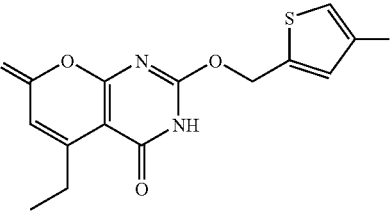 | B | 384 |
| 535 | 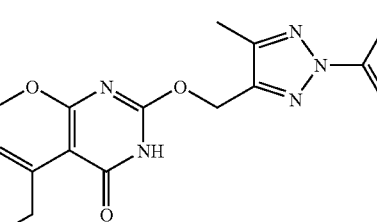 | B | 380 |
| 536 | 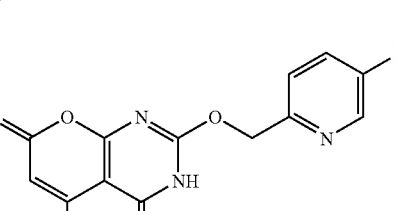 | B | 379 |
| 537 | 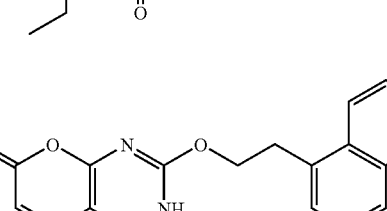 | C | 363 |

-continued

| Compound No. | Structure | NA EC50 camp (nM) | Electrospray LCMS [M + 1]+ |
|---|---|---|---|
| 538 | 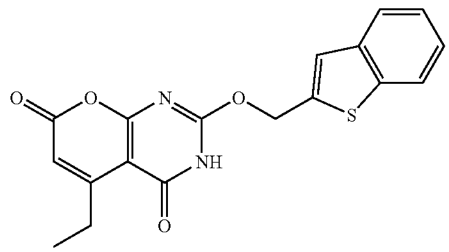 | B | 355 |
| 539 | 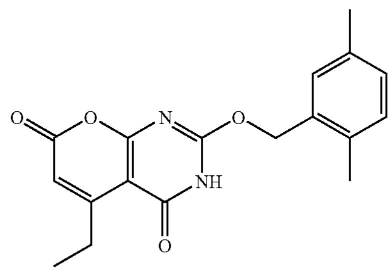 | B | 327 |
| 540 | 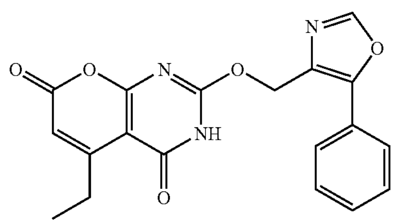 | B | 366 |
| 541 | 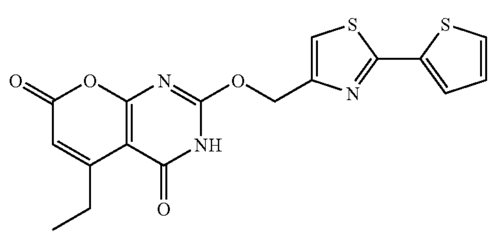 | B | 388 |
| 542 | 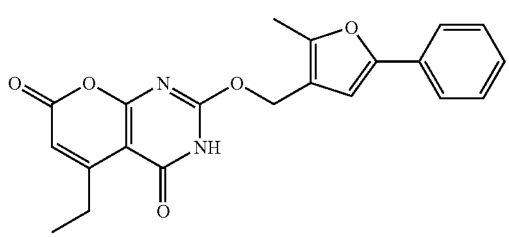 | C | 379 |
| 543 | 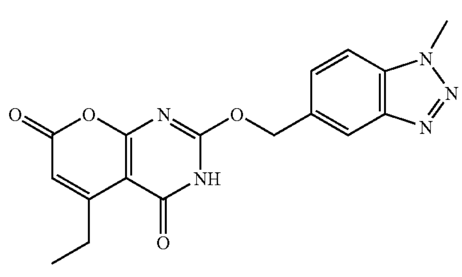 | B | 354 |

-continued

| Compound No. | Structure | NA EC50 camp (nM) | Electrospray LCMS [M + 1]+ |
|---|---|---|---|
| 544 | 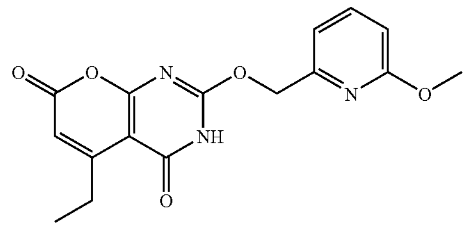 | B | 330.2 |
| 545 | 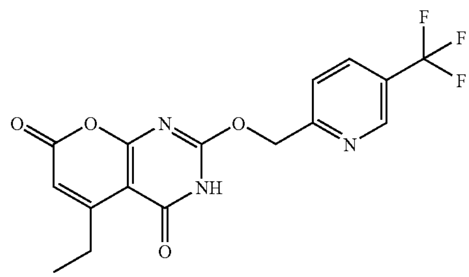 | B | 368.2 |
| 546 | 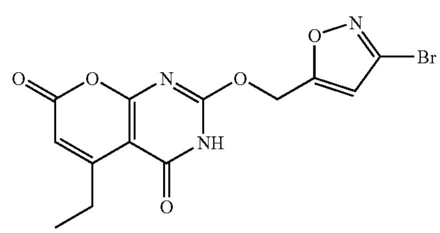 | B | 369.99 |
| 547 | 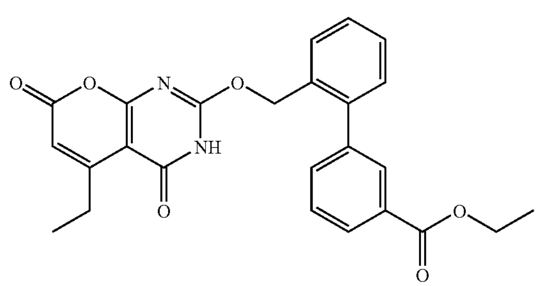 | B | 447 |
| 548 | 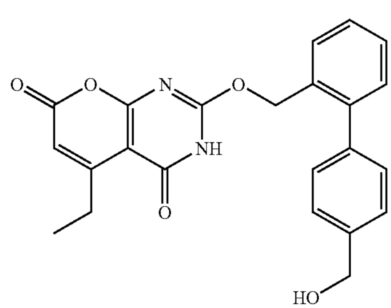 | B | 405 |

-continued

| Compound No. | Structure | NA EC50 camp (nM) | Electrospray LCMS [M + 1]+ |
|---|---|---|---|
| 549 | 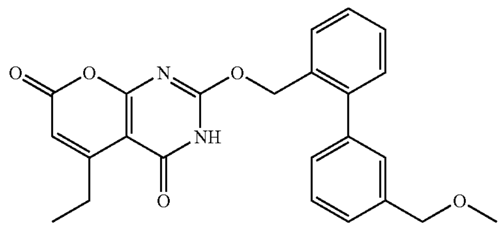 | B | 419 |
| 550 | 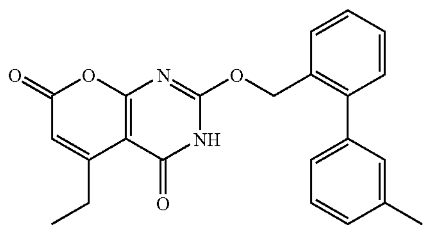 | C | 389 |
| 551 | 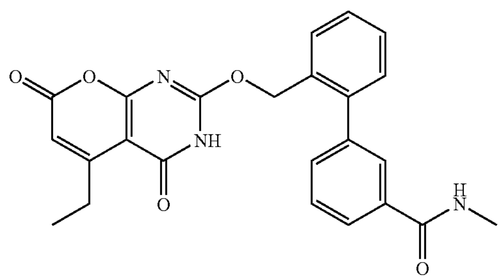 | B | 432 |
| 552 | 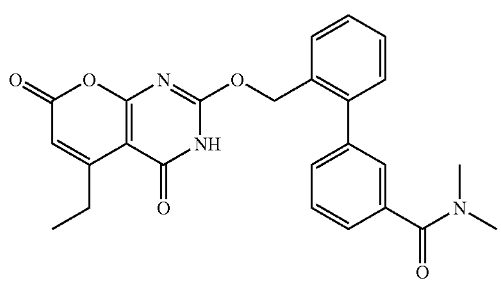 | B | 446 |
| 553 | 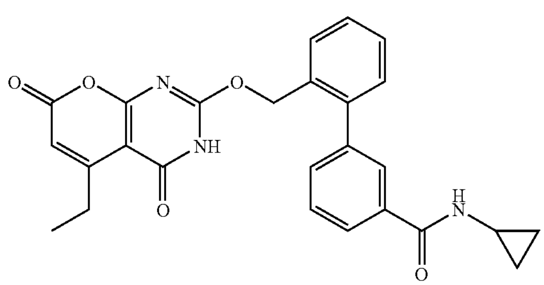 | C | 458 |

-continued
| Compound No. | Structure | NA EC50 camp (nM) | Electrospray LCMS [M + 1]+ |
|---|---|---|---|
| 554 | 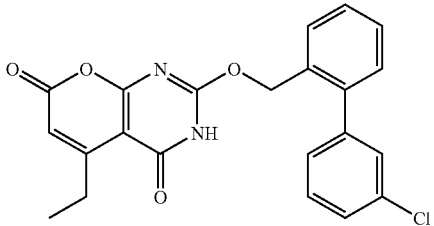 | C | 409 |
| 555 | 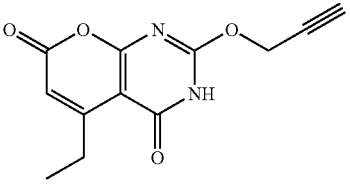 | B | 247 |
| 556 | 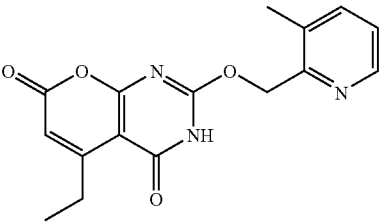 | C | 314.2 |
| 557 | 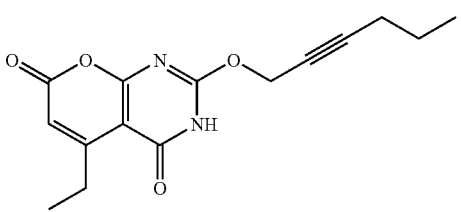 | A | 289 |
| 558 | 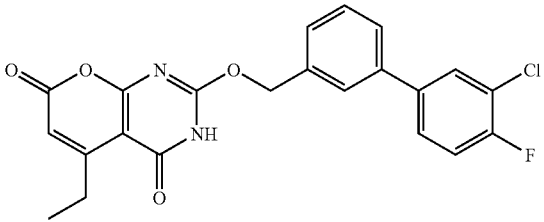 | C | 427 |
| 559 | 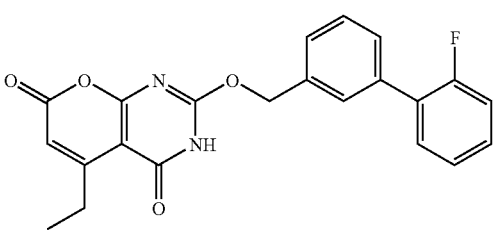 | B | 393 |

-continued

| Compound No. | Structure | NA EC50 camp (nM) | Electrospray LCMS [M + 1]+ |
|---|---|---|---|
| 560 | 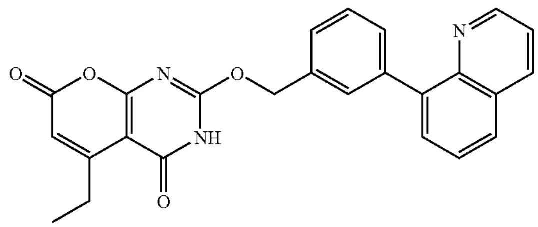 | C | 426 |
| 561 | 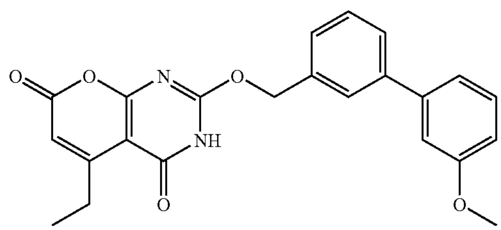 | B | 405 |
| 562 | 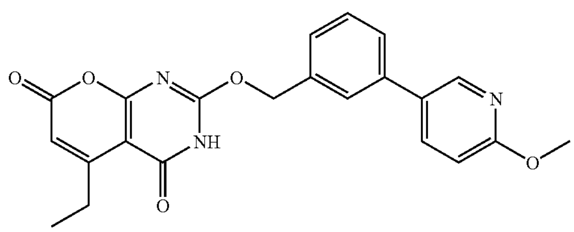 | B | 406 |
| 563 | 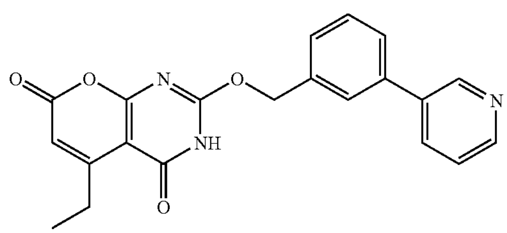 | B | 376 |
| 564 | 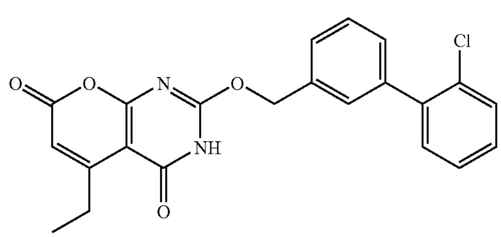 | B | 409 |
| 565 | 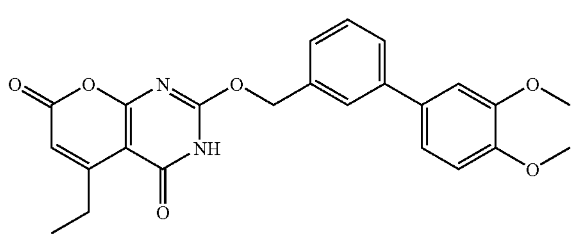 | B | 435 |

| Compound No. | Structure | NA EC50 camp (nM) | Electrospray LCMS [M + 1]+ |
|---|---|---|---|
| 566 | 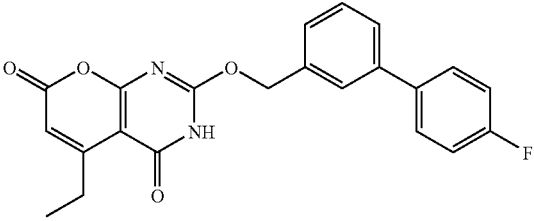 | C | 393 |
| 567 | 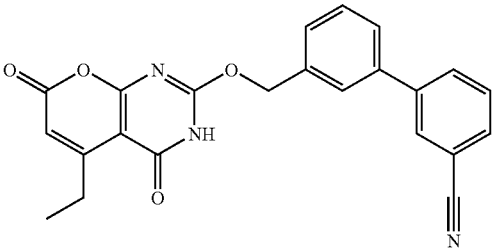 | B | 400 |
| 568 | 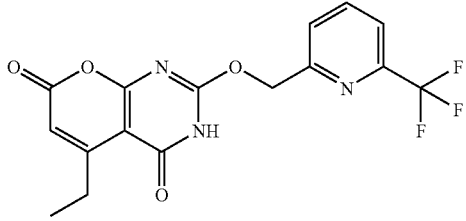 | B | 368.2 |
| 569 | 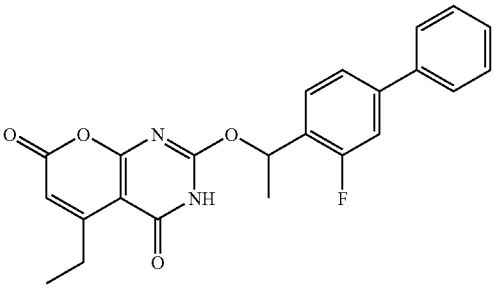 | A | 407.2 |
| 570 | 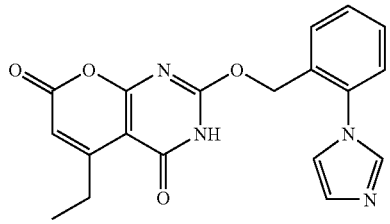 | B | 365.1 |
| 571 | 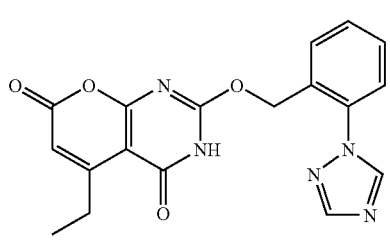 | B | 366.1 |

-continued

| Compound No. | Structure | NA EC50 camp (nM) | Electrospray LCMS [M + 1]+ |
|---|---|---|---|
| 572 | 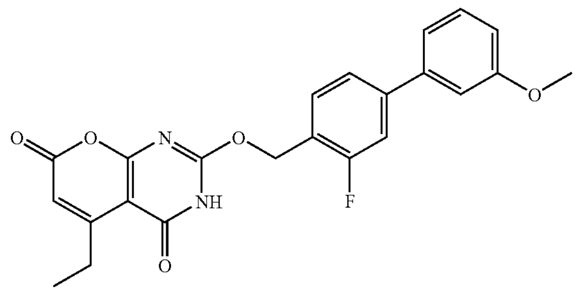 | B | 423.1 |
| 573 | 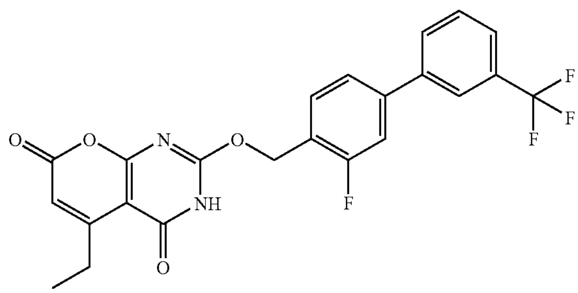 | B | 461.1 |
| 574 | 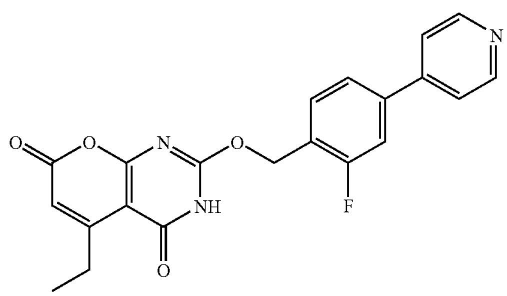 | B | 394.1 |
| 575 | 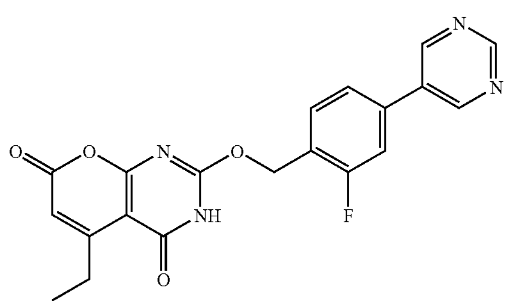 | B | 395.1 |
| 576 | 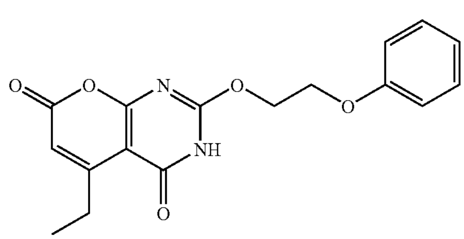 | C | 343.2 |

-continued

| Compound No. | Structure | NA EC50 camp (nM) | Electrospray LCMS [M + 1]+ |
|---|---|---|---|
| 577 | 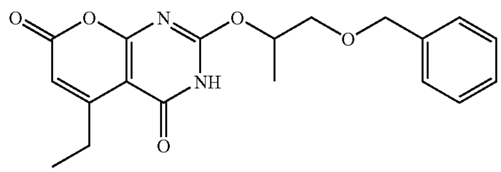 | B | 343.2 |
| 578 | 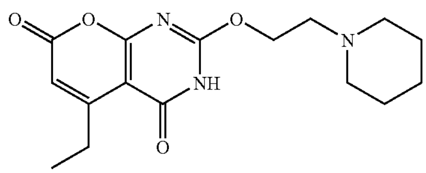 | C | 320.2 |
| 579 | 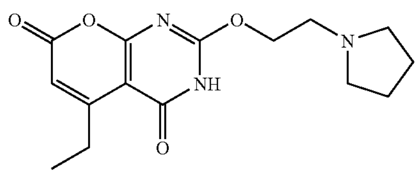 | C | 306.2 |
| 580 | 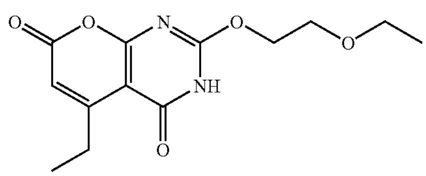 | C | 281.2 |
| 581 | 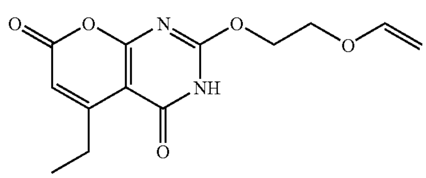 | C | 279.2 |
| 582 | 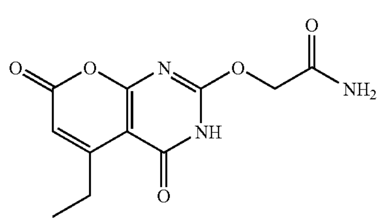 | B | 266.1 |
| 583 | 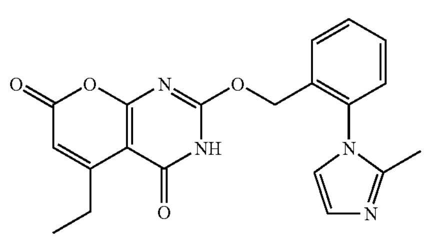 | B | 379.2 |

-continued

| Compound No. | Structure | NA EC50 camp (nM) | Electrospray LCMS [M + 1]+ |
|---|---|---|---|
| 584 | 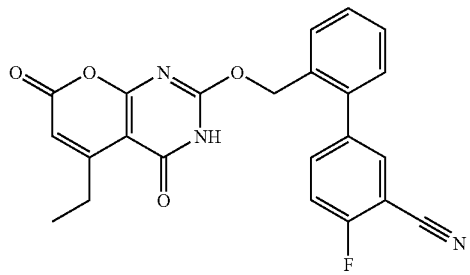 | B | 418 |
| 585 | 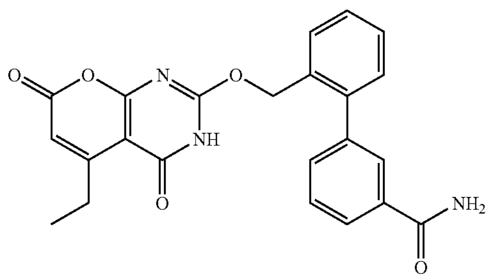 | B | 418 |
| 586 | 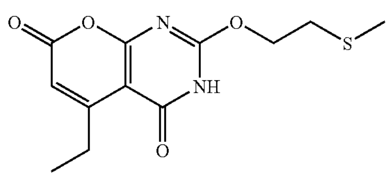 | A | 383.1 |
| 587 | 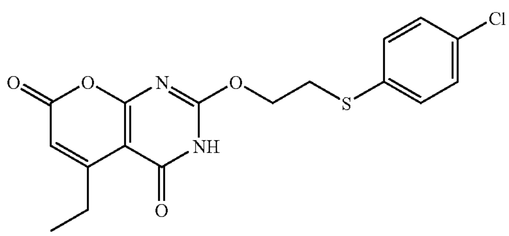 | C | 379.1 |
| 588 | 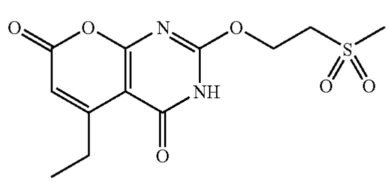 | C | 315.1 |
| 589 | 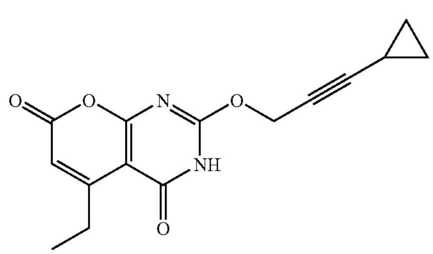 | A | 287 |

-continued

| Compound No. | Structure | NA EC50 cAMP (nM) | Electrospray LCMS [M + 1]+ |
|---|---|---|---|
| 590 | 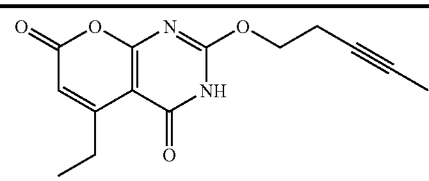 | B | 275 |
| 591 | 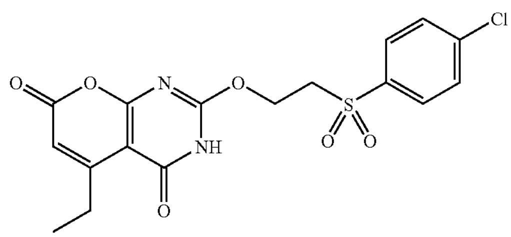 | A | 411.1 |
| 592 | 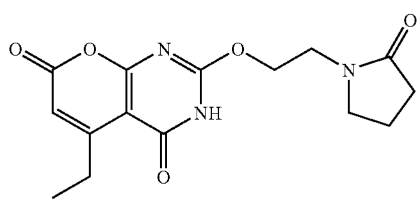 | B | 320.2 |
| 593 | 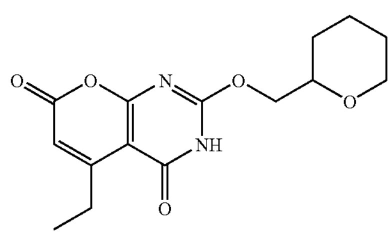 | C | 307.2 |
| 594 | 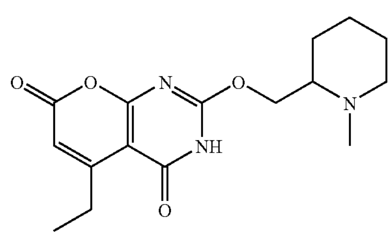 | C | 320.2 |
| 595 | 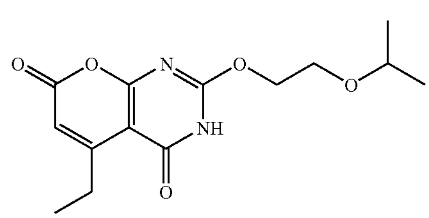 | B | 295.2 |
| 596 | 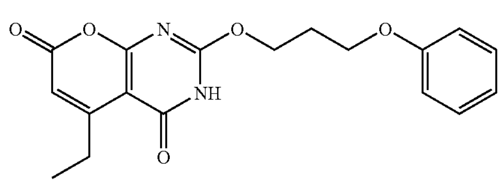 | B | 343.2 |

-continued

| Compound No. | Structure | NA EC50 camp (nM) | Electrospray LCMS [M + 1]+ |
|---|---|---|---|
| 597 | 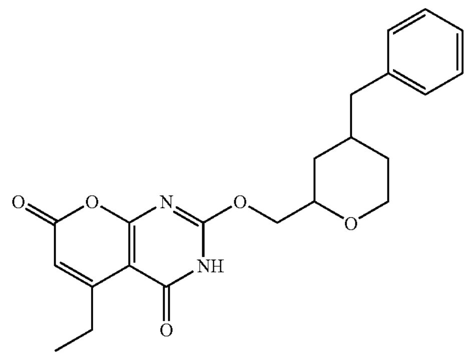 | C | 398.1 |
| 598 | 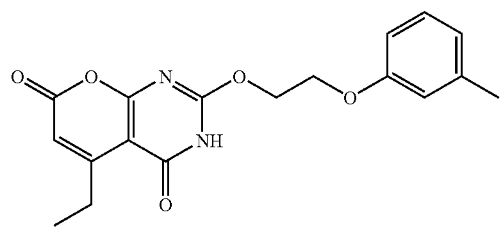 | B | 343.1 |
| 599 | 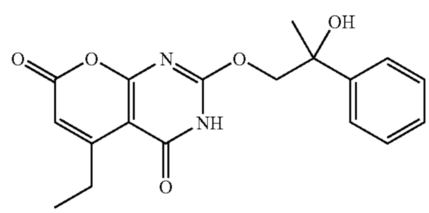 | B | 343.1 |
| 600 | 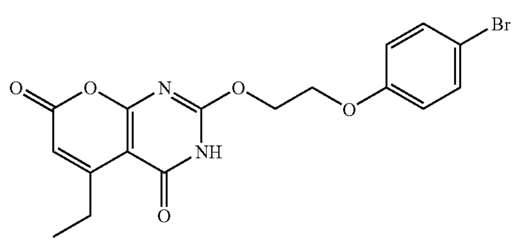 | C | 409.1 |
| 601 | 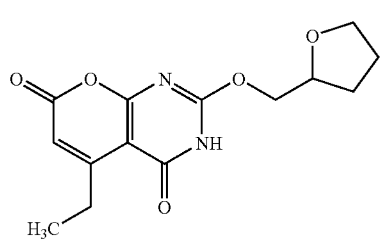 | C | 293.1 |

-continued

| Compound No. | Structure | NA EC50 camp (nM) | Electrospray LCMS [M + 1]+ |
|---|---|---|---|
| 602 | 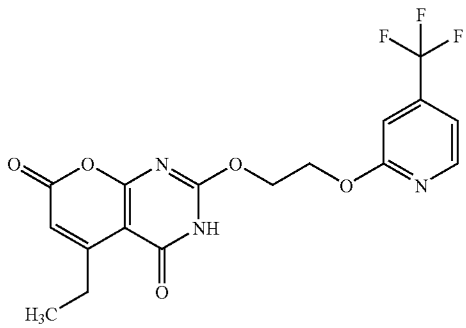 | B | 398.1 |
| 603 | 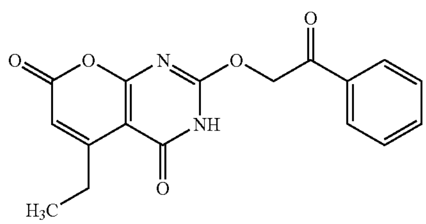 | B | 327.2 |
| 604 | 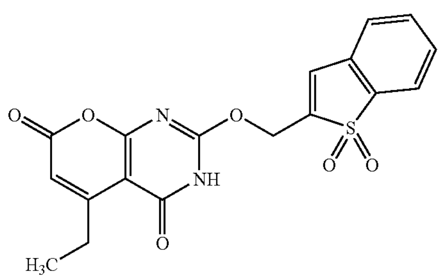 | B | 387.2 |
| 605 | 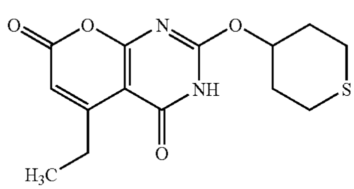 | C | 309.2 |
| 606 | 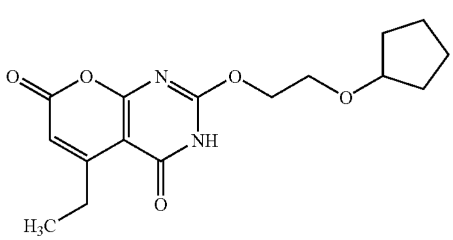 | C | 321 |
| 607 | 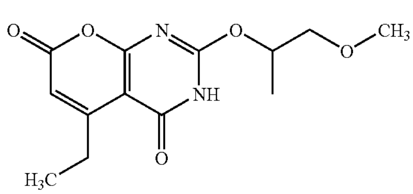 | B | 281.2 |

-continued

| Compound No. | Structure | NA EC50 camp (nM) | Electrospray LCMS [M + 1]+ |
|---|---|---|---|
| 608 | 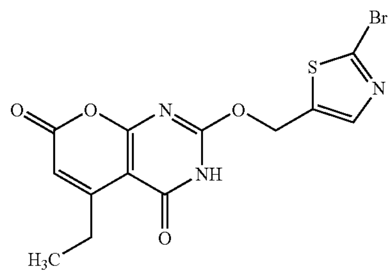 | B | 384.2 |
| 609 | 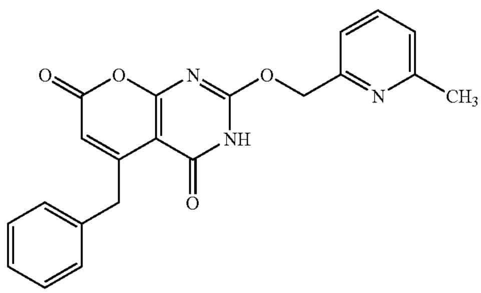 | C | 376.1 |
| 610 | 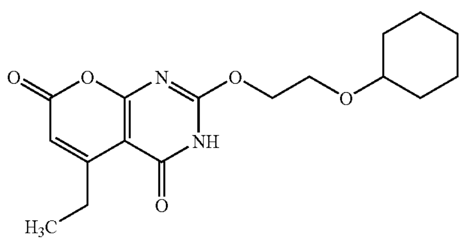 | C | 335 |
| 611 | 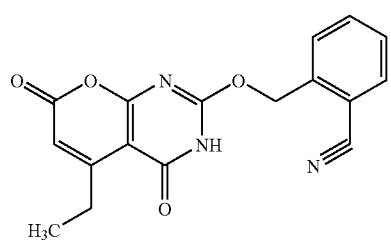 | C | 324.2 |
| 612 | 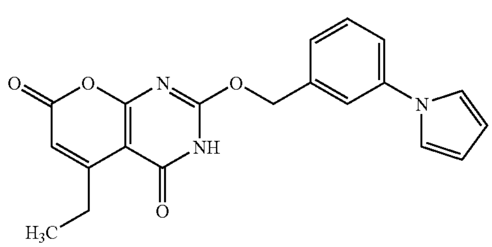 | C | 364.2 |

-continued

| Compound No. | Structure | NA EC50 camp (nM) | Electrospray LCMS [M + 1]+ |
|---|---|---|---|
| 613 | 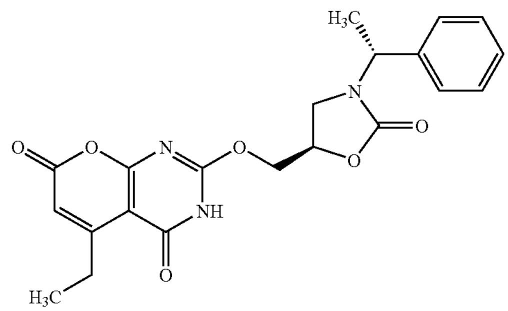 | B | 412.1 |
| 614 | 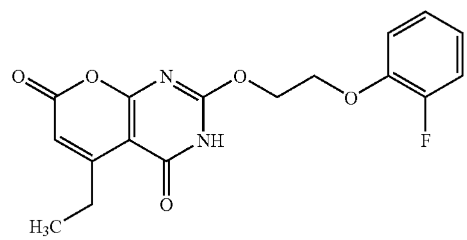 | B | 347.1 |
| 615 | 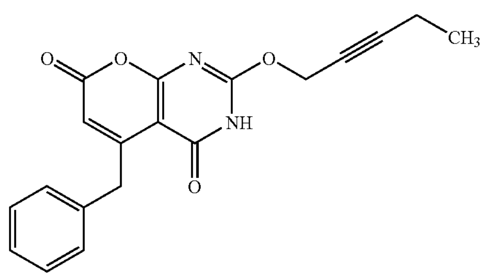 | B | 337.1 |
| 616 | 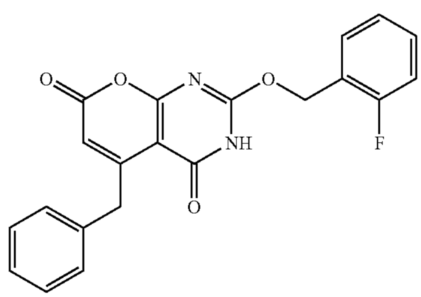 | B | 379.2 |
| 617 | 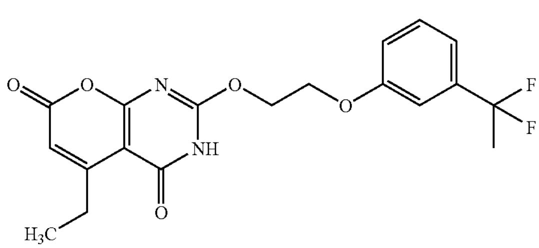 | B | 397.2 |

-continued

| Compound No. | Structure | NA EC50 camp (nM) | Electrospray LCMS [M + 1]+ |
|---|---|---|---|
| 618 | 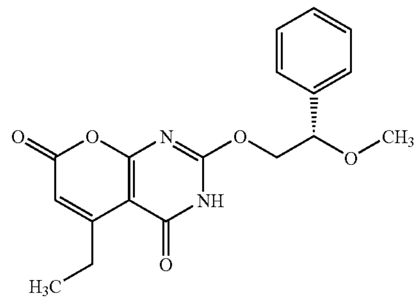 | B | 343.2 |
| 619 | 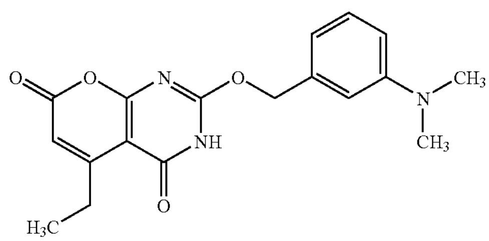 | B | 342.2 |
| 620 | 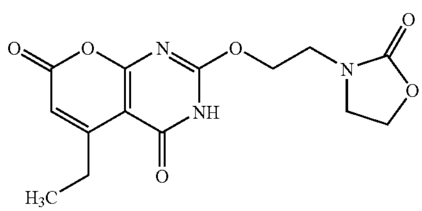 | C | 322.2 |
| 621 | 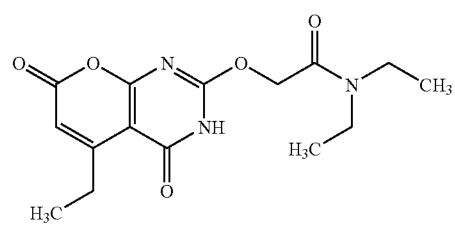 | B | 322.2 |
| 622 | 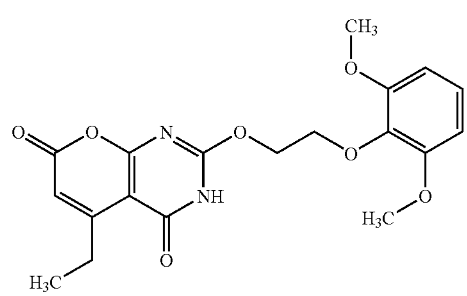 | B | 389.2 |

-continued
| Compound No. | Structure | NA EC50 camp (nM) | Electrospray LCMS [M + 1]+ |
|---|---|---|---|
| 623 | 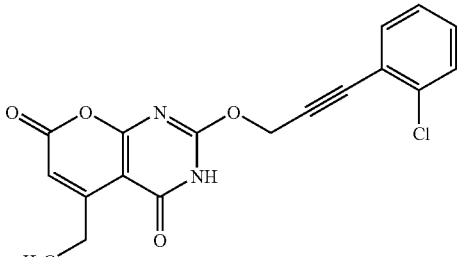 | A | 357.2 |
| 624 | 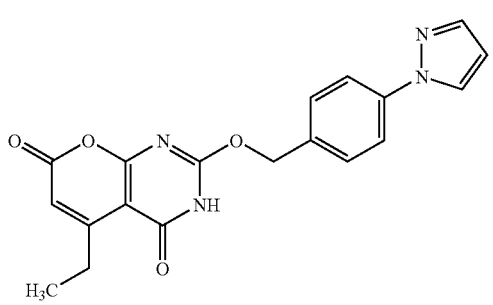 | B | 365.2 |
| 625 | 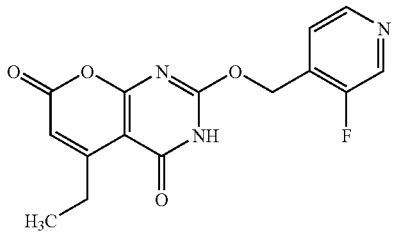 | B | 318.2 |
| 626 | 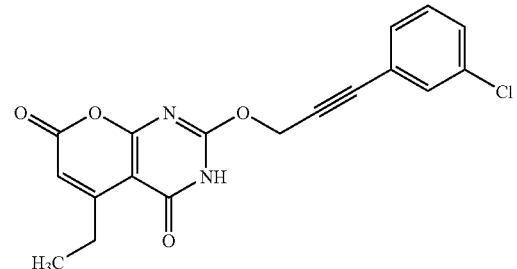 | A | 358 |
| 627 | 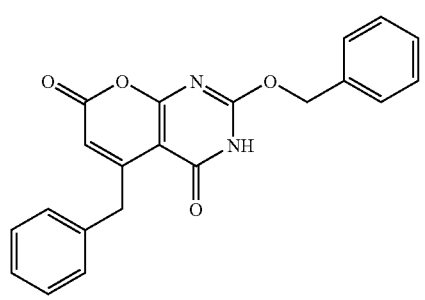 | C | 361.2 |

-continued

| Compound No. | Structure | NA EC50 camp (nM) | Electrospray LCMS [M + 1]+ |
|---|---|---|---|
| 628 | 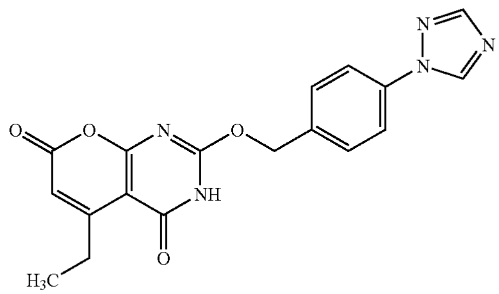 | C | 366.2 |
| 629 | 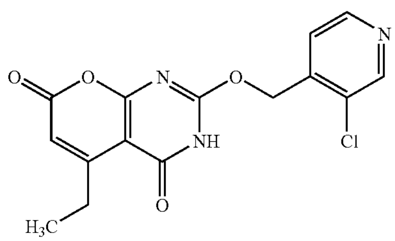 | B | 334.2 |
| 630 | 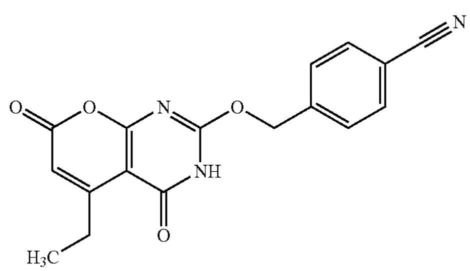 | C | 324.2 |
| 631 | 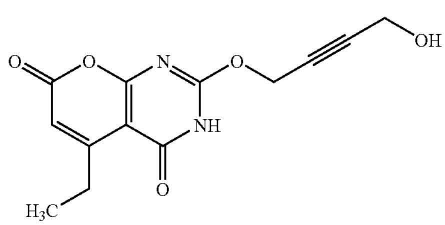 | B | 277 |
| 632 | 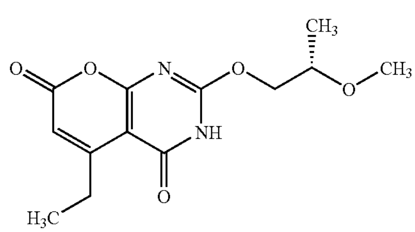 | B | 281.2 |

-continued

| Compound No. | Structure | NA EC50 camp (nM) | Electrospray LCMS [M + 1]+ |
|---|---|---|---|
| 633 | 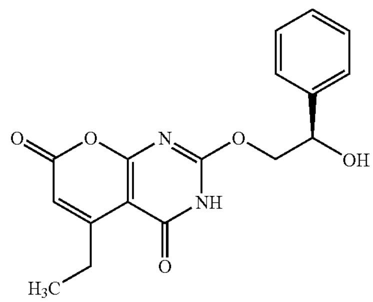 | B | 329.2 |
| 634 | 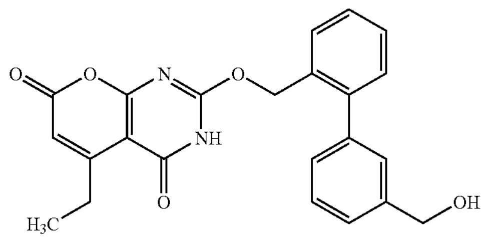 | B | 405 |
| 635 | 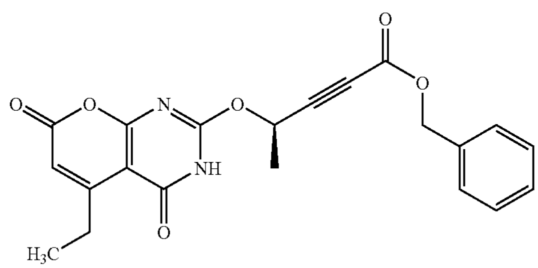 | C | 395 |
| 636 | 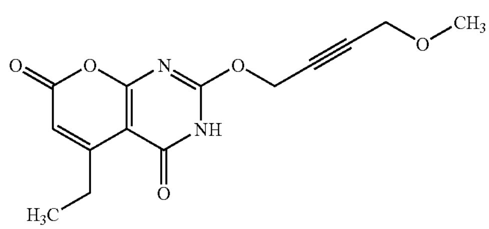 | B | 291 |
| 637 | 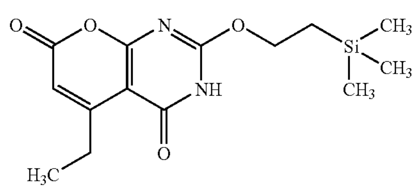 | B | 309.2 |
| 638 | 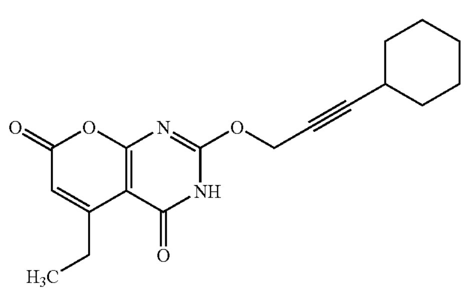 | B | 329 |

-continued

| Compound No. | Structure | NA EC50 camp (nM) | Electrospray LCMS [M + 1]+ |
|---|---|---|---|
| 639 | 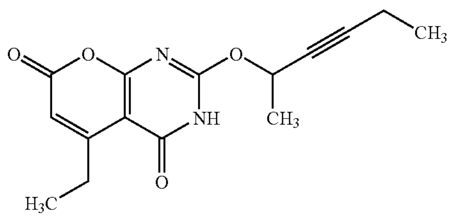 | B | 283 |
| 640 | 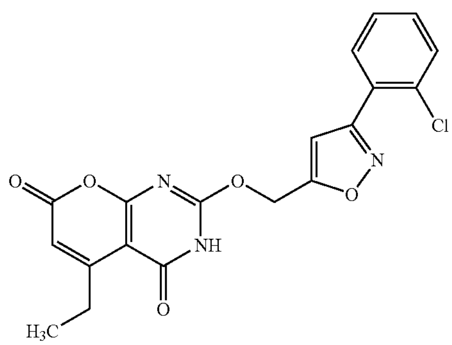 | B | 400.1 |
| 641 | 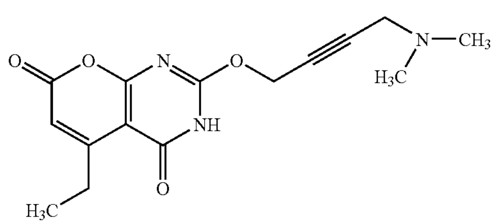 | A | 304 |
| 642 | 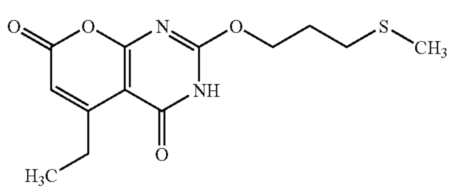 | B | 297.2 |
| 643 | 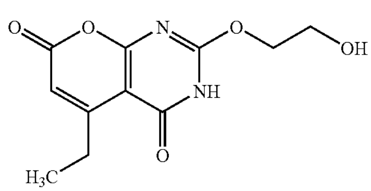 | B | 253.1 |
| 644 | 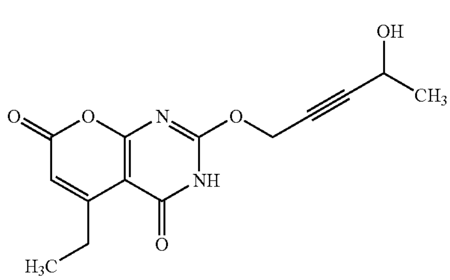 | A | 291 |

| Compound No. | Structure | NA EC50 camp (nM) | Electrospray LCMS [M + 1]+ |
|---|---|---|---|
| 645 | 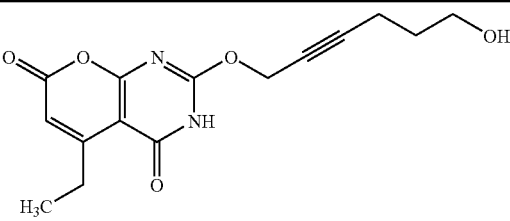 | A | 305 |
| 646 | 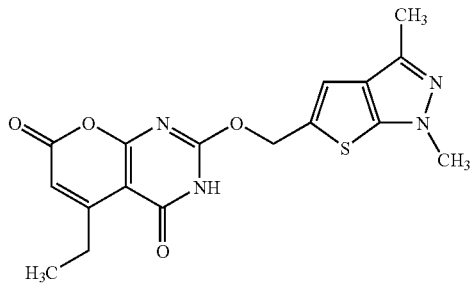 | C | 373.2 |
| 647 | 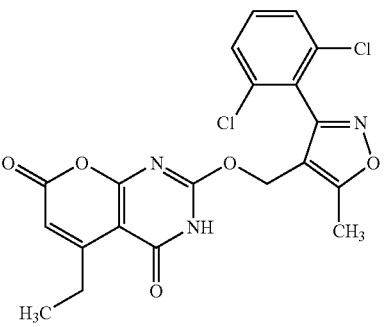 | B | 448.2 |
| 648 | 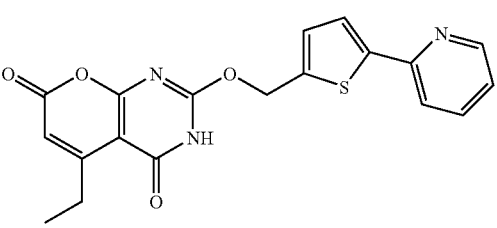 | B | 382.2 |
| 649 | 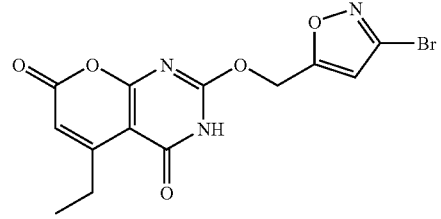 | B | 368 |
| 650 | 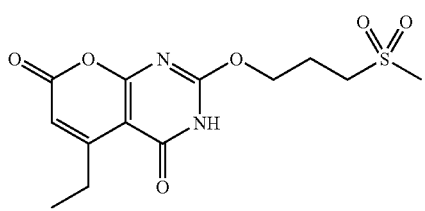 | B | 329.2 |

-continued

| Compound No. | Structure | NA EC50 camp (nM) | Electrospray LCMS [M + 1]+ |
|---|---|---|---|
| 651 | 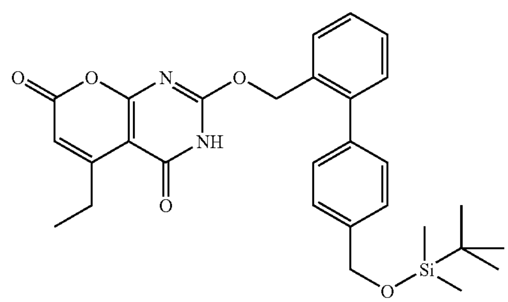 | B | 520 |
| 652 | 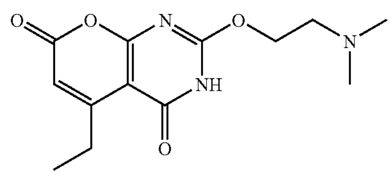 | A | 280.1 |
| 653 | 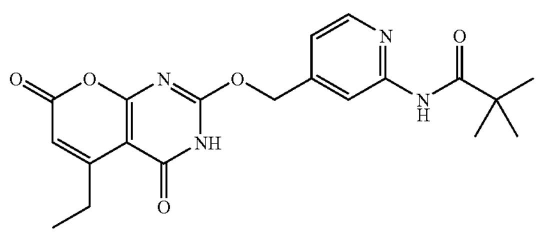 | C | 399.2 |
| 654 | 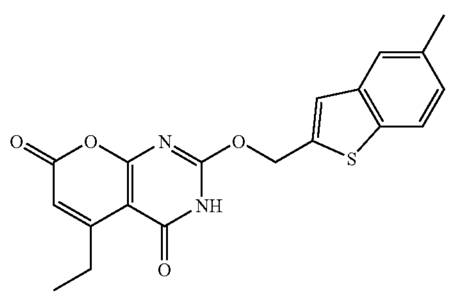 | A | M + Na 391.2 |
| 655 | 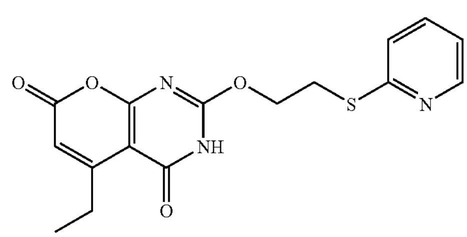 | B | 346.2 |
| 656 | 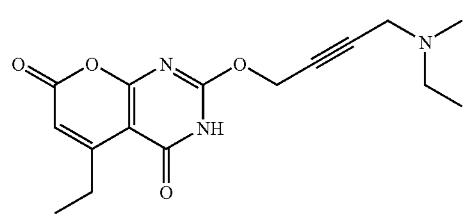 | C | 332 |

-continued

| Compound No. | Structure | NA EC50 camp (nM) | Electrospray LCMS [M + 1]+ |
|---|---|---|---|
| 657 | 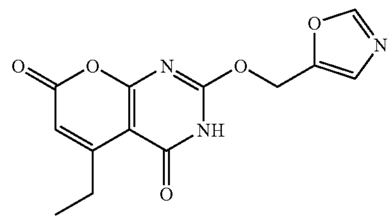 | C | 290 |
| 658 | 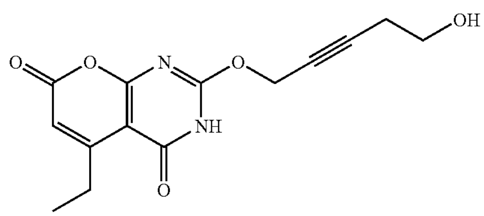 | B | 291 |
| 659 | 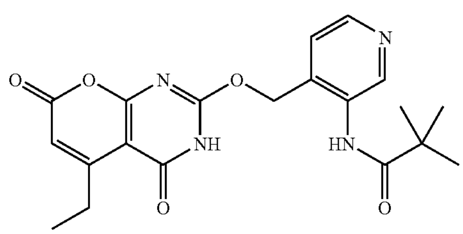 | C | 399.2 |
| 660 | 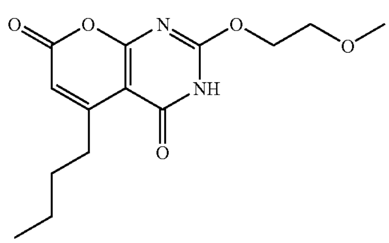 | C | 317.2 (M + Na) |
| 661 | 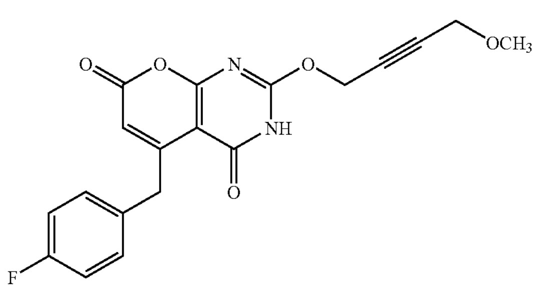 | B | 371.2 |
| 662 | 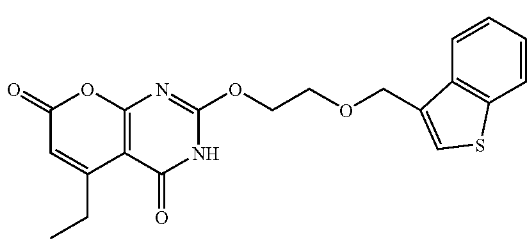 | A | 399.2 |

-continued

| Compound No. | Structure | NA EC50 camp (nM) | Electrospray LCMS [M + 1]+ |
|---|---|---|---|
| 663 | 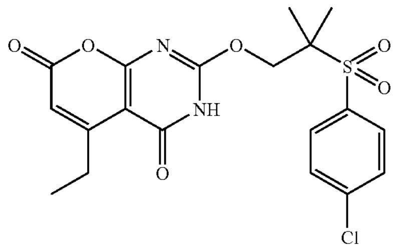 | C | 439.2 |
| 664 | 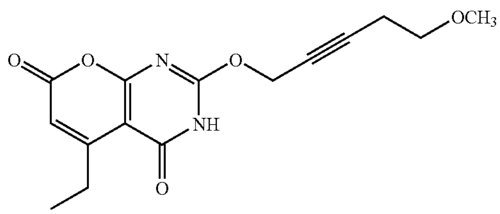 | B | 305 |
| 665 | 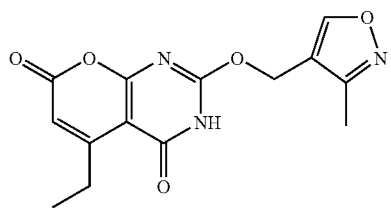 | C | 304 |
| 666 | 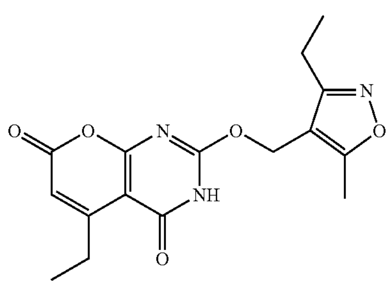 | A | 332 |
| 667 | 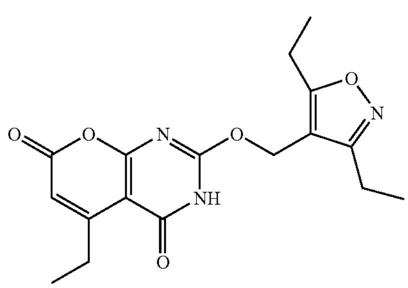 | B | 346 |
| 668 | 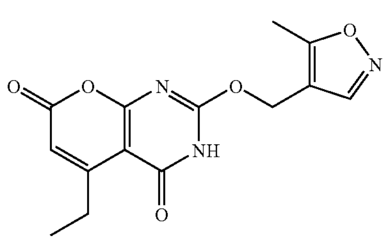 | C | 304 |

-continued
| Compound No. | Structure | NA EC50 camp (nM) | Electrospray LCMS [M + 1]+ |
|---|---|---|---|
| 669 | 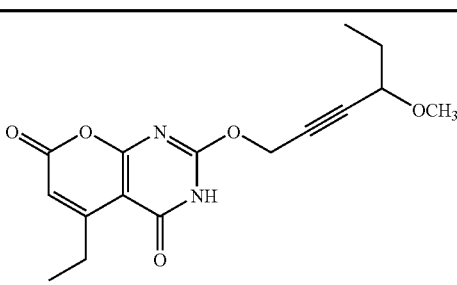 | B | 319 |
| 670 | 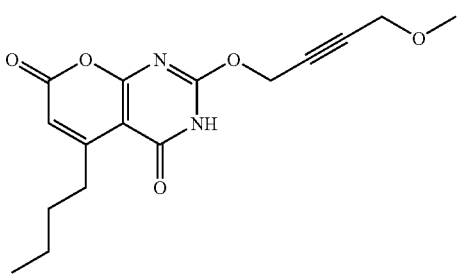 | A | 319.2 |
| 671 | 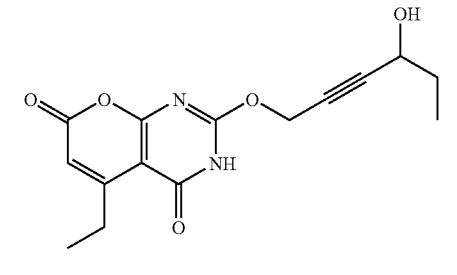 | A | 305 |
| 672 | 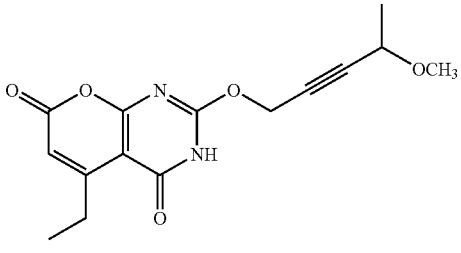 | B | 305 |
| 673 | 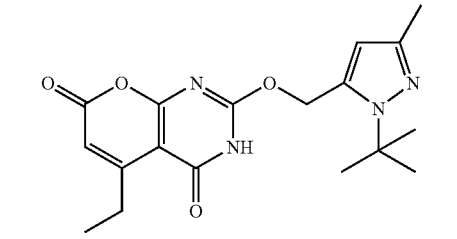 | B | 359 |
| 674 | 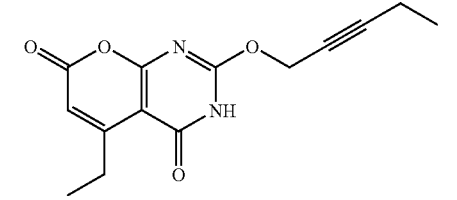 | A | 303 |

-continued
| Compound No. | Structure | NA EC50 camp (nM) | Electrospray LCMS [M + 1]+ |
|---|---|---|---|
| 675 | 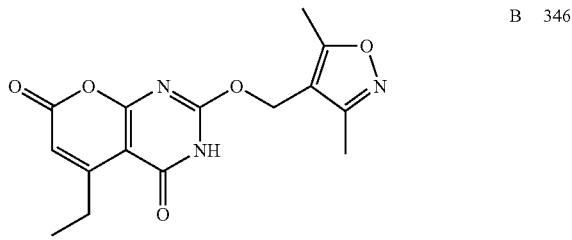 | B | 346 |
| 676 | 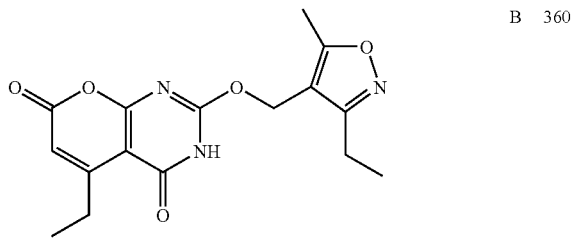 | B | 360 |
| 677 | 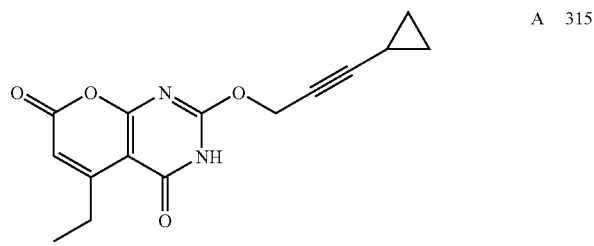 | A | 315 |
| 678 | 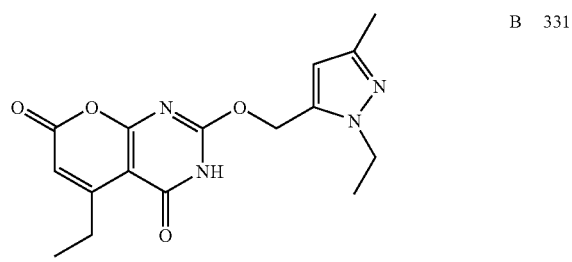 | B | 331 |
| 679 | 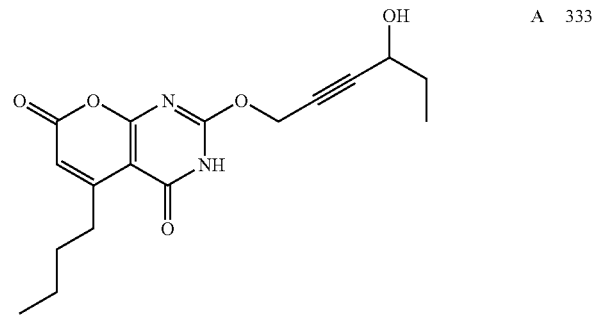 | A | 333 |

-continued

| Compound No. | Structure | NA EC50 camp (nM) | Electrospray LCMS [M + 1]+ |
|---|---|---|---|
| 680 | 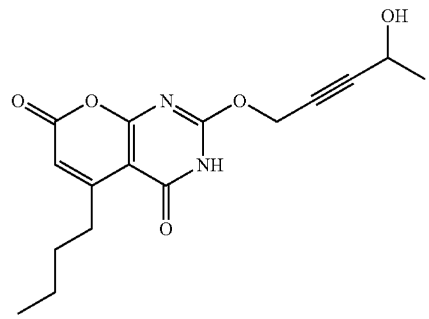 | A | 319 |
| 681 | 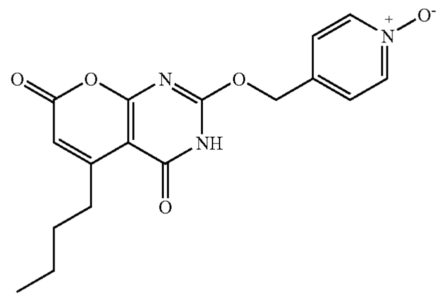 | C | 344.2 |
| 682 | 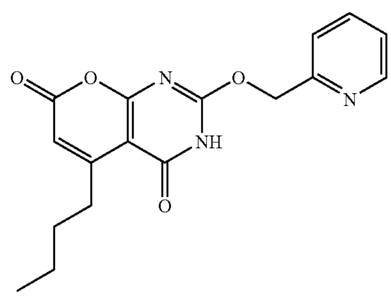 | C | 328.2 |
| 683 | 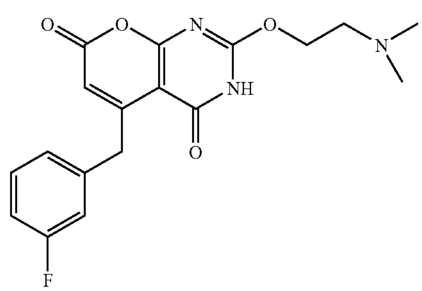 | C | 360.2 |
| 684 | 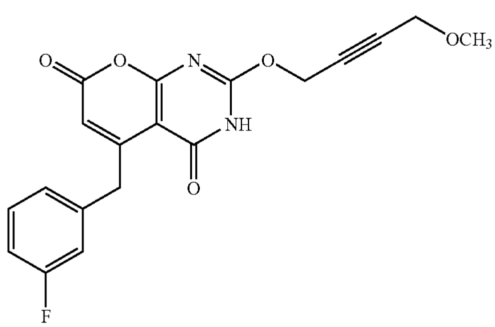 | A | 371.2 |

-continued
| Compound No. | Structure | NA EC50 camp (nM) | Electrospray LCMS [M + 1]+ |
|---|---|---|---|
| 685 | 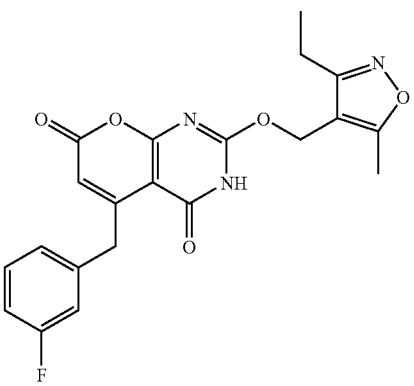 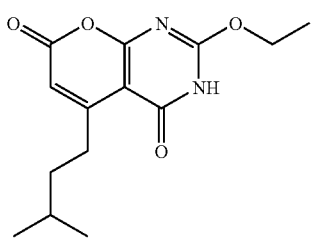 | B | 412.2 |
| 686 | 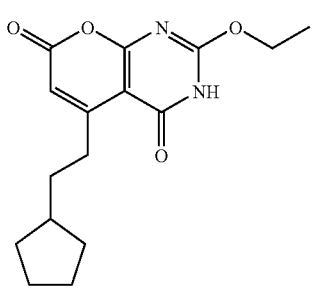 | B | 279.2 |
| 687 | 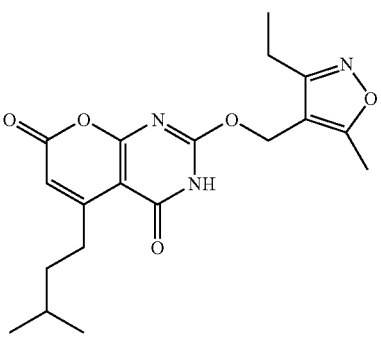 | B | 305.2 |
| 688 | 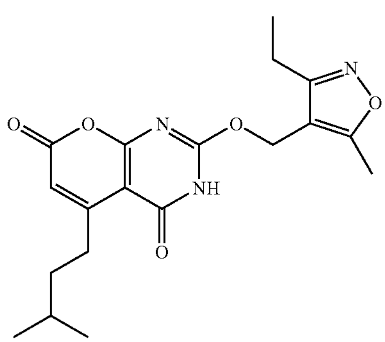 | B | 374.2 |

-continued
| Compound No. | Structure | NA EC50 camp (nM) | Electrospray LCMS [M + 1]+ |
|---|---|---|---|
| 689 | 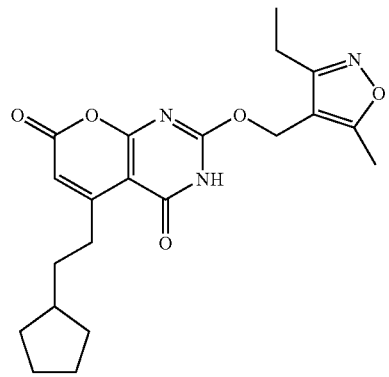 | B | 400.2 |
| 690 | 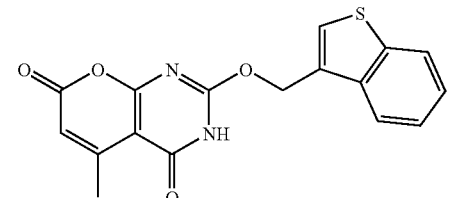 | C | 241.1 |
| 691 | 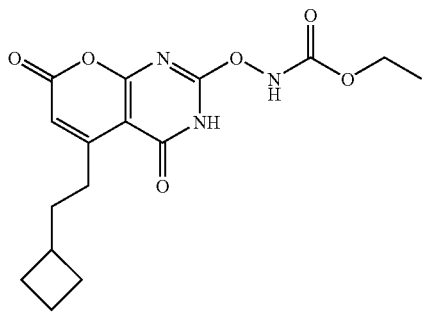 | A | 350.2 |
| 692 | 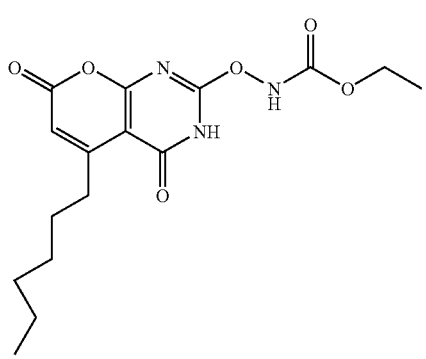 | A | 352.2 |

-continued

| Compound No. | Structure | NA EC50 camp (nM) | Electrospray LCMS [M + 1]+ |
|---|---|---|---|
| 693 | 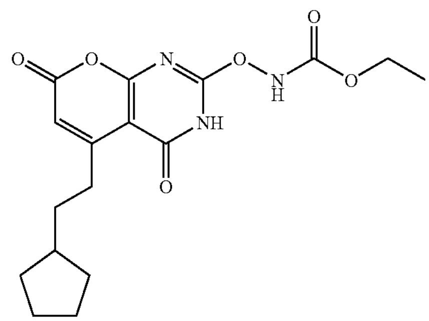 | B | 364.2 |
| 694 | 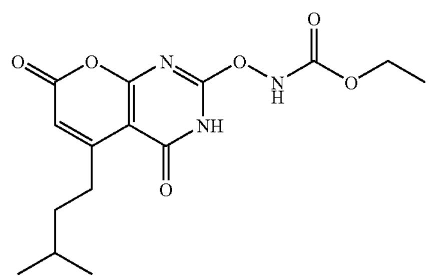 | C | 338.2 |
| 695 | 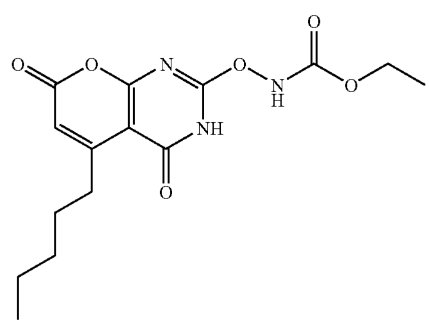 | A | 338.2 |
| 696 | 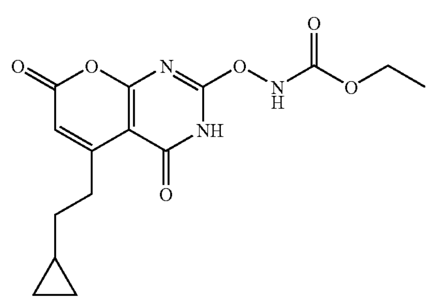 | B | 336.2 |
| 697 | 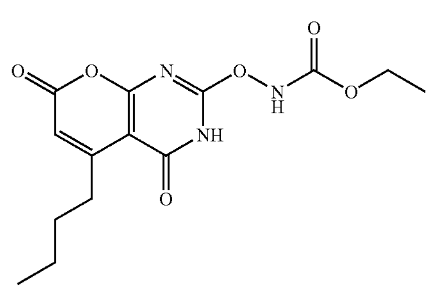 | — | 324.2 |

| Compound No. | Structure | NA EC50 camp (nM) | Electrospray LCMS [M + 1]+ |
|---|---|---|---|
| 698 | 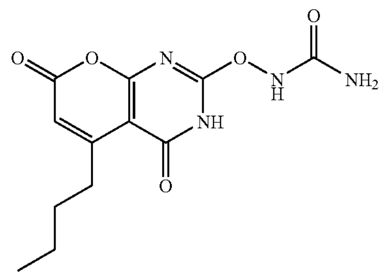 | — | 295.2 |

-continued

Preparative Example 699

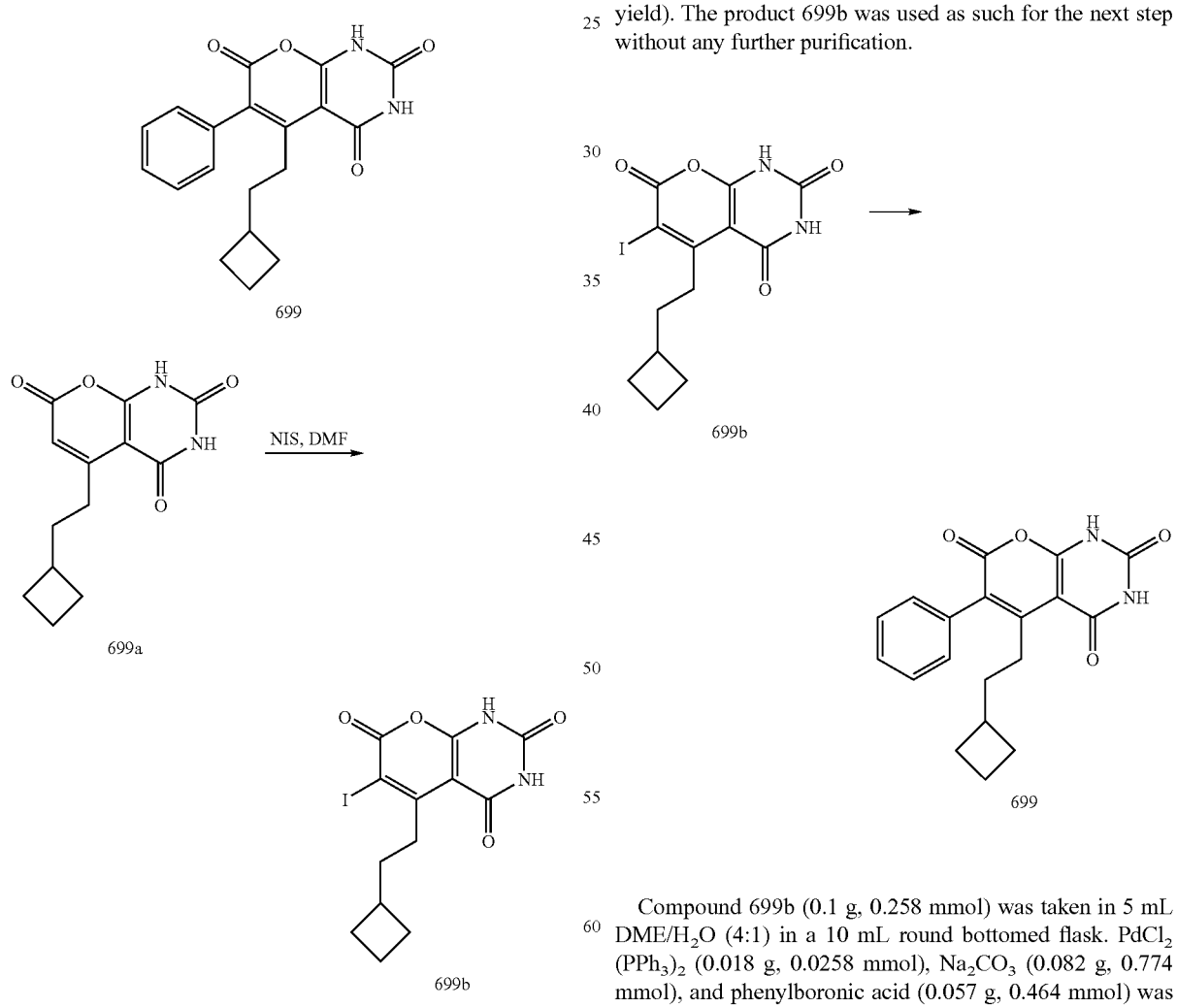

Compound 699a (0.925 g, 3.53 mmol) was taken in DMF (10 mL) in a round bottomed flask equipped with a magnetic stirring bar. N-Iodosuccinimide (1.59 g, 7.05 mmol) was added portionwise and the reaction mixture was heated to 50° C. overnight. After cooling to ambient temperature, H₂O (25 mL) was added. The product was filtered, washed with water followed by ether to give a white powdery mixture (>95% yield). The product 699b was used as such for the next step without any further purification.

Compound 699b (0.1 g, 0.258 mmol) was taken in 5 mL DME/H₂O (4:1) in a 10 mL round bottomed flask. PdCl₂(PPh₃)₂ (0.018 g, 0.0258 mmol), Na₂CO₃ (0.082 g, 0.774 mmol), and phenylboronic acid (0.057 g, 0.464 mmol) was added, and the reaction mixture was allowed to reflux (80° C.) for 6 h. After cooling, the mixture was concentrated and purified by flash chromatography (CH₂Cl₂ to 5% MeOH/CH₂Cl₂) to yield compound 699.

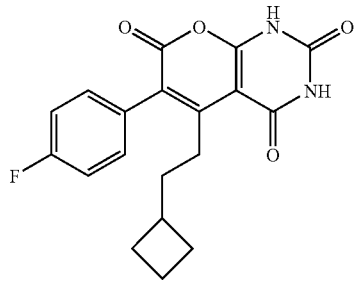

700

Compound 700 was prepared in the same manner as in example 699.

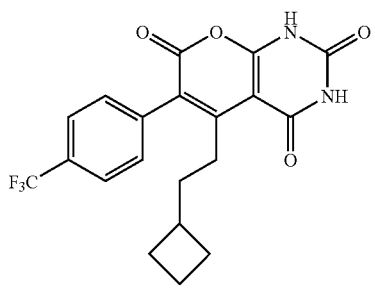

701

Compound 701 was prepared in the same manner as in example 699.

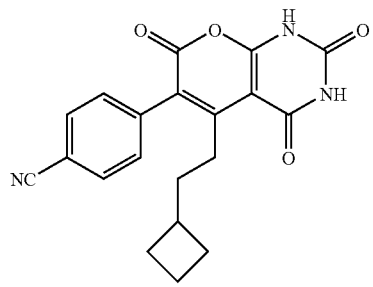

702

Compound 702 was prepared in the same manner as in example 699.

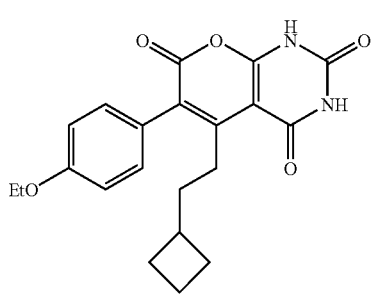

703

Compound 703 was prepared in the same manner as in example 699.

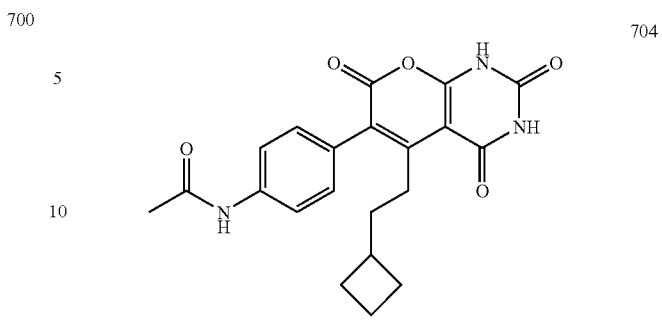

704

Compound 704 was prepared in the same manner as in example 699.

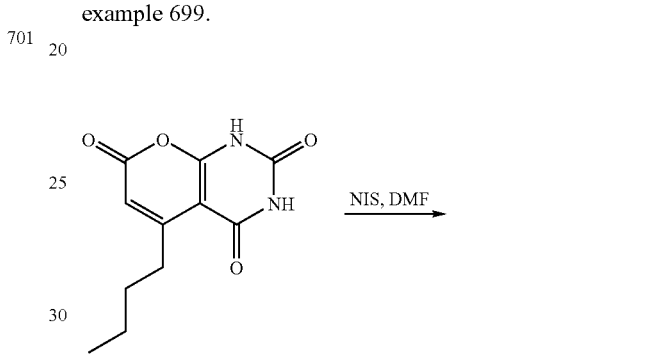

705a

705b

Compound 705b was prepared in the same manner as in example 699b.

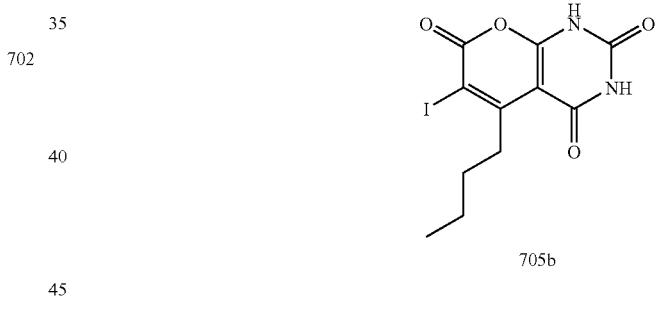

705

Compound 705 was prepared in the same manner of compound 699.

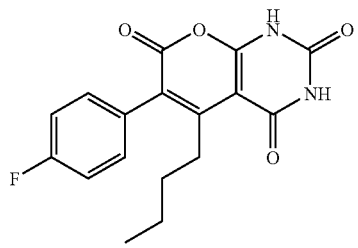
The compound 706 was prepared in the same manner of compound 699.
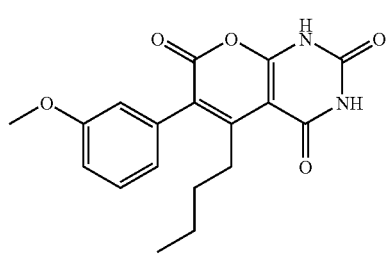
The compound 707 was prepared in the same manner of compound 699.
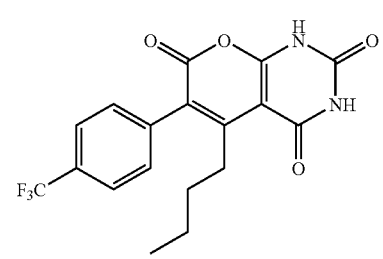
The compound 708 was prepared in the same manner of compound 699.
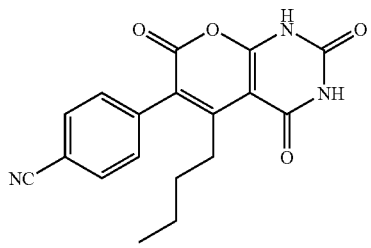
The compound 709 was prepared in the same manner of compound 699.
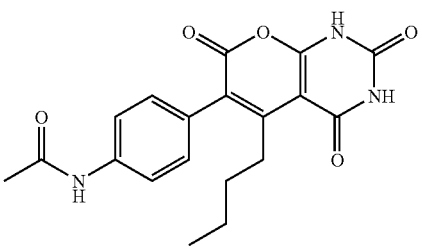
The compound 710 was prepared in the same manner of compound 699.
| Compound No. | STRUCTURE | NA EC$_{50}$ camp (nM) | Electrospray LCMS [M+]+ |
|---|---|---|---|
| 699 | 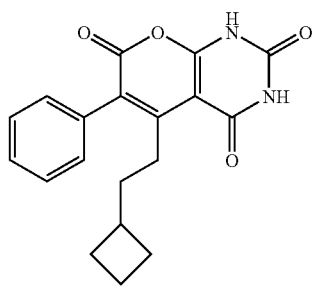 | C | 339.2 |

-continued

| Compound No. | STRUCTURE | NA EC$_{50}$ camp (nM) | Electrospray LCMS [M+]+ |
|---|---|---|---|
| 700 | 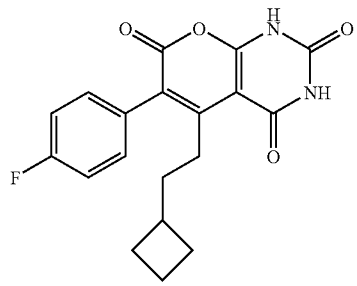 | C | 357.2 |
| 701 | 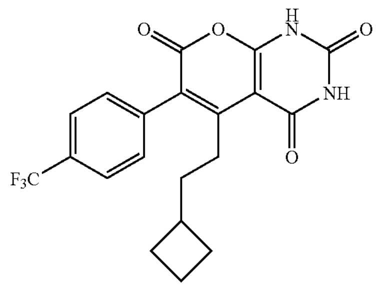 | C | 407.2 |
| 702 | 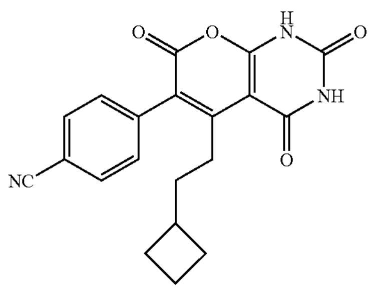 | C | 364.2 |
| 703 | 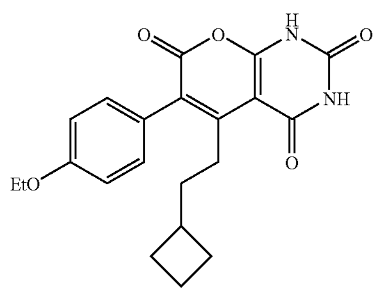 | C | 383.2 |
| 704 | 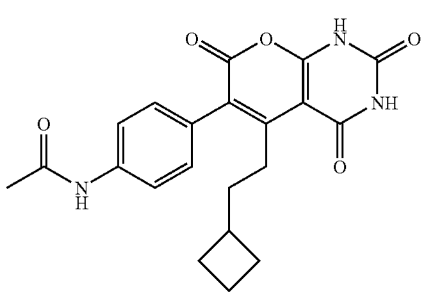 | C | 396.2 |

-continued

| Compound No. | STRUCTURE | NA EC$_{50}$ camp (nM) | Electrospray LCMS [M + ]+ |
|---|---|---|---|
| 705 | 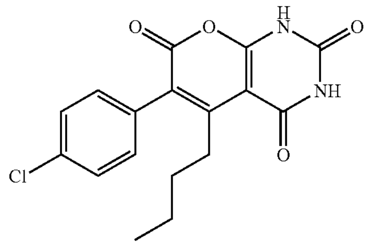 | C | 347.2 |
| 706 | 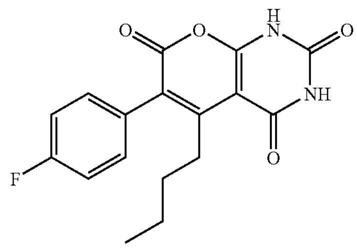 | C | 331.2 |
| 707 | 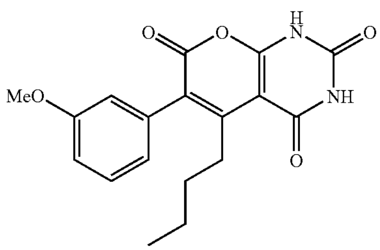 | C | 343.2 |
| 708 | 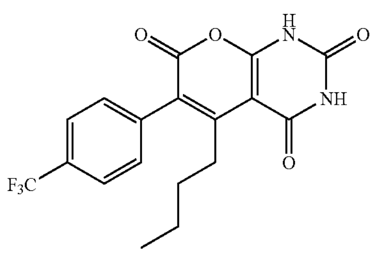 | B | 381.2 |
| 709 | 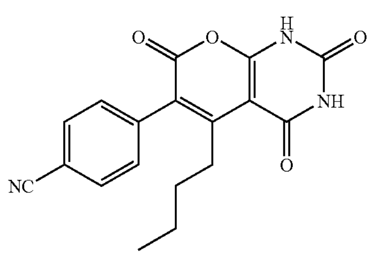 | C | 338.2 |
| 710 | 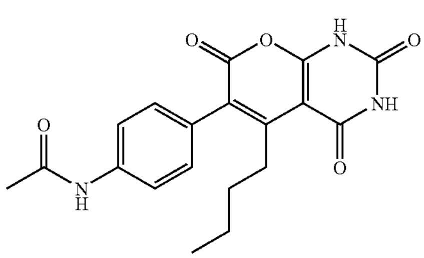 | C | 370.2 |

Preparative Example 711

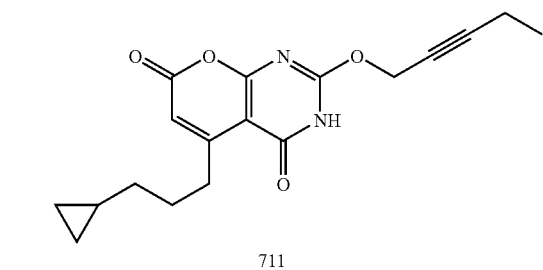

Step A:

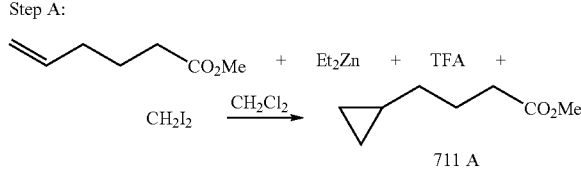

To a solution of diethyl zinc (3.0 eq, 1.0 M in THF) in CH₂Cl₂ (0.2 M) at 0° C., was added TFA (3.0 equiv, drop wise via an addition funnel). The resulting mixture was allowed to stir at 0° C. for 15 minutes after the addition was complete. CH₂I₂ (3.0 equiv) was then added to the reaction mixture drop wise via syringe and the resulting reaction was allowed to stir at 0° C. for 10 minutes. To the resulting reaction was added hex-5-enoic acid methyl ester (1.0 equiv) and the reaction mixture was stirred for about 15 hours, allowing the mixture to increase to room temperature. The reaction was then quenched by careful addition of aqueous 1 N HCl and the aqueous layer was extracted with CH₂Cl₂ (3×). The combined organic phases were washed with water, then brine, then dried over MgSO₄ and concentrated in vacuo to provide compound 711A in quantitative yield.

Step B:

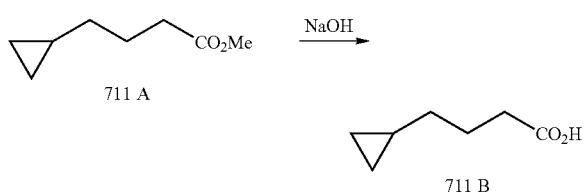

Aqueous NaOH solution (2.0 equiv, 2.0 N) was added to a solution of 711A (1.0 equiv) in THF and MeOH (v/v=2/1, 0.2 M) at room temperature. The mixture was allowed to stir for 4 hours and the solvent was then removed in vacuo. The resulting aqueous solution was extracted with ether and the resulting solution was then acidified using 5 M HCl. The aqueous layer was extracted with ether (3×) and the combined organic phases were washed with water, then brine, then dried over MgSO₄ and concentrated in vacuo to provide compound 711B in quantitative yield.

Step C:

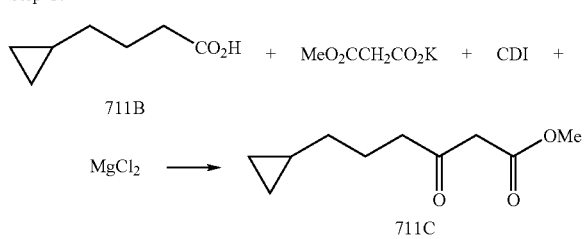

CDI (1.2 equiv) was added to a solution of 711B in THF (0.5 M) at room temperature. The reaction mixture was allowed to stir for 1 hour, then monomethyl melonate ester potassium salt (1.5 equiv) and MgCl₂ (1.0 equiv) were added. The resulting reaction was allowed to stir for about 15 hours and was then quenched with aqueous HCl (1.0 N). The aqueous layer was extracted with EtOAc (3×). The combined organic phases were washed with water, then brine, then dried over MgSO₄ and concentrated in vacuo to provide compound 711C in quantitative yield.

Step D:

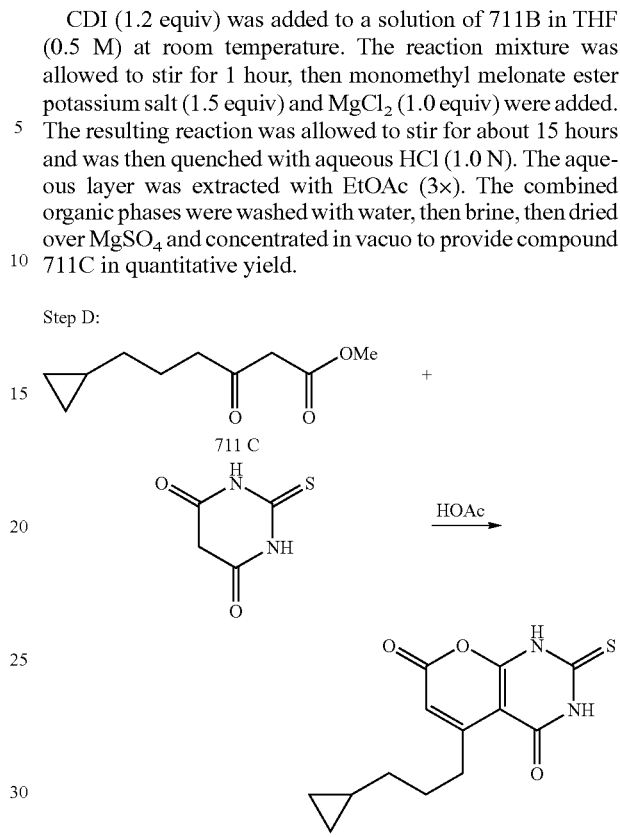

A mixture of 4,6-dihydroxy-2-mercapto-pyrimidine (1.0 eq) and 711C (1.25 equiv) in HOAc (1.0 M) was heated to reflux and allowed to stir at this temperature for about 15 hours. The reaction mixture was then cooled and concentrated in vacuo and the resulting residue was purified using flash column chromatography on silica gel to provide compound 711D (37% yield).

Step E:

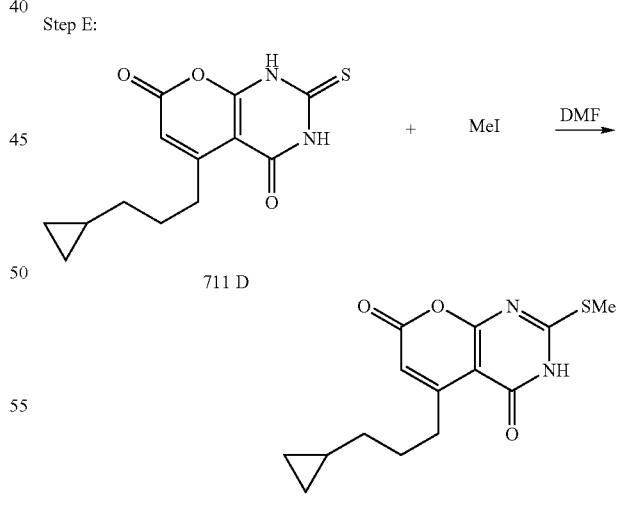

MeI (1.8 equiv) was added to a suspension of 711D (4.0 g, 17.86 mmol) in DMF (0.3 M) at room temperature. The reaction mixture was allowed to stir at room temperature for about 15 hours, then poured into water and the resulting solution was filtered through a sintered funnel. The collected solid material was washed with water and dried under vacuum to provide compound 711E (96% yield).

Step F:

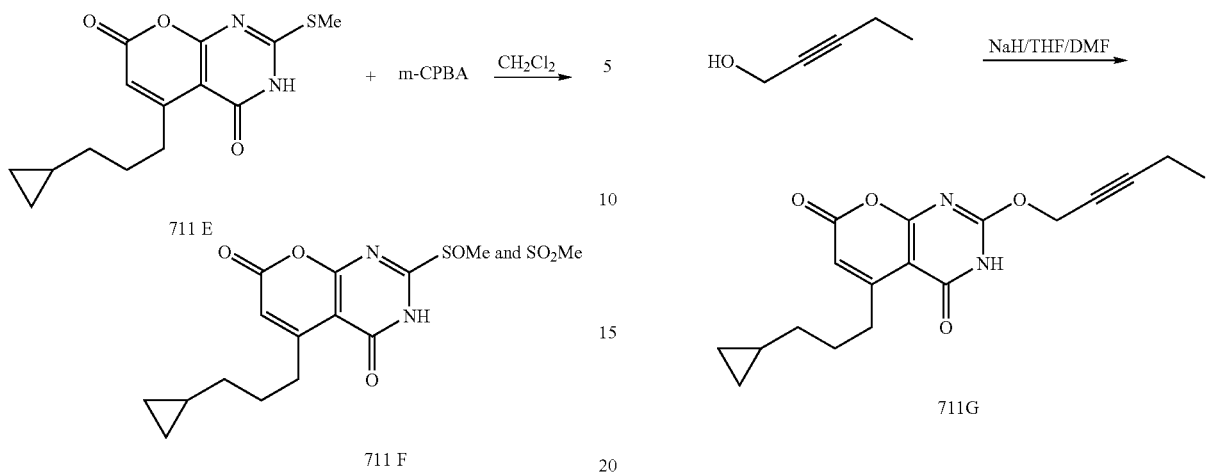

m-CPBA (2.0 equiv) was added to a suspension of 711E (1.0 equiv) in CH₂Cl₂ (0.15 M) at room temperature. After stirring for 3 hours, the reaction was quenched with Me₂S (3.0 eq) and concentrated in vacuo to provide a crude product which was washed with Hexane/EtOAc (v/v=3/1) to provide compound 711F as a mixture of sulfone and sulfoxide (90% yield, w/w=1/2).

Step G:

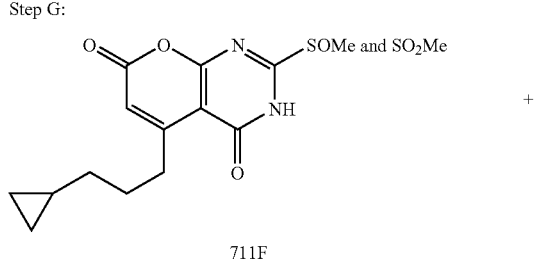

Pent-2-yne-1-ol (2.0 equiv) was added drop wise to a suspension of NaH (2.0 equiv) in THF at room temperature. The reaction mixture was stirred for 1 hour to provide a clear solution to which was then added drop wise a solution of 711F (1.0 equiv) in DMF. The reaction mixture was stirred for about 2 hours at room temperature and was then quenched with HOAc (2.0 equiv). The resulting solution was diluted with EtOAc and washed sequentially with 0.1 M HCl, water and brine, then dried over MgSO₄ and concentrated in vacuo. The resulting residue was purified using flash column chromatography on silica gel (eluent: hexane/CH₂Cl₂/EA (v/v/v=7/3/2)) to provide compound 711 (50% yield). Electrospray MS [M+1]⁺ 329.2.

Using the method described above, and appropriate materials, Compounds 712-739 were prepared:

| Compound No. | Structure | Electrospray LCMS [M + ]⁺ |
|---|---|---|
| 712 | 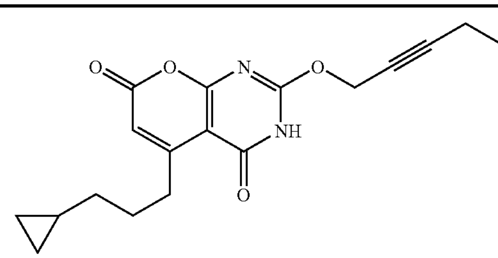 | 329.2 |
| 713 | 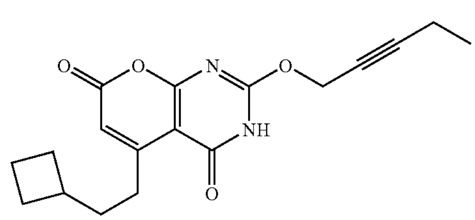 | 329.2 |

-continued

| Compound No. | Structure | Electrospray LCMS [M + ]+ |
|---|---|---|
| 714 | 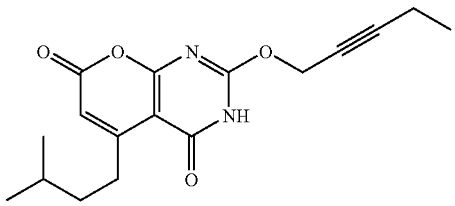 | 317.2 |
| 715 | 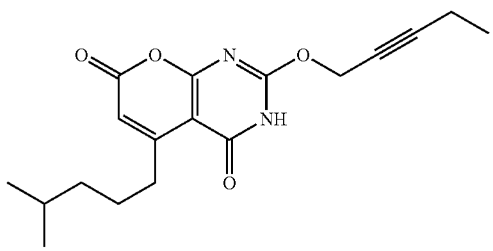 | 331.2 |
| 716 | 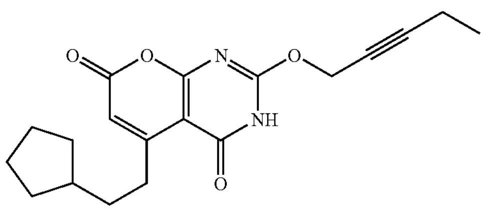 | 343.2 |
| 717 | 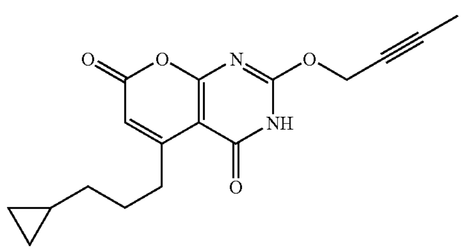 | 315.2 |
| 718 | 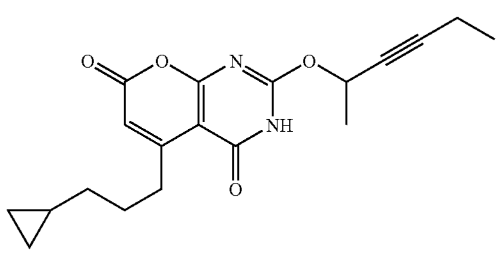 | 343.2 |
| 719 | 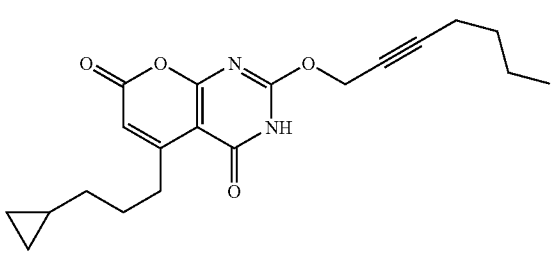 | 357.2 |

-continued

| Compound No. | Structure | Electrospray LCMS [M + ]+ |
|---|---|---|
| 720 | 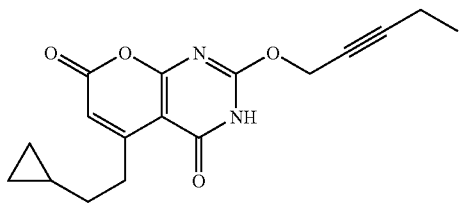 | 315.2 |
| 721 | 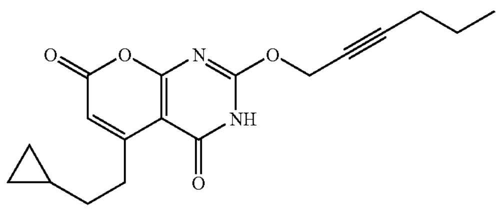 | 329.2 |
| 722 | 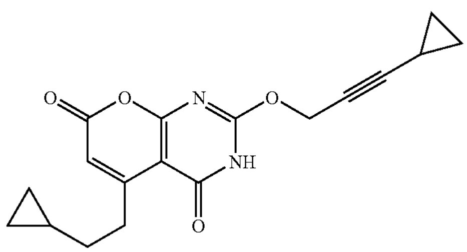 | 327.2 |
| 723 | 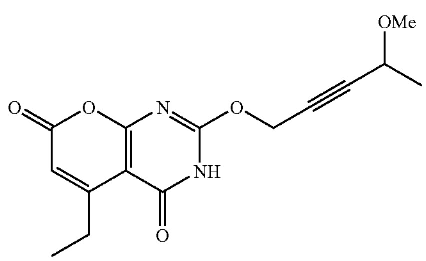 | 305 |
| 724 | 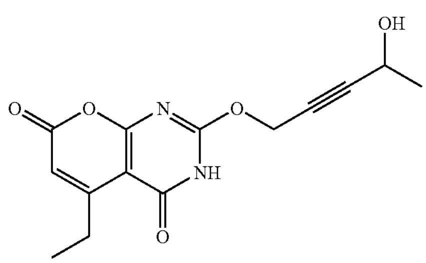 | 305 |
| 725 | 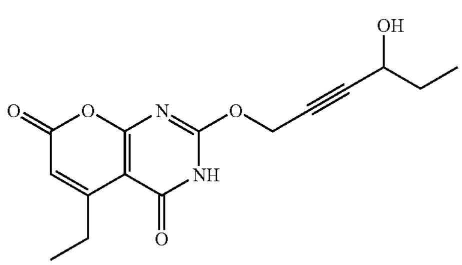 | 319 |

-continued

| Compound No. | Structure | Electrospray LCMS [M + ]+ |
|---|---|---|
| 726 | 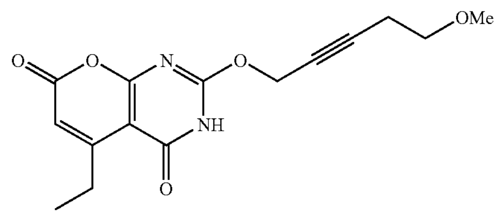 | 305 |
| 727 | 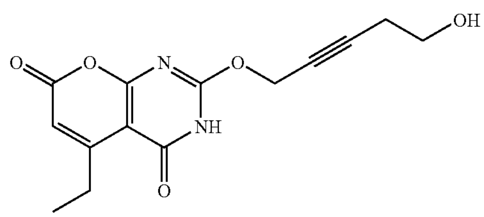 | 291 |
| 728 | 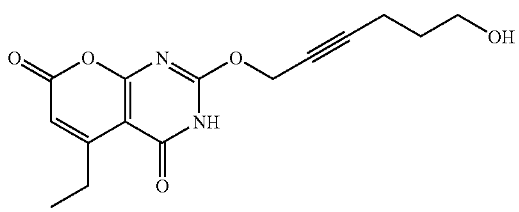 | 305 |
| 729 | 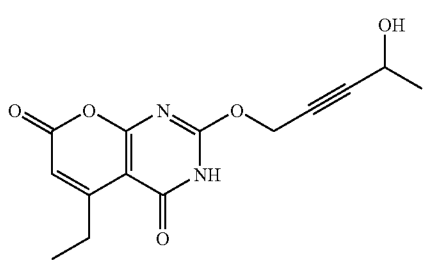 | 291 |
| 730 | 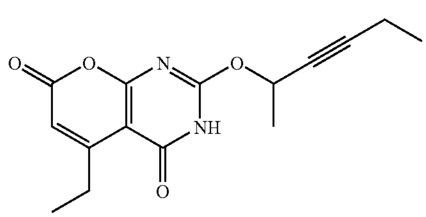 | 289 |
| 731 | 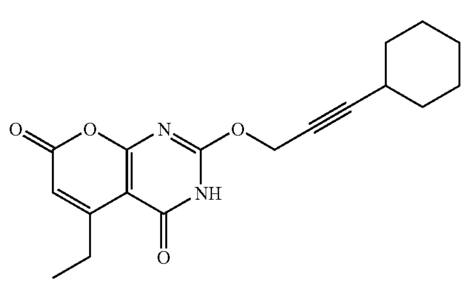 | 329 |

-continued

| Compound No. | Structure | Electrospray LCMS [M + ]+ |
|---|---|---|
| 732 | 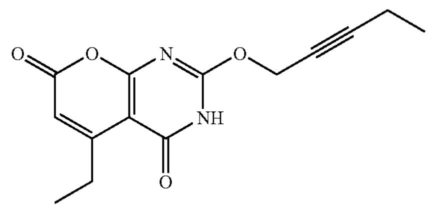 | 275 |
| 733 | 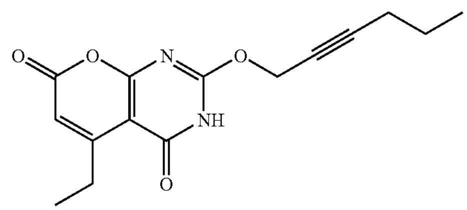 | 289 |
| 734 | 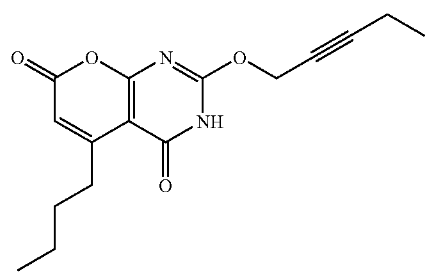 | 303 |
| 735 | 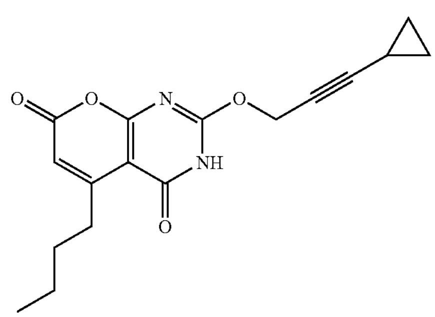 | 315 |
| 736 | 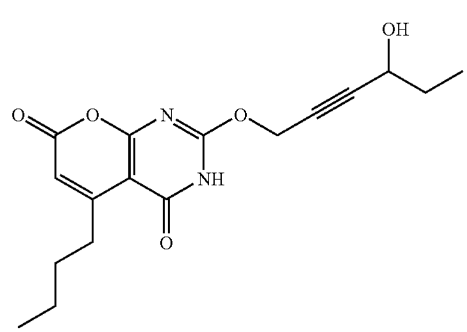 | 333 |

| Compound No. | Structure | Electrospray LCMS [M + ]+ |
|---|---|---|
| 737 | 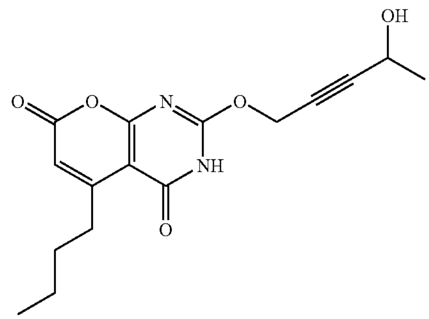 | 319 |
| 738 | 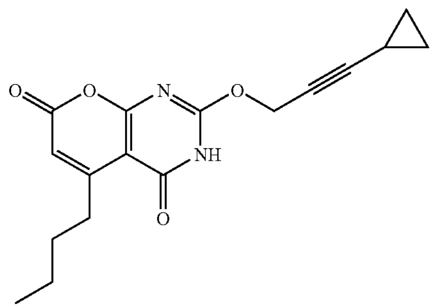 | 287 |
| 739 | 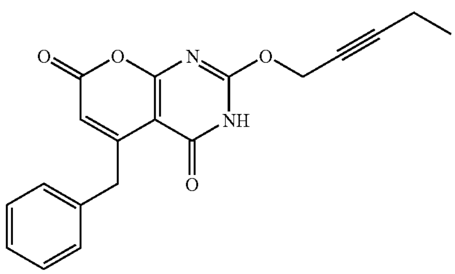 | 337.1 |

Preparative Example 740

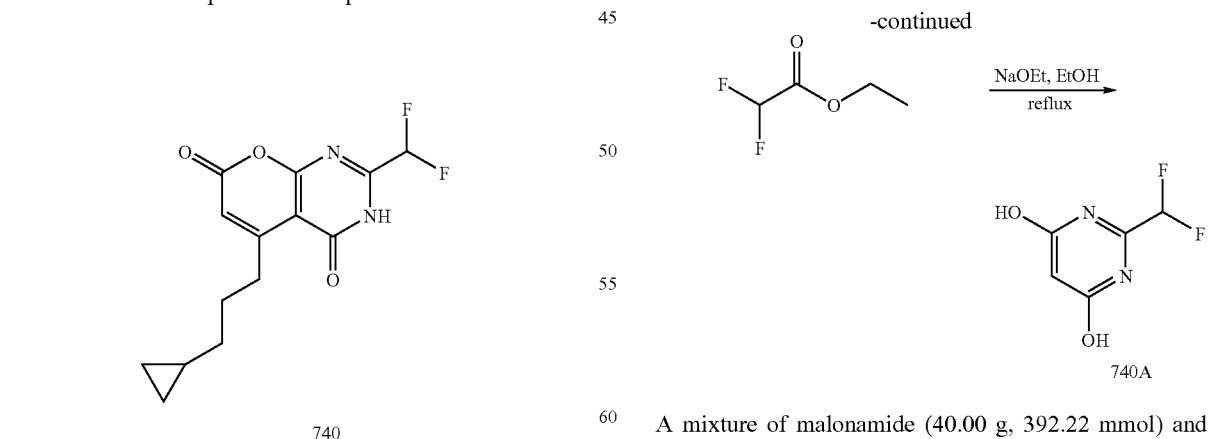

Step: 1

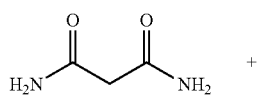

A mixture of malonamide (40.00 g, 392.22 mmol) and NaOEt (21%, 292.00 ml, 784.53 mmol) in MeOH (1 L) was stirred at room temperature for 1 hour. Difluoroacetic acid ethyl ester (58.00 g, 467.74 mmol) was then added to the reaction mixture and the reaction was heated to reflux and allowed to stir at this temperature for about 15 hours. The reaction mixture was cooled to room temperature and the solid product was collected by filtration and washed sequentially with EtOH, EtOAc and hexane, then sucked dry under vacuum to provide 45.0 g product as white powder (71% yield).

Step: 2

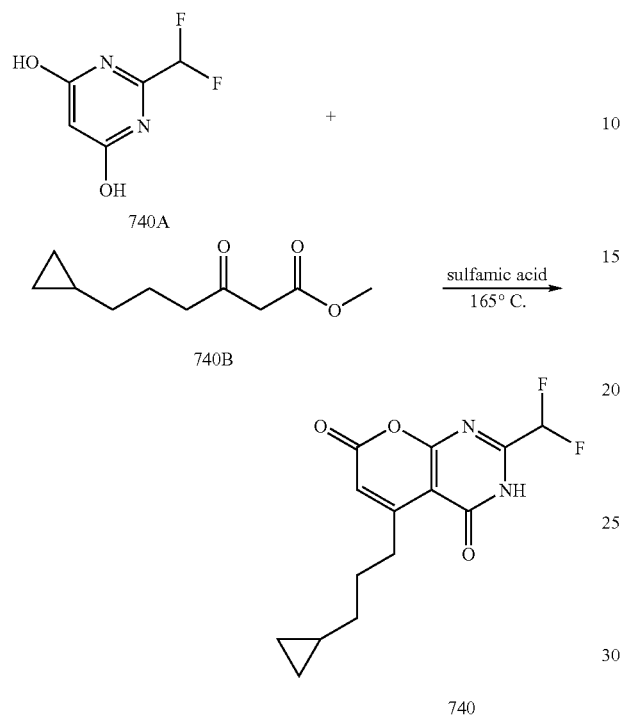

740

A mixture of compound 740A (10.50 g, 64.81 mmol), compound 740B (14.90 g, 80.98 mmol), and sulfamic acid (6.29 g, 64.84 mmol) was heated to 165° C. and allowed to stir at this temperature for 30 minutes. The reaction mixture was then cooled to about 70° C., then poured into a mixture of CH$_2$Cl$_2$/MeOH (1:1, 50 mL) and the resulting solution was filtered. The solid collected by filtration was then washed repeatedly with CH$_2$Cl$_2$/MeOH (1:1) and the eluates were combined and concentrated in vacuo to provide compound 740 as white crystals (3.30 g, 17%).

Using the method described above, and appropriate materials, Compounds 742, 743, 745, 746, 748, 750, 752, 754, 757 and 812 were prepared:

| Compound No. | Structure | Electrospray LCMS [M + ]$^+$ |
|---|---|---|
| 742 | | 405.2 |
| 743 | 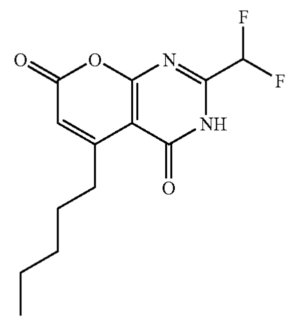 | 285.1 |
| 745 | 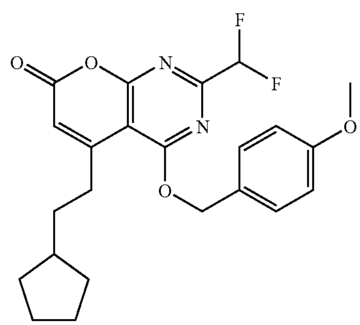 | 431.2 |
| 746 | 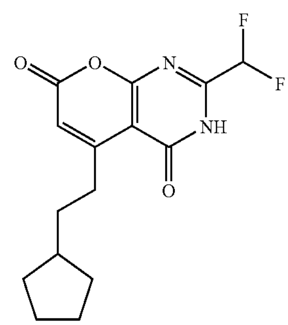 | 311.2 |
| 748 | 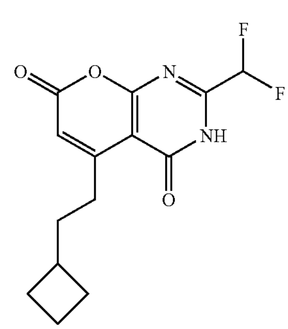 | 297.2 |

353

-continued

| Compound No. | Structure | Electrospray LCMS [M + ]+ |
|---|---|---|
| 750 | 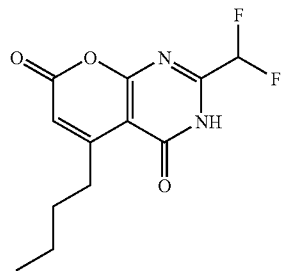 | 271.1 |
| 752 | 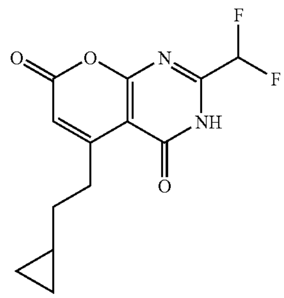 | 283.2 |
| 754 | 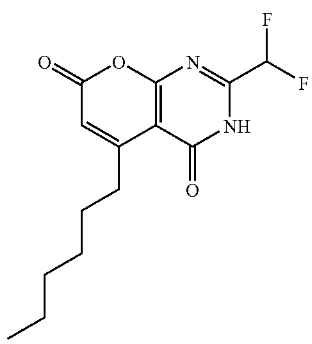 | 299.2 |
| 757 | 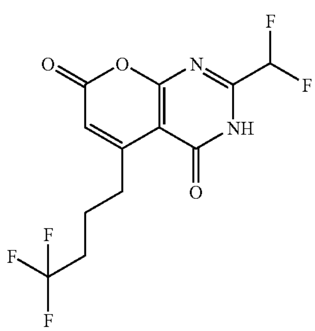 | 325.2 |
| 812 | 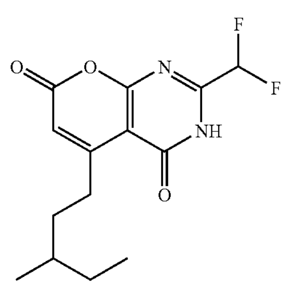 | 299.2 |

354

Preparative Example 758

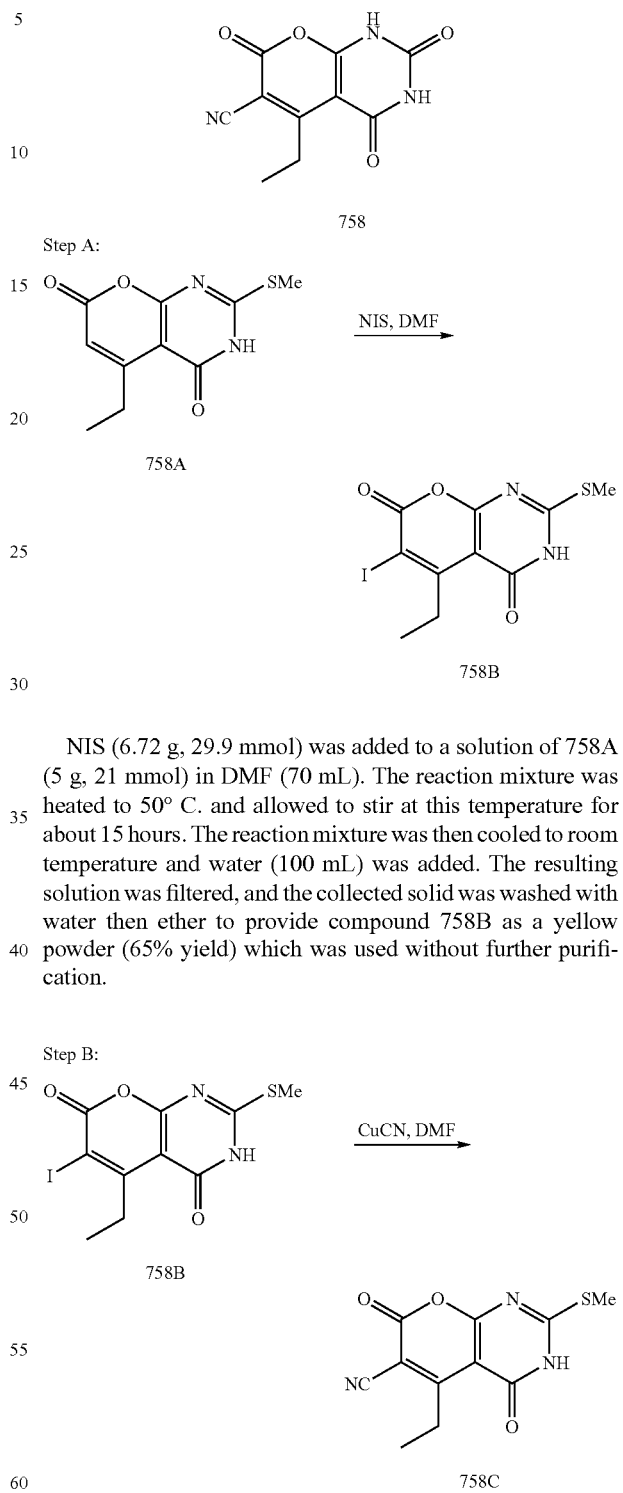

Step A:

NIS (6.72 g, 29.9 mmol) was added to a solution of 758A (5 g, 21 mmol) in DMF (70 mL). The reaction mixture was heated to 50° C. and allowed to stir at this temperature for about 15 hours. The reaction mixture was then cooled to room temperature and water (100 mL) was added. The resulting solution was filtered, and the collected solid was washed with water then ether to provide compound 758B as a yellow powder (65% yield) which was used without further purification.

Step B:

CuCN (0.246 g, 2.75 mmol) was added to a solution of 758B (1.0 g, 2.75 mmol) in DMF (10 mL). The reaction was refluxed for 2 h, under $N_2$. After cooling to room temperature, $H_2O$ (50 mL) was added. The precipitated product was filtered, washed with water then ether to afford 16 (95% yield).

Step C:

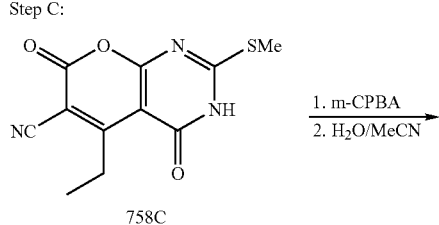

m-CPBA (0.936 g, 4.18 mmol) was added to a solution of 758C (0.55 g, 2.09 mmol) in CH$_2$Cl$_2$ (15 mL). The resulting reaction was allowed to stir at room temperature for 4 hours, then Me$_2$S was added and the resulting solution was allowed to stir for an additional 10 minutes and concentrated in vacuo. The resulting residue was diluted with 10 mL CH$_3$CN/H$_2$O (1:1) and the resulting solution was stirred at room temperature for 12 hours then concentrated in vacuo and purified by preparative TLC (15% MeOH/DCM) to provide compound 758. Electrospray MS. [MH$^+$]=262.1

Using the method described above, and appropriate materials, compounds 759 and 760 were prepared:

| Compound No. | Structure | Electrospray LCMS [M + ]$^+$ |
|---|---|---|
| 759 | 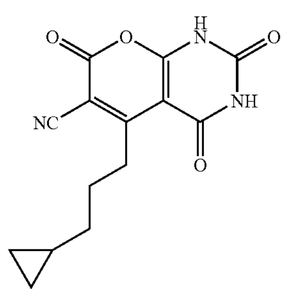 | 288.2 |
| 760 | 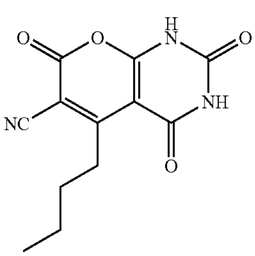 | 262.1 |

Preparative Example 761

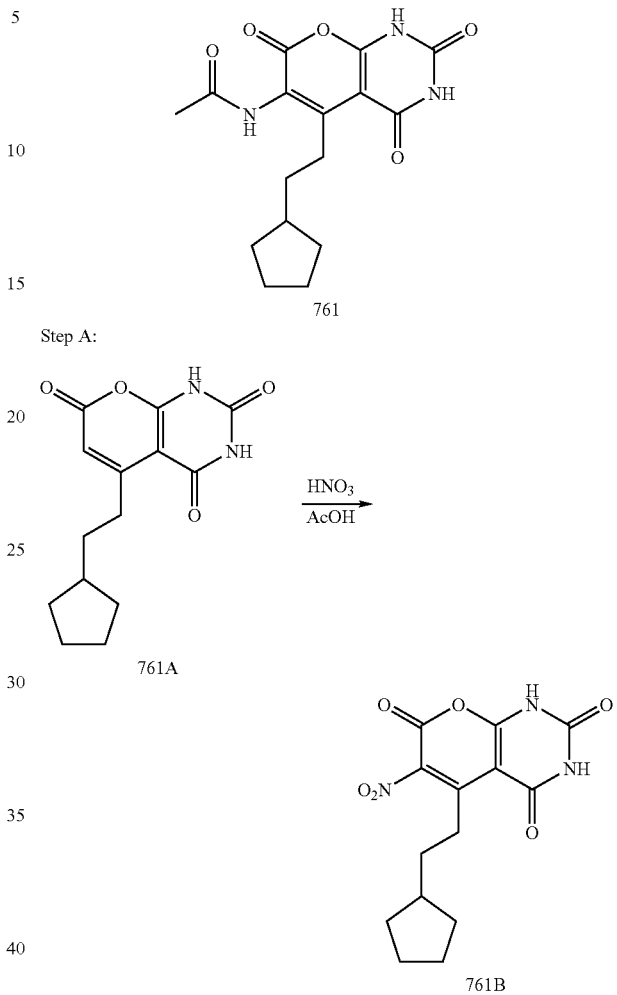

Step A:

Fuming HNO$_3$ (0.9 mL) was added drop wise to a solution of 761A (0.5 g, 1.81 mmol) in HOAc (1.8 mL) under N$_2$. The reaction was heated to 100° C. and allowed to stir at this temperature for 30 minutes, then the reaction mixture was poured into cold water (5 mL). The precipitate formed was isolated and washed with acetonitrile (1 mL) to afford compound 761B (0.3 g, 51%). Electrospray MS: [MH$^+$]=322.2

Step B:

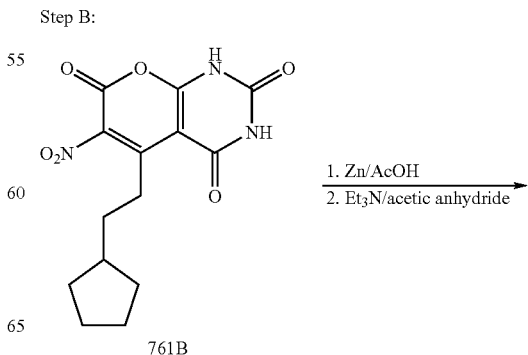

-continued

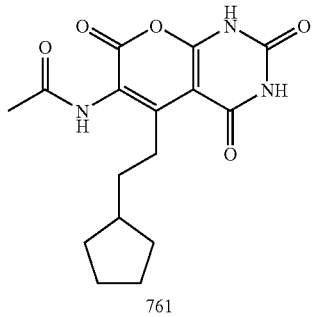
761

Zn dust (0.47 g, 7.2 mmol) was added to a solution of 761B (0.23 g, 0.72 mmol) in HOAc (3 mL) and MeOH (2 mL), and the resulting reaction was stirred at room temperature for about 18 hours. The reaction was filtered and the filtrate was concentrated in vacuo to provide a residue which was dissolved in $CH_2Cl_2$ (2 mL). To the resulting solution was added $Et_3N$ (2 mL) followed by acetic anhydride (2 mL). The resulting reaction was allowed to stir at room temperature for 24 hours, then was concentrated in vacuo and the resulting residue was purified using flash column chromatography on silica gel (eluent:MeOH/$CH_2Cl_2$ (v/v=10/97)) to provide compound 761 (0.15 g, 62%).

Electrospray MS: $[MH^+]=334.2$

Preparative Example 762

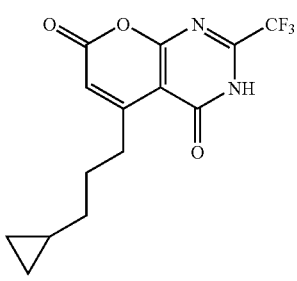
762

Step A:

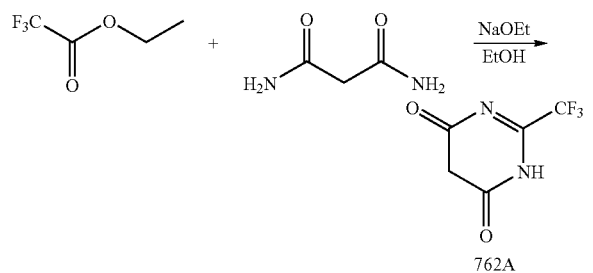
762A

Trifluoroacetic acid ethyl ester (8.8 ml, 73.5 mmol) was slowly added to a suspension of malonamide (5 g, 49 mmol) and NaOEt (21% in EtOH, 36.5 ml, 98 mmol) in EtOH (50 mL). The resulting reaction was put under nitrogen atmosphere, heated to reflux, and allowed to stir at this temperature for about 20 hours. The reaction mixture was then filtered and the collected yellow solid was washed with EtOAc, then EtOH to provide compound 762A.

Step B:

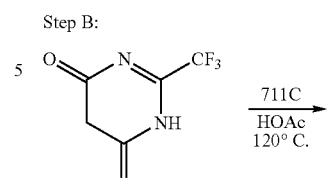
762A

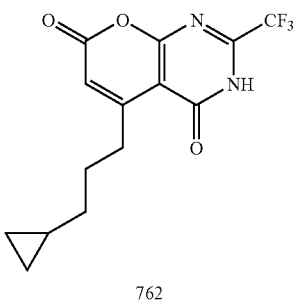
762

Compound 711C (0.8 g, 4.2 mmol, prepared as described above in preparative example 711, step C) was added to a solution of 762A (0.5 g, 2.8 mmol) in HOAc (1.5 mL). The resulting reaction was heated to 120° C. and allowed to stir at this temperature for 20 hours, then the reaction was cooled to room temperature and concentrated in vacuo. The resulting residue was purified using flash column chromatography on silica gel (eluent: 3% MeOH/$CH_2Cl_2$) followed by preparative TLC (5% MeOH/$CH_2Cl_2$) to provide compound 762.

Using the method described above, and appropriate materials, compounds 763 and 764 were prepared:

| Compound No. | Structure | Electrospray LCMS $[M+]^+$ |
|---|---|---|
| 763 | 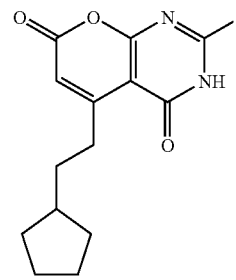 | 329.2 |
| 764 | 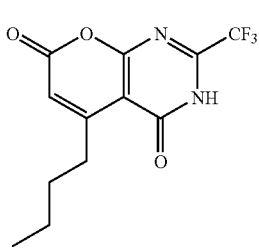 | 289.2 |

Preparative Example 765

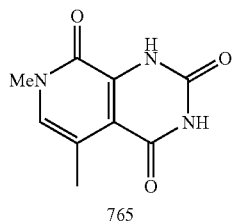

765

Step A:

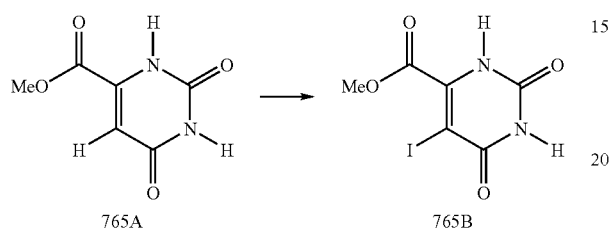

N-Iodosuccinimide (40 g, 177 mmol) was added to a solution of 765A (15 g, 88 mmol) in a mixture of TFA-TFAA (300 mL, 30 mL) and the resulting reaction was heated to 85° C. and allowed to stir at this temperature for about 15 hours. The reaction was then cooled to room temperature and concentrated in vacuo. The resulting residue was partitioned between 200 mL of H$_2$O and 100 mL of EtOAc. The precipitate was collected and washed with H$_2$O and EtOAc, then dried in vacuo to afford compound 765B (20.2 g, 78%).

Step B:

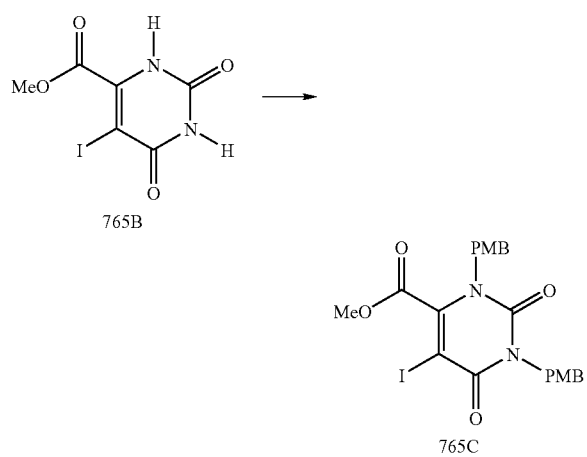

Na$_2$CO$_3$ (27 g, 300 mmol) and PMBCl (34 mL, 300 mmol) were added to a solution of 765B (20 g, 100 mmol) in DMF (300 mL). The resulting slurry was heated to 50° C. and allowed to stir at this temperature for about 15 hours. The reaction was then cooled to room temperature and partitioned between H$_2$O (250 mL) and EtOAc (500 mL). The organic layer was separated and washed with H$_2$O, then brine, then dried over MgSO$_4$, filtered and concentrated in vacuo. The resulting residue was filtered through a pad of silica gel, eluted with EtOAc-hexanes (1:10) followed by EtOAc-hexanes (1:1). The filtrate was concentrated in vacuo and the residue was recrystallized from DCM and hexanes to afford 765C (16.6 g, 31%).

Step C:

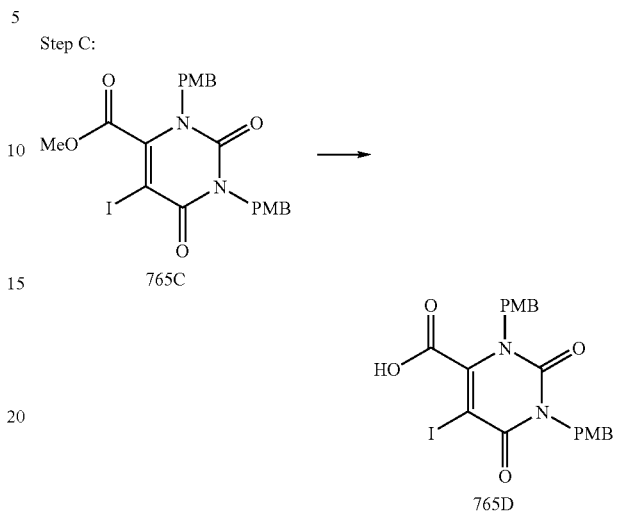

Lithium iodide (15.3 g, 114 mmol) was added to a solution of 765C (15.3 g, 28.5 mmol) in EtOAc (300 mL). The resulting slurry was stirred heated to 85° C. and allowed to stir at this temperature for about 15 hours. The reaction mixture was cooled to room temperature; then water (100 mL) was added and the resulting solution was transferred to a separatory funnel. The aqueous layer was separated and brought to a basic pH by the addition of 1 N NaOH, then the basified solution was washed with ether. The aqueous layer was then adjusted to pH=1 by addition of 1 N HCl and the resulting acidic solution was extracted with EtOAc. The combined organic extracts were washed with 1 N sodium thiosulfate solution, dried over MgSO$_4$, then filtered and concentrated in vacuo to provide compound 765D (13.5 g, 90%).

Step D:

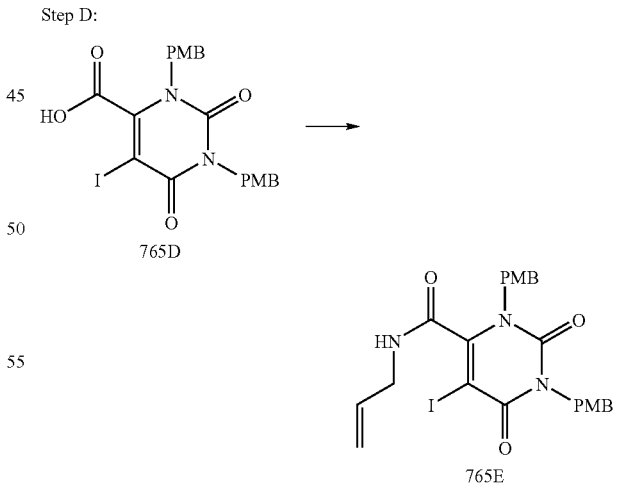

Oxalyl chloride (0.2 mL, 2.32 mmol) was added to a solution of 765D (1.0 g, 1.91 mmol) in CH$_2$Cl$_2$ (10 mL), followed by addition of a drop of DMF. The resulting mixture was allowed to stir at room temperature for 30 minutes, then concentrated in vacuo. The resulting residue was dissolved in CH$_2$Cl$_2$ (10 mL), and to the resulting solution was added allylamine (0.2 mL, 19.8 mmol). The resulting reaction was allowed to stir at room temperature for about 15 hours, then the reaction mixture was diluted with CH₂Cl₂ (10 mL) and washed with 1 N HCl. The organic layer was separated, washed with brine, dried over MgSO₄, and concentrated in vacuo. The resulting residue was purified using flash column chromatography on silica gel (eluent: EtOAc-hexanes, 1:1), to provide compound 765E (0.61 g, 60%).

Step E:

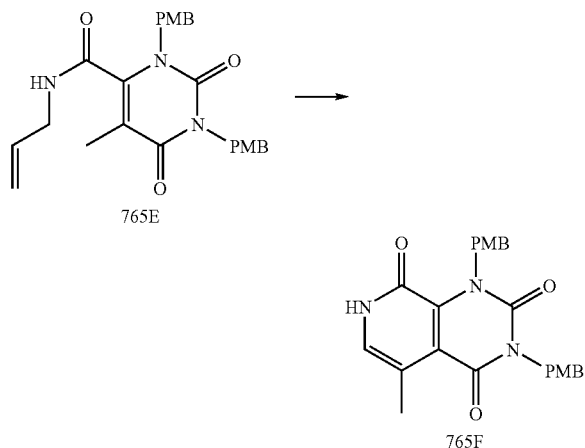

In a sealed tube, Et₃N (0.42 ml, 2.99 mmol) and Pd(OAc)₂ (38 mg, 0.17 mmol) were added to a solution of 765E (1.0 g, 1.91 mmol) in DMF (6 mL). The resulting reaction was heated at 85° C. and allowed to stir at this temperature for about 15 hours, then cooled to room temperature and filtered through Celite. The filtrate was concentrated in vacuo and the resulting residue was purified using flash column chromatography on silica gel (eluent:EtOAc-hexanes, 1:1) to provide compound 765F (0.27 g, 36%).

Step F:

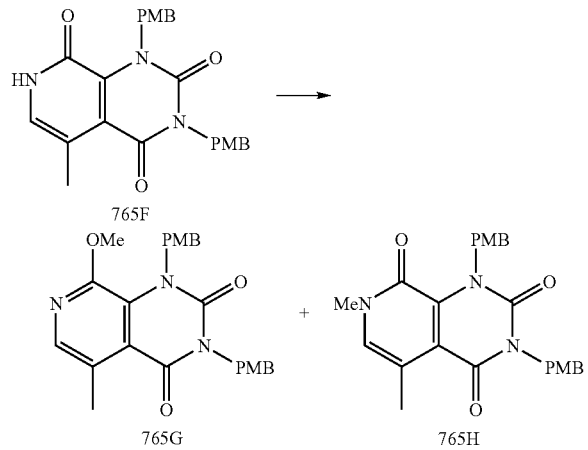

A solution of 765F (262 mg, 0.60 mmol) in DMF/THF (1:1, 12 mL) was cooled to 0° C. and NaH (30 mg, 1.18 mmol, 95% oil dispersion) was added. The resulting reaction was allowed to stir at 0° C. was stirred for about 30 minutes, then iodomethane (0.1 mL, 1.60 mmol) was added and the reaction was allowed to stir at room temperature for about 15 hours.

The reaction was quenched with water, and the aqueous layer was separated and extracted with CH₂Cl₂. The combined organic extracts were dried over MgSO₄ and concentrated in vacuo. The resulting residue was purified using flash column chromatography on silica gel (eluent:EtOAc-hexanes, 1:1) to provide compounds 765G (5 mg, 4% yield) and 765H (121 mg, 90%).

Step G:

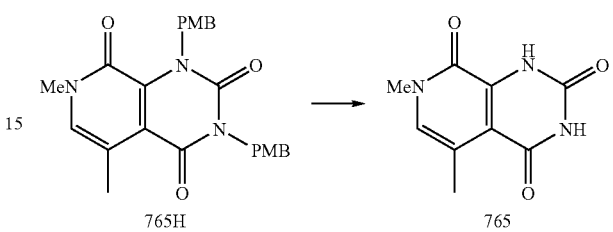

TFA (0.5 mL) and TfOH (0.1 mL) were added to a solution of 765H (100 mg, 0.22 mmol) in CH₂Cl₂ (6 mL). The resulting reaction was allowed to stir at room temperature for about 15 hours, then concentrated in vacuo to provide a crude residue which was purified using preparatory TLC (eluent: acetic acid/CH₂Cl₂/EtOAc, 1:10:10) to provide compound 765 (12 mg, 26%).

Electrospray MS [M+1]⁺ 208.1

Preparative Examples 766 and 767

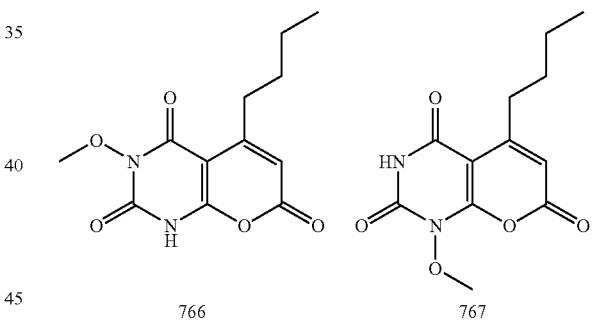

Step A:

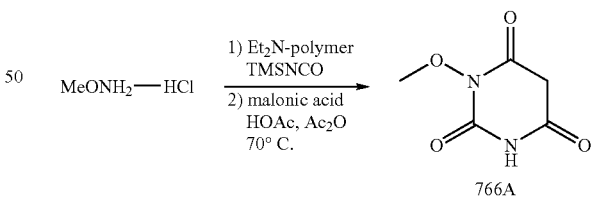

Diethylaminomethyl-polystyrene (40 g, 3.2 mmol/g, 128 mmol) was added to a solution of methoxylamine hydrochloride (5.0 g, 60 mmol) in MeOH (300 mL). The reaction mixture was stirred for 1 h. Then, TMSNCO (8.1 mL, 60 mmol) was added and the solution was stirred for 4 h. The polymer was filtered and washed twice with MeOH (50 mL, each) The volatiles were removed and the residue was dissolved in acetic acid (40 mL) then malonic acid (5.1 g, 60 mmol) and Ac₂O (40 mL) were added. The mixture was heated at 70° C. for 10 h. The reaction was concentrated in vacuo and the residue was dissolved in MeOH (100 mL), stirred for 10 min. and concentrated. The resulting residue was triturated in 1:1 EtOAc/Et2O and filtered to obtain 34 (4.2 g).

Step B:

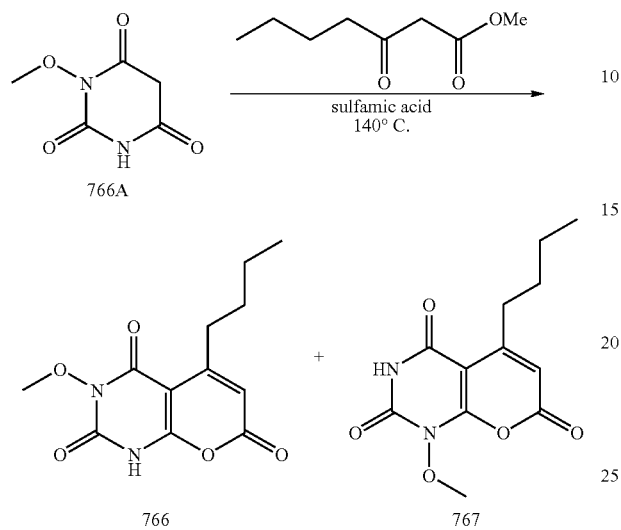

Sulfamic acid (613 mg, 6.32 mmol) was added to a mixture of 3-oxo-heptanoic acid methyl ester (2.0 g, 12.6 mmol) and 766A (109 go 6.32 mmol). The mixture was heated at 140° C. for 4 hours. The resulting residue was dissolved in 10 mL of MeOH, filtered and separated using a Gilson HPLC to obtain pure 766 and 767. Electrospray MS [M+1]$^+$ 267.1

Using the method described above, and appropriate materials, compounds 768-779 were prepared:

| Compound No. | Structure | Electrospray LCMS [M + ]$^+$ |
|---|---|---|
| 768 | 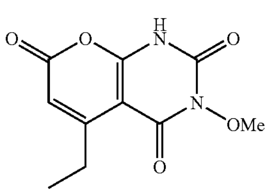 | 239.1 |
| 769 | 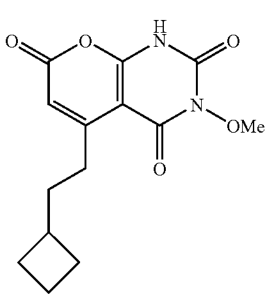 | 293.1 |

-continued

| Compound No. | Structure | Electrospray LCMS [M + ]$^+$ |
|---|---|---|
| 770 | 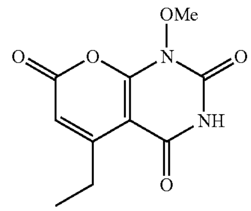 | 293.1 |
| 771 | 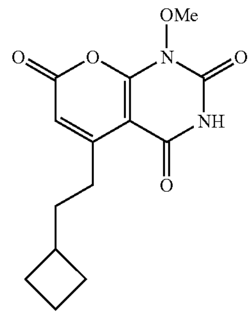 | 292.2 |
| 772 | 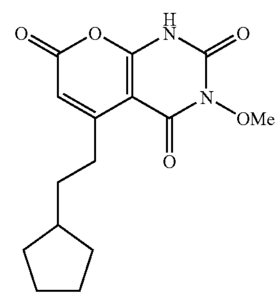 | 306.3 |
| 773 | 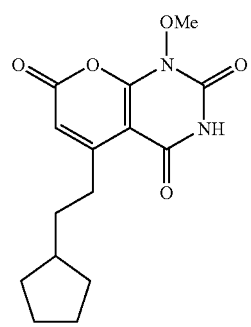 | 306.31 |
| 774 | 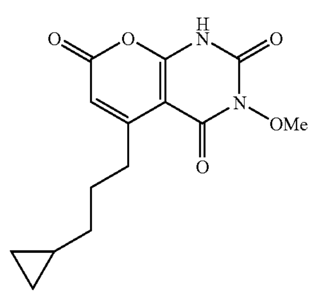 | NA |

-continued

| Compound No. | Structure | Electrospray LCMS [M + ]+ |
|---|---|---|
| 775 | (structure with OMe) | NA |
| 776 | (structure with OEt, cyclobutyl) | 307.1 |
| 777 | (structure with N-OEt, cyclobutyl) | 307.1 |
| 778 | (structure with OEt, butyl) | 281.1 |
| 779 | (structure with N-OEt, butyl) | 281.1 |

NA = not available

Other illustrative compounds of formula (I), include but are not limited to compounds 796-810, which are depicted below:

| Compound No. | Structure | Electrospray LCMS [M + ]+ |
|---|---|---|
| 796 | (morpholine structure, butyl) | 322.2 |
| 797 | (morpholine structure, butyl) | 322.2 |
| 798 | (benzyloxy structure, butyl) | 343.2 |
| 799 | (N-benzyloxy structure, butyl) | 343.2 |

-continued

| Compound No. | Structure | Electrospray LCMS [M + ]+ |
|---|---|---|
| 800 | 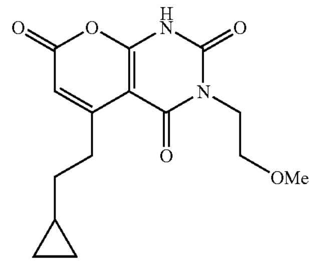 | 307.2 |
| 801 | 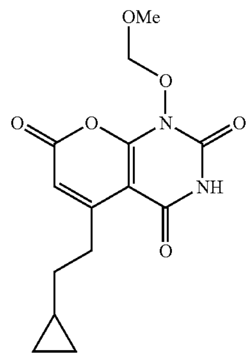 | 307.2 |
| 802 | 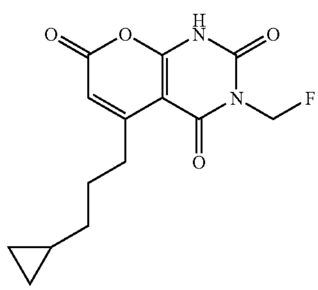 | 295.2 |
| 803 | 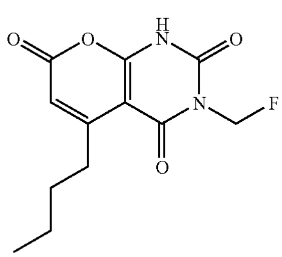 | 269.1 |
| 804 | 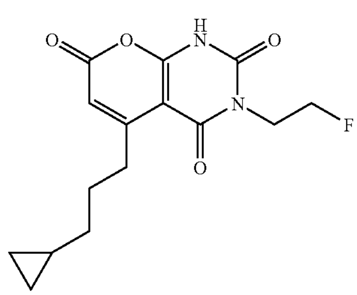 | 309.2 |

-continued

| Compound No. | Structure | Electrospray LCMS [M + ]+ |
|---|---|---|
| 805 | 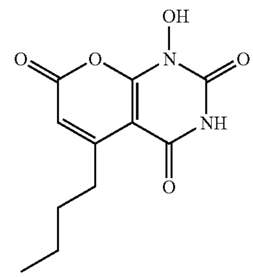 | 253.1 |
| 806 | 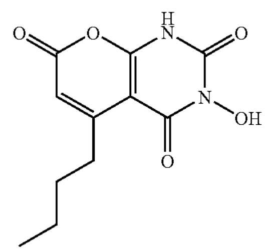 | 253.1 |
| 807 | 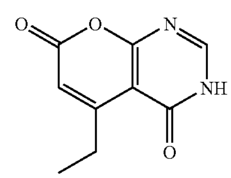 | 193.1 |
| 808 | 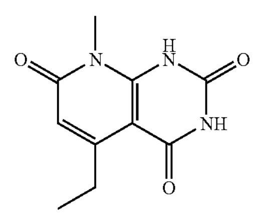 | 222.2 |
| 809 | 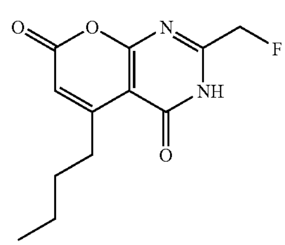 | 253.1 |
| 810 | 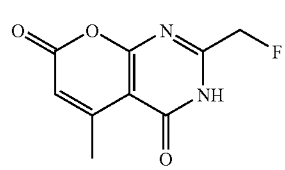 | 211.1 |

Preparative Example 811

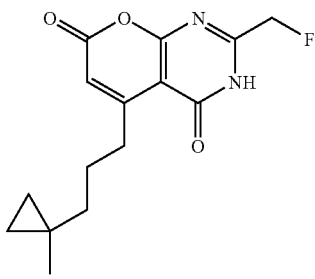

811

Step A:

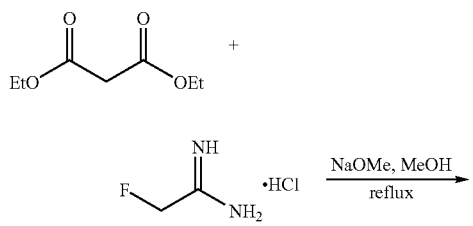

A solution of diethylmalonate (2.96 g, 18.48 mmol) and NaOMe (25 wt % in MeOH, 10.75 g, 49.76 mmol) was added to a solution of 2-fluoroacetamidine hydrochloride (2.0 g, 17.77 mmol) in MeOH (20 mL). The resulting reaction was heated to reflux and allowed to stir at this temperature for about 15 hours. The reaction mixture was cooled to room temperature, concentrated in vacuo, and the resulting residue was diluted with water (20 mL). The resulting solution was neutralized using concentrated HCl and the solid formed was collected by filtration, washed sequentially with $H_2O$ and $Et_2O$, then sucked dry to provide compound 811A as a pale brown powder (1.8 g, 69%).

Step B

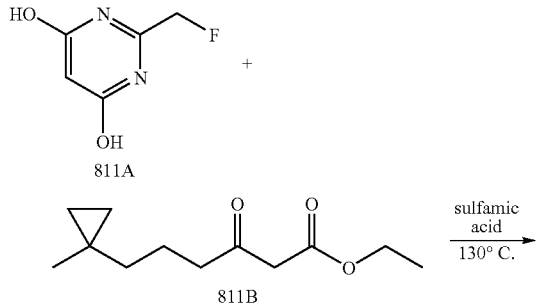

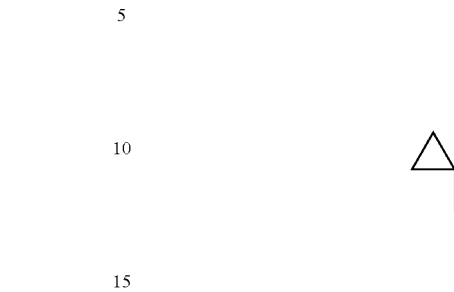

811

A mixture of compound 811A (0.1 g, 0.694 mmol), compound 811B (0.295 g, 1.39 mmol) and sulfamic acid (0.034 g, 0.347 mmol) was heated to 130° C. and allowed to stir at this temperature for about 2 hours. The reaction mixtures was then cooled to room temperature and poured into a mixture of $CH_2Cl_2$/MeOH (1:1, 1 mL). The resulting solution was purified using flash column chromatography (eluent: gradient of from 20% to 50% EtOAc/hexanes) to provide compound 811 product as a white solid.

Using the method described above, and appropriate materials, Compounds 741, 744, 747, 749, 751, 753, 755 and 756 were prepared:

| Compound No. | Structure | Electrospray LCMS $[M+]^+$ |
|---|---|---|
| 741 | 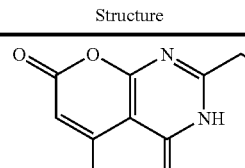 | 279 |
| 744 | 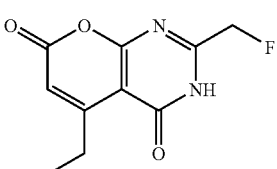 | 267.1 |
| 747 | 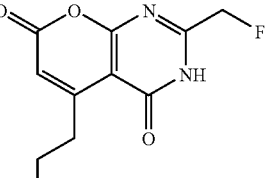 | 293.2 |

-continued

| Compound No. | Structure | Electrospray LCMS [M + ]⁺ |
|---|---|---|
| 749 | 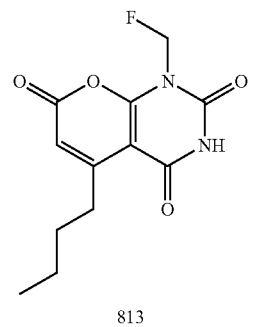 | 279.2 |
| 751 | 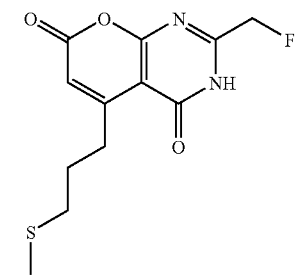 | 285.2 |
| 753 | 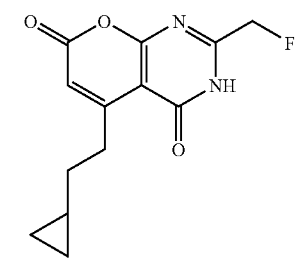 | 265.1 |
| 755 | 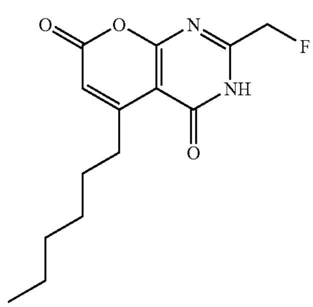 | 281.2 |
| 756 | 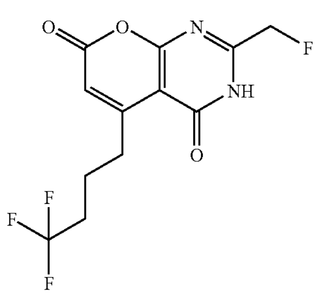 | 307.2 |

Preparative Example 813

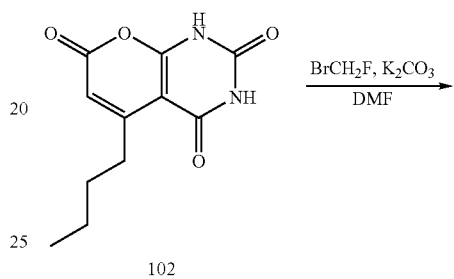

813

Step A:

BrCH₂F, K₂CO₃
DMF

102

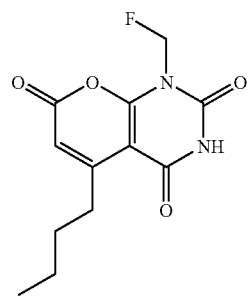

813

K₂CO₃ (0.35 g, 2.54 mmol) was added to a solution of compound 102 (0.4 g, 1.69 mmol) and BrCH₂F (0.21 g, 1.86 mmol) in DMF (5.0 mL) at room temperature. The resulting mixture was stirred overnight. The reaction mixture was diluted with ethyl acetate and neutralized with aqueous HCl solution (0.5 N). The organic phase was washed with water (3×), dried (Mg₂SO₄), and concentrated under vacuo to provide crude product which was purified with PTLC (CH2Cl2/MeOH=20/1) to give product 813 (5 mg), Electrospray MS [M+1]⁺ 269.1.

Preparative Example 814

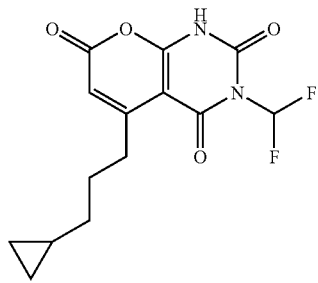

814

Step A:

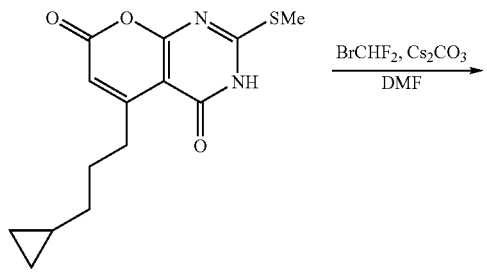

711E

Cs₂CO₃ (1.30 g, 3.99 mmol) was added to a solution of compound 711E (0.39 g, 1.33 mmol) and BrCHF₂ (0.79 g, 6.05 mmol) in DMF (5.0 mL) at room temperature. The resulting mixture was stirred overnight. The reaction mixture was diluted with ethyl acetate and neutralized with aqueous HCl solution (0.5 N). The organic phase was washed with water (3×), dried (Mg₂SO₄), and concentrated under vacuo to provide crude product which was purified with silica gel column chromatography (EtOAc/hexane gradient) to provide compound 814A (0.15 g).

Step B:

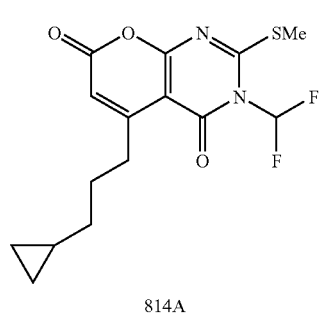

CH₃CO₃H (0.30 mL, 1.4 mmol) was added at room temperature to a solution of 814A (80 mg, 0.234 mmol) in CH₂Cl₂ (2.0 mL). The mixture was stirred for 3 hours before it was quenched with Me₂S (10.0 eq.) The reaction mixture was diluted with ethyl acetate and washed with water (3×). The organic phase was washed with brine, dried (Mg₂SO₄), and concentrated under vacuo to provide crude product which was taken up in DMF (2.0 mL) and treated with Cs₂CO₃ (91.6 mg, 0.281 mmol). The mixture was stirred for 1 hour before it was diluted with ethyl acetate and neutralized with aqueous HCl solution (0.5 N). The organic phase was washed with water (3×), dried (Mg₂SO₄), and concentrated under vacuo to provide crude product which was purified with reverse phase Gilson separation to provide compound 814 (60 mg), Electrospray MS [M+1]⁺ 313.2.

Using the method described above in Preparative Examples 813 and 814, and substituting the appropriate bromo compound in Step A, Compounds 815-833 were prepared:

| Compound No. | Structure | Electrospray LCMS [M + ]⁺ |
|---|---|---|
| 815 | 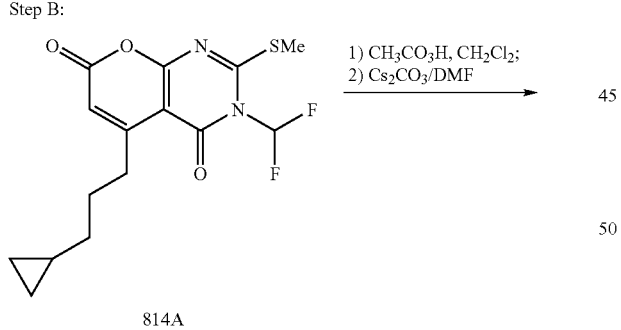 | 297.2 |
| 816 | 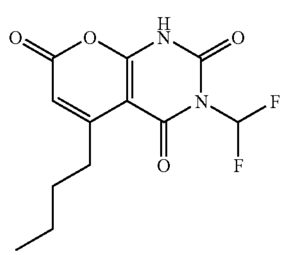 | 287.2 |
| 817 | 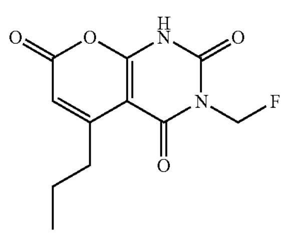 | 255.1 |
| 818 | 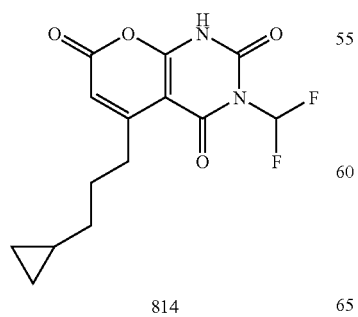 | 283.2 |

-continued
| Compound No. | Structure | Electrospray LCMS [M + ]⁺ |
|---|---|---|
| 819 | 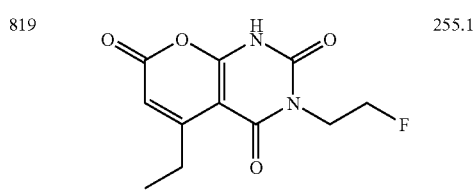 | 255.1 |
| 820 | 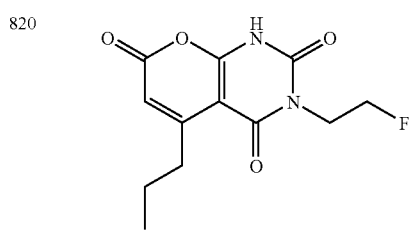 | 269.1 |
| 821 | 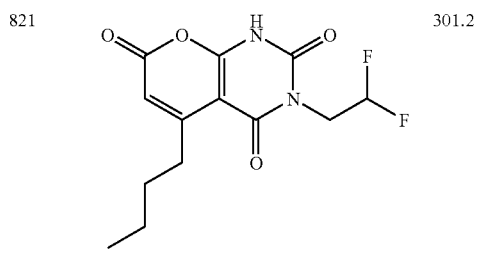 | 301.2 |
| 822 | 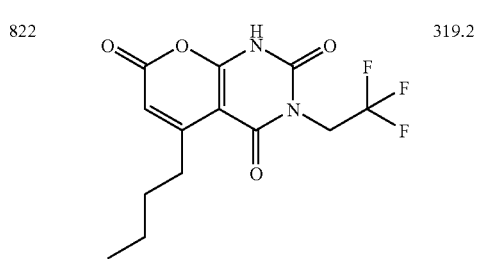 | 319.2 |
| 823 | 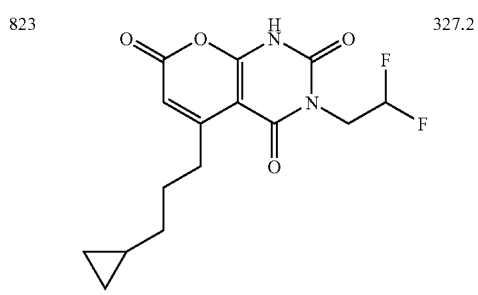 | 327.2 |
| 824 | 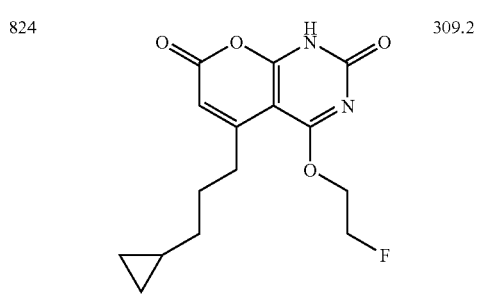 | 309.2 |
-continued
| Compound No. | Structure | Electrospray LCMS [M + ]⁺ |
|---|---|---|
| 825 | 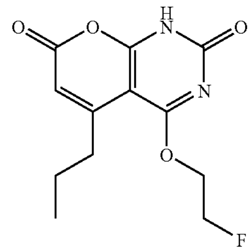 | 269.1 |
| 826 | 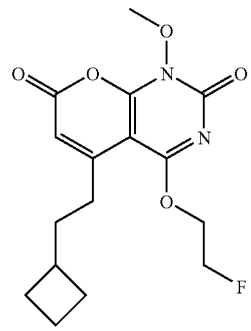 | 339.2 |
| 827 | 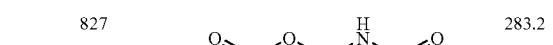 | 283.2 |
| 828 | 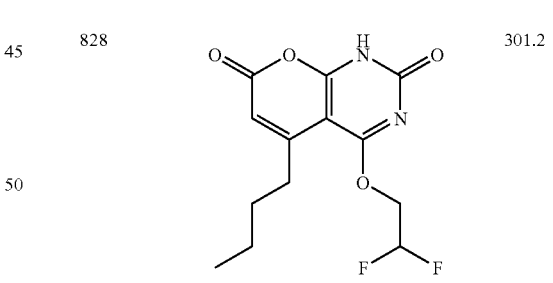 | 301.2 |
| 829 | 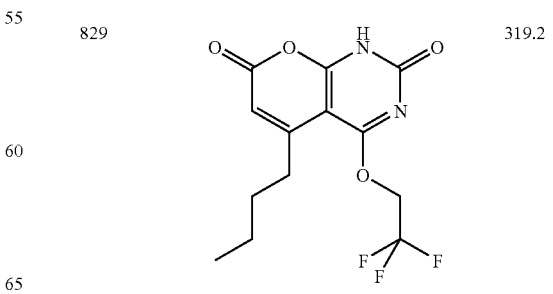 | 319.2 |

-continued

| Compound No. | Structure | Electrospray LCMS [M + ]+ |
|---|---|---|
| 830 | 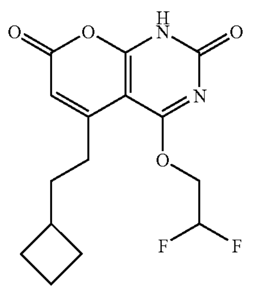 | 327.2 |
| 831 | 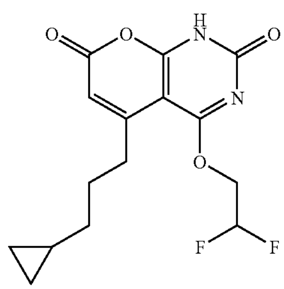 | 327.2 |
| 832 | 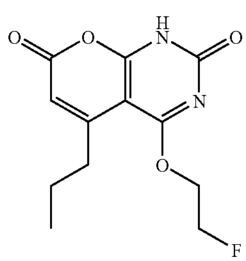 | 255.1 |
| 833 | 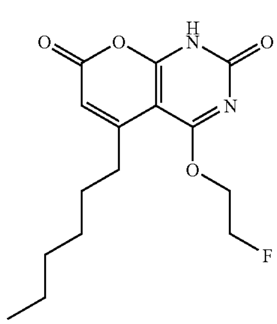 | 297.2 |

Preparative Example 834

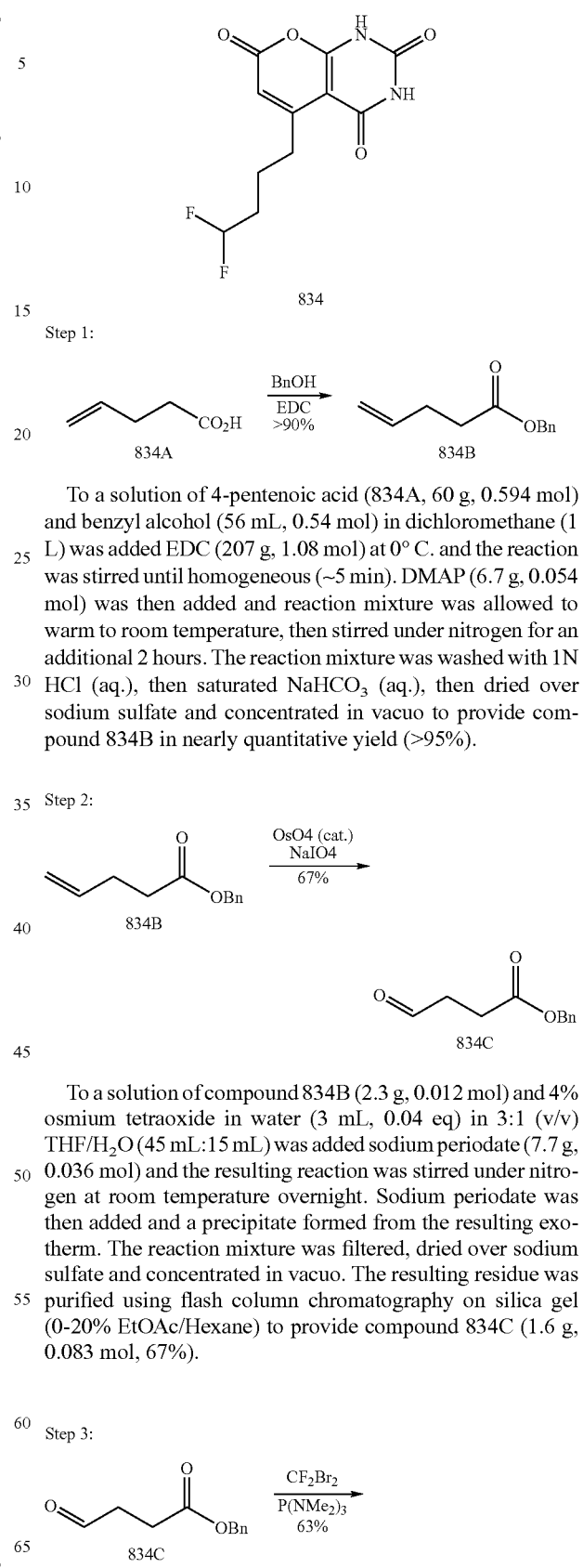

Step 1:

To a solution of 4-pentenoic acid (834A, 60 g, 0.594 mol) and benzyl alcohol (56 mL, 0.54 mol) in dichloromethane (1 L) was added EDC (207 g, 1.08 mol) at 0° C. and the reaction was stirred until homogeneous (~5 min). DMAP (6.7 g, 0.054 mol) was then added and reaction mixture was allowed to warm to room temperature, then stirred under nitrogen for an additional 2 hours. The reaction mixture was washed with 1N HCl (aq.), then saturated $NaHCO_3$ (aq.), then dried over sodium sulfate and concentrated in vacuo to provide compound 834B in nearly quantitative yield (>95%).

Step 2:

To a solution of compound 834B (2.3 g, 0.012 mol) and 4% osmium tetraoxide in water (3 mL, 0.04 eq) in 3:1 (v/v) THF/$H_2O$ (45 mL:15 mL) was added sodium periodate (7.7 g, 0.036 mol) and the resulting reaction was stirred under nitrogen at room temperature overnight. Sodium periodate was then added and a precipitate formed from the resulting exotherm. The reaction mixture was filtered, dried over sodium sulfate and concentrated in vacuo. The resulting residue was purified using flash column chromatography on silica gel (0-20% EtOAc/Hexane) to provide compound 834C (1.6 g, 0.083 mol, 67%).

Step 3:

-continued

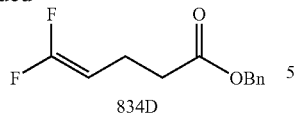
834D

To a solution of hexamethyl phosphorous triamide (25.4 g, 0.156 mol) in THF (300 mL) at −78° C. was added dibromodifluoromethane (16.4 g, 0.078 mol) and the resulting suspension was allowed to warm to room temperature. Compound 834C (7.5 g, 0.039 mol) was added and RM refluxed at 66° C. under nitrogen overnight. The reaction mixture was filtered, dried over sodium sulfate and concentrated in vacuo. The resulting residue was purified using flash column chromatography on silica gel (0-10% EtOAc/Hexane) to provide compound 834D (5.5 g, 0.024 mol, 62%).

Step 4:

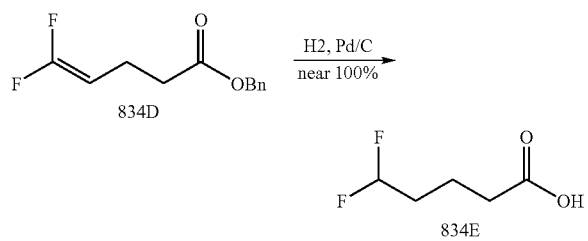

To a solution of compound 834D (5.5 g, 0.024 mol) in EtOAc (120 mL) was added 10% Pd/C (1.3 g, 0.05 eq) and the resulting solution was placed on Parr shaker under 50 psi hydrogen gas overnight. The reaction mixture was then filtered and the filtrate was concentrated in vacuo to provide compound 834E (3.3 g, 0.024 mol, >99%).

Step 5

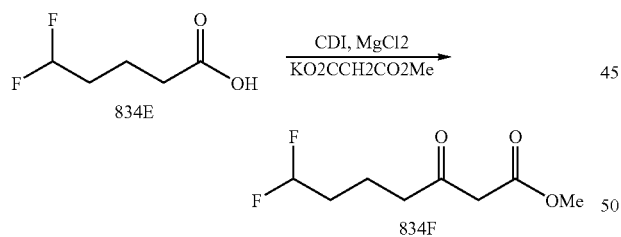

To solution of compound 834E (6 g, 0.0434 mol) in THF (150 mL) was added CDI (8.5 g, 1.2 eq) and the resulting reaction was stirred at room temperature under nitrogen for 1 hour. MgCl$_2$ (4.1 g, 1 eq) and monomethyl malonate potassium salt (10.2 g, 1.5 eq) were than added and the resulting reaction was stirred at room temperature under nitrogen overnight. The reaction mixture was then partitioned between 1N HCl (aq.) (200 mL) and EtOAc (200 mL). The aqueous layer was collected and extracted with EtOAc (3×100 mL) and the combined organic layers were washed with brine (50 mL), dried over sodium sulfate, filtered and concentrated in vacuo. The crude residue obtained was purified using flash chromatography on silica gel (0-20% EtOAc/Hexane) to provide compound 834F (6.7 g, 0.0347, 80%)

Step 6:

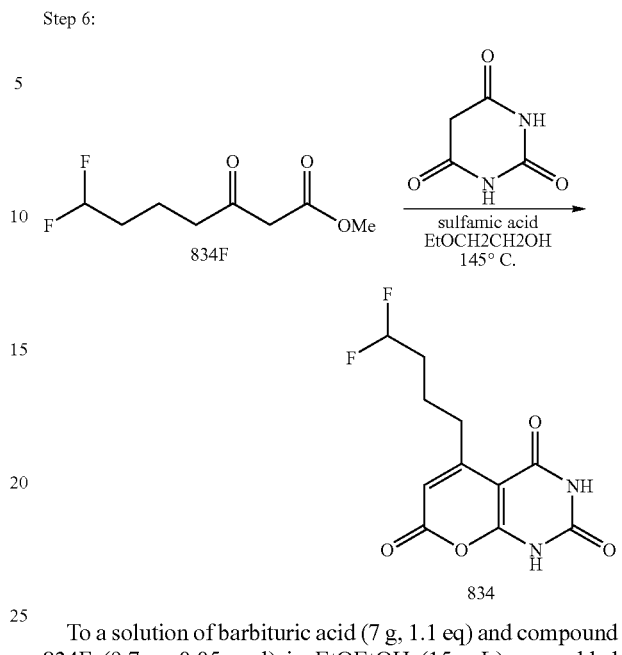

To a solution of barbituric acid (7 g, 1.1 eq) and compound 834F (9.7 g, 0.05 mol) in EtOEtOH (15 mL) was added sulfamic acid (2.4 g, 0.5 eq) and the resulting reaction was stirred at 147° C. for 4 hours. The reaction mixture was concentrated in vacuo and the resulting residue triturated with hot water three times to provide compound 834 (2 g, 0.007 mol. 15%).

Preparative Example 835

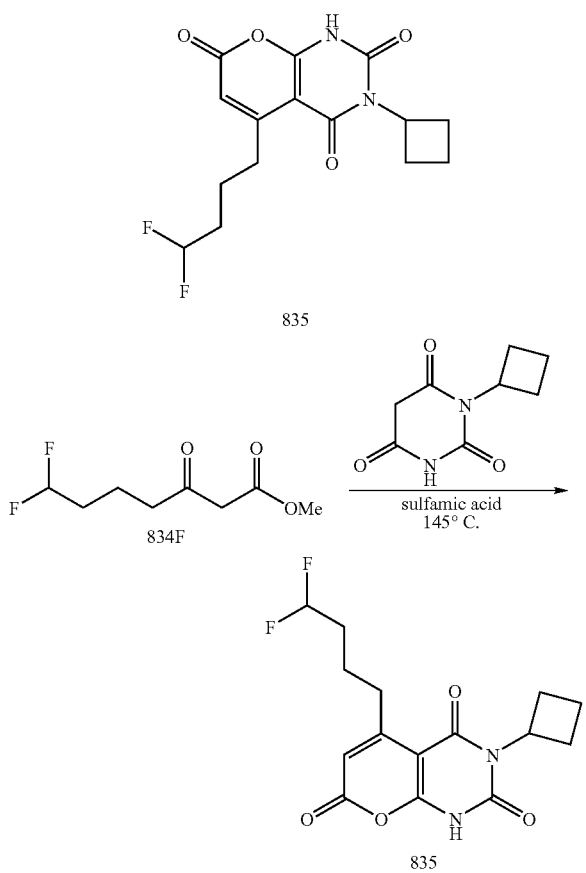

N-cyclobutyl barbituric acid (782, 4.3 mmol) and compound 834F (1 g, 1.2 eq) were heated at 140° C. for 2 hours in the presence of sulfamic acid (417 mg, 1 eq). The mixture was suspended in 10 mL DMF and the suspension was then filtered. The filtrate was injected into a Gilson HPLC in twenty injections and purified on a C18 column eluted with 0.1% TFA in water/acetonitrile (gradient 10-100% water/acetonitrile at a flow rate of 25 mL/min) to provide compound 835 (retention time: 10.1 min; 120 mg, 0.037 mmol, 9%).

Preparative Example 836

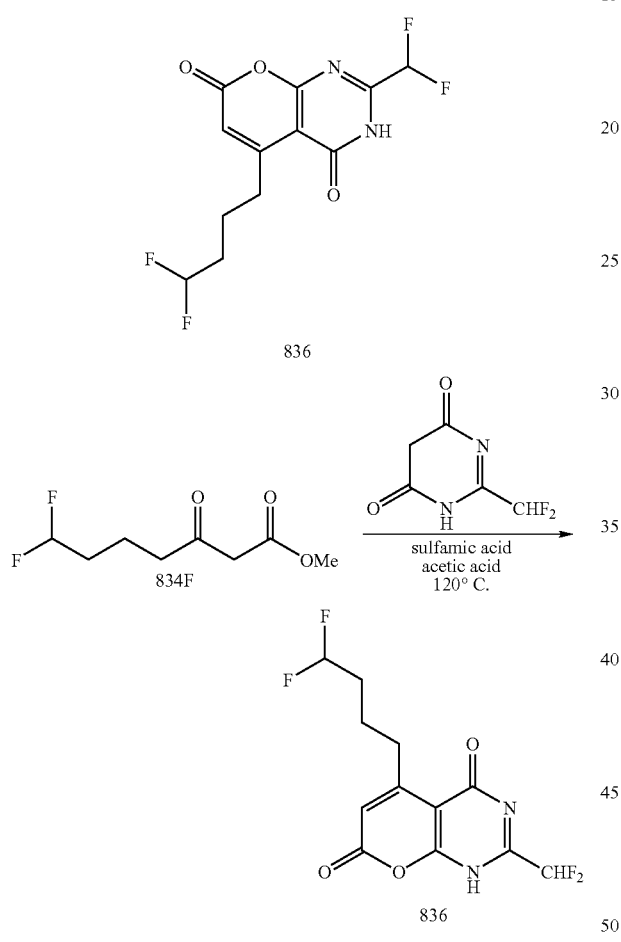

To a mixture of difluorobarbituric acid (1 g) and compound 834F (1 g) in a 15 mL microwave vial was added acetic acid (3 mL). The vial was sealed and the resulting solution was microwaved at 180° C. for 20 minutes The reaction mixture was then concentrated in vacuo and purified using flash chromatography on silica gel (gradient elution of 0-80% EtOAC/Hexane). The blue UV band that eluted off the column was collected and concentrated in vacuo and the resulting residue was purified using preparative TLC (2:1 EtOAc/Hexane) to provide compound 836 (40 mg, 3%).

Using the methods described above in Preparative Examples 834-836 with the appropriate difluoro β-keto ester and barbituric acid or barbituric acid derivative, Compounds 837-844 were prepared:

| Compound No. | Structure |
|---|---|
| 837 | 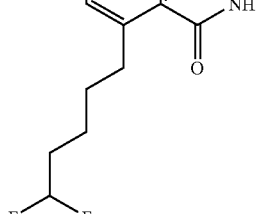 |
| 838 | 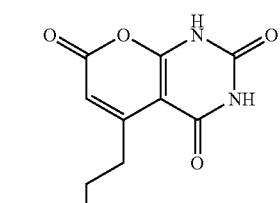 |
| 839 | 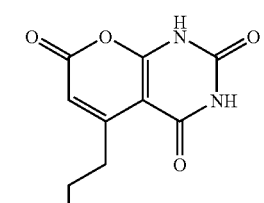 |
| 840 | 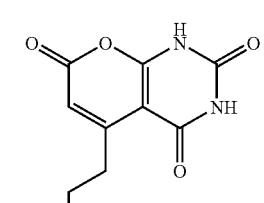 |
| 841 | 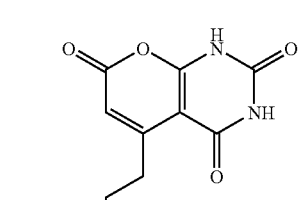 |

Nicotinic Acid Receptor Assay

The nicotinic acid receptor agonist activity of the inventive compounds was determined by following the inhibition of forskolin-stimulated cAMP accumulation in cells using the MesoScale Discovery cAMP detection kit following the manufacture's protocol. Briefly, Chinese Hamster Ovary (CHO) cells expressing recombinant human nicotinic acid receptor (NAR) were harvested enzymatically, washed 1× in phosphate buffered saline (PBS) and resuspended in PBS containing 0.5 mM IBMX at $3 \times 10^6$ cells/mL. Ten μL of cell suspension was added to each well of a 384-well plate which contained 10 μL of test compounds. Test compounds were diluted with PBS containing 6 μM of forskolin. Plates were incubated for 30 minutes at room temperature after the addition of cells. Lysis buffer containing cAMP-Tag was added to each well (10 μL/well) as per the manufacturer's protocol. Plates were then incubated from 45 minutes to overnight. Prior to reading, 10 μL of read buffer was added to each well, and the plate was read in a Sector 6000 plate imager. The signal was converted to cAMP concentration using a standard curve run on each plate. Compound $EC_{50}$ values were determined from concentration gradients of test compounds.

Compounds of Formula (I) of the present invention, and salts, solvates, or esters thereof, have cAMP $EC_{50}$ values of less than about 10,000 nM, preferably about 1000 nM or less, more preferably about 500 nM or less, even more preferably about 100 nM or less.

Examples 1, 5, 10, 29, 39, 71, 101-116, and 118-135 have cAMP $EC_{50}$ values of 100 nM or less.

The activity of selected illustrative compounds of the invention as determined using the above-described assay is presented in the following Table.

Nicotinic Receptor Agonist Activity of Selected Illustrative Compounds of the Invention -continued

| Compound No. | Structure | NA EC$_{50}$ camp (nM) |
| --- | --- | --- |
| 90 | 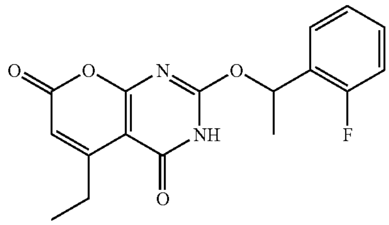 | 475.3 |
| 74 | 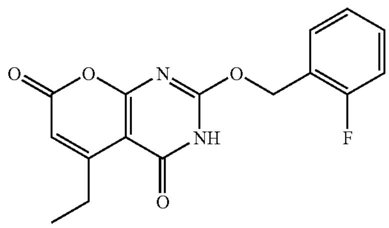 | 183.0 |
| 102 | 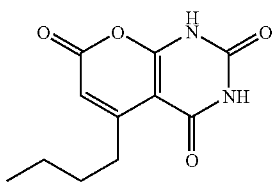 | 31.0 |
| 103 | 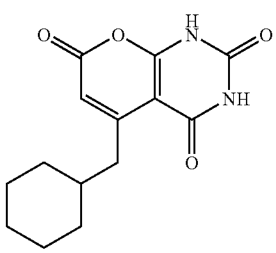 | 74.3 |
| 104 | 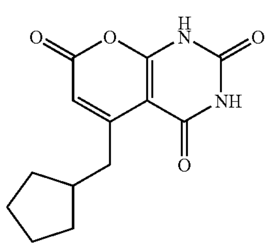 | 47.0 |
| 107 | 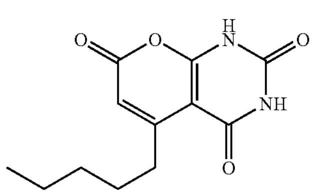 | 18.7 |

-continued

| Compound No. | Structure | NA EC$_{50}$ camp (nM) |
|---|---|---|
| 108 | 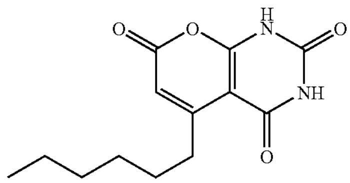 | 28.0 |
| 112 | 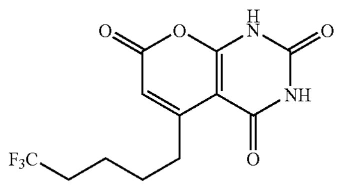 | 14.4 |
| 116 | 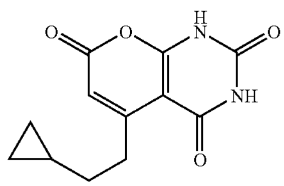 | 12.6 |
| 117 | 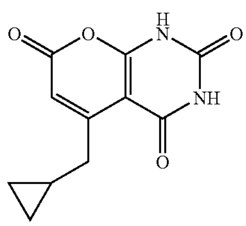 | 155.0 |
| 118 | 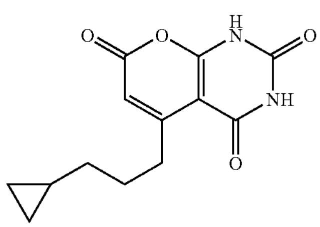 | 4.2 |
| 119 | 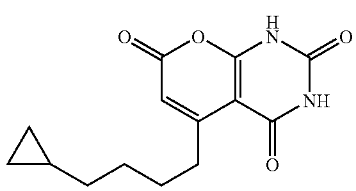 | 10.1 |
| 122 | 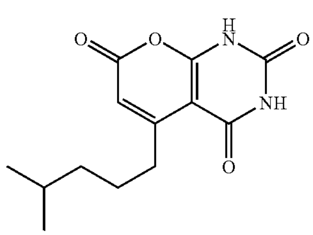 | 5.3 |

-continued

| Compound No. | Structure | NA EC$_{50}$ camp (nM) |
|---|---|---|
| 123 | 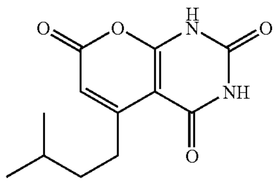 | 4.3 |
| 124 | 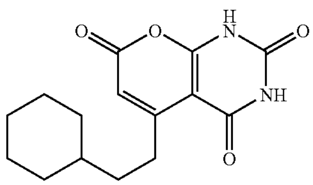 | 78.5 |
| 125 | 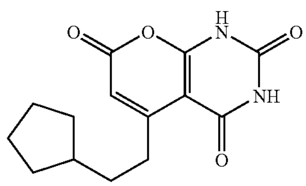 | 1.2 |
| 126 | 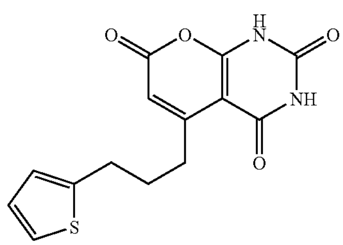 | 26.5 |
| 127 | 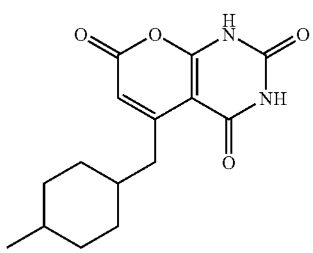 | 57.3 |
| 128 | 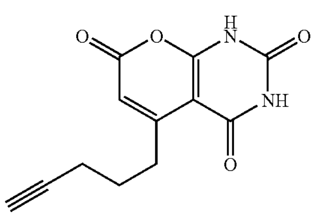 | 6.3 |
| 129 | 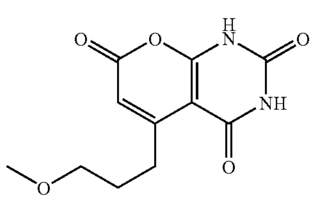 | 106.5 |

-continued

| Compound No. | Structure | NA EC$_{50}$ camp (nM) |
|---|---|---|
| 135 | 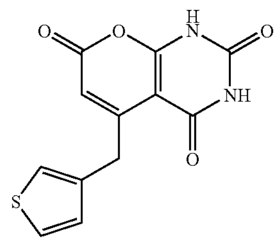 | 4.8 |
| 223 | 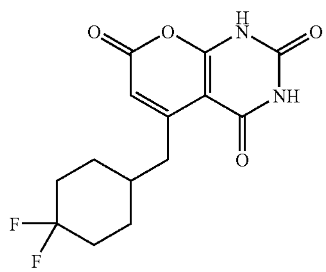 | 26.45 |
| 229 | 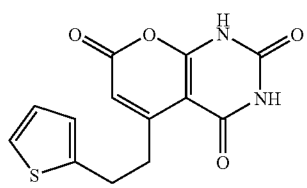 | 47.4 |
| 241 | 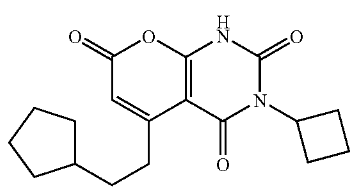 | 12.95 |
| 262 | 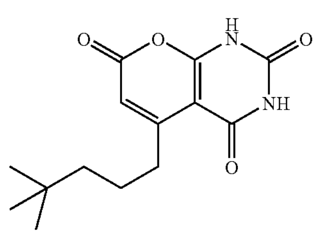 | 49.9 |
| 266 | 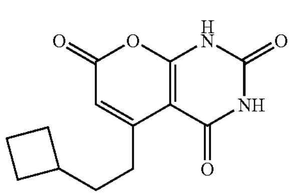 | 1.2 |

-continued

| Compound No. | Structure | NA EC$_{50}$ camp (nM) |
|---|---|---|
| 268 | (pyrano-pyrimidine-dione with 3-(1-methylcyclopropyl)propyl substituent) | 2.1 |
| 292 | (pyrano-pyrimidine-dione with phenyl and butyl substituents) | 300 |
| 297 | (pyrano-pyrimidine-dione with 3-cyclopentylpropyl substituent) | 56.75 |
| 512 | (pyrano-pyrimidinone with ethyl and O-CH$_2$-C≡C-CH$_2$CH$_3$ substituents) | 95.5 |
| 589 | (pyrano-pyrimidinone with ethyl and O-CH$_2$-C≡C-cyclopropyl substituents) | 33.8 |
| 645 | (pyrano-pyrimidinone with ethyl and O-CH$_2$-C≡C-CH$_2$CH$_2$OH substituents) | 26.2 |

-continued

| Compound No. | Structure | NA EC$_{50}$ camp (nM) |
|---|---|---|
| 666 | 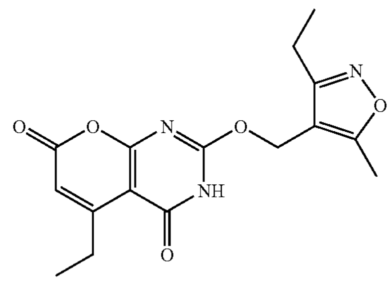 | 63.3 |
| 691 | 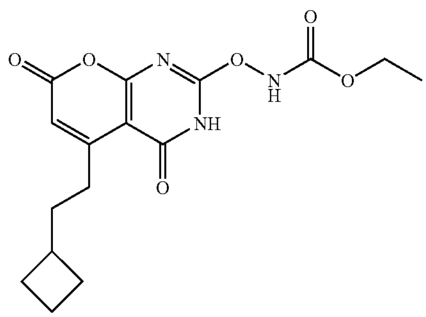 | 47.5 |
| 712 | 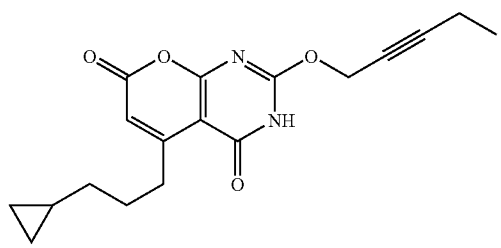 | 57.0 |
| 713 | 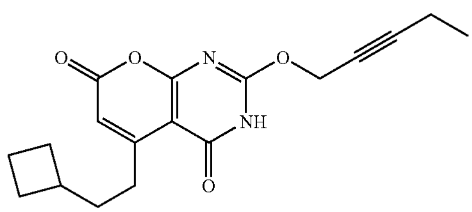 | 22.0 |
| 714 | 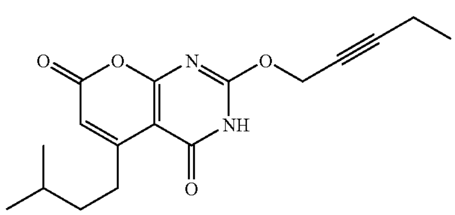 | 66.0 |
| 715 | 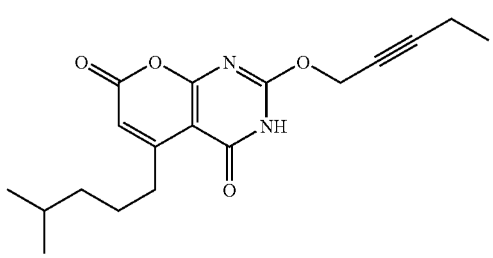 | 671.0 |

-continued

| Compound No. | Structure | NA EC$_{50}$ camp (nM) |
|---|---|---|
| 716 | 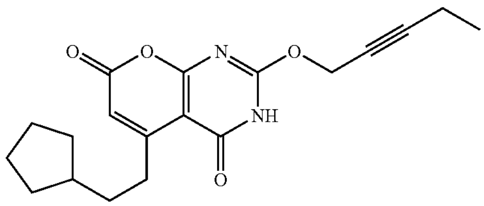 | 171.5 |
| 717 | 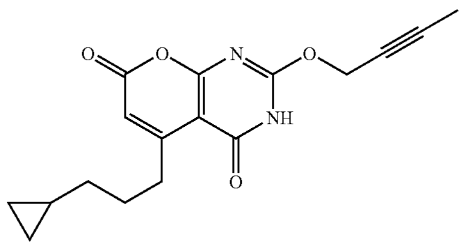 | 259.0 |
| 718 | 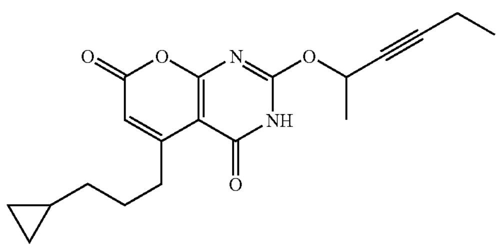 | 162.5 |
| 719 | 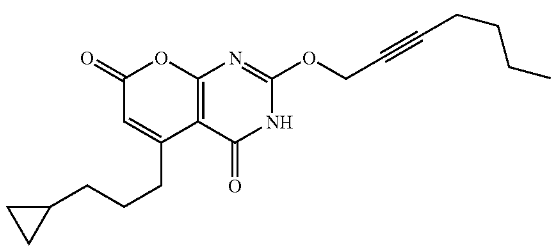 | 152.0 |
| 720 | 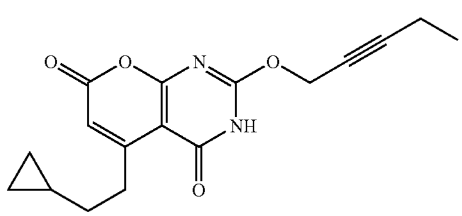 | 89.5 |
| 721 | 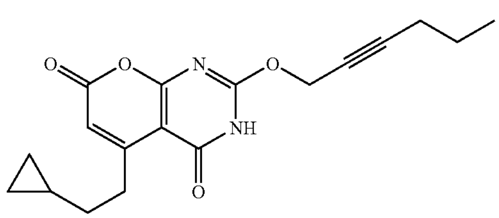 | 225.5 |

| Compound No. | Structure | NA EC$_{50}$ camp (nM) |
|---|---|---|
| 722 | 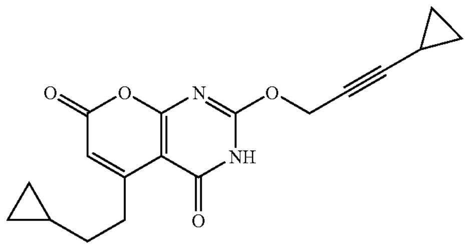 | 111.5 |
| 723 | 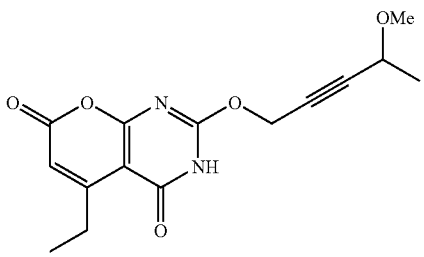 | 296 |
| 724 | 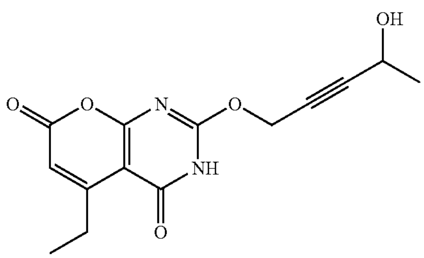 | 59.5 |
| 725 | 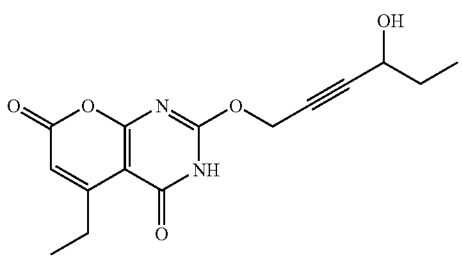 | 675 |
| 726 | 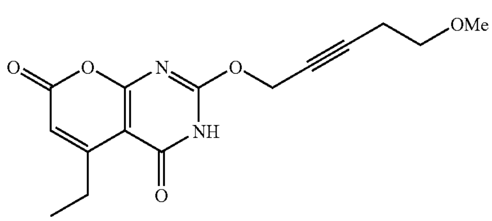 | 219 |
| 727 | 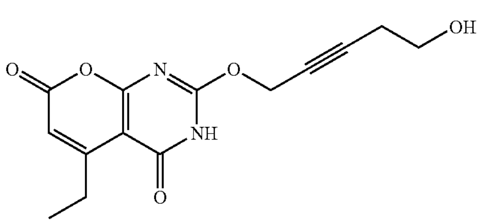 | 179 |

-continued

| Compound No. | Structure | NA EC$_{50}$ camp (nM) |
|---|---|---|
| 728 | 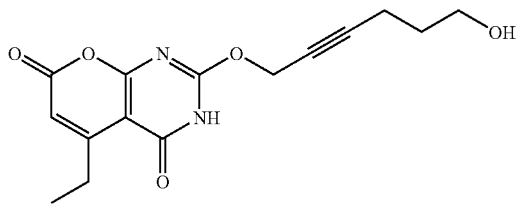 | 26.2 |
| 729 | 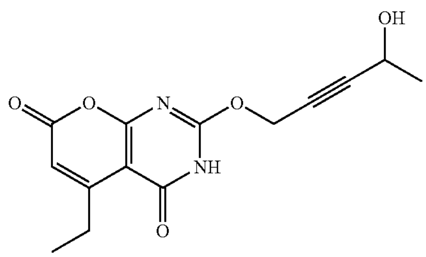 | 49.9 |
| 730 | 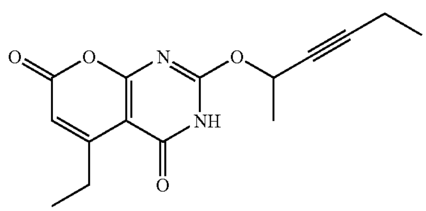 | 155.8 |
| 731 | 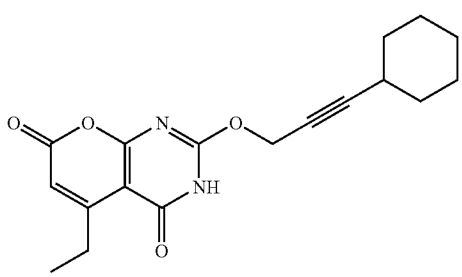 | 177.4 |
| 732 | 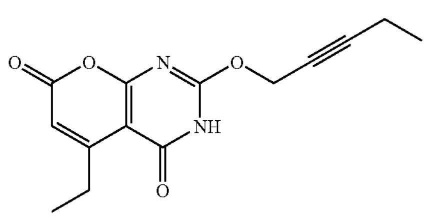 | 95.5 |
| 733 | 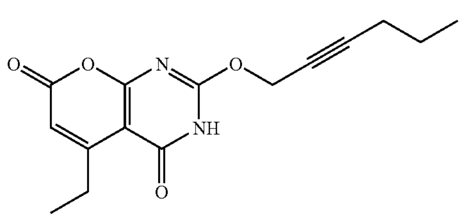 | 52.6 |

| Compound No. | Structure | NA EC$_{50}$ camp (nM) |
|---|---|---|
| 734 | 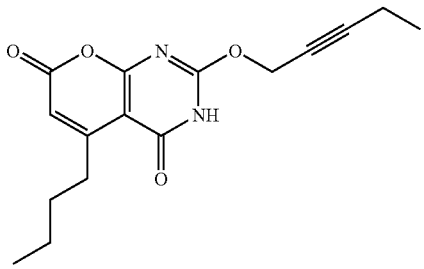 | 71.8 |
| 735 | 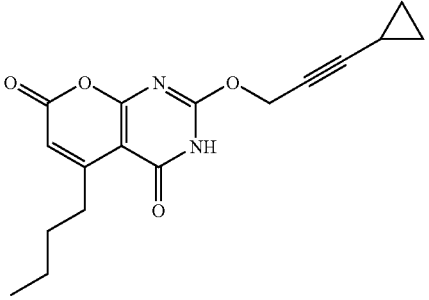 | 94 |
| 736 | 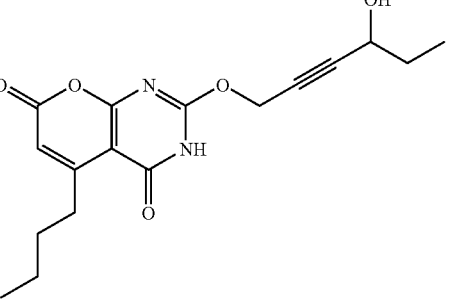 | 32.9 |
| 737 | 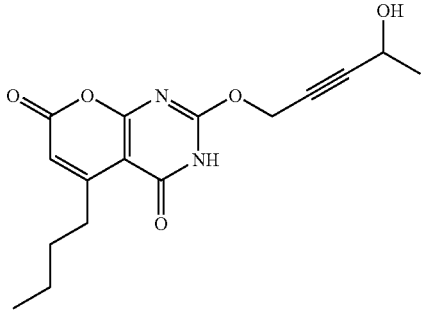 | 59.5 |
| 738 | 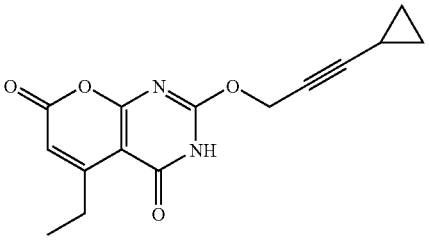 | 33.8 |

-continued

| Compound No. | Structure | NA EC$_{50}$ camp (nM) |
|---|---|---|
| 739 | 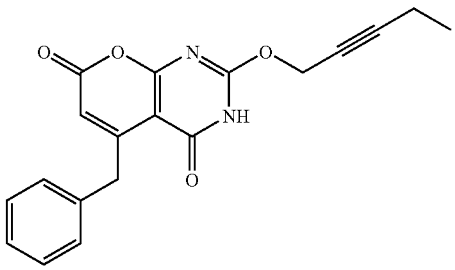 | 136.8 |
| 740 | 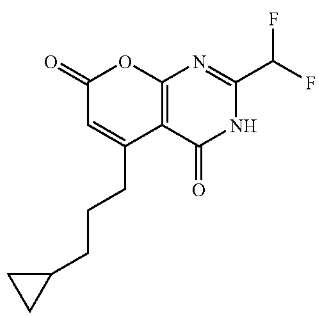 | 130 |
| 741 | 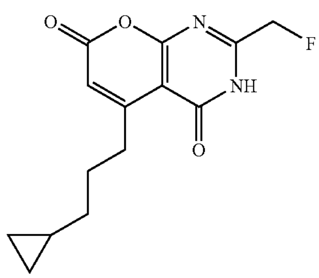 | 123 |
| 742 | 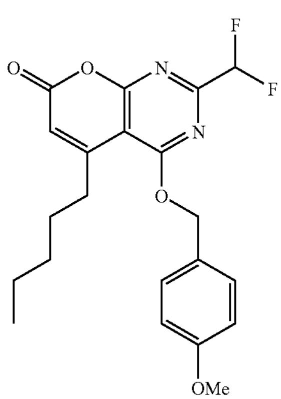 | 1068 |

-continued

| Compound No. | Structure | NA EC$_{50}$ camp (nM) |
|---|---|---|
| 743 | 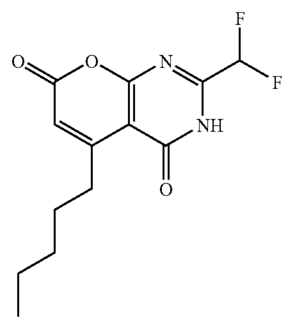 | 212.5 |
| 744 | 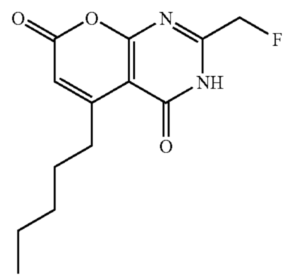 | 128 |
| 745 | 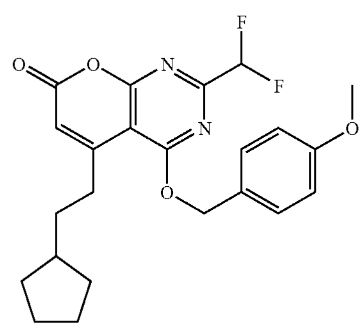 | 10000 |
| 746 | 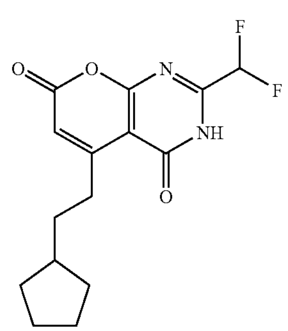 | 1402 |
| 747 | 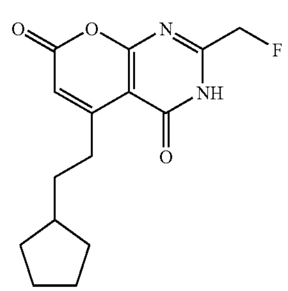 | 1233 |

-continued

| Compound No. | Structure | NA EC$_{50}$ camp (nM) |
|---|---|---|
| 748 | 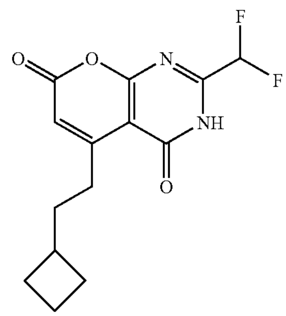 | 286 |
| 749 | 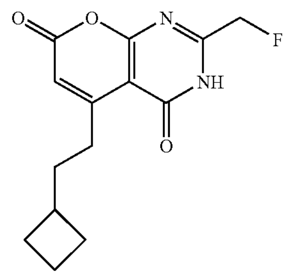 | 182.5 |
| 750 | 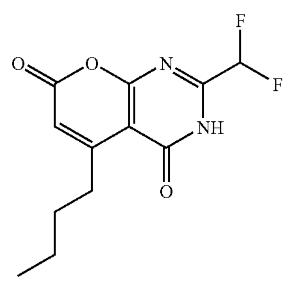 | 1892.5 |
| 751 | 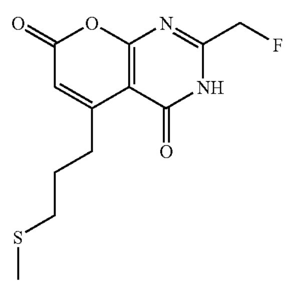 | 487 |
| 752 | 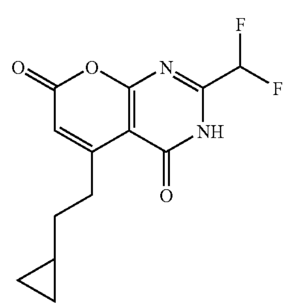 | 248 |

-continued
| Compound No. | Structure | NA EC$_{50}$ camp (nM) |
|---|---|---|
| 753 | 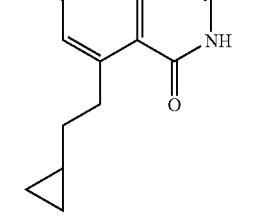 | 228 |
| 754 | 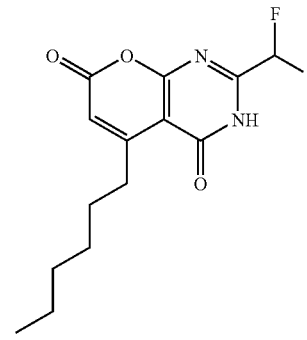 | 308 |
| 755 | 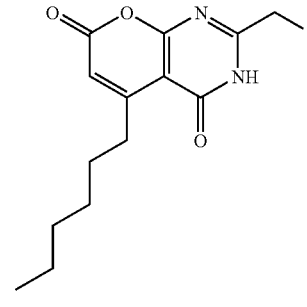 | 286 |
| 759 | 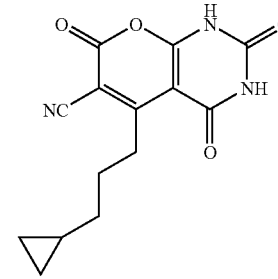 | 2326 |
| 760 | 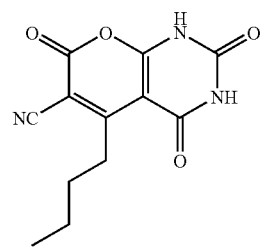 | 10000 |

| Compound No. | Structure | NA EC$_{50}$ camp (nM) |
|---|---|---|
| 763 | 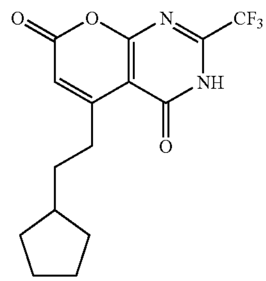 | 7734 |
| 764 | 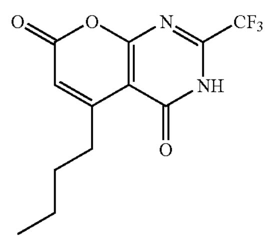 | 8922 |
| 768 | 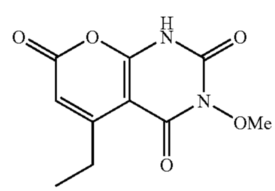 | 383.5 |
| 769 | 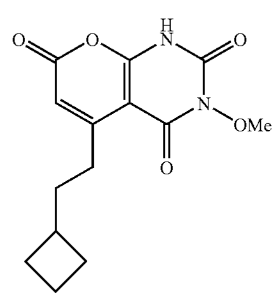 | 19 |
| 770 | 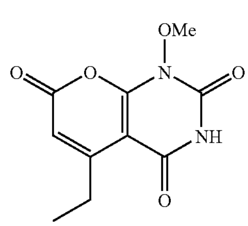 | 908 |

| Compound No. | Structure | NA EC$_{50}$ camp (nM) |
|---|---|---|
| 771 | 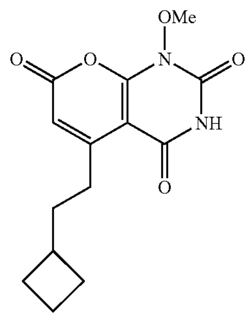 | 17 |
| 772 | 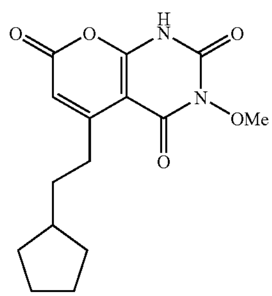 | 39 |
| 773 | 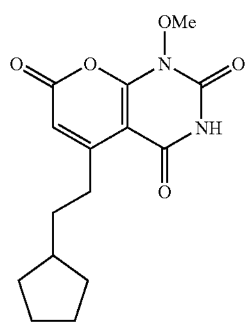 | 48.5 |
| 774 | 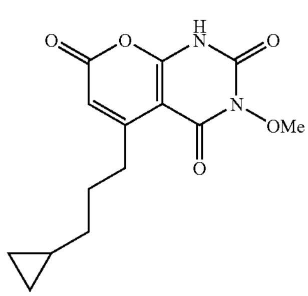 | 28.0 |

| Compound No. | Structure | NA EC$_{50}$ camp (nM) |
|---|---|---|
| 776 | 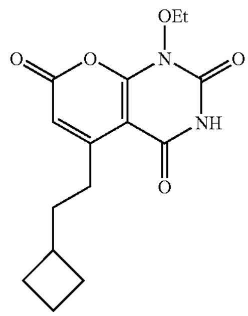 | 10000 |
| 777 | 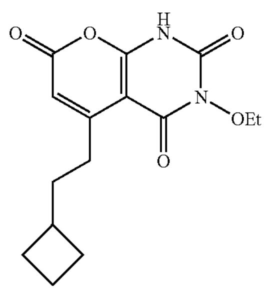 | 5600 |
| 778 | 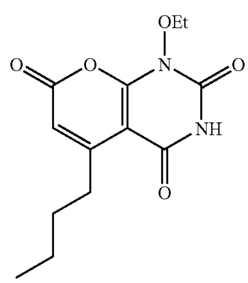 | 9150 |
| 779 | 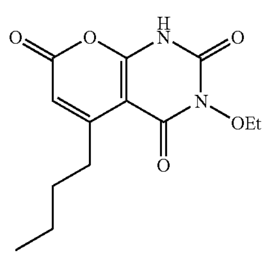 | 2851 |
| 780 | 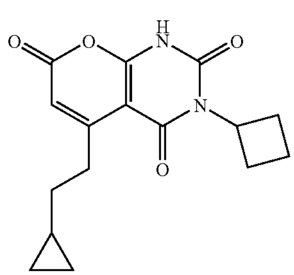 | 36 |

| Compound No. | Structure | NA EC$_{50}$ camp (nM) |
|---|---|---|
| 781 | 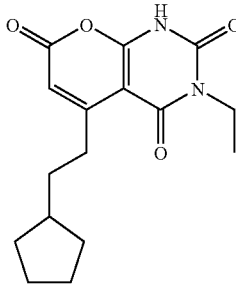 | 68 |
| 782 | 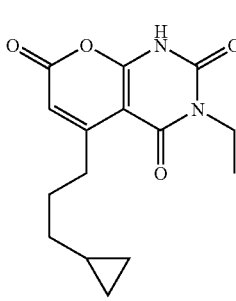 | 94 |
| 783 | 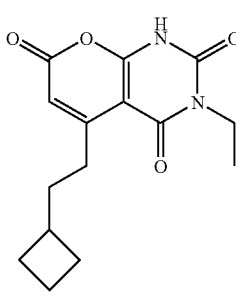 | 64 |
| 784 | 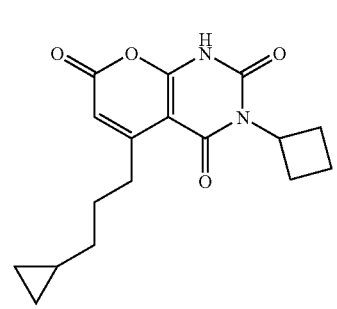 | 17.9 |
| 786 | 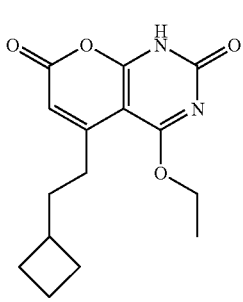 | 5331 |

-continued

| Compound No. | Structure | NA EC$_{50}$ camp (nM) |
|---|---|---|
| 787 | 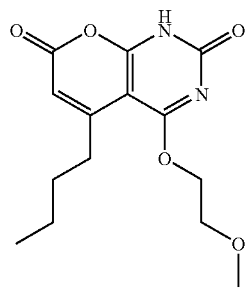 | 681.5 |
| 788 | 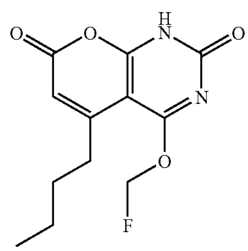 | 38.5 |
| 789 | 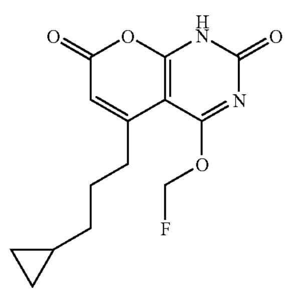 | 88 |
| 791 | 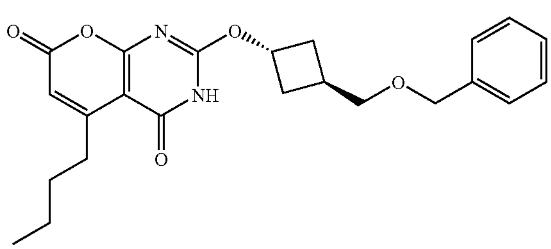 | 50 |
| 792 | 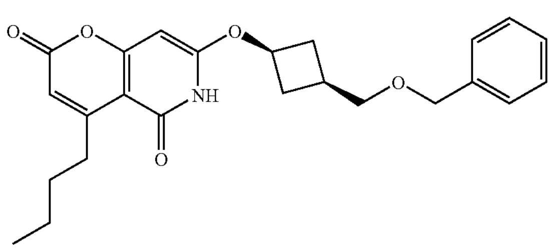 | 44 |

-continued

| Compound No. | Structure | NA EC$_{50}$ camp (nM) |
|---|---|---|
| 796 | 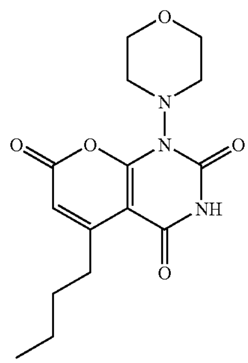 | >10000 |
| 797 | 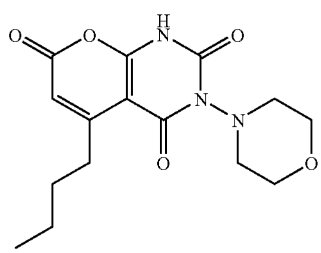 | >1000 |
| 798 | 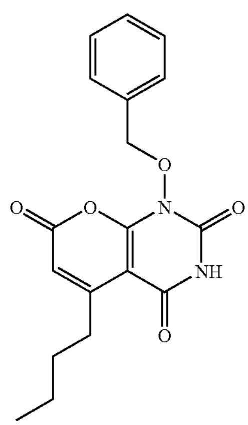 | >10000 |
| 799 | 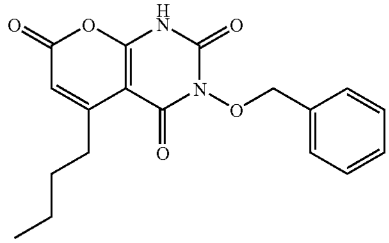 | >10000 |

-continued

| Compound No. | Structure | NA EC$_{50}$ camp (nM) |
|---|---|---|
| 800 | 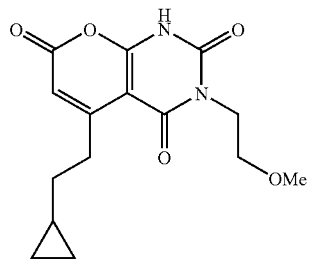 | >10000 |
| 801 | 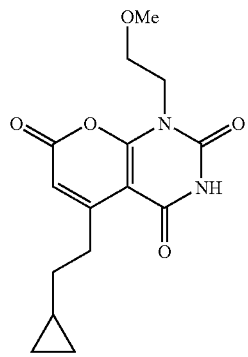 | >10000 |
| 802 | 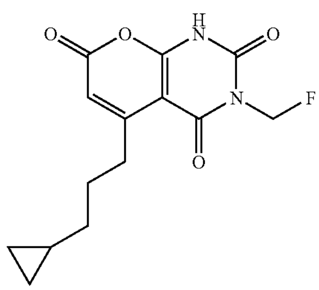 | 12 |
| 803 | 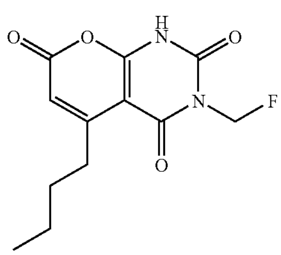 | 3450 |
| 804 | 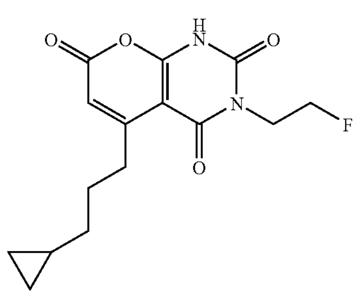 | 178 |

-continued

| Compound No. | Structure | NA EC$_{50}$ camp (nM) |
| --- | --- | --- |
| 805 | 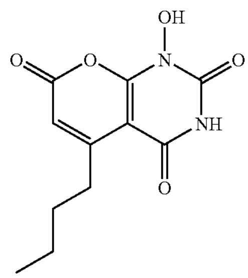 | 2063 |
| 806 | 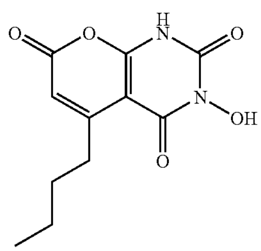 | 256 |
| 807 | 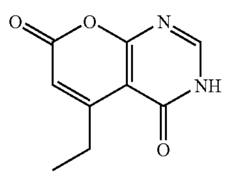 | >10000 |
| 808 | 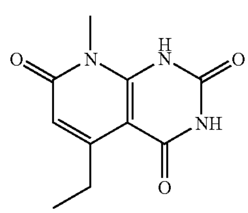 | >10000 |
| 809 | 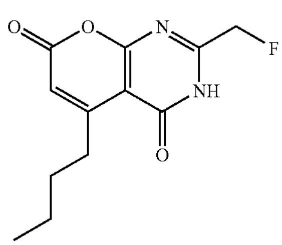 | 187 |
| 810 | 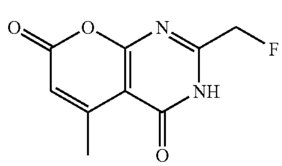 | >10000 |

-continued

| Compound No. | Structure | NA EC$_{50}$ camp (nM) |
|---|---|---|
| 811 | 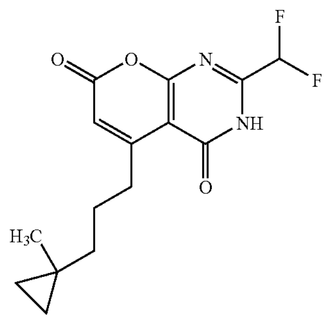 | 22 |
| 812 | 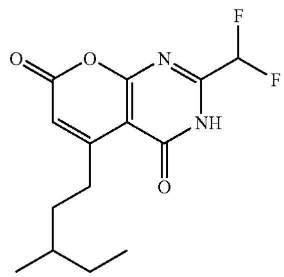 | 40 |
| 813 | 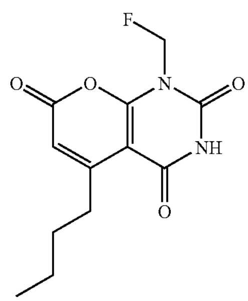 | 256 |
| 814 | 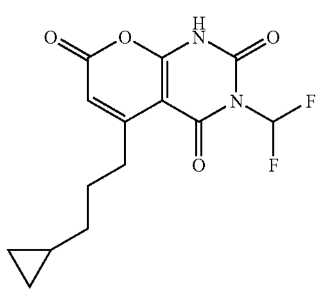 | 161 |
| 815 | 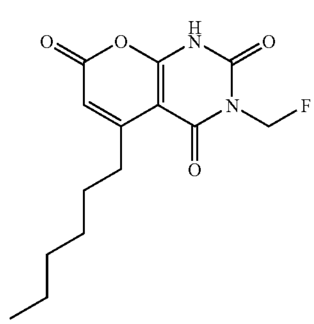 | 10000 |

-continued

| Compound No. | Structure | NA EC$_{50}$ camp (nM) |
|---|---|---|
| 816 | 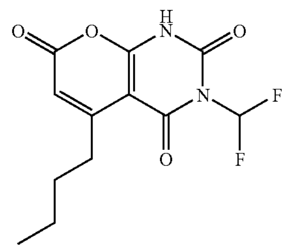 | 291 |
| 817 | 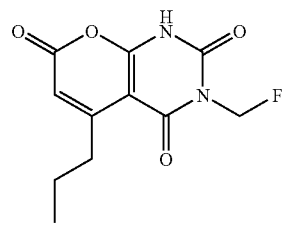 | 1450 |
| 818 | 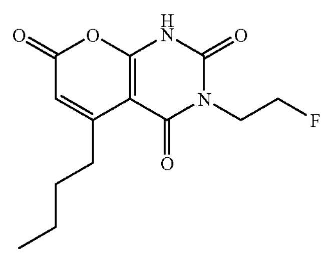 | 308 |
| 819 | 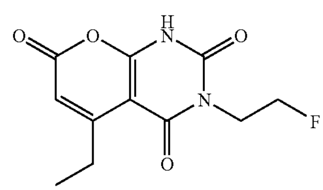 | 1536 |
| 820 | 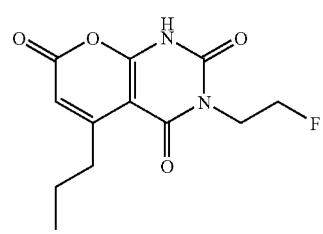 | 10000 |
| 821 | 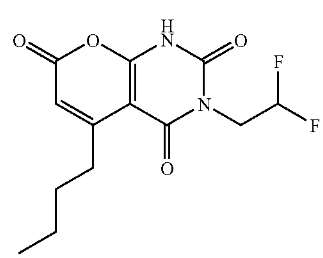 | 142 |

| Compound No. | Structure | NA EC$_{50}$ camp (nM) |
|---|---|---|
| 822 | 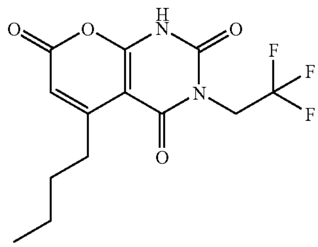 | 10000 |
| 823 | 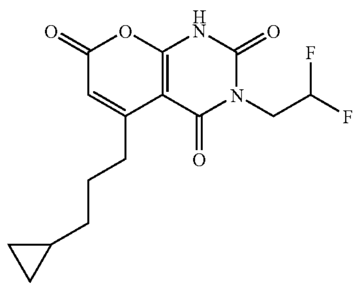 | 10000 |
| 824 | 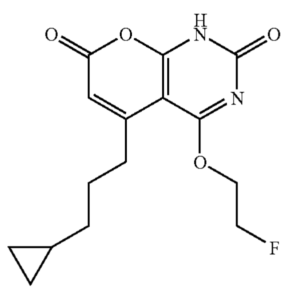 | 91 |
| 825 | 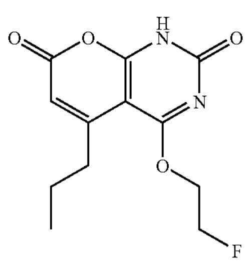 | 616 |
| 826 | 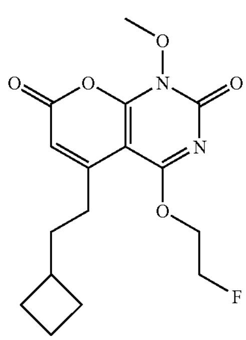 | 3251 |

-continued

| Compound No. | Structure | NA EC$_{50}$ camp (nM) |
|---|---|---|
| 827 | 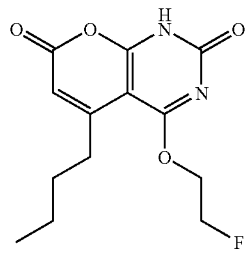 | 690 |
| 828 | 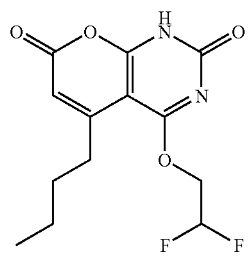 | 407 |
| 829 | 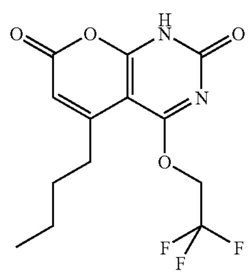 | 882 |
| 830 | 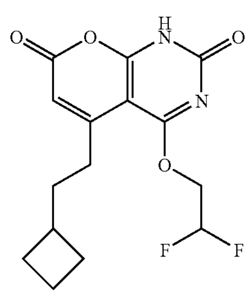 | 112 |
| 831 | 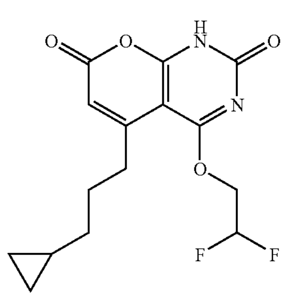 | 531 |

-continued

| Compound No. | Structure | NA EC$_{50}$ camp (nM) |
|---|---|---|
| 832 | 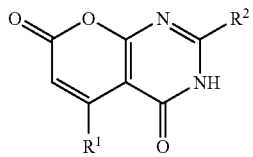 | 304 |
| 833 | 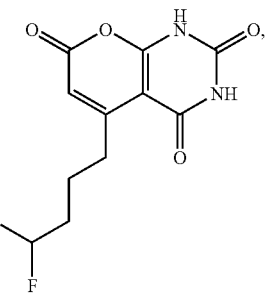 | 511 |

The activity of compounds 834-844 was also determined using the above-described assay and the EC$_{50}$ values measured ranged from about 3 nM to about 1600 nM.

The activity of several other compounds of the present invention is shown earlier in this specification as A, B or C. It will be appreciated by those skilled in the art that the herein-described inventive compounds exhibit excellent nicotinic acid receptor agonist activity. While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound having the formula:

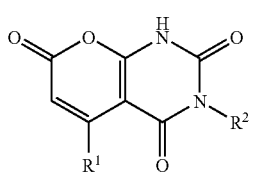

(IV)

or a pharmaceutically acceptable salt thereof, wherein:
R$^1$ is haloalkyl; and
R$^2$ is H or cycloalkyl.

2. A compound having the formula:

(V)

or a pharmaceutically acceptable salt thereof, wherein:
R$^1$ and R$^2$ are each, independently, haloalkyl.

3. The compound of claim 1, wherein R$^1$ is fluoroalkyl.
4. The compound of claim 2, wherein R$^1$ is -alkylene-CF$_2$.
5. The compound of claim 2, wherein R$^1$ is -alkylene-F.
6. The compound of claim 4, wherein R$^1$ is —(CH$_2$)$_3$—CF$_2$, —(CH$_2$)$_4$—CF$_2$ or —(CH$_2$)$_5$—CF$_2$.
7. The compound of claim 1, wherein R$^2$ is H.
8. The compound of claim 1, wherein R$^2$ is cycloalkyl.
9. The compound of claim 8, wherein R$^2$ is cyclobutyl.
10. The compound of claim 2, wherein R$^2$ is H.
11. The compound of claim 3, wherein R$^2$ is H.
12. The compound of claim 2, wherein R$^2$ is cycloalkyl.
13. The compound of claim 3, wherein R$^2$ is cycloalkyl.
14. A compound having the structure:

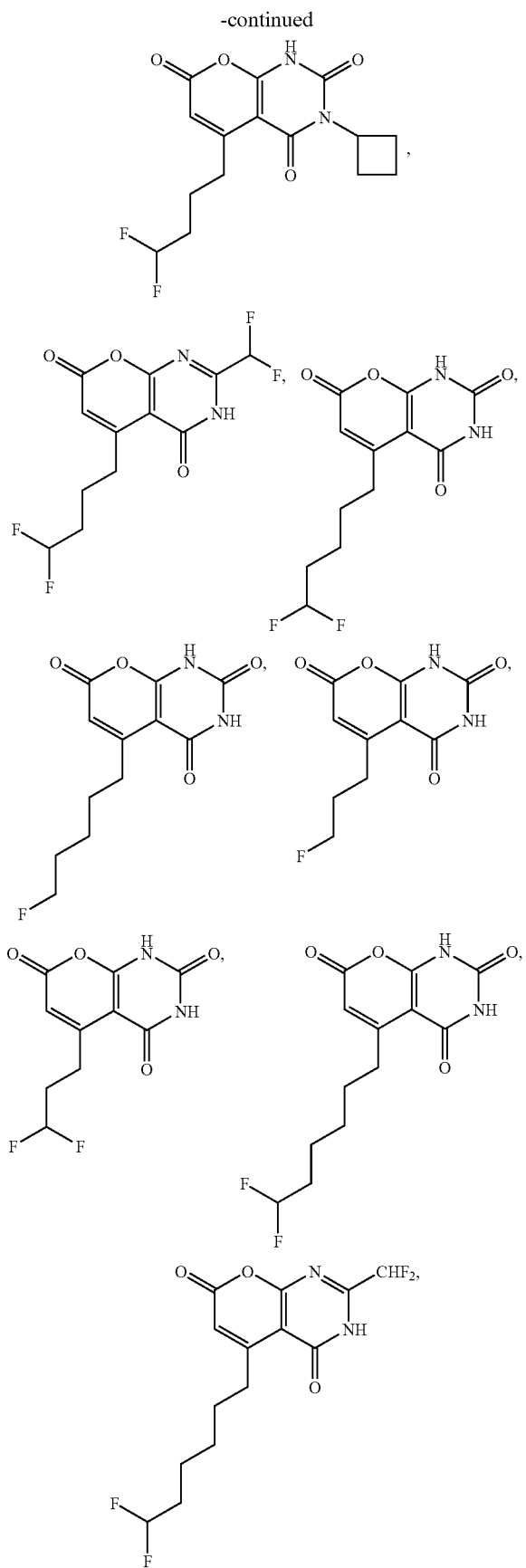

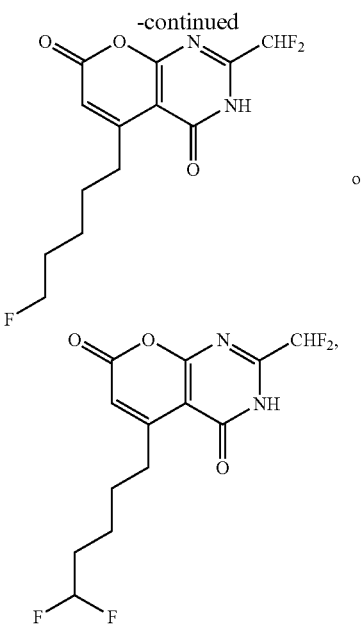

or a pharmaceutically acceptable salt thereof.

15. A composition comprising at least one compound of claim 1 and a pharmaceutically acceptable carrier.

16. A composition comprising at least one compound of claim 2 and a pharmaceutically acceptable carrier.

17. A composition comprising at least one compound of claim 14 and a pharmaceutically acceptable carrier.

18. The composition of claim 15, further comprising at least one additional therapeutic agent selected from the group consisting of HMG CoA reductase inhibitor compounds, HMG CoA synthetase inhibitors, squalene synthesis inhibitors, squalene epoxidase inhibitors, sterol biosynthesis inhibitors, bile acid sequestrants, aspirin, NSAID agents, ezetimibe, a combination of simvastatin and ezetimibe, inorganic cholesterol sequestrants, AcylCoA:Cholesterol O-acyltransferaseinhibitors, cholesteryl ester transfer protein inhibitors, fish oils containing Omega 3 fatty acids, natural water soluble fibers, plant stanols and/or fatty acid esters of plant stands, anti-oxidants, PPAR a agonists, PPAR γ-agonists, FXR receptor modulators, LXR receptor agonists, lipoprotein synthesis inhibitors, renin angiotensin inhibitors, microsomal triglyceride transport inhibitors, bile acid reabsorption inhibitors, PPAR δ agonists, triglyceride synthesis inhibitors, squalene epoxidase inhibitors, low density lipoprotein receptor inducers or activators, platelet aggregation inhibitors, 5-LO or FLAP inhibitors, PPAR δ partial agonists, niacin or niacin receptor agonists, 5HT transporter inhibitors, NE transporter inhibitors, $CB_1$ antagonists/inverse agonists, ghrelin antagonists, $H_3$ antagonists/inverse agonists, MCH1R antagonists, MCH2R agonists/antagonists, NPY1 antagonists, NPY5 antagonists, NPY2 agonists, NPY4 agonists, mGluR5 antagonists, leptins, leptin agonists/modulators, opioid antagonists, orexin receptor antagonists, BRS3 agonists, CCK-A agonists, CNTF, CNTF agonists/modulators, 5HT2c agonists, Mc4r agonists, monoamine reuptake inhibitors, serotonin reuptake inhibitors, GLP-1 mimetics, phentermine, topiramate, phytopharm compound 57, ghrelin antibodies, Mc3r agonists, ACC inhibitors, β3 agonists, DGAT1 inhibitors, DGAT2 inhibitors, FAS inhibitors, PDE inhibitors, thyroid hormone β agonists, UCP-1 activators, UCP-2 activators, UCP-3 activators, acyl-estrogens, glucocorticoid agonists/antagonists, 11β HSD-1 inhibitors, SCD1 inhibitors, lipase inhibitors, fatty acid transporter inhibitors, dicarboxylate transporter inhibitors, glucose transporter inhibitors, phosphate transporter inhibitors, antidiabetic agents, anti-hypertensive agents, anti-dyslipidemic agents, DPP-IV inhibitors, apolipoprotein-B secretionlmicrosomal triglyceride transfer protein (apo-B/MTP) inhibitors, sympathomimetic agonists, dopamine agonists, melanin concentrating hormone antagonists, leptons, galanin receptor antagonists, bombesin agonists, neuropeptide-Y antagonists, thyromimetic agents, dehydroepiandrosterone, urocortin binding protein antagonists, glucagons-like peptide-1 receptor agonists, human agouti-related proteins (AGRP), neuromedin U receptor agonists, noradrenergie anorectic agents, appetite suppressants, hormone sensitive lipase antagonists, α-glucosidase inhibitors, apo A1 milano reverse cholesterol transport inhibitors, fatty acid binding protein inhibitors (FABP), and fatty acid transporter protein inhibitors (FATP).

19. The composition of claim 18, wherein the at least one additional therapeutic agent is an HMG CoA reductase inhibitor selected from the group consisting of lovastatin, simvastatin, pravastatin, atorvastatin, fluvastatin, cerivastatin, rivastatin, rosuvastatin calcium, and pitavastatin.

20. The composition of claim 19, wherein the at least one additional therapeutic agent is simvastatin.

21. The composition of claim 18, wherein the at least one additional therapeutic agent is a cholesteryl ester transfer protein inhibitor.

22. The composition of claim 18, wherein the at least one additional therapetuic agent is ezetimibe, a combination of simvastatin and ezetimibe, aspirin, ibuprofen or acetaminophen or a combination thereof.

23. The composition of claim 18, wherein the at least one additional therapeutic agent is a DPP-IV inhibitor or a GLP-1 mimetic.

24. The composition of claim 16, further comprising at least one additional therapeutic agent selected from the group consisting of HMG CoA reductase inhibitor compounds, HMG CoA synthetase inhibitors, squalene synthesis inhibitors, squalene epoxidase inhibitors, sterol biosynthesis inhibitors, bile acid sequestrants, aspirin, NSAID agents, ezetimibe, a combination of simvastatin and ezetimibe, inorganic cholesterol sequestrants, AcylCoA:Cholesterol O-acyltransferaseinhibitors, cholesteryl ester transfer protein inhibitors, fish oils containing Omega 3 fatty acids, natural water soluble fibers, plant stanols and/or fatty acid esters of plant stanols, anti-oxidants, PPAR α agonists, PPAR γ-agonists, FXR receptor modulators, LXR receptor agonists, lipoprotein synthesis inhibitors, renin angiotensin inhibitors, microsomal triglyceride transport inhibitors, bile acid reabsorption inhibitors, PPAR δ agonists, triglyceride synthesis inhibitors, squalene epoxidase inhibitors, low density lipoprotein receptor inducers or activators, platelet aggregatidn inhibitors, 5-LO or FLAP inhibitors, PPAR δ partial agonists, niacin or niacin receptor agonists, 5HT transporter inhibitors, NE transporter inhibitors, $CB_1$ antagonists/inverse agonists, ghrelin antagonists, $H_3$ antagonists/inverse agonists, MCH1R antagonists, MCH2R agonists/antagonists, NPY1 antagonists, NPY5 antagonists, NPY2 agonists, NPY4 agonists, mGluR5 antagonists, leptins, leptin agonists/modulators, opioid antagonists, orexin receptor antagonists, BRS3 agonists, CCK-A agonists, CNTF, CNTF agonists/modularors, 5HT2c agonists, Mc4r agonists, monoamine reuptake inhibitors, serotonin reuptake inhibitors, GLP-1 mimetics, phentermine, topiramate, phytopharm compound 57, ghrelin antibodies, Mc3r agonists, ACC inhibitors, β agonists, DGAT1 inhibitors, DGAT2 inhibitors, FAS inhibitors, PDE inhibitors, thyroid hormone β agonists, UCP-1 activators, UCP-2 activators, UCP-3 activators, acyl-estrogens, glucocorticoid agonists/antagonists, 11β HSD-1 inhibitors, SCD-1 inhibitors, lipase inhibitors, fatty acid transporter inhibitors, dicarboxylate transporter inhibitors, glucose transporter inhibitors, phosphate transporter inhibitors, antidiabetic agents, anti-hypertensive agents, anti-dyslipidemic agents, DPP-IV inhibitors, apolipoprotein-B secretion/microsomal triglyceride transfer protein (apo-B/MTP) inhibitors, sympathomimetic agonists, dopamine agonists, melanin concentrating hormone antagonists, leptons, galanin receptor antagonists, bombesin agonists, neuropeptide-Y antagonists, thyromimetic agents, dehydroepiandrosterone, urocortin binding protein antagonists, glucagons-like peptide-1 receptor agonists, human agouti-related proteins (AGRP), neuromedin U receptor agonists, noradrenergic anorectic agents, appetite suppressants, hormone sensitive lipase antagonists, α-glucosidase inhibitors, apo A1 milano reverse cholesterol transport inhibitors, fatty acid binding protein inhibitors (FABP), and fatty acid transporter protein inhibitors (FATP).

25. The composition of claim 24, wherein the at least one additional therapeutic agent is an HMG CoA reductase inhibitor selected from the group consisting of lovastatin, simvastatin, pravastatin, atorvastatin, fluvastatin, cerivastatin, rivastatin, rosuvastatin calcium, and pitavastatin.

26. The composition of claim 25, wherein the at least one additional therapeutic agent is simvastatin.

27. The composition of claim 24, wherein the at least one additional therapeutic agent is a cholesteryl ester transfer protein inhibitor.

28. The composition of claim 24, wherein the at least one additional therapetuic agent is ezetimibe, a combination of simvastatin and ezetimibe, aspirin, ibuprofen or acetaminophen or a combination thereof.

29. The composition of claim 24, wherein the at least one additional therapeutic agent is a DPP-IV inhibitor or a GLP-1 mimetic.

30. The composition of claim 17, further comprising at least one additional therapeutic agent selected from the group consisting of HMG CoA reductase inhibitor compounds, HMG CoA synthetase inhibitors, squalene synthesis inhibitors, squalene epoxidase inhibitors, sterol biosynthesis inhibitors, bile acid sequestrants, aspirin, NSAID agents, ezetimibe, a combination of simyastatin and ezetimibe, inorganic cholesterol sequestrants, AcylCoA:Cholesterol O-acyltransferaseinhibitors, cholesteryl ester transfer protein inhibitors, fish oils containing Omega 3 fatty acids, natural water soluble fibers, plant stanols and/or fatty acid esters of plant stanols, anti-oxidants, PPAR α agonists, PPAR γ-agonists, FXR receptor modulators, LXR receptor agonists, lipoprotein synthesis inhibitors, renin angiotensin inhibitors, microsomal triglyceride transport inhibitors, bile acid reabsorption inhibitors, PPAR δ agonists, triglyceride synthesis inhibitors, squalene epoxidase inhibitors, low density lipoprotein receptor inducers or activators, platelet aggregation inhibitors, 5-LO or FLAP inhibitors, PPAR δ partial agonists, niacin or niacin receptor agonists, 5HT transporter inhibitors, NE transporter inhibitors, $CB_1$ antagonists/inverse agonists, ghrelin antagonists, $H_3$ antagonists/inverse agonists, MCH1R antagonists, MCH2R agonists/antagonists, NPY1 antagonists, NPY5 antagonists, NPY2 agonists, NPY4 agonists, mGluR5 antagonists, leptins, leptin agonists/modulators, opioid antagonists, orexin receptor antagonists, BRS3 agonists, CCK-A agonists, CNTF, CNTF agonists/modulators, 5HT2c agonists, Mc4r agonists, monoamine reuptake inhibitors, serotonin reuptake inhibitors, GLP-1 mimeties, phentermine, topiramate, phytopharm compound 57, ghrelin antibodies, Mc3r agonists, ACC inhibitors, β agonists, DGAT1 inhibitors, DGAT2 inhibitors, FAS inhibitors, PDE inhibitors, thyroid hormone β agonists, UCP-1 activators, UCP-2 activators, UCP-3 activators, acyl-estrogens, glucocorticoid agonists/antagonists, 11β HSD-1 inhibitors, SCD-1 inhibitors, lipase inhibitors, fatty acid transporter inhibitors, dicarboxylate transporter inhibitors, glucose transporter inhibitors, phosphate transporter inhibitors, antidiabetic agents, anti-hypertensive agents, anti-dyslipidemic agents, DPP-IV inhibitors, apolipoprotein-B secretion/microsomal triglyceride transfer protein (apo-B/MTP) inhibitors, sympathomimetic agonists, dopamine agonists, melanin concentrating hormone antagonists, leptons, galanin receptor antagonists, bombesin agonists, neuropeptide-Y antagonists, thyromimetic agents, dehydroepiandrosterone, urocortin binding protein antagonists, glucagons-like peptide-1 receptor agonists, human agouti-related proteins (AGRP), neuromedin U receptor agonists, noradrenergic anorectic agents, appetite suppressants, hormone sensitive lipase antagonists, α-glucosidase inhibitors, apo A1 milano reverse cholesterol transport inhibitors, fatty acid binding protein inhibitors (FABP), and fatty acid transporter protein inhibitors (FATP).

31. The composition of claim 30, wherein the at least one additional therapeutic agent is an HMG CoA reductase inhibitor selected from the group consisting of lovastatin, simvastatin, pravastatin, atorvastatin, fluvastatin, cerivastatin, rivastatin, rosuvastatin calcium, and pitavastatin.

32. The composition of claim 31, wherein the at least one additional therapeutic agent is simvastatin.

33. The composition of claim 30, wherein the at least one additional therapeutic agent is a cholesteryl ester transfer protein inhibitor.

34. The composition of claim 30, wherein the at least one additional therapetuic agent is ezetimibe, a combination of simvastatin and ezetimibe, aspirin, ibuprofen or acetaminophen or a combination thereof.

35. The composition of claim 30, wherein the at least one additional therapeutic agent is a DPP-IV inhibitor or a GLP-1 mimetic.

* * * * *